(12) United States Patent
Fujisawa et al.

(10) Patent No.: US 7,605,226 B2
(45) Date of Patent: Oct. 20, 2009

(54) MELTRINS

(75) Inventors: Atsuko Fujisawa, Tokyo (JP); Toru Yamakawa, Tokyo (JP); Kamon Shirakawa, Tokyo (JP); Chitose Orii, Tokyo (JP); Naoki Ogawa, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 12 days.

(21) Appl. No.: 11/276,738

(22) Filed: Mar. 13, 2006

(65) Prior Publication Data

US 2006/0247164 A1    Nov. 2, 2006

Related U.S. Application Data

(60) Division of application No. 09/983,531, filed on Oct. 24, 2001, now Pat. No. 7,060,791, which is a continuation of application No. 09/138,675, filed on Aug. 24, 1998, now abandoned, which is a continuation of application No. PCT/JP96/03017, filed on Oct. 17, 1996.

(30) Foreign Application Priority Data

Feb. 23, 1996  (JP) .................................. 8/61756

(51) Int. Cl.
   A61K 38/04    (2006.01)
   A07K 14/00    (2006.01)
(52) U.S. Cl. ........................ 530/324; 530/350
(58) Field of Classification Search .................. None
   See application file for complete search history.

(56) References Cited

U.S. PATENT DOCUMENTS

| 5,883,241 | A  | 3/1999 | Docherty et al. |
| 6,191,113 | B1 | 2/2001 | Nakahara et al. |
| 7,060,791 | B2* | 6/2006 | Fujisawa et al. ............ 530/324 |

FOREIGN PATENT DOCUMENTS

| WO | 97/31109 | 8/1997 |
| WO | 97/40072 | 10/1997 |

OTHER PUBLICATIONS

Gilpin et al. A Novel, Secreted Form of Human ADAM 12 (Meltrin ) Provokes Myogenesis in Vivo . J. Biol. Chem. 1998 273: 157-166.*
Paine et al. Purification, cloning, and molecular characterization of a high molecular weight hemorrhagic metalloprotease, jararhagin, from Bothrops jararaca venom. Insights into the disintegrin gene family.. J Biol Chem. Nov. 15, 1992;267(32):22869-22876.*
Murray RK et al. Harper's Biochemistry, 23ed., Prentic-Hall International Inc., London, 1993, p. 431.*
Lewin B. Genes V, Oxford University Press, Oxford, 1994, pp. 281-282.*
Alberts B et al., Molecular Biology of the Cell., Garland Publishing, Inc., New York 1994, pp. 628-629.*
Office Action issued in corresponding Canadian Application No. 2,247,067, dated Jun. 13, 2005.
Nomura, N. et al., GenBank database entry, Accession # D14665, May 14, 1993.
Hillier, L. et al., GenBank database entry, Accession #R28537, Apr. 25, 1995.
S. Fujisawa, "Mouse mRNA for Meltrin Alpha", EMBL Database Accession No. D50411, Sequence Identity MMMAB, Nov. 6, 1995, XP002151067.
S. Fujisawa, "Mouse mRNA for Meltrin Beta", EMBL Database Accession No. D50410, Sequence Identity MMMBA, Nov. 6, 1995, XP002151068.
S. Fujisawa, "Mouse mRNA for Meltrin Gamma", EMBL Database Accession No. D50412, Sequence Identity MMMGC, Nov. 6, 1995, XP002151069.
G. Weskamp et al., "MDC9, A Widely Expressed Cellular Disintegration Containing Cytoplasmic SH3 Ligand Domains", The Journal of Cell Biology, vol. 132, No. 4, Feb. 1, 1996, 717-726, XP000644308, Rockefeller University Press.
N. Nomura et al., "Prediction of the Coding Sequences of Unidentified Human Genes. . .", DNA Research, JP, Universal Academy Press, vol. 1, No. 1, 1994, 27-35, XP002049267.
N. Nomura et al., "Prediction of New Human Genes. . .", EMBL Database Accession No. D14665, Sequence Identity HSORF09, Mar. 31, 1993, XP002151071.
"Cellular Disintegration-Related Protein Precursor", SWISSPROT Database Accession No. Q13443, Nov. 1, 1996, XP002151071.
T. Yagami-Hiromasa et al., "A metalloprotease-disintegrin participating in myoblast fusion", Nature 377, pp. 652-656, 1995.
Mizushima et al., Nucleic Acid Res. 18, 5322, 1990.
Knudsen et al., Exp. Cell. Res., 188, 175-184, 1990.
Mege et al., J. Cell. Sci., 103, 897-906, 1992.
Donalies et al., Pro. Natl. Acad., Sci, 88, 8024-8028, 1991.
Rosen et al., Cell, 69, 1107-1119, 1992.
Smith, Donald B. et al., "Single-step purification of polypeptides expressed in *Escherichia coli* as fusions with glutathione S-transferase", Gene, 67, (1998) pp. 31-40.
T. Yagami-Hiromasa et al., "Meltrina, A Novel Metalloprotease-Disintegrin, Participates in Myotube Formation", Cell Structure and Function, vol. 20 No. 6, 1995, p. 585, 2A-1345.

(Continued)

Primary Examiner—Maher M Haddad
(74) Attorney, Agent, or Firm—Birch, Stewart, Kolasch & Birch, LLP

(57) ABSTRACT

The purpose of the present invention is to provide a novel protein involved in adhesion and fusion between myoblasts in the course of the formation of byotube. The present invention relates to Meltrins, which a membrane protein having fusion, adhesion and aggregation activity of cells, especially myoblast; and to polypeptides of their domains, DNAs encoding them, antisense RNA for these DNAs, various antibodies to Meltrins and the polypeptides of their domains, expression vectors containing these DNAs, and transformants by these vectors; as well as to the process for producing Meltrins and the polypeptides of their domains using those transformants and medical compositions comprising Meltrins or antagonist against them as an effective ingredient.

7 Claims, 90 Drawing Sheets

OTHER PUBLICATIONS

Kurizaki Tomohiro et al., "A Novel Cellular Adhesive Molecule Meltrin belonging to Metalloprotease Dysintegrain Family", Experimental Medicine 14 (10), pp. 1352-1356, Jan. 7, 1996.

Endo, Tsuyoshi, "ADAM Family and Cell Fusion", Biochemistry, vol. 68, No. 8, pp. 1453-1458, Aug. 1996.

Cho, Chunghee et al., "Chromosomal Assignment of Four Testis-Expressed Mouse Genes from a New Family of Transmembrane Proteins (ADAMs) Involved in Cell-Cell Adhesion and Fusion", Genomics, 34, Apr. 10, 1996, pp. 413-417.

J. Fujisawa et al., "Molecular Mechanism of Differentiation and Formation of Skeletal Muscle" Generalized Research Report in Fiscal Years Heisei 5 to 7, Morphological and Biochemical and Molecular Biological Basic Research on Muscular Dystrophy, Mar. 1996, pp. 85-88.

Morrison, T. G., "Structure, function, and introcellular processing of paramyxovirus membrane proteins", Virus Research, 10 (1988), pp. 113-136.

Blobel, Carl P. et al., "A potential fusion peptide and an integrin ligand domain in a protein active in sperm-egg fusion", Nature, vol. 356, Mar. 19, 1992, pp. 248-252.

G. Weskamp et al., "A Family of Cellular Proteins Related to Snake Venom Disintegerins", Proc. Natl. Acad. Sci. USA 91, 1994.

International Search Report in corresponding application No. PCT/JP96/03017 completed Jan. 16, 1997 and mailed Jan. 28, 1997.

T. Kurisaki et al., "Cloning of Meltrins, Novel Members of Metalloprotease-Disintegrin Family Involved in Myogenesis", Cell Structure and Function, vol. 20 No. 6, 1995, p. 585, 2A-1330.

Seiler-Tuyns, Anne et al., Expression and Regulation of Chicken Actin Genes Introduced into Mouse Myogenic and Nonmyogenic Cells, Proceedings of the National Academy of Sciences, May 15, 1984, vol. 81, No. 10, 2980-2984.

Kurisaki et al., "Cloning of novel members of metalloprotease-disintegrin family which are involved in myotube formation", 2A-1330 Abstract of the 48th Annual Meeting of the Japan Societ for Cell Biology, 1995.

Yagami et al., "Function analysis of meltrin genes which participate in myogenesis", 2A-1345 Abstract of the 48th Annual Meeting of the Japan Society for Cell Biology, 1995.

* cited by examiner

| | | | | | | | | |
|---|---|---|---|---|---|---|---|---|
| Mα | HGRGVCNNRK | NCHCEAHWAP | PFCDKFCFGG | STDSGPIRQA | DNQGLTVGIL | VSILCLIAAG | FVVYLKRKTL | MRLLFTHKKT | TMEKLRCVHP | SRTPSGPHLG | 762 |
| MS2 | NH-GVCNHKR | ECHCHKGWAP | PNCVQ----R | LADVSDEQAA | STSLPVSVVV | VLVILVAPMV | IVAGIVIYRK | APRQIQRRSV | APKPIS---- | ---------- | 707 |
| Fα | NENGICNNLG | HCHCGDGFAP | PNCKEQCTGG | SIDSGPPPPS | SPTAPPKPT | QTTKASSENL | ALIGLILLVI | LILLVICAI | CLGIPAEEAP | PPPEEEAGE | 783 |

| | | | | | | | |
|---|---|---|---|---|---|---|---|
| Mα | QAHHTPGKGL | LMNRAPHFNT | PKDRHSLKCQ | NMDISRPLDA | RAVPQIQSPQ | RVLLPLHQTP | RAPSGPARPL | PASPAVRQAQ | GIRKPSPPQK | PLPADPLSRT | 862 |
| MS2 | ---GLSNPLF | YTRDSSL-PA | KNRPDPSET | VSTNQPPRPI | AKPKRP----- | ---------- | ---------- | PVPVYAPKIP | NQFRPDPPTK | PLPELKPKQV | 792 |
| Fα | LEEEPEPEPE | PEEEAAEEE | D | | -----PPAP | PGAVSSS-PL | | | | | 804 |

| | | | | | |
|---|---|---|---|---|---|
| Mα | SRLTSALVRT | PGQQEPGHRP | APIRPAPKHQ | VPRPSHNAYI | K | 903 |
| MS2 | KPTFAPPTPP | VKPGTGGTVP | GATQGAGPK | VALKVPIQK- | R | 832 |

Fig. 2a

```
        190       200       210       220       230       240
CGGGGGCCCCGAAGCAGCAGCTGCACGCCCAGGCCCGGGCGACAATGGCAGAGGCCGGCGCG
                                            M  A  E  R  P  A  R    7

250       260       270       280       290       300
GCGCGGCCGCCCCGCGCCCTCCTGCTGGCCCTGGCTGGGGCCCTGCTGGCGCCCCG
 R  A  P  P  A  R  A  L  L  L  L  A  L  A  G  A  L  L  A  P  R   27

310       320       330       340       350       360
TGCAGCCCGAGGGATGAGTTTGTGGGACCAGAGAGGAGCTTACGAAGTGGCCAGAGCCTC
 A  A  R  G  M  S  L  W  D  Q  R  G  A  Y  E  V  A  R  A  S    47

370       380       390       400       410       420
CCTTCTGAGCAAGGACCCTGGGATCCCAGGACAGAGCATCCCAGCCAAGGATCATCCAGA
 L  L  S  K  D  P  G  I  P  G  Q  S  I  P  A  K  D  H  P  D   67

430       440       450       460       470       480
CGTGCTGACTGTGCAACTGCAGCTGGAGAGCCGAGACCTGATCCTCAGCCTGGAAAGGAA
 V  L  T  V  Q  L  Q  L  E  S  R  D  L  I  L  S  L  E  R  N   87
```

Fig. 2b

```
       490       500       510       520       530       540
TGAGGGACTCATTGCCAATGGCTTCACGGAGACCCATTATCTGCAAGATGGTACTGATGT      107
 E  G  L  I  A  N  G  F  T  E  T  H  Y  L  Q  D  G  T  D  V 550       560       570       580       590       600
CTCTCTCACTCGAAATCACACGGATCATTGTTACTACCATGGACATGTGCAAGGAGATGC      127
 S  L  T  R  N  H  T  D  H  C  Y  Y  H  G  H  V  Q  G  D  A 610       620       630       640       650       660
TGCATCAGTGGTCAGCCTCAGTACTTGCTCTGATCTCCGGGACTTATCATGTTTGAAAA      147
 A  S  V  V  S  L  S  T  C  S  D  L  R  G  L  I  M  F  E  N 670       680       690       700       710       720
TAAAACGTACAGCTTAGAGCCAATGAAAAACACCACTGACAGCTACAAACTCGTCCCAGC      167
 K  T  Y  S  L  E  P  M  K  N  T  T  D  S  Y  K  L  V  P  A 730       740       750       760       770       780
TGAGAGCATGACGAACATCCAAGGGCTGTGTGGTCACAGCATAACAAGTCCAACCTCAC      187
 E  S  M  T  N  I  Q  G  L  C  G  S  Q  H  N  K  S  N  L  T
```

Fig. 2c

```
           790         800         810         820         830         840
CATGGAAGATGTCTCCCCCTGGAACCTCTCAAATGCGGGCAAGAAGGCATAAGAGAGAGAC       207
 M  E  D  V  S  P  G  T  S  Q  M  R  A  R  R  H  K  R  E  T 850         860         870         880         890         900
CCTTAAGATGACCAAGTACGTGGTTATTGTGCAGACAACAGAGAGTTTCAGAG              227
 L  K  M  T  K  Y  V  E  L  V  I  V  A  D  N  R  E  F  Q  R 910         920         930         940         950         960
GCAAGGAAAAGACCTGGAGAAAAGTTAAGCAGCGATTAATAGAGATCGCCAATCACGTTGA      247
 Q  G  K  D  L  E  K  V  K  Q  R  L  I  E  I  A  N  H  V  D 970         980         990        1000        1010        1020
CAAGTTTTACAGACGTCCTCTATAAGCCACTGAACATCCGGATCCGTGCTGGTAGGAGTGGAAGTGTGGAATGA   267
 K  F  Y  R  P  L  N  I  R  I  V  L  V  G  V  E  V  W  N  D 1030        1040        1050        1060        1070        1080
CATCGACAAATGCTCTATAAGCCAGGACCCATTCACCAGGCTCCATGAGTTTCTAGACTG       287
 I  D  K  C  S  I  S  Q  D  P  F  T  R  L  H  E  F  L  D  W
```

Fig. 2d

```
              1090       1100       1110       1120       1130       1140
        GAGAAAGATAAAGCTTCTACCTCGAAAATCCCACGACAATGCTCAGCTTATCAGTGGGT       307
         R  K  I  K  L  L  P  R  K  S  H  D  N  A  Q  L  I  S  G  V 1150       1160       1170       1180       1190       1200
        TTATTCCAAGGAACCACCATCGGCATGGCACCCATCATGAGCATGTGCACTGCAGAACA       327
         Y  F  Q  G  T  T  I  G  M  A  P  I  M  S  M  C  T  A  E  Q 1210       1220       1230       1240       1250       1260
        GTCTGGAGGAGTTGTGTCATGGACCATTCAGACAGCCCCTTGGTGCCAGTGACCTTGGC       347
         S  G  G  V  V  M  D  H  S  D  S  P  L  G  A  A  V  T  L  A 1270       1280       1290       1300       1310       1320
        ACATGAGCTGGGCCACAACTTCGGGATGAACCATGACACACTGGAGAGGGGCTGCAGCTG       367
         H  E  L  G  H  N  F  G  M  N  H  D  T  L  E  R  G  C  S  C 1330       1340       1350       1360       1370       1380
        CAGAATGGCCGCAGAGAAAGGAGGCTGCATCATGAACCCGTCCACGGGGTTCCCATTCCC       387
         R  M  A  A  E  K  G  G  C  I  M  N  P  S  T  G  F  P  F  P
```

Fig. 2e

```
      1390      1400      1410      1420      1430      1440
CATGGTGTTCAGCAGCTGCAGCAGGAAGGACCTGGAGGCTAGCCTGGAGAAGGGCATGGG      407
 M  V  F  S  S  C  S  R  K  D  L  E  A  S  L  E  K  G  M  G 1450      1460      1470      1480      1490      1500
GATGTGCCTCTTCAACCTACCAGAGGTCAAGCAGGCCTTTGGGGGCCGGAAGTGTGGAAA      427
 M  C  L  F  N  L  P  E  V  K  Q  A  F  G  G  R  K  C  G  N 1510      1520      1530      1540      1550      1560
TGGCTATGTGGAAGAGGGAGAAGAGTGTGACTGCGGAGAACCGGAGGAATGCACGAATCG      447
 G  Y  V  E  E  G  E  E  C  D  C  G  E  P  E  E  C  T  N  R 1570      1580      1590      1600      1610      1620
CTGCTGTAACGCTACCACCTGTACTCTGAAGCCAGATGCTGTGTGCGCGCACGGGCAGTG      467
 C  C  N  A  T  T  C  T  L  K  P  D  A  V  C  A  H  G  Q  C 1630      1640      1650      1660      1670      1680
CTGTGAAGACTGTCAGCTGAAGCCTCCAGGAACTGCATGCAGGGGCTCCAGCAACTCCTG      487
 C  E  D  C  Q  L  K  P  P  G  T  A  C  R  G  S  S  N  S  C
```

Fig. 2f

```
      1690      1700      1710      1720      1730      1740
TGACCTCCCAGAATTCTGCACAGGGACTGCCCCTCACTGTCCAGCCAATGTGTACCTACA    507
 D   L   P   E   F   C   T   G   T   A   P   H   C   P   A   N   V   Y   L   H 1750      1760      1770      1780      1790      1800
TGATGGCCACCCGTGTCAGGGCGTGTACTGTTACTGCTACAACGGCATCTGCCAGACCCA    527
 D   G   H   P   C   Q   G   V   D   G   Y   C   Y   N   G   I   C   Q   T   H 1810      1820      1830      1840      1850      1860
TGAGCAGCAGTGTGTCACGCTCTGGGGACCAGGTGCTAAACCGGCTCCTGGCATCTGCTT    547
 E   Q   Q   C   V   T   L   W   G   P   G   A   K   P   A   P   G   I   C   F 1870      1880      1890      1900      1910      1920
TGAGCGAGTCAACTCTGCAGGAGATCCTTATGGTAACTGTGGCAAAGACTCCAAGAGCGC    567
 E   R   V   N   S   A   G   D   P   Y   G   N   C   G   K   D   S   K   S   A 1930      1940      1950      1960      1970      1980
CTTCGCCAAATGTGAGCTGAGAGATGCCAAGTGTGGGAAAATCCAGTGTCAAGGTGGTGC    587
 F   A   K   C   E   L   R   D   A   K   C   G   K   I   Q   C   Q   G   G   A
```

Fig. 2g

```
      1990        2000        2010        2020        2030        2040
AAGCCGACCTGTCATTGGTACCAATGCTGTGTTCCATAGAAACAAATATCCCACAGCAGGA         607
 S  R  P  V  I  G  T  N  A  V  S  I  E  T  N  I  P  Q  Q  E 2050        2060        2070        2080        2090        2100
AGGAGGTCGGATTCTGTGCCGGGGGAGACCCATGTGTACTTGGGTGATGACATGCCAGACCC         627
 G  G  R  I  L  C  R  G  T  H  V  Y  L  G  D  D  M  P  D  P 2110        2120        2130        2140        2150        2160
AGGGCTTGTGCTTGCAGGAACAAAGTGTGCAGAAGGAAAAATCTGCCTCAATCGTCGATG         647
 G  L  V  L  A  G  T  K  C  A  E  G  K  I  C  L  N  R  R  C 2170        2180        2190        2200        2210        2220
TCAGAATATCAGTGTCTTCGGCGTTCACAAGTGTGCCATGCAGTGCCACGGCCGAGGGGT         667
 Q  N  I  S  V  F  G  V  H  K  C  A  M  Q  C  H  G  R  G  V 2230        2240        2250        2260        2270        2280
ATGTAACAACAGGAAGAATTGCCACTGTGAAGCCCACTGGGCTCCACCCTTCTGTGACAA         687
 C  N  N  R  K  N  C  H  C  E  A  H  W  A  P  P  F  C  D  K
```

Fig. 2h

```
      2290       2300       2310       2320       2330       2340
GTTTGGCTTTGGAGGAAGCACAGACAGTGGTCCCATCAGGCAAGCAGATAACCAGGGCT      707
 F  G  F  G  G  S  T  D  S  G  P  I  R  Q  A  D  N  Q  G  L 2350       2360       2370       2380       2390       2400
GACTGTAGGAATCCTCGGTGAGCATCCTGTGTCTGCTGGCTGCTGGATTTGTGGTGTATCT    727
 T  V  G  I  L  V  S  I  L  C  L  L  A  A  G  F  V  V  Y  L 2410       2420       2430       2440       2450       2460
CAAAAGGAAGACGTTGATGCGGGTGCTGTTCACACATAAAAAACCACCATGGAAAAGCT      747
 K  R  K  T  L  M  R  L  L  F  T  H  K  K  T  T  M  E  K  L 2470       2480       2490       2500       2510       2520
AAGGTGTGTGCACCCTTCCCGACACCAGTGGCCCTCACCTTGGCCCAGGCTCACCACAC      767
 R  C  V  H  P  S  R  T  P  S  G  P  H  L  G  Q  A  H  H  T 2530       2540       2550       2560       2570       2580
CCCCGGGAAAGGCCTGCTGATGAACCGGGCACCACATTTCAATACCCCCAAGGACAGGCA    787
 P  G  K  G  L  L  M  N  R  A  P  H  F  N  T  P  K  D  R  H
```

Fig. 2i

```
     2590      2600      2610      2620      2630      2640
CTCGCTGAAATGCCAGAACATGGACATCAGCAGGCCCCTCGACGCTCGAGCGTCCACA
 S  L  K  C  Q  N  M  D  I  S  R  P  L  D  A  R  A  V  P  Q     807

2650      2660      2670      2680      2690      2700
GCTTCAGTCACCTCAGGGAGTGCTCCTGCCTCTCCACCAGACCCCACGTGCACCCAGTGG
 L  Q  S  P  Q  R  V  L  L  P  L  H  Q  T  P  R  A  P  S  G     827

2710      2720      2730      2740      2750      2760
CCCTGCCAGGCCCCTGCCCGCCAGTCCTGCAGTCCAGGCAGGCCCCAGGGCATTCGAAAACC
 P  A  R  P  L  P  A  S  P  A  V  R  Q  A  Q  G  I  R  K  P     847

2770      2780      2790      2800      2810      2820
CAGTCCTCCTCAGAAGCCTCTGCCTGATCCACTGAGCAGGACTTCTCGGCTCACTAG
 S  P  P  Q  K  P  L  P  A  D  P  L  S  R  T  S  R  L  T  S     867

2830      2840      2850      2860      2870      2880
TGCCTTGGTGAGGACCCCAGGGCAGCAGGAACCTGGGCACCGCCCAGCCCCCATCAGACC
 A  L  V  R  T  P  G  Q  Q  E  P  G  H  R  P  A  P  I  R  P     887
```

Fig. 2j

```
          2890       2900       2910       2920       2930       2940
TGCCCCTAAGCATCAAGTACCCAGACCTTCCCACAATGCCTATATCAAGTGAGAAGCCAG
 A  P  K  H  Q  V  P  R  P  S  H  N  A  Y  I  K  ***  903
```

Fig. 3a

```
         70         80         90         100        110        120
TCATGCCCGGCGCGGGGCGCGGGGGTCGCCGGTTCTGCTTGCTCTGCTCTGCAGCTAC
     M  P  G  R  A  G  V  A  R  F  C  L  L  A  L  Q  L  H   20

130        140        150        160        170        180
ATTGGCCGCTGGGCGGTGCGAGCCGGATGGACCACAAGAGGAAGCCAAGAAGGTAGCC
  W  P  L  A  A  C  E  P  G  W  T  T  R  G  S  Q  E  G  S  P   40

190        200        210        220        230        240
CTCCGCTACAGCATGAACTCATAATACCTCAGTGGCGACTTCAGAAAGCCCTGGGAGAG
  P  L  Q  H  E  L  I  I  P  Q  W  R  T  S  E  S  P  G  R  G   60

250        260        270        280        290        300
GAAAGCATCCACTCAGAGCAGAGCTCAGGGTCATGGCTGAAGGGCGAGAGCTGATCCTAG
  K  S  I  H  S  E  Q  S  S  G  S  W  L  K  G  E  S  D  P  E
GAAAGCATCCACTCAGAGCAGAGCTCAGGGTCATGGCTGAAGGGCGAGAGCTGATCCTAG
  E  S  P  L  R  A  E  L  R  V  M  A  E  G  R  E  L  I  L  D   80

310        320        330        340        350        360
ACCTGGAGAAGAACGAGCACCTTTTGCTCCAGCCTACACAGAAACCTGCTACACTGCAA
  K  H  P  L  R  A  E  L  R  V  M  A  E  G  R  E  L  I  L  D
ACCTGGAGAAGAACGAGCACCTTTTGCTCCAGCCTACACAGAAACCTGCTACACTGCAA
  L  E  K  N  E  H  L  F  A  P  A  Y  T  E  T  C  Y  T  A  S  100
```

Fig. 3b

```
     370        380        390        400        410        420
GTGGCAATCCTCAAACCAGCACGCTGAAGTCTGAGGATCACTGCTTTTACCACGGAACTG                    120
 G  N  P  Q  T  S  T  L  K  S  E  D  H  C  F  Y  H  G  T  V 430        440        450        460        470        480
TGAGGGACGTGGATGAGTCAAGTGTCCAGTGTCACGCTCAGCACCTGCCGGGGAATTAGAGGACTGA              140
 R  D  V  D  E  S  S  V  T  L  S  T  C  R  G  I  R  G  L  I 490        500        510        520        530        540
TTATAGTGAGAAGTAACCTCAGCTACATCATCGAGCCCGTCCCTAACAGGACAGCCAAC                      160
 I  V  R  S  N  L  S  Y  I  I  E  P  V  P  N  S  D  S  Q  H 550        560        570        580        590        600
ACCGTATTACAGATCCGAACATCTCACGCTGCCCCCGGGAACTGTGGGTTCGAGCACT                       180
 R  I  Y  R  S  E  H  L  T  L  P  P  G  N  C  G  F  E  H  S 610        620        630        640        650        660
CCGGGCCACCTCGAAGGACTGGGCCCTTCAGTTTACACATCAGACCACAAAAAGCAACCTC                    200
 G  P  T  S  K  D  W  A  L  Q  F  T  H  Q  T  K  K  Q  P  R
```

Fig. 3c

```
           670       680       690       700       710       720
GCAGAATGAAACGGGAAGATCTACACTCTATGAAGTACGTGGAGCTTTACCTGGTGGCTG      220
  R  M  K  R  E  D  L  H  S  M  K  Y  V  E  L  Y  L  V  A  D 730       740       750       760       770       780
ATTATGCAGAGTTTCAGAAGAATCGACATGACCAGGATGCCACCAAACGCAAGCTCATGG      240
  Y  A  E  F  Q  K  N  R  H  D  Q  D  A  T  K  R  K  L  M  E 790       800       810       820       830       840
AGATTGCCAACTATGTTGATAAGTTTTACCGTCCCTGAACATCCGAATTGCACTTGTCG      260
  I  A  N  Y  V  D  K  F  Y  R  S  L  N  I  R  I  A  L  V  G 850       860       870       880       890       900
GCTTGGAGGTGTGGACGCATGGGAGATAAGTGTGAAGTTTCAGAGAATCCCTACTCTACCC    280
  L  E  V  W  T  H  G  D  K  C  E  V  S  E  N  P  Y  S  T  L 910       920       930       940       950       960
TCTGGTCCTTTCTTAGTTGGAGGCGCAAGCTGCTTGCTCAGAAGAGCCATGACAATGCTC     300
  W  S  F  L  S  W  R  R  K  L  L  A  Q  K  S  H  D  N  A  Q
```

Fig. 3d

```
        970       980       990      1000      1010      1020
AGCTAATCACGGGGCAGGTCCTTCCAAGGCACCACCATTGGCCTGGCCCCTCATGGCCA        320
 L   I   T   G   R   S   F   Q   G   T   T   I   G   L   A   P   L   M   A   M 1030      1040      1050      1060      1070      1080
TGTGCTCCGTGTACCAGTCTGGAGGAGTTAGCATGGACCACTCCGAGAATGCCATTGGTG        340
 C   S   V   Y   Q   S   G   G   V   S   M   D   H   S   E   N   A   I   G   V 1090      1100      1110      1120      1130      1140
TAGCCTCCACTGTGGCCCATGAGATTGGCCACAACTTTGGCATGAGCCATGATTCTGCAC        360
 A   S   T   V   A   H   E   I   G   H   N   F   G   M   S   H   D   S   A   H 1150      1160      1170      1180      1190      1200
ACTGCTGTTCTGCCAGTGCAGCCGATGGCGGCTGCATCATGGCCGCCGCCACCGGGCACC        380
 C   C   S   A   S   A   A   D   G   G   C   I   M   A   A   A   T   G   H   P 1210      1220      1230      1240      1250      1260
CTTTCCCCAAAGTGTTCAGTTGGTGTAACAGGAAGGAGCTGGACAGGTATCTGCAGACAG        400
 F   P   K   V   F   S   W   C   N   R   K   E   L   D   R   Y   L   Q   T   G
```

Fig. 3e

```
      1270      1280      1290      1300      1310      1320
GAGGAGGGATGTGTCTCTCCAACATGCCGGACACTAGGACGCTGTATGGAGGCCGGAGGT     420
  G  G  M  C  L  S  N  M  P  D  T  R  T  L  Y  G  G  R  R  C 1330      1340      1350      1360      1370      1380
GTGGCAACGGGTACCTGGAAGACGCTGAAGAATGTGACTGTGGAGAAGAGGAGAATGTA     440
  G  N  G  Y  L  E  D  G  E  E  C  D  C  G  E  E  E  E  C  K 1390      1400      1410      1420      1430      1440
AGAACCCTTGCTGCAATGCCTCCAACTGCACTCTGAAGGAAGGGGCAGAGTGTGCCATG     460
  N  P  C  C  N  A  S  N  C  T  L  K  E  G  A  E  C  A  H  G 1450      1460      1470      1480      1490      1500
GTTCCTGCTGCCACCAGTGCAAGCTGGTGGCCCCAGTGCCTGGAACCCAGTGTCGGGAGCAGGTTC     480
  S  C  C  H  Q  C  K  L  V  A  P  G  T  Q  C  R  E  Q  V  R 1510      1520      1530      1540      1550      1560
GGCAATGTGACCTCCCCGAGTTCTGCACCGGCAAGTCTCCCCACTGCCCCACCAACTATT     500
  Q  C  D  L  P  E  F  C  T  G  K  S  P  H  C  P  T  N  Y  Y
```

Fig. 3f

```
        1570      1580      1590      1600      1610      1620
ATCAGATGGATGGCACCCCCTGCGAGGGTGGCCAGGCCTACTGTCAACGGCATGTGCC         520
  Q  M  D  G  T  P  C  E  G  G  Q  A  Y  C  Y  N  G  M  C  L 1630      1640      1650      1660      1670      1680
TCACTTACCAGGAACAGTGCCAGCAGCTGTGGGGACCTGGAGCCCGGCCCTGCCCTCGATC      540
  T  Y  Q  E  Q  C  Q  Q  L  W  G  P  G  A  R  P  A  L  D  L 1690      1700      1710      1720      1730      1740
TTTGCTTTGAGAGGGTGAATGCTGCTGGTGACACCTATGGAAACTGTGGCAAGGGCTTGA      560
  C  F  E  R  V  N  A  A  G  D  T  Y  G  N  C  G  K  G  L  N 1750      1760      1770      1780      1790      1800
ATGGCCAATACAGGAAGTGCAGTCCCAGGGATGCCAAGTGTGGSAAGATTCAGTGCCAGA      580
  G  Q  Y  R  K  C  S  P  R  D  A  K  C  G  K  I  Q  C  Q  S 1810      1820      1830      1840      1850      1860
GCACCCAGGCCCGGCCCCTGGAATCCAACGCAGTATCTATTGACACCATCACCTTGA         600
  T  Q  A  R  P  L  E  S  N  A  V  S  I  D  T  T  I  T  L  N
```

Fig. 3g

```
     1870      1880      1890      1900      1910      1920
ACGGGAGGCGGATCCACTGTCGGGGCACCCACGTCTACCGGGGTCCTGAGGAGGAAG        620
  G   R   R   I   H   C   R   G   T   H   V   Y   R   G   P   E   E   E   E   G 1930      1940      1950      1960      1970      1980
GGGAAGGTGACATGCTGGACCCAGGGCTGGTGATGACTGGAACCAAGTGTGGCCACAACC
  E   G   D   M   L   D   P   G   L   V   M   T   G   T   K   C   G   H   N   H    640

1990      2000      2010      2020      2030      2040
ATATTTGCTTCGAGGGCCAGTGCAGGAACACCTCCTTTGAGACGGAAGGCTGTGGGA
  I   C   F   E   G   Q   C   R   N   T   S   F   F   E   T   E   G   C   G   K    660

2050      2060      2070      2080      2090      2100
AAAAGTGCAATGGCCACGGGGTCTGCAACAACAAGAACTGTCATTGCTTCCCTGGCT
  K   C   N   G   H   G   V   C   N   N   K   N   C   H   C   F   P   G   W    680

2110      2120      2130      2140      2150      2160
GGTCTCCACTTTCTGTAACACCCCGGGAGATGGTGGCAGCGTCGACAGTGGTCCTTTGC
  S   P   P   F   C   N   T   P   G   D   G   G   S   V   D   S   G   P   L   P    700
```

Fig. 3h

```
      2170      2180      2190      2200      2210      2220
CCCTAAGAGTGTGGGTCCCGTGATCGCTGGGGTGTTTTCAGCTCTCTTCGTGTTGGCAG
  P   K   S   V   G   P   V   I   A   G   V   F   S   A   L   F   V   L   A   V 2230      2240      2250      2260      2270      2280
TTCTGGTGTGCTACTGTGTCACTGCTACAGACAGAGCCACAAACTGGGCAAACCCTCGCTC
  L   V   L   L   C   H   C   Y   R   Q   S   H   K   L   G   K   P   S   A   L 2290      2300      2310      2320      2330      2340
TCCCTTTCAAGCTGCGGCATCAGTTCAGTTGTCCCTTCAGGGTATCTCAGAGTGGTGGAA
  P   F   K   L   R   H   Q   F   S   C   P   F   R   V   S   Q   S   G   G   T 2350      2360      2370      2380      2390      2400
CTGGCCATGCCAACCCAACTTTCAAGTTGCAGACCCCCAGGGCAAGGCGAAAGGTGACTA
  G   H   A   N   P   T   F   K   L   Q   T   P   Q   G   K   R   K   V   T   N 2410      2420      2430      2440      2450      2460
ACACCCCTGAATCCCTCCGGAAGCCGTCCCACCCCCCCTCCGGCCCTCCAGACTACC
  T   P   E   S   L   R   K   P   S   H   P   P   L   R   P   P   P   D   Y   L
```

```
       2470        2480        2490        2500        2510        2520
TGCGGGTTGAATCGCCACCTGCACCATTGTCGGCACATCTGAACAGGGCTGTGGGAGCT
  R  V  E  S  P  P  A  P  L  S  A  H  L  N  R  A  A  G  S  S           820

2530        2540        2550        2560        2570        2580
CCCCAGAAGCTGGGGGCTCGAATAGAAAAGGAGTCAGCCAGGAGGCCTCCCCAAGCC
  P  E  A  G  A  R  I  E  R  K  E  S  A  R  R  P  P  P  S  R           840

2590        2600        2610        2620        2630        2640
GACCCATGCCCCCTGCACCTAACTGCCTACTGTCCCAGGACTTCTCCAGGCCTCGACCAC
  P  M  P  P  A  P  N  C  L  L  S  Q  D  F  S  R  P  R  P  P           860

2650        2660        2670        2680        2690        2700
CTCAGAAGGCACTCCCAGCCAATCCGGTGCCAGGCCAAAGGACCGGTCCCAGGTCAGGAG
  Q  K  A  L  P  A  N  P  V  P  G  Q  R  T  G  P  R  S  G  G           880

2710        2720        2730        2740        2750        2760
GCACCTCCCCTGCTTCAGCCCCTACTTCTGGTCCTCCAGCCCCCCAGGCCTCCAGCCAGTGC
  T  S  L  L  Q  P  P  T  S  G  P  P  Q  P  P  R  P  P  A  V  P        900
```

Fig. 3j

```
        2770      2780      2790      2800      2810      2820
CTGTTCCAAAGCTACTACCGAGTACCGAGATCACAGAGGGTTGGAGCAATAATTAGCTCCAAGA
 V   P   K   L   P   E   Y   R   S   Q   R   V   G   A   I   I   S   S   K   I 2830      2840      2850      2860      2870      2880
TCTAGAAGTGTCGAGAAGTTTCTTGTTCCGATGGAAGACTCCGGATGCCATGGAAGGTCC
```

```
            70         80         90        100        110        120
CCCTCGGCTATGGGGCCGGCGCGCTCTCGGCCCCTTGCCTCTCTGCCGACTAAGGTGGCTGC
         M  G  P  R  A  L  S  P  L  A  S  L  R  L  R  W  L  L      18

130        140        150        160        170        180
TGGCGTGTGGCTTGCTGGGCCCAGTCCTCGAGGCCGGACCAGACTTGGAACAGACTG
  A  C  G  L  L  G  P  V  L  E  A  G  R  P  D  L  E  Q  T  V       38

190        200        210        220        230        240
TCCATCTTCTTCTTATGAAATTATTACTCCTTGGAGATTAACTAGAGAAAGAAGGGAAG
  H  L  S  S  Y  E  I  I  T  P  W  R  L  T  R  E  R  R  E  A       58

250        260        270        280        290        300
CTCTGGGGCCCAGTTCACAGCAGATCTCTTACGTCATCCAGGCCCAAGGAAAACAGCATA
  L  G  P  S  S  Q  Q  I  S  Y  V  I  Q  A  Q  G  K  Q  H  I       78

310        320        330        340        350        360
TTATTCACTTGGAAAGAAACACAGACCTTTACCTAATGATTTGTAGTTTACACCTACG
  I  H  L  E  R  N  T  D  L  L  P  N  D  F  V  V  Y  T  Y  D       98
```

Fig. 4b

```
         370       380       390       400       410       420
ACAAGGAAGGCTCCCTACTCTCTGACCATCCCAACGTACAGAGCCATTGTCACTATCGAG      118
 K  E  G  S  L  L  S  D  H  P  N  V  Q  S  H  C  H  Y  R  G 430       440       450       460       470       480
GCTATGTGGAGGGAGTGCAGAATTCCGGGTTGCTGTGAGCGCCTGCTTTGGACTCAGAG      138
 Y  V  E  G  V  Q  N  S  A  V  A  V  S  A  C  F  G  L  R  G 490       500       510       520       530       540
GCTTGCTGCATTTGGAGAATGCCAGTTTTGGAATTGAACCTCTGCACAACAGCTCACACT      158
 L  L  H  L  E  N  A  S  F  G  I  E  P  L  H  N  S  S  H  F 550       560       570       580       590       600
TTGAGCACATATTTTACCCCATGGATGGCATCCACCAGGAGCCTCTGAGATGTGGAGTCT      178
 E  H  I  F  Y  P  M  D  G  I  H  Q  E  P  L  R  C  G  V  S 610       620       630       640       650       660
CTAACAGGGACACAGAGAAGGAAGGCACACAGGGGATGAGGAGGAGCATCCGAGTGTCA      198
 N  R  D  T  E  K  E  G  T  Q  G  D  E  E  E  H  P  S  V  T
```

Fig. 4c

```
           670        680        690        700        710        720
     CTCAGCTGCTGCGCAGAAGAGAGCTGTTCTACCACAGACCCGCTATGTGTGGAGCTGTTCA      218
       Q  L  L  R  R  R  R  A  V  L  P  Q  T  R  Y  V  E  L  F  I 730        740        750        760        770        780
     TTGTTGTAGACAAGGAAAGGTACGACATGATGGGACGGAACCAGACTGCTGTGAGAGAAG      238
       V  V  D  K  E  R  Y  D  M  M  G  R  N  Q  T  A  V  R  E  E 790        800        810        820        830        840
     AGATGATTCGCTTAGCAAACTACCTGGATAGCATGTACATCATGTTAAACATTCGAATTG      258
       M  I  R  L  A  N  Y  L  D  S  M  Y  I  M  L  N  I  R  I  V 850        860        870        880        890        900
     TGCTGGTTGGACTAGAAATTTGGACAGACAGAAATCCTATCAATATAATTGGAGGAGCTG      278
       L  V  G  L  E  I  W  T  D  R  N  P  I  N  I  I  G  G  A  G 910        920        930        940        950        960
     GAGATGTGCTGGGCAACTTTGTTCAGTGGCGGGAAAAGTTCCTTATAACTCGTCGGAGAC      298
       D  V  L  G  N  F  V  Q  W  R  E  K  F  L  I  T  R  R  R  H
```

Fig. 4d

```
        970         980         990        1000        1010        1020
ACGGACAGTGCACAGTTGGTTTTGAAGAAAGGCTTTGGTGGAACTGCAGGAATGGCGTTTG                    318
 D  S  A  Q  L  V  L  K  K  G  F  G  G  T  A  G  M  A  F  V 1030        1040        1050        1060        1070        1080
TAGGAACAGTATGTTCAAGGAGCCACGGTGGATCAATGTGTTTGGGCAAATCACTG                         338
 G  T  V  C  S  R  S  H  A  G  G  I  N  V  F  G  Q  I  T  V 1090        1100        1110        1120        1130        1140
TGGAGACATTTGCATCCATTGTTGCTCATGAATTGGGCATAACCTTGAATGAATCATG                       358
 E  T  F  A  S  I  V  A  H  E  L  G  H  N  L  G  M  N  H  D 1150        1160        1170        1180        1190        1200
ATGATGGGAGAGAGTGTTTCTGTGGAGCAAAGAGCTGTATCATGAATTCAGGAGCATCCG                     378
 D  G  R  E  C  F  C  G  A  K  S  C  I  M  N  S  G  A  S  G 1210        1220        1230        1240        1250        1260
GGTCCAGAAACTTAGCAGTGCGGAGGACTTTGAGAAGTTAACGTTGAATAAGG                            398
 S  R  N  F  S  S  C  S  A  E  D  F  E  K  L  T  L  N  K  G
```

Fig. 4e

```
      1270       1280       1290       1300       1310       1320
GAGGAAGCTGCCTGCTTAACATCCCGAAGCCTGACGAAGCCTACAGCGCGGCCCTCCTGTG      418
 G  S  C  L  L  N  I  P  K  P  D  E  A  Y  S  A  P  S  C  G 1330       1340       1350       1360       1370       1380
GTAATAAGCTGGTGGACCCTGGAGAGGAGTGTGACTGCGGCACAGCGAAGGAGTGTGAGG      438
 N  K  L  V  D  P  G  E  E  C  D  C  G  T  A  K  E  C  E  V 1390       1400       1410       1420       1430       1440
TGGACCCATGCTGTGAAGGAAGCACTTGTAAGCTCAAGTCATTTGCTGAGTGTGCATATG      458
 D  P  C  C  E  G  S  T  C  K  L  K  S  F  A  E  C  A  Y  G 1450       1460       1470       1480       1490       1500
GCGACTGTTGTAAAGATTGCCAGTTCCTTCCAGGAGGCTCCATGTGCAGAGGGAAGACCA      478
 D  C  C  K  D  C  Q  F  L  P  G  G  S  M  C  R  G  K  T  S 1510       1520       1530       1540       1550       1560
GTGAGTGTGATGTTCCTGAGTACTGCAACGGTTCCTCTCAGTTCTGCCCGCCAGATGTCT      498
 E  C  D  V  P  E  Y  C  N  G  S  S  Q  F  C  P  P  D  V  F
```

Fig. 4f

```
      1570      1580      1590      1600      1610      1620
TCATTCAGAATGGATATCCTTGCCAGAACAGCAAAGCCTACTGTCACAATGGCATGTGCC    518
 I  Q  N  G  Y  P  C  Q  N  S  K  A  Y  C  Y  N  G  M  C  Q 1630      1640      1650      1660      1670      1680
AATATTATGACGGCCAGTGTCAGGTCATCTTTGGTTCAAAGGCTAAGGCTGCCCAAGAG    538
 Y  Y  D  A  Q  C  Q  V  I  F  G  S  K  A  K  A  A  P  R  D 1690      1700      1710      1720      1730      1740
ATTGCTTCATTGAAGTCAATTCTAAAGGTGACAGATTGGCAACTGTGGTTTCCGGCA    558
 C  F  I  E  V  N  S  K  G  D  R  F  G  N  C  G  F  S  G  S 1750      1760      1770      1780      1790      1800
GTGAGTACAAGAAGTGTGCCACTGGGAACGCGCTGTGTGGAAAGCTTCAATGCGAGAATG    578
 E  Y  K  K  C  A  T  G  N  A  L  C  G  K  L  Q  C  E  N  V 1810      1820      1830      1840      1850      1860
TACAGGACATGCCGGGTGTTTGGAATAGTACCAGCTATCATTCAGACACCCAGTCGAGGCA    598
 Q  D  M  P  V  F  G  I  V  P  A  I  I  Q  T  P  S  R  G  T
```

Fig. 4g

```
      1870       1880       1890       1900       1910       1920
CCAAATGCTGGGGTGTGGATTTCCAGCTTGGTTCCGACGTTCCAGACCCAGGGATGGTGA        618
  K   C   W   G   V   D   F   Q   L   G   S   D   V   P   D   P   G   M   V   N 1930       1940       1950       1960       1970       1980
ATGAAGGCACCAAATGTGATGCTGGCAAGATTTGCAGGAATTTCAGTGTGTAAATGCTT        638
  E   G   T   K   C   D   A   G   K   I   C   R   N   F   Q   C   V   N   A   S 1990       2000       2010       2020       2030       2040
CTGTCCTGAATTATGACTGTGACATTCAGGGAAAAATGTCATGGCCATGGGGTATGTAACA        658
  V   L   N   Y   D   C   D   I   Q   G   K   C   H   G   H   G   V   C   N   S 2050       2060       2070       2080       2090       2100
GCAATAAGAATTGTCACTGTGAAGATGGCTGGGCTCCCCCACACTGTGACACCAAAGGAT        678
  N   K   N   C   H   C   E   D   G   W   A   P   P   H   C   D   T   K   G   Y 2110       2120       2130       2140       2150       2160
ATGGAGGAAGCGTGGACAGCGGGCCGACGTATAATGCAAAGAGCACTGCACTGAGGGACG        698
  G   G   S   V   D   S   G   P   T   Y   N   A   K   S   T   A   L   R   D   G
```

Fig. 4h

```
      2170        2180        2190        2200        2210        2220
GGCTTCTGGTCTCTTCTTCTTCCTAATCGTCCCCCTTGTTGCGGCTGCCATTTTCCTCTTTA    718
 L  L  V  F  F  F  L  I  V  P  L  V  A  A  A  I  F  L  F  I 2230        2240        2250        2260        2270        2280
TCAAGAGAGATGAACTACGGAAAAACCTTCAGGAAGAAGATCACAAATGTCAGATGGCA       738
 K  R  D  E  L  R  K  K  T  F  R  K  K  R  S  Q  M  S  D  G  R 2290        2300        2310        2320        2330        2340
GAAATCAAGCAAACGTCTCTAGACAGCCAGGAGATCCTAGTATCTCCAGACCCAGGGG        758
 N  Q  A  N  V  S  R  Q  P  G  D  P  S  I  S  R  P  P  G  G 2350        2360        2370        2380        2390        2400
GCCCAAATGTCTCCAGACCACCAGGGGGCCCAGGTGTCTCCAGACCACCAGGGGCCCAG       778
 P  N  V  S  R  P  P  G  G  P  G  V  S  R  P  P  G  G  P  G 2410        2420        2430        2440        2450        2460
GTGTCTCCAGACCACCAGGGGGCCCAGGTGTCTCCAGACCGCCACCTGGGCATGGAAACA     798
 V  S  R  P  P  G  G  P  G  V  S  R  P  P  P  G  H  G  N  R
```

Fig. 4i

```
        2470      2480      2490      2500      2510      2520
GATTCCAGTACCAACCTACGCCGCCAAGCAGCCTGCGCAGTTCCCGTCAAGGCCACCTC
  F   P   V   P   T   Y   A   A   K   Q   P   A   Q   F   P   S   R   P   P   P   818

2530      2540      2550      2560      2570      2580
CACCACAACCGAAAATATCTTCTCAGGGAAACTTGATTCCGGCTCGGCCCGCTCCTGCAC
  P   Q   P   K   I   S   S   Q   G   N   L   I   P   A   R   P   A   P   A   P   838

2590      2600      2610      2620      2630      2640
CTCCTTTATATAGCTCCCTCACCTGATAGTAGAATATTAGAATCTTATTTTTTAAATGTC
  P   L   Y   S   S   L   T   845
```

Fig. 5a

```
GCCAGAGTAG CGCGGCGGCG CACGCACACA CACGGGGGAGG GGAGAAAGTT    50
TTTTTTGAA AAAATGAAAG GCTAGACTCG CTGCTCAGCG ACCCGGGCGC      100
TGCGCGAGGG GGTCGCGGGCA GACTCAGGGC AGTAGGACTT CCCCCAGCTC    150
GGCGCCCGCG TGGGATGCTG CAGCGCTGGC CGCGGGGCCC CCGAAGCAGC     200

┌─ READING FRAME
TGCACGCCAG GCCGGCGACA ATGGCAGAGC GCCGGCGGCG GCGGCGGCCC     250
CCCGCCCCGC CCCTCCTGCT GGCCCCTGGCT GGGGCCCTGC TGGCGCCCCG    300
CCCAGCCCGA GGGATGAGTT TGTGGGACCA GAGAGGAGCT TACGAAGTGG     350
CCAGAGCCTC CCTTCTGAGC AAGGACCCTG GGATCCCCAGG ACAGAGCATC    400
CCAGCCAAGG ATCATCCAGA CGTGCTGACT GTGCAACTGC AGCTGGAGAG     450
CCGAGACCTG ATCCCTCAGCC TGGAAAGGAA TGAGGGACTC ATTGCCAATG    500
GCTTCACGGA GACCCATTAT CTGCAAGATG GTACTGATGT CTCTCTCACT     550
CGAAATCACA CGGATCATTG TTACTACCAT GGACATGTGC AAGGAGATGC    600
TGCATCAGTG GTCAGCCTCA GTACTTGCTC TGATCTGCTC GGACTTATCA     650
```

Fig. 5b

```
TGTTTGAAAA TAAAACGTAC AGCTTAGAGC CAATGAAAAA CACCACTGAC     700
AGCTACAAAC TCGTCCCAGC TGAGAGCATG ACGAACATCC AAGGGCTGTG     750
TGGGTCACAG CATAACAAGT CCAACCTCAC CATGGAAGAT GTCTCCCCTG     800
GAACCTCTCA AATGCGGGCA AGAAGGCATA AGAGAGAGAC CCTTAAGATG     850
ACCAAGTACG TAGAGCTGGT TATTGTGGCA GACAACAGAG AGTTTCAGAG     900
GCAAGGAAAA GACCTGGAGA AAGTTAAGCA GCGATTAATA GAGATCGCCA     950
ATCACGTTGA CAAGTTTTAC AGACCACTGA ACATCCCGGAT CGTGCTGGTA   1000
GGAGTGGAAG TGTGGAATGA CATCGACAAA TGCTCTATAA GCCAGGACCC    1050
ATTCACCAGG CTCCATGAGT TTCTAGACTG GAGAAAGATA AAGCTTCTAC    1100
CTCGAAAATC CCACGACAAT GCTCAGCTTA TCAGTGGGGT TTATTTCCAA    1150
GGAACCACCA TCGGCATGGC ACCCATCATG AGCATGTGCA CTGCAGAACA    1200
GTCTGGAGGA GTTGTCATGG ACCATTCAGA CAGCCCCCTT GGTGCCGGCAG   1250
TGACCTTGGC ACATGAGCTG GGCCACAACT TCGGGATGAA CCATGACACA    1300
CTGGAGAGGG GCTGCAGCTG CAGAATGGCC CAGAGAAAAG GAGGCTGCAT    1350
CATGAACCCG TCCACGGGGT TCCCATTCCC GCAGAGAAAG AGCAGCTGCA    1400
```

Fig. 5c

| | | | | |
|---|---|---|---|---|
| GCAGGAAGGA | CCTGGGAGGCT | AGCCTGGAGA | AGGGCATGGG | GATGTGCCTC | 1450
| TTCAACCTAC | CAGAGGTCAA | GCAGGCCTTT | GGGGGCCCGGA | AGTGTGGAAA | 1500
| TGGCTATGTG | GAAGAGGGAG | AAGAGTGTGA | CCGGGAGAA | CCGGAGGAAT | 1550
| GCACGAATCG | CTGCTGTAAC | GCTACCACCT | GTACTCTGAA | GCCAGATGCT | 1600
| GTGTGCCGCGC | ACGGGCAGTG | CTGTGAAGAC | TGTCAGCTGA | AGCCTCCAGG | 1650
| AACTGCATGC | AGGGGCTCCA | GCAACTCCTG | TGACCTCCCA | GAATTCTGCA | 1700
| CAGGGACTGC | CCCTCACTGT | CCAGCCAATG | TGTACCTACA | TGATGGCCAC | 1750
| CCGTGTCAGG | GCGTGGATGG | TTACTGCTAC | AACGGGCATCT | GCCAGACCCA | 1800
| TGAGCAGCAG | TGTGTCACGC | TCTGGGGACC | AGGTGCTAAA | CCGGCTCCTG | 1850
| GCATCTGCTT | TGAGCGAGTC | AACTCTGCAG | GAGATCCTTA | TGGTAACTGT | 1900
| GGCAAAGACT | CCAAGAGCGC | CTTCGCCAAA | AAGGTGGTGC | GAGATGCCAA | 1950
| GTGTGGGAAA | ATCCAGTGTC | AAGGTGGTGC | ACACAGCAGGA | GTCATTGGTA | 2000
| CCAATGCTGT | TTCCATAGAA | ACAAATATCC | CACAGCAGGA | AGGAGGTCGG | 2050
| ATTCTGTGCC | GGGGACCCA | TGTGTACTTG | GGTGATGACA | TGCCAGACCC | 2100
| AGGGCTTGTG | CTTGCAGGAA | CAAAGTGTGC | AGAAGGAAAA | ATCTGCCTCA | 2150

Fig. 5d

| | | | | |
|---|---|---|---|---|
| ATCGTCGATG | TCAGAATATC | AGTGTCTTCG | GCGTTCACAA | GTGTGCCATG | 2200
| CAGTGCCACG | GCCGAGGGGT | ATGTAACAAC | AGGAAGAATT | GCCACTGTGA | 2250
| AGCCCACTGG | GCTCCACCCT | TCTGTGACAA | GTTTGGCTTT | GGAGGAAGCA | 2300
| CAGACAGTGG | TCCCATCAGG | CAAGCAGATA | ACCAGGGCTT | GACTGTAGGA | 2350
| ATCCTGGTGA | GCATCCTGTG | TCTGCTTGCT | GCTGGATTTG | TGGTGTATCT | 2400
| CAAAAGGAAG | ACGTTGATGC | GGCTGCTGTT | CACACATAAA | AAAACCACCA | 2450
| TGGAAAAGCT | AAGGTGTGTG | CACCCCTTCCC | GGACACCCAG | TGGCCCCTCAC | 2500
| CTTGGCCAGG | CTCACCACAC | CCCCGGGAAA | GGCCTGCTGA | TGAACCGGGC | 2550
| ACCACATTTC | AATACCCCCA | AGGACAGGCA | CTCGCTCGAG | TGCCAGAACA | 2600
| TGGACATCAG | CAGGCCCCTC | GACGCTCGAG | CCGTCCCACA | GCTTCAGTCA | 2650
| CCTCAGCGAG | TGCTCCCTGCC | TCTCCACCAG | ACCCCACGTG | CACCCAGTGG | 2700
| CCCTGCCAGG | CCCCTGCCCG | CCAGTCCTGC | AGTCAGGCAG | GCCCAGGGCA | 2750
| TTCGAAAACC | CAGTCCTCCT | CAGAAGCCCTC | TGCCTGCTGA | TCCACTGAGC | 2800
| AGGACTTCTC | GGCTCACTAG | TGCCTTGGTG | AGGACCCCAG | GGCAGCAGGA | 2850

Fig. 5e  READING FRAME

| | | | | |
|---|---|---|---|---|
|ACCTGGGCAC|CGCCCCAGCCC|CCATCAGACC|TGCCCCTAAG|CATCAAGTAC| 2900
|CCAGACCTTC|CCACAATGCC|TATATCAAGT|GAGAAGCCAG|CCCAGACCGG| 2950
|TCCTCAACAG|TGAAGACAGA|AGTTTGCACT|ATCTTCAGCT|CCATTGGAGT| 3000
|TGTGTTGTA|CCAACTTTCC|GAGTTTCTAA|AGTGTTTAAA|ACACCATTCT| 3050
|CTCCAGACCC|TGGAGCCACT|GCCATCGGTG|CTGTGCTGTG|GTGCTTTGTG| 3100
|TACTTGCTCA|GGAACTTGTA|AGTTATTAAT|TTATGCAGAG|TGTCTATTAC| 3150
|TGCGCAGGGC|GCCGTAGCAG|GCATTTGTAC|CATCACAGGG|CTTTTCTACA| 3200
|GAAGGAAGGC|TCCTCGTGCT|TTTGTTTTTC|TGGAGGACTT|GAAATACCCT| 3250
|GCTTGATGGG|ACCTAAGATG|AGATGTTTAC|TTTCTATTCA|AGGCCTTATC| 3300
|GGAAAATAGC|TCCCCACCTT|CCCAAGGCTG|TTATGGTACC|AGACACACAG| 3350
|CTCAGGACAC|CCCAGGGAGA|ACCTGGCATG|GGTTTTCTTT|GTTGCTTTC| 3400
|ATTTTATCTT|TTATATTTTG|GTATCCCTAT|CTTGGGTTGT|AGCCAGGGCC| 3450
|TTCAGGAAGG|TCTTGGGCCA|CTGCATGCTA|ATGGCCTTCA|GGTCCTGCAC| 3500

Fig. 5f

```
CCTGAAGCTC TCAGACAACA AGTAGGATCT GCTTTCTAGC CAGCAGCTTT    3550
GGAGAGAAAC TGGGGTACTG AAAAGAAGGT TTGGGGTGTG GTTATACCAG    3600
GATGGAGACT GGAATCCTAA TCTGGGCAAA CATCTGACCT TGAGCTGAGC    3650
AGCCATGAGC ACCTCTAGGA AGCAAGGACG GCTGAGGTGC TGCACAAGGC    3700
TCTGCTTTGA GAGCTGGCAG GGGCTTCTCT GTTACATCG TTTGCAGAGT    3750
GCTAGCTGGC ATGGCATGTT GTTACATCG CTGCAGACCT TGTTTCTACA    3800
AGAAAGCCAC TGCCTGGGCA TGCCTGGGCA CCGTCTCCTG CCCATTTAGA    3850
GCTAAGCAAA TTACCACATT GTCTTCTGGA CTGTAATACA ATGACCCTGT    3900
GTTCTGACAG ATAGAGGAGG CTTTCTATGG AACCATAACT ATTTTCANAT    3950
GTGAACTAGT AACCAGATCT AGTCGATCAA CTCTGGAGAT AGAAATCTCC    4000
TTTTACTGC AAGGCTCGAC TTATTAAAAA TTAGGCAGAA TCCATATGCT    4050
TGCAAAAGCT ATAACCACGT GGAATGCTCT TCTCATGGCA CAGCCTGAGT    4100
CTGGTATCCT TATTAGTAGC CATTGGACAA AGCACCCAAA GTTACCTGTG    4150
TGTTCTCTTC AAGGCATCCT AATTTCTTCA GCATAGAGAG ACTCGGTCTT    4200
CCTCACATTC TGAACATACC TATCAATGAC TAAGNCAGCA AGGCAATCCG    4250
```

Fig. 5g

| | | | | |
|---|---|---|---|---|
| TTTCCGAATA | CTGAGTTGCT | CACGGNAAGG | CAACCCTCAGC | CCAGGNAAAC | 4300 |
| TTTTTCCTC | TGNTCTTTCA | GTATGTGACT | GGGGAGCTAC | CTTCAGAAGC | 4350 |
| AAATTTTCAA | GGTGGNCTCA | ACCCCATNGG | ATGAAAGNTA | TTTTTTAAA | 4400 |
| AAATAATTAA | TGGTAATGCC | AGAGGGCTTT | CCTGGCNTCC | AGATNGGGGC | 4450 |
| GTAGGNTTGA | CTAGCTTTCA | CGACAGAAGG | TAAATGACAG | CAGTCCTCTA | 4500 |
| CCTCGTCTGA | CTGCTTTAAG | ATCAAGGCTT | CTTTGGAAGG | GTAACTAACA | 4550 |
| TTAATGGCTG | GCCTGTGCCT | TGAAGCAGAA | GGGAAAATAC | AGATAAGGAA | 4600 |
| TTTGGTTTGC | TTTCTAGAAT | CCAAAACTGT | ATCCAGCATT | GGGAAGCATG | 4650 |
| GTCTTCATGA | CTGGGTAAAT | AAATCCACGT | CACAGATGCA | TAAAAGAATA | 4700 |
| ACTCTTATGA | CATGCCTCTT | TTTGTGGCAC | AGAGACAATA | TTGCTGCCAC | 4750 |
| TGAGATGCAT | ACAAAATTTC | TGTAACTGAT | ATGTCATTCA | GTAGTTGTAT | 4800 |
| TAAGGCCAAA | CATCCACAAC | TGTAAAGACT | TATAGAGTTG | TGTGGGCGTT | 4850 |
| GTCTTGTGAG | ACACACAAAG | CCTCAGCTGA | AGCCGTATGAG | CTCCTCCTCC | 4900 |
| AGGTGGGAGT | GATGGGGAGG | CTAGAAACAC | ACAAAGACAA | CAGAAGAGCT | 4950 |
| TTGGTTTGGG | GGGGGTGCAG | AGAGAGTGTG | GTTTAGAGGA | AGTTGGAGCC | 5000 |

Fig. 5h

| | | | | |
|---|---|---|---|---|
| ATGATCTTCT | GCCATCTCCC | CAGTGTCCAC | TAAGGATGCC | GATGGTGCCT | 5050
| TACCAGCTGT | GCAGTGCTGG | CTGCTTGCTT | TTACAGAGCC | ATGCATTCAT | 5100
| TTCTGAATAA | GAACATATTT | AATCCCTGAAA | TTCCCTTACA | GGACAGACAG | 5150
| TGTTACTAAA | GGAATTCCTC | TAAGATACAG | TAGTTGTCAA | TTAAAGCATA | 5200
| TTTAGCAGTA | ACTTCAATTT | TAACAAAATT | GGGACCCAAT | AGCCAGCATG | 5250
| AGGGTTCTTT | GACAGAGGGT | AGTTTCTCTC | TCCCTTTCTC | CATCCTTCAA | 5300
| ATGACAAGAC | GTCAAAACTA | ATACAGTTCA | TTTGCAGTCC | ATCTCATGCT | 5350
| TATACATACT | AGAGGTATGA | CTAAAGTTGG | TTGAGTCATG | GGAGACCATC | 5400
| CCTGAGAAAG | TCCAGTCGGT | CAAGAGCCTT | GCCAGGTGGC | GTGGCTGGAC | 5450
| GTCCTCCTTT | TGTTCCTGCA | CTGAGGAATA | GTTATAGGTT | ATGTGACCCC | 5500
| ACTTCACAGG | CAAGTGGGAG | GCGAACCCTG | CAGGCATGCC | CCTTAAAAGC | 5550
| TGGTCTCAGA | CCTACAATAG | TCCTGAGTCT | GTTTTCCCAG | CACACAGAGA | 5600
| GCAACAATGC | AGTTTTCCAT | TTCAAAATAT | GCATGCCGAG | TTTGCGCTCT | 5650
| GTGTGAGTGT | TTCCAGGTTA | CACATATGGG | ATGACATCAC | AGAAACCACA | 5700
| CAAGCAACAA | ATTAAATTCT | ACGGGAAGAA | ATCCCTCCTGA | CTGGTCTCTG | 5750

Fig. 5i

| | | | | |
|---|---|---|---|---|
| AGGAGACATT | TTTATGCCTT | CTTAACTTTA | TTAGGAACTC | TCAGGCTGAA | 5800
| GCTAGGGGTC | ATTGTCCCCC | AACAAATCAA | TACAAAGCCA | TCAATGNACT | 5850
| CTCGAAGAAC | TGCCAAACCC | TGATCTGTGT | GAATGTTCTC | AGGAGCCTGT | 5900
| GATCCCCATG | GTGCTANAAA | GAGGCTGGAG | CTGGGCCAAC | AAGAAGGCCT | 5950
| AAGAGTCCTC | CTGCCTCTCA | GCAGATGTTT | ACTGAGCACT | CTGAGCCAGA | 6000
| AGCACCCCGA | CAACCAGGAG | GACGATNGCT | GGGCAGTAGG | GCGCCCCAGCC | 6050
| ACTTGCAGCT | CTTTCCTCTG | AGGCCCGCTT | TGTGTTTTAA | TTCCCTTCTG | 6100
| TCAGGCCCCA | ANCAGNGGAC | ACTGTCCTAT | AGACCTCCCT | CTNAGTTTTC | 6150
| AGACGGCCTA | AGCCATACAC | AAATGCCCCA | GACTAAGAAA | CACCAATACN | 6200
| TCCCAGCAGT | CCCCAAGAAC | TGGTTTTAA | ACACTATGAC | AAGTAGAAGA | 6250
| GGGTGTCACA | GAGGCCATTT | TTTTCTTTT | CTTTCCACTC | ATACTGGAAC | 6300
| CTAGGTCCTC | TCTCTACACT | CCTAGTTCCT | TTACACAACT | CGGCAGTGGC | 6350
| TCCATTACAC | CAAGGACACA | GAAAAACACA | GGTACCGATT | TGCCTTCCTC | 6400
| TCCTGCCAAT | CACAAGTGCC | TTACTCTGAC | CAGACCCATG | ACAAAACCTC | 6450
| TGTCATCCAA | GAGAGCCAAC | TCTCTACCTT | TGTTACTACT | TCAAGCCAAT | 6500

Fig. 5j

```
GTGGTAACTG CTAACCTTCA AGGGTCACCT AAACAGTATA GTCCAACCTT    6550
CACCAGGACC ATAGCACAGA GCAACCTCCA GNACACACAC ACACACACAC    6600
CTTGAATCTA TCCCACAGCA TATCAACCCA CAGTGACCCTC CCTCCCACCG   6650
CCTTGTTCTA ATTACAAGGT GAAGATGGCC ATAGAAAATC AAGTTAGCAC    6700
TAATTACAAA ATGCTTTTGA TGCAACCTGA ATTTCCCAAT GGCACCTATT    6750
GCTTTGAAAC TCTGATGAGT TAAGTCATGC TCTGGGAGCT GTGAGCCCCA    6800
TGCTCAGATC CACTGGGCAG GGGGACTCC TTGCAGGAGA CATGGGCACA     6850
CATATGAATG TACCATTTCC ATGCCTTTTG TGGAGTACAG ACATATAAAC    6900
ATAAATACTT CCATT                                          6915
```

Fig. 6a

```
GGCCCGGGGGC AGGCAATGGC AGGGGATGTG TGATTGCCGGA CAGTGAGAGG GCCGTTGCTA    60
           └─ READING FRAME
TCATGCCCGG GCGGCGGGGC GTCGCCCCGT TCTGCTTGCT GGCTCTCGCT CTGCAGCTAC   120
ATTGGCCGCT GGCGGCGTGC GAGCCGGGAT GGACCACAAG AGGAAGCCAA GAAGGTAGCC   180
CTCCGCTACA GCATGAACTC ATAATACCTC AGTGGCGGAC TTCAGAAAGC CCTGGGAGAG   240
GAAAGCATCC ACTCAGAGCA GAGCTCAGGG TCATGGCTGA AGGGCGAGAG CTGATCCTAG   300
ACCTGGAGAA GAACGAGCAC CTTTTTGCTC CAGCCTACAC AGAAACCTGC TACACTGCAA   360
GTGGCAATCC TCAAACCAGC ACGCTGAAGT CTGAGGATCA CCGGGGAATT CACGGGACTG   420
TGAGGGACGT GGATGAGTCC AGTGTCACGC TCAGCACCTG CCGGGGAATT AGAGGACTGA   480
TTATAGTGAG AAGTAACCTC AGCTACATCA TCGAGCCCGC CCCTAACAGC GACAGCCAAC   540
ACCGTATTTA CAGATCCGAA CATCTCCACG TGCCCCCGGG GAACTGTGGG TTCGAGCACT   600
CCGGGCCCAC CTCGAAGGAC TGGGCCCTTC AGTTTACACA TCAGACCAAA AAGCAACCTC   660
GCAGAATGAA ACGGGAAGAT CTACACTCTA TGAAGTACGT GGAGCTTTAC CTGGTGGCTG   720
ATTATGCAGA GTTTCAGAAG AATCGACATG ACCAGGATGC CACCAAACGC AAGCTCATGG   780
```

Fig. 6b

| | | | | |
|---|---|---|---|---|
| AGATTGCCAA | CTATGTTGAT | AAGTTTTACC | GCTCCCTGAA | CATCCGAATT | GCACTTGTCG | 840 |
| GCTTGGAGGT | GTGGACGCCAT | GGGATAAGT | GTGAAGTTTC | AGAGAATCCC | TACTCTACCC | 900 |
| TCTGGTCCTT | TCTTAGTTGG | AGGCGCAAGC | TGCTTGCTCA | GAAGAGCCAT | GACAATGCTC | 960 |
| AGCTAATCAC | GGGCAGGTCC | TTCCAAGGCA | CCACCATTGG | GCATGGACCA | CTCATGGCCA | 1020 |
| TGTCTCCGT | GTACCAGTCT | GGAGGAGTTA | GCATGGACCA | CTCCGAGAAT | GCCATTGGTG | 1080 |
| TAGCCTCCAC | TGTGGCCCAT | GAGATTGGCC | ACAACTTTGG | CATGAGCCAT | GATTCTGCAC | 1140 |
| ACTGCTGTTC | TGCCAGTGCA | GCCGATGGCG | GCTGCATCAT | GGCCGCCGCC | ACCGGGCACC | 1200 |
| CTTCCCCAA | AGTGTTCAGT | TGGTGTAACA | GGAAGGAGCT | GGACAGGTAT | CTGCAGACAG | 1260 |
| GAGGAGGAT | GTGTCTCTCC | AACATGCCGG | ACACTAGGAC | GCTGTATGGA | GGCCCGGAGGT | 1320 |
| GTGGCAACGG | GTACCTGGAA | GACGGTGAAG | AATGTGACTG | TGGAGAAGAG | GAGGAATGTA | 1380 |
| AGAACCCTTG | CTGCAATGCC | TCCAACTGCA | AGGGGCAGAG | AGGGGCAGAG | TGTGCCCATG | 1440 |
| GTTCCTGCTG | CCACCAGTGC | AAGCTGGTGG | CTCCCTGGAAC | CCAGTGTCGG | GAGCAGGTTC | 1500 |
| GGCAATGTGA | CCTCCCCGAG | TTCTGCACCG | GCAAGTCTCC | CCACTGCCCC | ACCAACTATT | 1560 |
| ATCAGATGGA | TGGCACCCCC | TGCGAGGGTG | GCCAGGCCTA | CTGCTACAAC | GGCATGTGCC | 1620 |
| TCACTTACCA | GGAACAGTGC | CAGCAGCTGT | GGGGACCTGG | AGCCCGGGCCT | GCCCTCGATC | 1680 |

Fig. 6c

```
TTTGCTTTGA GAGGGTGAAT GCTGCTGGTG ACACCTATGG AAACTGTGGC AAGGGCTTGA 1740
ATGGCCAATA CAGGAAGTGC AGTCCCAGGG ATGCCAAGTG TGGSAAGATT CAGTGCCAGA 1800
GCACCCAGGC CCGGCCCCTG GAATCCAACG CAGTATCTAT TGACACCACC ATCACCTTGA 1860
ACGGGAGGCG GATCCACTGT CGGGGCACCG ACGTCTACCG GGGTCCTGAG GAGGAGGAAG 1920
GGGAAGGTGA CATGCTGGAC CCAGGGCTGG TGATGACTGG AACCAAGTGT GGCCACAACC 1980
ATATTTGCTT CGAGGGGCAG TGCAGGAACA CCTCCTTCTT TGAGACGGAA GGCTGTGGGA 2040
AAAAGTGCAA TGCCACGGG GTCTGCAACA ACAACAAGAA CTGTCATTGC TTCCCTGGCT 2100
GGTCTCCACC TTTCTGTAAC ACCCCGGGAG ATGGTGGCAG CGTCGACAGT GGTCCTTTGC 2160
CCCCTAAGAG TGTGGGTCCC GTGATCGCTG GGGTGTTTTC AGCTCTCTTC GTGTTGGCAG 2220
TTCTGGTGCT ACTGTGTCAC TGCTACAGAC AGAGCCACAA ACTGGGCAAA CCCCTCGGCTC 2280
TCCCTTTCAA GCTGCGGCAT CAGTTCAGTT GTCCCTTCAG GGTATCTCAG AGTGGTGGAA 2340
CTGGCCATGC CAACCCAACT TTCAAGTTGC AGACCCCCCA GGGCAAGCGA AAGGTGACTA 2400
ACACCCCTGA ATCCCTCCGG AAGCCGTCCC ACCCCCTCT CCGGCCCCCT CCAGACTACC 2460
TGCGCGTTGA ATCGCCACCT GCACCATTGT CGGCACATCT GAACAGGGCT GCTGGGAGCT 2520
CCCCAGAAGC TGGGGCTCGA ATAGAAAGAA AGGAGTCAGC CAGGAGGCCT CCCCCAAGCC 2580
```

Fig. 6d

| | | | | |
|---|---|---|---|---|
|GACCCATGCC|CCCTGCACCT|AACTGCCTAC|TGTCCCAGGA|CTTCTCCAGG|CCTCGACCAC|2640|
|CTCAGAAGGC|ACTCCCAGCC|AATCCCAGCC|CAGGCCAAAG|GACCGGTCCC|AGGTCAGGAG|2700|
|GCACCTCCCT|GCTTCAGCCC|CCTACTTCTG|GTCCCTCAGCC|CCCCAGGCCT|CCAGCAGTGC|2760|

READING FRAME ⟶

CTGTTCCAAA GCTACCCGAG TACCGATCAC AGAGGGTTGG AGCAATAATT AGCTCCAAGA  2820

TCTAGAAGTG TCGAGAAGTT TCTTGTTCCG ATGGAAGACT CCGGATGCCA TGGAAGGTCC  2880
AGAAGAAAGA CGCCTTCTCA CCCATCCTGA AGCTTTGGCA GCCTTCTGGA ACGTCCCTCA  2940
TCCCCAGAAT CTCCCTTCTT ACCCGAGTGC CTCCTGCTTC CTCCGAGGCC CAGGGGGACT  3000
CATATCCAAT GGCTCCTAAG TGTTTGTCCT GTGCAATATA CAGCCCAGGG AGGGAAGGGA  3060
AGCACGGGCGA GGAGGGTGGG AAAGGTTCTC CCTCAGCCCA CTAGCCAAGA GCTACCAGCG  3120

Fig. 6e

| | | | | | |
|---|---|---|---|---|---|
| ATGCTCAGGG | AAGGCTTGAG | CTGGGGTCCT | CCTCTGCGGA | GCTTGGAGAA | GGTACCCATC | 3180
| CTGGTCCTAT | GCTGGCAGGA | ACACACGCGA | GTGTCACTGA | TTGGCCTCCT | TCTGGGATCC | 3240
| CAGGCTGCTG | AGGAAGCTAC | TGCTACATCC | CTACCCCAAG | GGGCTTGGTC | AAGGTGCCTG | 3300
| TYCCTGGCTC | TCTGGCTGCA | TGTAATAAGC | CATGCTCCCC | TCCCCTGCCT | TTCTTCACAT | 3360
| TCCCACTCCC | ATATTACAC | GGGTCACTCT | GACTCAGACA | GGTACTATTT | GTAAGTAGCA | 3420
| TAGACAGCAG | GGGGGTGGGG | TGGTCAACCT | GTGTCCCCTC | GTGTCCCGTTA | TGCCAAAGGT | 3480
| CACTAAGGAC | ATTTAGAATC | CCCATCCATC | GTGTCCCCTC | TCCATCCATC | CATCCATTCA | 3540
| TCCATCCCCA | GTGTTCCATG | TGTCACCTTC | TCCTTTTCCA | GCATCCCTAT | CCTATGGTGC | 3600
| TTTGGTGGTG | AACTATGGCA | GTCCTGACTT | GCTGATGACC | ATATGCTGGT | GACCTACAAA | 3660
| TCGGGATCCT | GCCATATGGG | GTCGCCACTG | GACTTTCTGC | ACTGGTTCTC | AAGAGCGTTG | 3720
| AGCCGAGTGG | GCGTGTATGT | TTGTGTGTGT | GTGTGTGTGT | GTGTGTGTGT | GTGTGTGTGT | 3780
| GTGTGTGTGT | GTGTGTGTGT | GTGAAAGAGA | CAGAGGCAAT | GAGAGAGACA | GACATGCAGG | 3840
| CAGGCCGACA | GCTCTGCATG | TACTTGTGTT | TTACGGCCTC | AAGCAGTATA | AGGGACCTCC | 3900
| TCCTTATTTC | TGACTCATAT | CTAAGTAAGG | TTCCCCAGGA | CMAGCCACAG | CTGTACTGAG | 3960
| GGGGCTGAC | ATGTTTGGCA | TCCTGGCTAT | AGTATTGTAT | ACACAGGGCC | ACCAGCCCCG | 4020

Fig. 6f

| | | | | |
|---|---|---|---|---|
|CCCTAGTGGT|CAGCTCTGAG|GGGGACTGG|TGACTCTGAA|CAGATCGATG|TCAACAGCCA|4080
TGGTGAACCA|GATCTGGGCA|GGGTTCCCCA|AACTCTATTC|AACCAGAGTT|TTATCACGCA|4140
NCTCATCGGG|TCTCTCCCTGG|TTGCTGCCCC|GAGGTGATCG|TCATGGAAAA|TGCTGAGAAG|4200
GTGGGAATGG|GATGGGGTGG|ACCTTCTCTT|GCTTGGTGCT|CCGCTATTTG|GAACAGTTCT|4260
TACACATTTG|CTGGGCCTGG|CCTCTGAGAG|GCCATCTTCC|ACCCCCAGAA|AGGTGCTAAT|4320
GGCACTGCAG|AGGGCTCTCT|AGGGGCCTCC|CCGCCCCAAC|AGCAAGCAGT|TGTTAGCTCT|4380
TGGAACCCTC|CAGAGGAAGA|GGCAAGCGTT|TGACTTCCCC|TTTACCACCT|GAGGCCTCCT|4440
TATATCTCTT|CCCAGAGTAA|GCTTTGGGAT|TGTAGACATG|TGGGAGCTAT|GACAGACGTG|4500
GCCTGGGGTA|GAAAGATCTC|AGGAAAGCAC|CTTTCTCCTT|TTCAGGGTGA|CCGTGCTCTT|4560
CACACTCTCT|GAGGCCTCAG|TCCATGTCCT|ATATCAGTTT|CTCTTTTGTG|TGCTTTACCA|4620
AGTGGCCGGT|GACTACAGGC|CACCCCGATT|CTCACCACAA|AGTTAGAAAC|CCTCCACTTT|4680
CTGTCCCTTG|AACCATATCA|GAAAAAGACC|CATTTCCTTG|CTCTTTGTA|ATCACTTCTG|4740
TTTTTCTTC|TTCATTACTG|TGCTACCACC|TCCATCCCAT|GACATTATTC|TGTGANGTGT|4800
AAGAGGACGG|TGTTTNTTA|NTCTTGGGAG|ANATGTCGGC|AGCTGCTCTA|CACACAACTT|4860
CACTCAAGGC|TTTGTCTCCA|GAGGCCAGCT|AGGCTGTCAC|AGGCAGGAAT|CCCTTCCCAT|4920

Fig. 6g

| | | | | |
|---|---|---|---|---|
| CTGCTTTGTG | AAGGGTCCCA | TACAGGTGTA | TCTAGACTTC | AAGGACAGGG | TTTGTCTCAC | 4980 |
| AGGATTGTCA | CTTAGGAGAT | GAAAGAATAT | TACCACATGA | GGAGGAGGGG | CAGTTGCAAC | 5040 |
| AGAACACTTT | GGTCTTCCTA | CACCAAGTCT | GTGAGGGCAT | CCAAGACTGA | ATGAAAGCGC | 5100 |
| TTTTCTTATG | CATACAATGT | GAGCAAGAAC | AAGAACTGTT | TAAGGCACCT | CTGTTCCCAG | 5160 |
| CCACTGAAGA | GAGACGTCAG | AAGATGTTAG | AATAGGTCAA | AACCAAGGCT | CTGGTGGACT | 5220 |
| GAGGGAAGGT | TTGTAGCTGC | GTTTAGTGGT | ATACATCTTT | AGTCCCAGCA | TAGGCAGGTG | 5280 |
| AATCTCGAGT | TTGAAGCTAG | CCTGGTCTAA | AAAGGAAGTT | CCAAGACTGC | CAGGGCCACA | 5340 |
| CAGAGGAAAA | AAAAAAACCC | TCTAGAAAAA | CAAAAATGAA | GACAGGTTCT | CATGTATCGT | 5400 |
| AGATTGGCCT | TTAAGTCACT | TTACCAAGGA | TGATCTTTGA | ACTCCTGAGT | ACAGACTGCG | 5460 |
| GGTGTGTGCT | ACCATGCTTT | ATGTGGCCCT | GGGTTCAAAC | ACAGCCCTTC | ATATGTATAT | 5520 |
| AGCCAAACAC | TCTACAACTG | AGCTACATCC | TCCAGCCTAG | GCTGTAAATG | TTTTTTGGAG | 5580 |
| CTAGATTAGC | TGCCTGCCAA | CCTTAGAACT | GCAAAGCCAT | TCCTGACCTG | TAAACCTCAG | 5640 |
| CTCTCCATCT | CTATAAGAGG | TATAGCCTGG | GCTAATACCG | TCCAAGTTAC | AACTCCTGC | 5700 |
| TTGCTTTCTG | TTCCTTCTAG | CCTTGGTGAC | TTCCACCAGG | AAGAGAATAC | CCCCTCTCTA | 5760 |
| CCCCTGCTCC | AAGACACTGT | AGATGCTAGT | GTCGGAGTGT | TCTCTGTAAC | GCGACAGTTC | 5820 |

Fig. 6h

| | | | | | |
|---|---|---|---|---|---|
|CTTCTGTTGC|AATAGCCCCC|CTGCAACACT|GCAATAATCC|TTCAGTGTCT|CCCCTGGGCT|5880|
|CAATTCACTT|CCTTATTTGA|CAAAGTGGAG|GTGAGACTTG|TATTCTTAAA|ATTGGAGGCT|5940|
|AGTTATTTTG|TCAAATGCAT|GTAATGAACA|GACCCGAAGG|AATCCTCCAC|ACACAAGCCA|6000|
|GGGAACACCA|ACTGGAAAGG|TACCCCGTCC|CAGGGAAGCC|TGCTAGGGAG|AGGTTCTGTA|6060|
|GAATCCGAGC|CTAGCACCCC|AAAGTCATGC|ACCCAGTATC|CTCTTGTATG|ACTGTATATG|6120|
|TCTATGTCTG|GGATCCAGGG|CAAATGTGAA|TTTCCTTTTG|ATTTGGGAGA|TTGTTCACAG|6180|
|GAAGTAGTCC|TCCCCTCTCA|TGTCCTCCTA|TTGATTGTTT|ACAATATTTG|TACATCTATG|6240|
|CAAAATACTT|GAATGGGCCA|TGGTGCCTTG|TTTTTTGTTG|TTGTTGTTAT|TTTTTCTCC|6300|
|TTGTTTGTAT|TTAATTAAAA|CAAATTGTCA|TGAGGAAAAA|AAAAAAAAAA|AA|6352|

Fig. 7a

| | | | | | |
|---|---|---|---|---|---|
| GTTGCAAGGA | TGACCGAAGN | NCGGAGGGCG | CGGCCGGGCG | TTGAGCGGAA | CCTGCCGAAG | 60

└─ READING FRAME

| | | | | | |
|---|---|---|---|---|---|
| CCCTCGCTAT | GGGGCCGCGC | GCGCTCTCGC | CCCTTGCCTC | TCTGCGACTA | AGGTGGCTGC | 120
| TGGCGTGTGG | CTTGCTGGGC | CCAGTCCTCG | AGGCCGGGCG | ACCAGACTTG | GAACAGACTG | 180
| TCCATCTTTC | TTCTTATGAA | ATTATTACTC | CTTGGAGATT | AACTAGAGAA | AGAAGGGAAG | 240
| CTCTGGGGCC | CAGTTCACAG | CAGATCTCTT | AGTCATCCA | GGCCCAAGGA | AAACAGCATA | 300
| TTATTCACTT | GGAAAGAAAC | ACAGACCTTT | TACCTAATGA | TTTTGTAGTT | TACACCTACG | 360
| ACAAGGAAGG | CTCCCTACTC | TCTGACCATC | CCAACGTACA | GAGCCATTGT | CACTATCGAG | 420
| GCTATGTGGA | GGGAGTGCAG | AATTCCGCGG | TTGCTGTGAG | CGCCTGCTTT | GGACTCAGAG | 480
| GCTTGCTGCA | TTTGGAGAAT | GCCAGTTTTG | GAATTGAACC | TCTGCACAAC | AGCTCACACT | 540
| TTGAGCACAT | ATTTACCCC | ATGGATGGCA | TCCACCAGGA | GCCTCTGAGA | TGTGGAGTCT | 600
| CTAACAGGGA | CACAGAGAAG | GAAGGCACAC | AGGGGGATGA | GGAGGAGCAT | CCGAGTGTCA | 660
| CTCAGCTGCT | GGGCAGAAGA | AGAGCTGTTC | TACCACAGAC | CCGCTATGTG | GAGCTGTTCA | 720
| TTGTTGTAGA | CAAGGAAAGG | TACGACATGA | TGGGACGGAA | CCAGACTGCT | GTGAGAGAAG | 780

Fig. 7b

| | | | | |
|---|---|---|---|---|
| AGATGATTCG | CTTAGCAAAC | TACCTGGATA | GCATGTACAT | CATGTTAAAC | ATTCGAATTG | 840
| TGCTGGTTGG | ACTAGAAATT | TGGACAGACA | GAAATCCTAT | CAATATAATT | GGAGGAGCTG | 900
| GAGATGTGCT | GGGCAACTTT | GTTCAGTGGC | GGGAAAAGTT | CCTTATAACT | CGTCGGAGAC | 960
| ACGACAGTGC | ACAGTTGGTT | TTGAAGAAAG | GCTTTGGTGG | AACTGCAGGA | ATGGGGTTTG | 1020
| TAGGAACAGT | ATGTTCAAGG | AGCCACGCAG | GTGGGATCAA | TGTGTTTGGG | CAAATCACTG | 1080
| ATGAGACATT | TGCATCCATT | GTTGCTCATG | AATTGGGGCA | TAACCTTGGA | ATGAATCATG | 1140
| ATGATGGGAG | AGAGTGTTTC | TGTGGAGCAA | AGAGCTGTAT | CATGAATTCA | GGAGCATCCG | 1200
| GGTCCAGAAA | CTTTAGCAGT | TGCAGTGCGG | AGGACTTTGA | GAAGTTAACG | CCCTCCTGTG | 1260
| GAGGAAGCTG | CCTGCTTAAC | ATCCCGAAGC | CTGACGAAGC | CTACAGCGCC | GAGTGTGAGG | 1320
| GTAATAAGCT | GGTGGACCCT | GGAGAGGAGT | GTGACTGCGG | CACAGCGAAG | TGTGCATATG | 1380
| TGGACCCATG | CTGTGAAGGA | AGCCACTTGTA | AGCTCAAGTC | ATTGCTGAG | GGGAAGACCA | 1440
| GCGACTGTTG | TAAAGATTGC | CAGTTCCTTC | CAGGAGGCTC | CATGTGCAGA | GGGAAGACCA | 1500
| GTGAGTGTGA | TGTTCCTGAG | TACTGCAACG | GTTCCTCTCA | GTCTGCCCG | CCAGATGTCT | 1560
| TCATTCAGAA | TGGATATCCT | TGCCAGAACA | GCAAAGCCTA | CTGCTACAAT | GGCATGTGCC | 1620
| AATATTATGA | CGCGCAGTGT | CAGGTCATCT | CAGGTTCAAA | GGCTAAGGCT | GCCCCAAGAG | 1680

Fig. 7c

| | | | | |
|---|---|---|---|---|
| ATTGCTTCAT | TGAAGTCAAT | TCTAAAGGTG | ACAGATTGG | CAACTGTGGT | TTCTCCGGCA | 1740 |
| GTGAGTACAA | GAAGTGTGCC | ACTGGGAACG | CGCTGTGTGG | AAAGCTTCAA | TGCGAGAATG | 1800 |
| TACAGGACAT | GCCGGTGTTT | GAATAGTAC | CAGCTATCAT | TCAGACACCC | AGTCGAGGCA | 1860 |
| CCAAATGCTG | GGGTGTGGAT | TCCAGCTTG | GTTCCGACGT | TCCAGACCCA | GGGATGGTGA | 1920 |
| ATGAAGGCAC | CAAATGTGAT | GCTGGCAAGA | TTTGCAGGAA | TTTTCAGTGT | GTAAATGCTT | 1980 |
| CTGTCCTGAA | TTATGACTGT | GACATTCAGG | GAAAATGTCA | TGGCCATGGG | GTATGTAACA | 2040 |
| GCAATAAGAA | TGTCACTGT | GAAGATGGCT | GGGCTCCCCC | ACACTGTGAC | ACCAAAGGAT | 2100 |
| ATGGAGGAAG | CGTGGACAGC | CTAATCGTCC | ATAATGCAAA | CCCTTGTTGC | CTGAGGGACG | 2160 |
| GGCTTCTGGT | CTCTTCTTC | CTAATCGTCC | GGAAGAAGAG | GGCTGCCATT | TTCCTCTTTA | 2220 |
| TCAAGAGAGA | TGAACTACGG | AAAACCTTCA | AGACAGCCAG | GAGATCCTAG | TCAGATGGCA | 2280 |
| GAAATCAAGC | AAACGTCTCT | AGACAGCCAG | CAGGTGTCTC | TATCTCCAGA | CCACCAGGGG | 2340 |
| GCCCAAATGT | CTCCAGACCA | CCAGGGGCC | CAGGTGTCTC | CAGACCACCA | GGGGGCCCAG | 2400 |
| GTGTCTCCAG | ACCACCAGGG | GGCCCAGGTG | TCTCCAGACC | GCCACCTGGG | CATGGAAACA | 2460 |
| GATTCCCAGT | ACCAACCTAC | GCCGCCAAGC | AGCCTGGGCA | GTTCCCGTCA | AGGCCACCTC | 2520 |
| CACCACAACC | GAAATATCT | TCTCAGGGAA | ACTTGATTCC | GGCTCGGCCC | GCTCCTGCAC | 2580 |

Fig. 7d
READING FRAME

| | | | | |
|---|---|---|---|---|
| CTCCTTTATA | TAGCTCCCTC | ACCTGATAGT | AGAATATTAG | AATCTTATTT | TTTAAATGTC | 2640 |
| TTCAGGGAAC | TGAGCAAATG | TTTGTTGTTT | TTTTTTCCT | GATGTTTCT | TGAAAAGCCT | 2700 |
| TTCTCTTCCA | ACCATGAATG | AACACAAACC | ACCACAAAAC | AAGCTTTATT | AACACAGGAG | 2760 |
| CCTAGTGGGG | ATTGCGAAAC | ACAGGAATGT | GCAGGCGCTC | CGGGGGGTGT | AAAGTGAACG | 2820 |
| TTTCCATCGT | TAGAATGTTT | TCTCTGGCCA | TTTGTGGATT | TAATGCACTT | GACGTGGATT | 2880 |
| AAGTTATTCT | GAGCATGTTA | CTGTAATGAT | TCTCAAATTA | ACTGTATTAG | TGTAAGCTTT | 2940 |
| GTCACTATGC | GCTAAACGTA | ATCCTGACTT | TTTGACCCCA | GTTACCATTA | ATAGTTTCTG | 3000 |
| GTTGACCATG | TGAACATGTA | TTAACTTAGG | AAGACTAATT | GCCAATAACG | TCTGCATTTT | 3060 |
| CATCTTGCAT | GGATTAACAG | CCATTTATAT | GGACTTATGT | CTCTTAATGC | ACAAAGAAGC | 3120 |
| AGATATCTCG | AAGGAGCTTA | CACAAGAACC | ACAATTACTA | GATCATGATA | TACTTGGAAA | 3180 |
| GTGTGAAATA | TGGTGTGTAC | TCAGTTATTG | GCTTCCATTT | TTWATGATCT | TTCAACTATA | 3240 |
| ACAATTATGA | TAGAAATCGA | TTTAACACAA | TCAGTTATGG | GCTTCCATTT | TCAAATATCT | 3300 |
| TTTCAACTGT | AATGACTATG | ACAGGAACTG | ATTCAACTCT | CAATTTTCTT | TATGCATCAT | 3360 |

Fig. 7e

```
GGTAAAGCAT TGCAGCAGTG TTGTTTTGTT TGAAGTGCAC ACTCTATGGT ACGAGGTGTT    3420
TAGTATACCC AAGCAGATAG GTGTCGATCG AACAGGAGCA GGGAGAATAC TTCCAACAGT    3480
TGAGGTGTTA CCAAACCACT TGAGAATTCA TGAGCACTTT AACTCTAAAC TCTGAATTTC    3540
AAAGCTTGAT GTGAAGTCCT CTAGAATGTT TACATTTACT AAGGTGTGCT GGGTCCTGTC    3600
TCTTTTGACT AATATTTTCG TAAACATTAG GCTGGAGAAA GGAAGGAAGC AGTGGTTTCC    3660
TTAGATAACT ACAGAATTAT ACTGGTCTCT GGGATTACTC TCTCAGCTGT ATTAAAATGA    3720
ATTTGTACTT TGAAAGGAAT GATATTGACA CTAAAATTTT AAACATTTAA ATTTTTTCAT    3780
AATCTTTCAT AAAGAAGTTT AATAATAGGT ATATTAACTG AATTTCATTA GTTTTTAAA    3840
ATAATATTGT TTGTGTATAT ATACATATTA AAATAAAAAC ATTTACAACA AATAAAATAC    3900
TTGAAATTCT AAAAAAAAAA AAAAAAAAA A                                    3931
```

Days in the differentiation medium

Fig. 12a

```
         10         20         30         40         50         60
AAGCCTGCAGGAACAGCGTGCAGGGACTCCAGCAACTCCTGTGACCTCCAGAGTTCTGC
 K  P  A  G  T  A  C  R  D  S  S  N  S  C  D  L  P  E  F  C 70         80         90        100        110        120
ACAGGGCCAGCCTCACTGCCCAGCCAACGTGTACCTGCACGATGGGCACTCATGTCAG
 T  G  A  S  P  H  C  P  A  N  V  Y  L  H  D  G  H  S  C  Q 130        140        150        160        170        180
GATGTGGACGGCTACTGCTANAAATGGCATCTGCCAGACTCACGAGCAGTGTGTCACG
 D  V  D  G  Y  C  X  N  G  I  C  Q  T  H  E  Q  C  V  T 190        200        210        220        230        240
CTCTGGGGACCAGGTGCTAAACCTGCCCCCTGGGATCTGCTTTGAGAGATCAATTCTGCA
 L  W  G  P  G  A  K  P  A  P  G  I  C  F  E  R  V  N  S  A 250        260        270        280        290        300
GGTGAACCTTATGGCAACTGTGGCAAAGTCTCGAAGAGTTCCTTTGCCAAATGCCAGAGATG
 G  E  P  Y  G  N  C  G  K  V  S  K  S  S  F  A  K  C  E  M
```

Fig. 12b

```
        310           320
AGAGATGCTAAAATGCGGGCAAG    107
 R   D   A   K   C   G   K
```

Fig. 13a

```
          10         20         30         40         50         60
GCAAAGAGCTGCATCATGAATTCAGGAGCATCGGGTTCCAGAAACTTTAGCAGTTGCAGT
 A  K  S  C  I  M  N  S  G  A  S  G  S  R  N  F  S  S  C  S     20

70         80         90        100        110        120
GCAGAGGACTTTGAGAAGTTAACTTTAAATAAGGAGAAACTGCCTTCTTAATATTCCA
 A  E  D  F  E  K  L  T  L  N  K  G  G  N  C  L  L  N  I  P     40

130        140        150        160        170        180
AAGCCTGATGAAGCCTATAGTGCTCCCTCCTGTGGTAATAAGTTGGTGGACGCTGGGGAA
 K  P  D  E  A  Y  S  A  P  S  C  G  N  K  L  V  D  A  G  E     60

190        200        210        220        230        240
GAGTGTGACTGTGGTACTCCAAAGGAAGAATGTGAATTGGACCCTTGCTGCGAAGGAAGTACC
 E  C  D  C  G  T  P  K  E  C  E  L  D  P  C  C  E  G  S  T     80

250        260        270        280        290        300
TGTAAGCTTAAATCATTGCTGAGTGTGCATATGGTGACTGTTGTAAAGACTGTCGGTTC
 C  K  L  K  S  F  A  E  C  A  Y  G  D  C  C  K  D  C  R  F    100
```

Fig. 13b

```
         310        320        330        340        350        360
CTTCCAGGAGTACTTTATGCCGAGGAAAAACCAGTGAGTGTGATGTTCCAGAGTACTGC        120
 L  P  G  G  T  L  C  R  G  K  T  S  E  C  D  V  P  E  Y  C 370        380        390        400        410        420
AATGGTTCTTCTCAGTTCTGTCAGCCAGATGTTTTATTCAGAATGGATATCCTTGCCAG        140
 N  G  S  S  Q  F  C  Q  P  D  V  F  I  Q  N  G  Y  P  C  Q 430        440        450        460        470        480
AATAACAAAGCCTATTGCTACAACGGCATGTGCCAGTATTATGATGCTCAATGTCAAGTC        160
 N  N  K  A  Y  C  Y  N  G  M  C  Q  Y  Y  D  A  Q  C  Q  V 490        500        510        520        530        540
ATCTTTGGCTCAAAAGCCAAGGCTGCCCCCAAAGATTGTTTCATTGAAGTGAATTCTAAA        180
 I  F  G  S  K  A  K  A  A  P  K  D  C  F  I  E  V  N  S  K 550        560        570        580        590        600
AATCTTGGCAATTGTGGTTTCTCTGGCAATGAATACAAGAAGTGTGCCACTGGG        200
 G  D  R  F  G  N  C  G  F  S  G  N  E  Y  K  K  C  A  T  G
```

Fig. 13c

```
              610        620        630        640        650        660
     AATGCTTTGTGTGGAAAGCTTCAGTGTGAGAATGTACAAGAGATACCTGTATTTGGAATT
      N  A  L  C  G  K  L  Q  C  E  N  V  Q  E  I  P  V  F  G  I   220

670        680        690        700        710        720
     GTGCCTGCTATTATTCAAACGCCTAGTCGAGGCACCAAATGTGGGGTGTGGATTCCAG
      V  P  A  I  I  Q  T  P  S  R  G  T  K  C  W  G  V  D  F  Q   240

730        740        750        760        770        780
     CTAGGATCAGATGTTCCAGATCCTGGGATGGTTAACGAAGGCACAAAATGTGGTGCTGGA
      L  G  S  D  V  P  D  P  G  M  V  N  E  G  T  K  C  G  A  G   260

790        800        810        820        830        840
     AAGATCTGTAGAAACTTCCAGTGTGTAGATGCTTCTGTTCTGAATTATGACTGTGATGTT
      K  I  C  R  N  F  Q  C  V  D  A  S  V  L  N  Y  D  C  D  V   280

850        860        870        880        890        900
     CAGAAAAAGTGTCATGGACATGGGGTATGTAATAGCAATAAGAATTGTCACTGTGAAAAT
      Q  K  K  C  H  G  H  G  V  C  N  S  N  K  N  C  H  C  E  N   300
```

Fig. 13d

```
          910       920       930       940       950       960
GGCTGGCTCCCCCAAATTGTGAGACTAAAGGATACGAGATCAAGCTTATCGATACCGTCG
 G  W  L  P  Q  I  V  R  L  K  D  T  R  S  S  L  S  I  P  S

ACCTCGA
 T  S
     322                                                      320
```

Fig. 15a

```
GGGGACCTCTGGATCCCAGTGAAGAGCTTCGACTCCAAGAATCATCCAGAAGTGCTGAAT      60
 G  D  L  W  I  P  V  K  S  F  D  S  K  N  H  P  E  V  L  N       20

ATTCGACTACAACGGGAAAGCAAAGAACTGATCATAAATCTGGAAAGAAATGAAGGTCTC     120
 I  R  L  Q  R  E  S  K  E  L  I  I  N  L  E  R  N  E  G  L       40

ATTGCCAGCAGTTTCACGGAAACCCACTATCTGCAAGACGGTACTGATGTCTCCCTCGCT     180
 I  A  S  S  F  T  E  T  H  Y  L  Q  D  G  T  D  V  S  L  A       60

CGAAATTACACGGGTCACTGTTACTACCATGGACATGTACGGGGATATTCTGATTCAGCA     240
 R  N  Y  T  G  H  C  Y  Y  H  G  H  V  R  G  Y  S  D  S  A       80

GTCAGTCTCAGCACGTGTTCTGGTCTCAGGGGACTTATTGGGTTTGAAAATGAAAAGCTAT   300
 V  S  L  S  T  C  S  G  L  R  G  L  I  G  F  E  N  E  S  Y      100

GTCTTAGAACCAATGAAAAGTGCAACAACAGATACAAACTCTTCCCAGCGAAGAAGCTG     360
 V  L  E  P  M  K  S  A  T  N  R  Y  K  L  F  P  A  K  K  L      120

AAAAGCGTCCGGGGATCATGTGGATCACATCACAACACCAAACCTCGCTGCAAAGAAT      420
 K  S  V  R  G  S  C  G  S  H  H  N  T  P  N  L  A  K  N        140
```

Fig. 15b

```
GTGTTTCCACCACCCTCTCAGACATGGGCAAGAAGGCATAAAAGAGAGACCCTCAAGGCA   480
 V  F  P  P  P  S  Q  T  W  A  R  R  H  K  R  E  T  L  K  A    160

ACTAAGTATGTGGAGCTGGTGATCGTGGCAGACAACCGAGAGTTTCAGAGGCAAGGAAAA   540
 T  K  Y  V  E  L  V  I  V  A  D  N  R  E  F  Q  R  Q  G  K    180

GATCTGGAAAAAGTTAAGCAGCGATTAATAGAGATTGCTAATCACGTTGACAAGTTTTAC   600
 D  L  E  K  V  K  Q  R  L  I  E  I  A  N  H  V  D  K  F  Y    200

AGACCACTGAACATTCGGATCGTGTTGGTAGGCGTGGAAGTGTGGAATGACATGGACAAA   660
 R  P  L  N  I  R  I  V  L  V  G  V  E  V  W  N  D  M  D  K    220

TGCTCTGTAAGTCAGGACCCATTCACCAGCCTCCATGAATTTCTGGACTGGAGGAAGATG   720
 C  S  V  S  Q  D  P  F  T  S  L  H  E  F  L  D  W  R  K  M    240

AAGCTTCTACCTCGCAAATCCCATGACAATGCGCAGCTTGTCAGTGGGGTTTATTCCAA   780
 K  L  L  P  R  K  S  H  D  N  A  Q  L  V  S  G  V  Y  F  Q    260

GGGACCACCATCGGGCATGCCCCAATCATGAGCATGTGCACGGGCAGACCAGTCTGGGGGA   840
 G  T  T  I  G  M  A  P  I  M  S  M  C  T  A  D  Q  S  G  G    280
```

Fig. 15c

```
ATGTCATTGGACCATTCAGACAATCCCCTTGGTCAGCCCTGACCCTGGCACATGAGCTG      900
 I  V  M  D  H  S  D  N  P  L  G  A  A  V  T  L  A  H  E  L       300

GGCCACAATTTCGGGATGAATCATGACACACTGGACAGGGGCTGTAGCTGTCAAATGGCG      960
 G  H  N  F  G  M  N  H  D  T  L  D  R  G  C  S  C  Q  M  A       320

GTTGAGAAAGGAGGCTGCATCATGAACGCTTCCACCGGGTACCCATTTCCCATGGTGTTC     1020
 V  E  K  G  G  C  I  M  N  A  S  T  G  Y  P  F  P  M  V  F       340

AGCAGTTGCAGCAGGAAGGACTTGGAGACCAGCCTGGAGAAAGGAATGGGGGTGTGCCTG     1080
 S  S  C  S  R  K  D  L  E  T  S  L  E  K  G  M  G  V  C  L       360

TTTAACCTGCCCGAAGTCAGGGAGTCTTTCGGGGGCCAGAAGTGTGGGAACAGATTTGTG     1140
 F  N  L  P  E  V  R  E  S  F  G  G  Q  K  C  G  N  R  F  V       380

GAAGAAGGAGAGGAGTGTGACTGTGGGGAGCCAGAGGAATGTATGAATCGCTGCTGCAAT     1200
 E  E  G  E  E  C  D  C  G  E  P  E  E  C  M  N  R  C  C  N       400

GCCACCACCTGTACCCTGAAGCCCGACGCTGTGCGCCACATGGGCTGTGCTGTGAAGAC     1260
 A  T  T  C  T  L  K  P  D  A  V  C  A  H  G  L  C  C  E  D       420
```

Fig. 15d

```
TGCCAGCTGAAGCCTGCAGGAACAGCGTGCAGGACTCCAGCAACTCCTGTGACCTCCCA    1320
 C  Q  L  K  P  A  G  T  A  C  R  D  S  S  N  S  C  D  L  P     440

GAGTTCTGCACAGGGGCCAGCCCTCACTGCCCAGCCAACGTGTACCTGCACGATGGGCAC    1380
 E  F  C  T  G  A  S  P  H  C  P  A  N  V  Y  L  H  D  G  H     460

TCATGTCAGGATGTGGACGGGCTACTGCTACAATGGCATCTGCCAGACTCACGAGCAGCAG    1440
 S  C  Q  D  V  D  G  Y  C  Y  N  G  I  C  Q  T  H  E  Q  Q     480

TGTGTCACGCTCTGGGGACCAGGTGCTAAACCTGCCCCTGGGATCTGCTTTGAGAGAGTC    1500
 C  V  T  L  W  G  P  G  A  K  P  A  P  G  I  C  F  E  R  V     500

AATTCTGCAGGTGATCCTTATGGCAACTGTGGCAAAGTCTCGAAGAGTTCCTTTGCCAAA    1560
 N  S  A  G  D  P  Y  G  N  C  G  K  V  S  K  S  S  F  A  K     520

TGCGAGATGAGAGATGCTAAATGTGGAAAAATCCAGTGTCAAGGAGGTGCCAGCCGGCCA    1620
 C  E  M  R  D  A  K  C  G  K  I  Q  C  Q  G  G  A  S  R  P     540

GTCATTGGTACCAATGCCCGTTTCCATAGAAACAAACATCCCCTGCAGCAAGGAGGCCGG    1680
 V  I  G  T  N  A  V  S  I  E  T  N  I  P  L  Q  Q  G  G  R     560
```

Fig. 15e

```
ATTCTGTGCCGGGGACCCACGTGTACTTGGGCGATGACATGCCGGACCCAGGGCTTGTG    1740
 I  L  C  R  G  T  H  V  Y  L  G  D  D  M  P  D  P  G  L  V     580

CTTGCAGGCACAAAGTGTGCAGATGGAAAAATCTGCCTGAATCGTCAAATGTCAAAATATT  1800
 L  A  G  T  K  C  A  D  G  K  I  C  L  N  R  Q  C  Q  N  I     600

AGTGTCTTTGGGGTTCACGAGTGTGCAATGCAGTGCCACGGCAGAGGGGTGTGCAACAAC   1860
 S  V  F  G  V  H  E  C  A  M  Q  C  H  G  R  G  V  C  N  N     620

AGGAAGAACTGCCACTGCGAGGCCCACTGGGCACCTCCCCTTCTGTGACAAGTTTGGCTTT  1920
 R  K  N  C  H  C  E  A  H  W  A  P  P  F  C  D  K  F  G  F     640

GGAGGAAGCACAGACAGCGGCCCCATCCGGCAAGCAGAAGGCAGGAAGCTGCAGAG       1980
 G  G  S  T  D  S  G  P  I  R  Q  A  E  A  R  Q  E  A  A  E     660

TCCAACAGGGAGCGCGGCCAGGGCCAGGAGCCCGTGGGATCCAGGAGCATGCGTCTACT    2040
 S  N  R  E  R  G  Q  G  Q  E  P  V  G  S  Q  E  H  A  S  T     680

GCCTCACTGACACTCATCTGAGCCCTCCCATGACACATGGGAGACCGTGACCAGTGCTGCTGC 2100
 A  S  L  T  L  I  *                                             686
```

Fig. 15f

```
AGAGGAGGTCACGCGTCCCCAAGGCCCTCCTGTGACTGGCAGCATTGACTCTGTGGCTTTG  2160
CCATCGTTTCCATGACAACAGACACAACAGTTCTCGGGCTCAGGAGGGAAGTCCAG       2220
CCTACCAGGCACGTCTGCAGAAACAGTGCAAGGAAGGGCAGCGACTTCCTGGTTGAGCTT   2280
CTGCTAAAACATGGACATGCTTCAGTGCTCCTGAGAGTAGCAGGTTACCACTCTG        2340
GCAGGCCCCAGCCTGCAGCAAGGAGGAAGAGGACTCAAAAGTCTGGCCTTTCACTGAGC    2400
CCCCACAGCAGTGGGGAGAAGCAAGGGTTGGGCCCAGTGTCCCCTTTCCCCAGTGACAC    2460
CTCAGCCCTTGGGCAGCCCTGATGACTCTCTGGCTGCAACTTAATGCTCTGATATGGCT    2520
TTTAGCATTTATTATGAAATAGCAGGTTTTAGTTTTAATTTATCAGAGACCCTGC        2580
CACCCATTCCATCTCCATCCAAGCAAACTGAATGGCATTGAAACAAACTGGAGAAGAAGG   2640
TAGGAGAAAGGGGTGAACTCTCTGGCTCTCTTTGCTGTGGACCCAGAGTCACCAGCAGTACTC 2700
AGGTTTGAGGGTTTGCAGAAAGCCAGGGAACCCACAGAGTCACCAACCCTTCATTAACA   2760
AGTAAGAATGTTAAAAGTGAAAACAATGTAAGAGCCTAACTCCATCCCCCGTGGCCATT   2820
ACTGCATAAAATAGAGTGCATCCCCGCCC  2848
```

Fig. 16

```
GGG GAA GAG TGT GAT TGT GGA GAA GAA GAG GAA TGT GGA AAC AAC CCC TGC AAT GCC TCT    60
 G   E   E   C   D   C   G   E   E   E   E   C   N   N   P   C   C   N   A   S    20

AAT TGT ACC CTG AGG CCG GGG GAG TGT GCT CAC GGC TCC TGC TGC CAC CAG TGT AAG       120
 N   C   T   L   R   P   G   E   C   A   H   G   S   C   C   H   Q   C   K        40

CTG TTC GCT CCT GGG ACC CTG TCC CCC GAG CAG GCC AGG CAG TGT GAC CTC CCG GAG TTC   180
 L   L   A   P   G   T   L   S   P   E   Q   A   R   Q   C   D   L   P   E   F    60

TGT ACC GGC AAG TCT CCC CAC TGC CCT AAC TTC TAC CAG ATG GAT GGT ACC CCC TGT       240
 C   T   G   K   S   P   H   C   P   T   N   F   Y   Q   M   D   G   T   P   C    80

GAG GGC GGC CAG GCc TAC TGC TAC AAC GGC ATG TGC CTC ACC TAC CAG GAG CAG TGC CAG   300
 E   G   G   Q   A   Y   C   Y   N   G   M   C   L   T   Y   Q   E   Q   C   Q   100

CAG CTG TGG GGA CCC GGA GCC CGA CCT GCC CCT GAC CTC TGC TTC GAG AAg GTG AAT GTG  360
 Q   L   W   G   P   G   A   R   P   A   P   D   L   C   F   E   K   V   N   V   120

GCA GGA GAC ACC TTT GGA AAC TGT GGA AAG GAC A                                    394
 A   G   D   T   F   G   N   C   G   K   D                                       131
```

Fig. 17a

```
CGGAGCTGCCACTGGGCACCCCTTTCCCAAAGTGTTCAATGGATGCAACAGGAGGAGCT  60
         G  A  T  G  H  P  F  P  K  V  F  N  G  C  N  R  R  E  L   20
GGACAGGTATCTGCAGTCAGGTGGTGGTGGAATGTGTCTCCAACATGCCAGACACCAGGAT  120
 D  R  Y  L  Q  S  G  G  G  M  C  L  S  N  M  P  D  T  R  M   40
GTTGTATGGAGGCCGGAGGTGTGGGAACGGGTATCTGGAAGATGGGGAAGAGTGTGACTG  180
 L  Y  G  G  R  R  C  G  N  G  Y  L  E  D  G  E  E  C  D  C   60
TGGAGAAGAAGAGGAATGTAACAACCCCTGCTGCAATGCCTCTAATTGTACCCTGAGGCC  240
 G  E  E  E  E  C  N  N  P  C  C  N  A  S  N  C  T  L  R  P   80
GGGGGCGGAGTGTGCTCACGGGTCCTGCCACCAGTGTAAGCTGTTGGCTCCTGGAC  300
 G  A  E  C  A  H  G  S  C  C  H  Q  C  K  L  L  A  P  G  T   100
CCTGTGCCCGAGCAGGCCAGGCAGTGTGACCTCCCGGAGTTCTGTACGGGCAAGTCTCC  360
 L  C  R  E  Q  A  R  Q  C  D  L  P  E  F  C  T  G  K  S  P   120
CCACTGCCCTACCAACTTCTACCAGATGGATGGTACCCCTGTGAGGGCGGGCCAGGCCTA  420
 H  C  P  T  N  F  Y  Q  M  D  G  T  P  C  E  G  G  Q  A  Y   140
```

Fig. 17b

```
CTGCTACAACGGCATGTGCCTCACCTACCAGGAGCAGTGCCAGCAGTGTGGGGACCCGG   480
 C  Y  N  G  M  C  L  T  Y  Q  E  Q  C  Q  Q  L  W  G  P  G    160

AGCCCGACCTGCCCCTGACCTCTGCTTCGAGAAGGTGAATGTGGCAGGAGACACCTTTGG   540
 A  R  P  D  L  C  F  E  K  V  N  V  A  G  D  T  F  G          180

AAACTGTGGAAAGGACATGAATGGTGAACACAGGAAGTGCAACATGAGAGATGCGAAGTG   600
 N  C  G  K  D  M  N  G  E  H  R  K  C  N  M  R  D  A  K  C    200

TGGGAAGATCCAGTGTCAGAGCTCTGAGGCCCCTGAGTCCAACGCGGTGCCCAT         660
 G  K  I  Q  C  Q  S  S  E  A  R  P  L  E  S  N  A  V  P  I    220

TGACACCACTATCATCATGAATGGGAGGCAGATCCAGTGCCGGGGCACCCACGTCTACCG   720
 D  T  T  I  I  M  N  G  R  Q  I  Q  C  R  G  T  H  V  Y  R    240

AGGTCCTGAGGAGGGTGACATGCTGGACCCAGGGCTGGTGATGACTGGAACCAAGTG     780
 G  P  E  E  G  D  M  L  D  P  G  L  V  M  T  G  T  K  C       260

TGGCTACAACCATATTTGCCTTGAGGGGCAGTGCAGGAACACCTCCTTCTTTGAAACTGA   840
 G  Y  N  H  I  C  L  E  G  Q  C  R  N  T  S  F  F  E  T  E    280
```

Fig. 17c

```
AGGCTGTGGGAAGAAGTGCAATGGCCATGGGTCTGTAACAACCAGAACTGCCACTG    900
 G  C  G  K  K  C  N  G  H  G  V  C  N  N  N  Q  N  C  H  C    300

CCTGCCGGGCTGGGCCCCGCCCTTCTGCAACACACCGGGCCACGGGCCAGTATCGACAG    960
 L  P  G  W  A  P  P  F  C  N  T  P  G  H  G  G  S  I  D  S    320

TGGGCCTATGCCCCCTGAGAGTGTGGGTCCTGTGGTAGCTGGAGTGTTGGTGGCCATCTT  1020
 G  P  M  P  P  E  S  V  G  P  V  V  A  G  V  L  V  A  I  L    340

GGTGCTGGTCCTCATGCTACTACTGCAGAACAACAAACTAGGCCA  1080
 V  L  V  L  M  Y  Y  C  C  R  Q  N  N  K  L  G  Q    360

ACTCAAGCCCTCAGCTCTCCCCTTCCAAGCTGAGGCAACAGTTCAGTTGTCCCTTCAGGGT  1140
 L  K  P  S  A  L  P  S  K  L  R  Q  Q  F  S  C  P  F  R  V    380

TTCTCAGAACAGCGGGACTGGTCATGCCAACCCAACTTTCAAG  1183
 S  Q  N  S  G  T  G  H  A  N  P  T  F  K    394
```

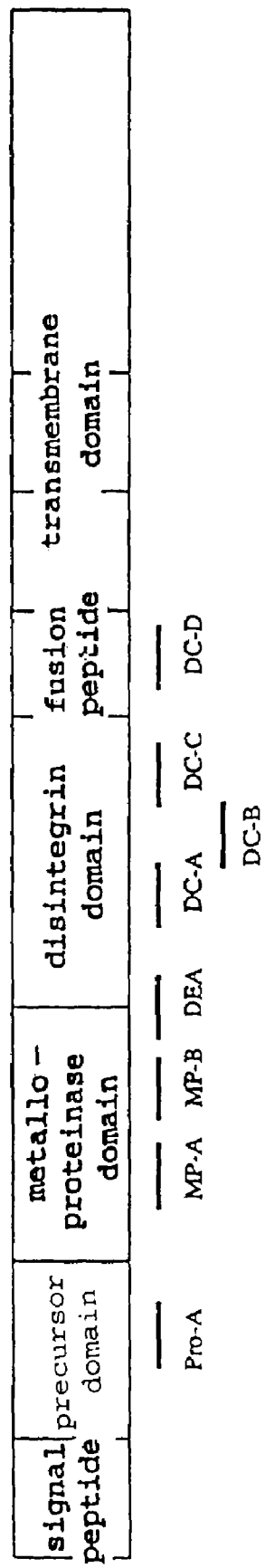
Fig. 18a    Peptides used for the preparation of monoclonal antibody

Fig. 18b  Peptide sequences used for the preparation of monoclonal antibody

| No. | Name | Sequence (N-terminal, C-terminal) |
|---|---|---|
| 1 | Pro-A | TTDSYKLVPAESMTNIC |
| 2 | NP-A | ADNREFQRQGKDLEKVKC |
| 3 | NP-B | FTRLHEFLDWRKIKC |
| 4 | DC-A | QLKPPGTACRGSSNSC |
| 5 | DC-B | GTACRGSSNSCDLPEFC |
| 6 | DC-C | GKDSKSAFAKCELRDAKC |
| 7 | DC-D | QGGASRPVIGTNAVSIETNIC |
| 8 | DE-A | LFNLPEVKQAFGGRKC |

Western blotting with anti-Meltrin monoclonal antibodies

Effects of anti-mouse Meltrin antibodies on the formation of pit (bone-resorption area) in mouse unfractionated bone cells

Fig. 23a

```
GCACAAAGTGTGCAGATGGAAAAATCTGCCTGAATGTCAATATTAGTGTCT      60
 T  K  C  A  D  G  K  I  C  L  N  R  Q  C  Q  N  I  S  V  F    20

TTGGGGTTCACGAGTGTGCAATGCAGTGCCACGGGCAGAGGGGTGTGCAACAACAGGAAGA     120
 G  V  H  E  C  A  M  Q  C  H  G  R  G  V  C  N  N  R  K  N    40

ACTGCCACTGCGAGGCCCACTGGGCCACCTCCCTTCTGTGACAAGTTTGGCTTTGGAGAA     180
 C  H  C  E  A  H  W  A  P  P  F  C  D  K  F  G  F  G  G  S    60

GCACAGACAGGCGGCCCCATCGGGCAAGCAGATAACCAAGGTTTAACCACTATAGGAATTCTGG    240
 T  D  S  G  P  I  R  Q  A  D  N  Q  G  L  T  I  G  I  L  V    80

TGACCATCCTGTGTCTTCTGCTGCCGATTGTGTTGTTTATCTCAAAGGAAGACCTTGA     300
 T  I  L  C  L  L  A  A  G  F  V  V  Y  L  K  R  K  T  L  I    100

TACGACTGCTGTTTACAAATAAGAGACCATTGAAAAACTAAGGTGTGTGCGCCCTT     360
 R  L  L  F  T  N  K  K  T  T  I  E  K  L  R  C  V  R  P  S    120

CCCGGGCCACCCCGTGCCTTCCAACCCTGTCAGGCTCACCTCGGCCACCTTGAAAAGGCC     420
 R  P  P  R  G  F  Q  P  C  Q  A  H  L  G  H  L  G  K  G  L    140
```

Fig. 23b

```
TGATGAGGAAGCCGCCCAGATTCCTACCCACGGAAGGACAATCCCAGGAGATTGCTGCAGT   480
 *  M  R  K  P  P  D  S  Y  P  P  K  D  N  P  R  R  L  L  Q  C   160

GTCAGAATGTTGACATCAGCAGACCCCTCAACGGCCTGAATGTCCTCAGCCCCAGTCAA    540
 Q  N  V  D  I  S  R  P  L  N  G  L  N  V  P  Q  P  Q  S  T    180

CTCAGGGAGTGCTTCCCCCTCCACCGGGCTCCACGTGCACCTAGGTCCTGCCAGAC       600
 Q  R  V  L  P  P  L  H  R  A  P  R  A  P  S  V  P  A  R  P    200

CCCTGCCCAGCCAAGCCCTGCACTTA   624
 L  P  A  K  P  A  L        207
```

Fig. 24a

| | |
|---|---|
| CGGAGCTGCCACTGGGCACCCCTTTCCCAAAGTGTTCAATGGATGCAACAGGAGGGAGCT | 60 |
| G  A  T  G  H  P  F  P  K  V  F  N  G  C  N  R  R  E  L | 20 |
| GGACAGGTATCTGCAGTCAGGTGGTTGGAATGTGTCTCTCCAACATGCCAGACACCAGGAT | 120 |
| D  R  Y  L  Q  S  G  G  M  C  L  S  N  M  P  D  T  R  M | 40 |
| GTTGTATGGAGGCCGGAGTGTGGGAACGGGTATCTGGAAGATGGGGAAGAGTGTGACTG | 180 |
| L  Y  G  G  R  R  C  G  N  G  Y  L  E  D  G  E  E  C  D  C | 60 |
| TGGAGAAGAGGAATGTAACAACCCCTGCTGCAATGCCTCTAATTGTACCCTGAGGCC | 240 |
| G  E  E  E  C  N  N  P  C  C  N  A  S  N  C  T  L  R  P | 80 |
| GGGGGCGGAGTGTGCTCACGGTGTCCTGCCACCAGTGTAAGCTGTTGGCTCCTGGGAC | 300 |
| G  G  G  E  C  A  H  G  S  C  C  H  Q  C  K  L  L  A  P  G  T | 100 |
| CCTGTGCCCGGAGCAGGCCAGGCAGTGACCTCCCGGAGTTCTGTACGGGCAAGTCTCC | 360 |
| L  C  R  E  Q  A  R  Q  C  D  L  P  E  F  C  T  G  K  S  P | 120 |
| CCACTGCCCTACCAACTTCTACCAGATGGATGGTACCCCCTGTGAGGGGCCAGGCCTA | 420 |
| H  C  P  T  N  F  Y  Q  M  D  G  T  P  C  E  G  G  Q  A  Y | 140 |

Fig. 24b

```
CTGCTACAACGGCATGTGCCTCACCTACCAGGAGCAGTGCCAGCAGCTGTGGGGACCCGG    480
 C  Y  N  G  M  C  L  T  Y  Q  E  Q  C  Q  Q  L  W  G  P  G    160

AGCCCGACCTGCCCCTGACCTCTGCTTCGAGAAGGTGAATGTGGCAGGAGACACCTTTGG    540
 A  R  P  A  P  D  L  C  F  E  K  V  N  V  A  G  D  T  F  G    180

AAACTGTGAAAGGACATGAATGGTGAACACAGGAAGTGCAACATGAGAGATGCGAAGTG    600
 N  C  G  K  D  M  N  G  E  H  R  K  C  N  M  R  D  A  K  C    200

TGGGAAGATCCAGTGTCAGAGCTCTGAGGCCCGGCCCCTGGAGTCCAACGCGGTGCCCAT    660
 G  K  I  Q  C  Q  S  S  E  A  R  P  L  E  S  N  A  V  P  I    220

TGACACCACTATCATCATGAATGGGAGGCAGATCCAGTGCCGGGGCACCCACGTCTACCG    720
 D  T  T  I  I  M  N  G  R  Q  I  Q  C  R  G  T  H  V  Y  R    240

AGGTCCTGAGGAGGGTGACATGCTGGACCCAGGGCTGGTGATGACTGGAACCAAGTG    780
 G  P  E  E  G  D  M  L  D  P  G  L  V  M  T  G  T  K  C    260

TGGCTACAACCATATTTGCCTTGAGGGGCAGTGCAGGAACACCTCCTTCTTTGAAACTGA    840
 G  Y  N  H  I  C  L  E  G  Q  C  R  N  T  S  F  F  E  T  E    280
```

Fig. 24c

```
AGGCTGTGGGAAGAAGTGCAATGGCCATGGGTCTGTAACAACCAGAACTGCCACTG    900
 G  C  G  K  K  C  N  G  H  G  V  C  N  N  Q  N  C  H  C    300

CCTGCCGGGCTGGGCCCCCTTCTGCAACACCGGGGGCAGTATCGACAG             960
 L  P  G  W  A  P  P  F  C  N  T  P  G  H  G  G  S  I  D  S  320

TGGGCCTATGCCCCCCTGAGAGTGTCCTGTGTAGCTGGAGTGTTGGTGGCCATCTT    1020
 G  P  M  P  P  E  S  V  G  P  V  V  A  G  V  L  V  A  I  L  340

GGTGCTGGCGGTCCTCATGCTACTACTGCTGCAGACAGAACAAACTAGGCCA         1080
 V  L  A  V  L  M  L  M  Y  Y  C  C  R  Q  N  N  K  L  G  Q  360

ACTCAAGCCCTCAGCTCTCCCTTCCAAGCTGAGGCAACAGTTCAGTTGTCCCTTCAGGGT 1140
 L  K  P  S  A  L  P  S  K  L  R  Q  Q  F  S  C  P  F  R  V  380

TTCTCAGAACAGGGGGACTGGTCATGCCAACCCAACTTTCAAGCCGGAATTCCGGGCCCC 1200
 S  Q  N  S  G  T  G  H  A  N  P  T  F  K  P  E  F  R  A  P  400

CCACAGCCCACACCACCATGACAAGGGCCACCAATTCCACGGCCACACCCCTCCACTC    1260
 H  S  P  H  H  H  D  K  G  H  Q  F  H  G  H  T  L  L  H  S  420
```

Fig. 24d

```
TGGGGACGACCCGGATCCTCACTGAGCTGACCACAACAGCCACTACAACTGCAGCCACTG  1320
 G  D  D  P  D  P  H  *                                        427

GATCCACGGGCCACCCTGTCCTCCACCCCAGGGACCACCTGGATCCTCACAGAGCCGAGCA  1380
CTATAGCCACCGTGATGGTGCCCACCCGGTTCCACGGGCCACCTCCTCCACTCTGGGAA    1440
CAGCTCACACCCCCAAAGTGGTGACCACCATGGCCCACTATGCCCACAGCCACTGCCTCCA  1500
CGGTTCCCAGCTCGTCCACGGGACCACCCGCACCCCGCAGTGCTCCCCAGCAGCC        1560
TGCCAACCTTCAGCGTGTCCACTGTCCTCCTCCAGTCCTCACACCCTGAGACCCACTG     1620
GCTTCCCCAGCTCCCACTTCTCTACTCCCTGCTTCTGCAGGGCATTTGGACAGTTTTCT    1680
CGCCCGGGAAGTCATCTACAATAAGACCGACGGGCTGCTGCCATTTCTACGCAGTGT      1740
GCAATCAGCACTGTGACATTGACCGCTTCCAGGGCGCCGCCTGTCCCCACCCCACCGCCAG  1800
TGTCCTCCGCCCCGTCCTCGCCCCCTGGCTGTGACAATGCCATCCCTC               1860
TCCGGGCAGGTGAATGAGACCTGGACCTGGCTGGACCCAAAGCCTCACCTGCGTGGGTG    1920
ACAACCCGTGTCCTGCTGGAGAACTGTGGCCAACGTCACCTGCGTGAACAAGC          1980
ACCTGCCCATCAAAGTGTCGGGGCGGCTCCACTATTCCCACCTTTGACGGCACTCTTACACCT 2040
GCATCTGCAGCATGTGGGGGCCTCCACCTATGTCCTCATGAGAGATCCATGCCACGCGCTTGC 2100
TCCGGGCAACTGCACCTGGACAACCACTACAAGTCCATGGATATCGTCCTCACTGTCGGTGC 2160
GCCTCTACCTGGACAATCCAGCATCCACTGCACGGCCCTCTGCCACTGCCGCCGCGCTGCC   2220
CCGGCGCCCTCAGCATCCACTACAAGTCCATGGATATCGTCCTCACTGTCACCATGGTGC   2280
ATGGGAAGGAGGGGCCCTGATCCTGTTTGACCAAATTCCGGTCCAGCCAGGGGTTTCAGCA 2340
```

Fig. 24e

```
AGAACGGGCGTGCTTGTGTCTGTGCTGGGGACCACCACCATGGTGTGGACATTCCTGCCC   2400
TGGGCGTGAGCGTCACCTTCAATGGCCAAGTCTTCCAGGCCCGGCTGCCCTACAGCCTCT   2460
TCCAACAACAACACCGAGGGCCAGTGCGGGCCACCTGCACCAACAACCAGAGGGACGACTGTC   2520
TCCAGCGGGACGGAACCACTGCCGCCAGTTGCAAGGACATGGCCAAGACGTGGCTGGTCC   2580
CCGACAGCAGAAAGGATGGCTGTGGGCTGCTGGGCACACCCCCACTGCCAGCCCCCG      2640
CAGCCCCCGGGTGTCTAGCACACCCACCCCCG  2669
```

MELTRINS

This application is a divisional of U.S. patent application Ser. No. 09/983,531, issued as U.S. Pat. No. 7,060,791, filed Oct. 24, 2001, which is a continuation of U.S. patent application Ser. No. 09/138,675, filed Aug. 24, 1998, now abandoned, which is a continuation of International Application No. PCT/JP96/03017, filed Oct. 17, 1996, which claims priority on Japanese Patent Application No. 8-61756, filed Feb. 23, 1996. The entire disclosures of the above patent applications are hereby incorporated by reference.

TECHNICAL FIELD

This invention relates to Meltrins and polypeptides of the respective domains thereof; DNAs encoding the same; antisense oligonucleotides for these DNAs; various antibodies against these Meltrins and the polypeptides of the respective domains thereof; expression vectors comprising the DNAs; transformants constructed by using these expression vectors; a process for producing the above-mentioned meltirins and the polypeptides of the respective domains thereof by means of the transformants; and medical compositions comprising the Meltrins or Meltrin antagonists as an effective ingredient.

BACKGROUND ART

In the course of myotube formation, myoblasts, which have divided from myogenic cells originating in undifferentiated mesodermal cells and grown to differentiate, will start synthesizing muscle-specific substances such as myosin and actin after its final division, and will lose cell boundaries at the fusion surface to be transformed into multinucleate syncytium named myotube through adhesion and fusion of cytoplasmic membranes with neighbouring cells of the same kind.

There have been already reported several kinds of membrane proteins involved in the myotube formation, such as N-Cadherin (Knudsen, K. A. et al., Expl. Cell Res., 188, 175-184 (1990), Merge, R. M. et al., J. Cell Sci., 103, 897-906 (1992)), M-Cadherin (Donalies, M. et al., Proc. Natl. Acad. Sci., U.S.A. 88, 8024-8028 (1991)), N-CAMs (Merge, R. M. et al., J. Cell Sci., 103, 897-906 (1992) and others), V-CAMs and Integrins (Rosen, G. D. et al., Cell 69, 1107-1119 (1992) and others).

However, the molecular mechanism has not yet been sufficiently understood concerning the course of formation of the multinucleate syncytium named myotube through adhesion and fusion of the cytoplasmic membranes of the myoblasts with each other.

On the other hand, the substances named "fusion peptides" have been known as an adhesion factor involved in the course of infection of cells with viruses (Morrison, T. G. Virus Res., 10, 113-136 (1988) and the others). Fertilin, which was recently isolated as a factor involved in sperm-egg adhesion, has been found to contain a sequence similar to the fusion peptide of rubella virus (Blobel, C. P. et al., Nature 356, 248-252 (1992) and the others).

Many substances having adhesion activity are known as mentioned above, and substances which may inhibit the activity of Integrins and the like have been developed and studied as potential medical agents.

The present inventors have now isolated novel substances involved in adhesion. Particularly, on the assumption that some fusion peptide-like adhesion factor like in sperm-egg adhesion may be involved in adhesion and fusion of the myoblasts with each other in the course of myotube formation, the novel substances involved in cell adhesion have been cloned and named "Meltrins", by using highly conserved sequences in Fertilin α and β as a probe.

DISCLOSURE OF INVENTION

The present invention relates to novel substances "Meltrins." "Meltrins" are characterized as proteins which are expressed in the course of differentiation-induction of muscle cells and to contain the highly conserved sequences in Fertilin α and β. Meltrins are also characterized as proteins which are involved in fusion, adhesion, or aggregation of cells. Thus, some kinds of cells such as muscle ones may fuse, aggregate or adhere via Meltrins.

Cell fusion means that more than two cells fuse with each other to form one multinucleate syncytium. Adhesion of cells means that more than two cells adhere to each other. Aggregation of cells means that more than two cells (particularly the cells present in liquid) flock together to form a mass of cells. It may be considered that cells adhere to each other, followed by cell fusion and aggregation.

The origin of the present Meltrins is not specifically limited. Accordingly, Meltrins in the present specification comprise polypeptides originating in any animals as long as they have the above features, unless otherwise particularly noted. As will be demonstrated in the following examples, at least three kinds of molecules (α, β and γ) have been isolated from one animal species. Meltrins in the present specification therefore comprise any one of the above three molecules.

The specific examples of Meltrins of the present invention are mouse Meltrins α, β and γ, which are characterized by amino acid sequences shown in FIG. 2a~FIG. 2j, FIG. 3a~FIG. 3j and FIG. 4a~FIG. 4i, respectively, or partial sequences thereof.

Other examples may contain human Meltrins α, β and γ, which are characterized by amino acid sequences shown in any one of FIG. 12a~FIG. 12b, FIG. 15a~FIG. 15f or FIG. 23a~FIG. 23b; any one of FIG. 16 or FIG. 17a~FIG. 17c; or FIG. 13a~FIG. 13d, respectively, or partial sequences thereof.

The above amino acid sequences should be considered only examples of Meltrins of the present invention. Any variant of the above amino acid sequences wherein a part of the sequences has changed due to deletion, substitution, addition, insertion and the like of amino acids is therefore contained in Meltrins of the present invention, as long as it is expressed in muscle cells, and have the highly conserved sequences in Fertilin α and β or is involved in fusion, adhesion or aggregation of cells. As cleared now by the present inventors, a high homology is seen in the part from disintegrin domain to cysteine-rich region of mouse amino acid sequences shown in FIG. 2a~FIG. 2j and human amino acid sequences shown in FIG. 12a~FIG. 12b. It is considered that such substances as showing homology of about 80% or more, preferably about 90% or more to the above amino acid sequences may keep the function as Meltrin. Particularly, it is believed that the substances having the sequences with homology of about 80% or more, preferably about 90% or more to the region from metalloproteinase domain to disintegrin domain of mouse or human Meltrins α, β and γ will have substantially the same activity, even if all of the other sequences are different from them. Accordingly, Meltrins of the present invention may include substances having a high homology to the above amino acid sequences or to a part thereof and showing substantially the same activity as mouse or human Meltrins.

In other words, Meltrins of the present invention may be characterized by having amino acid sequences encoded by base sequences that may hybridize the sequences complementary to the base sequences encoding any one of the amino acids shown in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c or FIG. 23a~FIG. 23b.

Meltrins exist in bodies as a membrane protein consisting of intracellular domain, transmembrane domain, and extracellular domain; and as a soluble protein having no transmembrane domain. The extracellular domain contains precursor domain, metalloproteinase domain, disintegrin domain, and cysteine-rich region. Meltrin α has a fusion peptide-like sequence in its cysteine-rich region (Refer to FIG. 8).

The disintegrin domain is indispensable for the function of Meltrins such as adhesion, fusion and aggregation of cells. On the other hand, the precursor and metalloproteinase domains are thought to be regulating sequences for Meltrins to show the activity in a specific organ or tissue, or under specific conditions. It is known that the disintegrin found in snake venom will adhere to platelet IIb/IIIa. It is therefore presumed that the disintegrin domain by itself may have the function to adhere to cells. The metalloproteinase domain may act by itself as a protease as such.

The present invention relates to polypeptides comprising any part of Meltrins. The present polypeptides include the respective domain per se of Meltrins, polypeptides comprising at least the respective domain of Meltrins, any part of the sequences of Meltrins, polypeptides comprising at least any part of the sequences of Meltrins, and polypeptides comprising at least the sequence having the combination of any of the respective domains of Meltrins and any part of Meltrins in any order. The present invention may further include the above polypeptides which are chemically modified or formed into salts thereof.

The preferable examples of the present polypeptides include polypeptides consisting of a part of the disintegrin domain, polypeptides consisting of the disintegrin domain per se, polypeptides comprising at least the disintegrin domain, polypeptides comprising at least the disintegrin and cysteine-rich regions, polypeptides comprising at least the metalloproteinase, disintegrin and cysteine-rich regions, polypeptides consisting of a part of the metalloproteinase domain, and polypeptides consisting of the metalloproteinase domain per se.

There may be mentioned as other preferable examples of the present polypeptides those comprising at least the disintegrin and cysteine-rich regions, but not comprising the transmembrane domain, or comprising neither the transmembrane domain nor intracellular domain; and those comprising at least the metalloproteinase, disintegrin and cysteine-rich regions, but not comprising the transmembrane domain, or comprising neither the transmembrane domain nor intracellular domain. Such polypeptides comprising no transmembrane domain are a soluble one which will be secreted through a cell membrane into an extracellular area. The soluble polypeptides may be collected from a supernatant of the culture medium of cells. When optionally combined downstream of a suitable signal sequence and expressed by cells in a genetic engineering process, it will be secreted into the culture supernatant and advantageously collected therefrom with a high efficiency.

The amino acid sequences in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c and FIG. 23a~FIG. 23b, which correspond to the precursor domain, metalloproteinase domain, disintegrin domain, cysteine-rich region, intracellular domain, and transmembrane domain of mouse and human Meltrins α, β and γ, are discussed in the Examples. It should be noted, however, that the polypeptides having the above corresponding amino acid sequences constitute only examples of the polypeptides of the present invention. The polypeptides essentially comprising the same amino acid sequences also belong to the scope of the present invention. Thus, the boundaries of each domain are not limited to those defined in the Examples. And the polypeptides comprising the domains wherein the boundaries are shifted to N-, C-terminals or both by 1 to about 20 amino acids from the boundaries defined in the Examples are contained in the polypeptides of the present invention, as long as they have substantially the same function as that of the above polypeptides. Similarly, the polypeptides wherein a part of the amino acid sequences has changed due to deletion, substitution, addition, insertion and the like of amino acids are therefore contained in the polypeptides of the present invention, as long as they have substantially the same function as that of each domain.

As it is considered that the polypeptides comprising such amino acid sequences as showing homology of about 80% or more, preferably about 90% or more to the amino acid sequences in each domain of the above figures may have the same function as that of the polypeptides of the present invention, they are also considered to be contained in the present invention.

Meltrins of the present invention may be used to bond cells to each other or to apparatuses such as a plate. They may be also fused with any other substances to efficiently deliver the substances to muscle cells upon its application into culture systems of the muscle cells, tissues or bodies.

On the other hand, the polypeptides comprising at least a part of Meltrins may be added to the culture systems to competitively inhibit the adhesion, fusion or aggregation of cells. Particularly, the disintegrin domain per se, a part thereof, or a soluble polypeptide comprising the disintegrin domain may be used as an effective ingredient in a medical composition for inhibiting the adhesion of cells. For example, such medical composition may be used as an anticoagulant to inhibit thrombus formation or blood coagulation, and be used to treat thrombosis, DIC and multi-organ failure. Furthermore, since it is considered that adhesion factors such as integrin family are involved in metastasis of cancer cells, the polypeptides comprising the disintegrin domain may be used as a drug for inhibiting the growth of cancers, or the adhesion of cancer cells to other cells so as to prevent their metastasis. In addition to the above, it is known that the adhesion of cells plays an important role in the formation of osteoclasts. The examples will demonstrate that Meltrins are involved in the adhesion in the formation of osteoclasts, and anti-Meltrin antibodies may inhibit the formation of osteoclasts and the increase of bone resorption Accordingly, the polypeptides of the present invention comprising disintegrin domain of Meltrins, particularly of Meltrins α or β, may be used as an effective ingredient in a medical composition for inhibiting the increase of bone resorption, like as anti-Meltrin antibodies.

Among the polypeptides comprising at least a part of Meltrins of the present invention, those comprising the metalloproteinase domain may act as a protease by itself, or be used to competitively inhibit the activity of other proteases so that they may be utilized as a drug for treating inflammatory diseases.

The polypeptides and Meltrins of the present invention may also be used as antigens for producing antibodies.

The present invention also relates to DNAs comprising the base sequences encoding the amino acid sequences of Meltrins of the present invention or the polypeptides comprising any parts thereof.

The above DNAs include any type of DNAs such as genomic DNAs and cDNAs.

The origin of the present DNAs is not specifically limited. The examples of the present DNAs are those encoding mouse Meltirns α, β, and γ, or the polypeptides comprising any parts thereof, which are characterized by the coding regions shown as the base sequences in FIG. 5a~FIG. 5j, FIG. 6a~FIG. 6h, and FIG. 7a~FIG. 7e, respectively, or partial sequences thereof. Other examples are those encoding human Meltirns α, β, and γ, or the polypeptides comprising any parts thereof, which are characterized by the coding regions of the sequences shown as the base sequences in any one of FIG. 12a~FIG. 12b, FIG. 15a~FIG. 15f or FIG. 23a~FIG. 23b; any one of FIG. 16 or FIG. 17a~FIG. 17c; or FIG. 13a~FIG. 13d, respectively, or partial sequences thereof.

The base sequences in the above figures, which correspond to the precursor domain, metalloproteinase domain, disintegrin domain, cystein-rich domain, intracellular domain, and transmembrane domain of mouse and human Meltrins α, β and γ, are discussed in the Examples. It should be noted, however, that they constitute only examples of the DNAs of the present invention. The DNAs essentially comprising the same base sequences also belong to the scope of the present invention. Thus, the boundaries of each domain are not limited to those defined in the Examples. And the DNAs comprising sequences encoding the domains wherein the boundaries are shifted to 5'-, and/or 3'-ends by 1 to about 60 base pairs from the boundaries defined in the Examples are contained in the DNAs of the present invention, as long as they encode the polypeptides having substantially the same function as that of each domain.

In addition of the above base sequences, the present DNAs include those comprising the base sequences or partial sequences thereof, which encode the same amino acid sequences as above prepared by means of chemical synthesis or genetic engineering in consideration of degeneracy of codons.

As cleared now by the present inventors, a high homology is seen in mouse and human Meltrins. It is therefore considered that the substances showing homology of about 80% or more, preferably about 90% or more to the above amino acid sequences may keep the function as Meltrin, and that DNAs encoding such homologous polypeptides will hybridize with each other. Accordingly, the present DNAs also include DNA fragments which may be obtained by hybridization under stringent conditions using the DNAs having the base sequences complementary to those in the above figures as a probe.

The DNAs of mouse or human Meltrins α, β and γ, or partial sequences thereof may be inserted into plasmid vectors. Strains of *E. coli* transformed by the same plasmid vectors have been deposited with the National Institute of Bioscience and Human-Technology, Agency of Industrial Science and Technology.

The present DNAs may be prepared by known methods. The cDNAs, for example, may be prepared by using cDNA library and known PCR (e.g., Michael A. I. et al., PCR Protocols, a guide to method and application, Academic Press, 1990) with degenerative primers for a part of the amino acid sequences (for example, the degenerative primer encoding the amino acid sequences of the disintegrin domain) shown in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c and FIG. 23a~FIG. 23b. The present DNAs may also be prepared by hybridization method using a probe prepared on the basis of the base sequences of the above amplified DNA fragments.

As demonstrated in the Examples, the preferable source of cDNA library include cells obtained by inducing myoblast to differentiate, bone marrow and fetal pulmonary cells. Known cDNA libraries prepared from placenta, chorionic cells and fetal cells may also serve as the source of cDNA library in the present invention.

Among the present DNA, one encoding the polypeptide in which any parts of Meltrins are combined in any order may be prepared by the following steps. That is, each DNA fragment encoding any part of Meltrins is amplified by PCR, in which the primers may be optionally modified in order to provide an appropriate restriction enzyme site. The amplified DNA fragments are ligated with each other by DNA ligase, so that a reading frame should not be shifted.

The present DNAs may be used for producing the Meltrins or polypeptides of the present invention by means of genetic engineering. Such production may be carried out with reference to known methods (for example, Sambrook J. et al., Molecular Cloning a Laboratory Manual 2nd ed., Cold Spring Harbor Laboratory, New York, 1989).

The present DNAs inserted into suitable vectors may also be used in gene therapy. The base sequence encoding any physiologically active substances is fused downstream of the present DNAs followed by insertion of the resulting fused DNA into a vector originated in an appropriate virus, and cells in a living body are transformed with the resulting vector, so that the physiologically active substances may be expressed as a fused protein with Meltrins of the present invention. The thus expressed physiologically active substances will be delivered near to the cells to which Meltrins adhere.

The present invention further relates to antisense oligonucleotides and derivatives thereof for the DNAs encoding Meltrins of the present invention or for the polypeptides comprising any part thereof.

The present antisense oligonucleotides and derivatives thereof are characterized by their base sequences complementary to those encoding Meltrins or a part thereof, or by their function to inhibit the expression of Meltrins or the polypeptides comprising any part thereof. The antisense oligonucleotides and derivatives thereof characterized by the latter feature include those complementarily bonding to the non-coding regions existing upstream or downstream of the coding regions of Meltrins as well as those complementarily bonding to the coding regions of Meltrins or any part thereof.

The examples of the present antisense oligonucleotides and derivatives thereof include the base sequences complementary to the DNAs of the present invention or any part thereof, particularly to those shown in FIG. 5a~FIG. 5j, FIG. 6a~FIG. 6h, FIG. 7a~FIG. 7e, FIG. 12aFIG. 12b, FIG. 13a~FIG. 13d, FIG. 15a~FIG. 15f, FIG. 16, FIG. 17a~FIG. 17c and FIG. 23a~FIG. 23b. Uracil (U) may be used instead of thymine (T) as a complementary base to adenine (A).

The derivatives of the present antisense oligonucleotides include any one that is similar to the antisense oligonucleotides in steric structure and function, such as those wherein other substances are bound to 3'- or 5'-end of the oligonucleotides; those wherein at least one of bases, sugars or phosphoric acids in the oligonucleotides has substitution or modification; those having non-naturally occurring bases, sugars or phosphoric acids; and those having back bone other than that of sugars-phosphoric acids.

The present antisense oligonucleotides and derivatives thereof may be prepared by known methods (for example, ed., Stanley T. Crooke and Bernald Lebleu, in Antisense Research and Applications, CRC Publishing, Florida, 1993).

The present antisense oligonucleotides of a naturally occurring type may be prepared by chemically synthesizing sense-primers and antisense-primsers having the base sequences complementary to 3'- or 5'-end of the antisense oligonucleotide sequences, followed by PCR using the Meltrin genes or RNAs encoding Meltrins as a template. Otherwise, the derivatives of the antisense oligonucleotides such as a methylphosphonate and phosphorothionate types may be prepared by means of a chemical synthesizer (e.g., Perkin Elmer Japan Co., Type 394) according to the manual attached to the chemical synthesizer, followed by, if necessary, purification of the synthesized products in HPLC method using reversed phase chromatography and the like.

The present antisense oligonucleotides and derivatives thereof may be labelled with radioisotopes, fluorescent substances, enzymes or luminescent substances and used as a probe for detecting the existence of Meltrins or any part thereof in a sample. The present antisense oligonucleotides may also be used as a medical composition for inhibiting the expression of Meltrins in a living body.

For the purpose of inhibiting the expression of Meltrins by using the present antisense oligonucleotides and derivatives, they may be solubilized or suspended in a suitable solvent, enclosed in a liposome, or inserted into a suitable vector.

It is preferred that the present antisense oligonucleotides and derivatives thereof used in the medical composition should have a pharmaceutically acceptable purity and be used in a pharmaceutically acceptable way.

As already mentioned in the above, it is considered that Meltrins are involved in formation of osteoclasts, growth and metastasis of cancers as well as skeletal myogenesis. Accordingly, the present antisense oligonucleotides and their derivatives which are capable of inhibiting the expression of Meltrins may be used in treatment and prevention of cancers, treatment of osteoporosis and hypercalcemia by inhibiting bone resorption.

The present invention also relates to antibodies recognizing Meltrins of the present invention or the polypeptides comprising at least any part thereof. In other words, they include those recognizing only Meltrins of the present invention, those recognizing only the polypeptides of the present invention and those recognizing both of them.

The present antibodies include those cross reacting with other polypeptides in addition to those specifically recognizing Meltrins and the polypeptides of the present invention. They also include those specifically recognizing any one of Meltrins α, β and γ, and those specifically recognizing more than two of Meltrins α, β and γ, as well as those recognizing only Meltrins originated in a particular animal such as human and mouse or only the polypeptides comprising at least any part thereof, and those recognizing Meltrins originated in more than two kinds of animals or the polypeptides comprising at least any part thereof.

The preferable present antibodies are those recognizing the amino acid sequences in FIG. 2a~FIG. 2j, FIG. 3a~FIG. 3j, FIG. 4a~FIG. 4i, FIG. 12a~FIG. 12b, FIG. 13a~FIG. 13d, FIG. 15a~FIG. 15f, FIG. 16, FIG. 17a~FIG. 17c or FIG. 23a~FIG. 23b, or any part thereof.

More preferably, the present antibodies are those obtained by immunization of animals with the polypeptides comprising said amino acid sequences or any part thereof as an antigen, which may be optionally conjugated with a suitable carrier.

Such preferred antibodies may be prepared by inserting DNA comprising the base sequences shown in FIG. 5a~FIG. 5j, FIG. 6a~FIG. 6h, FIG. 7a~FIG. 7e, FIG. 12a~FIG. 12b, FIG. 13a~FIG. 13d, FIG. 15a~FIG. 15f, FIG. 16, FIG. 17a~FIG. 17c or FIG. 23a~FIG. 23b or any part thereof into a suitable expression vector, transforming a suitable host cell by the vector to produce Meltrins, which are purified from cell bodies of the transformant or culture medium and administered as an antigen. The cell bodies per se of the transformant or any cells expressing Meltrins per se may be administered as an antigen. Such transformant or cells may express any one of Meltrins α, β and γ, or more than two kinds of them. The present antibodies may be also prepared by chemically synthesizing the polypeptides having a part of the amino acid sequences of Meltrins, conjugating them with a carrier such as KLH (Keyhole Limpet Hemocyanin) and administering them as an antigen.

It is possible to prepare the present antibody that may recognize the whole of Meltrins even when the part of Meltrins is used as an antigen to be administered. It is also possible to prepare the present antibody that may recognize human Meltrins or any part thereof even when mouse Meltrins or any part thereof are used as an antigen to administered.

The antibodies of the present invention include monoclonal and polyclonal ones, and may belong to any class or subclass.

The antibodies of the present invention may be prepared according to known methods (e.g., "Meneki jikkenho (Laboratory manual of Immunology)" published by Japan Immunological Society). An example of the known methods will be described below.

A suitable cell is transformed by an expression vector comprising the coding regions of the base sequences shown in FIG. 5a~FIG. 5j, FIG. 6a~FIG. 6h, FIG. 7a~FIG. 7e, FIG. 12a~FIG. 12b, FIG. 13a~FIG. 13d, FIG. 15a~FIG. 15f, FIG. 16, FIG. 17a~FIG. 17c or FIG. 23a~FIG. 23b or any part thereof, and used as an antigen as such. Alternatively, Meltrins produced by the transformant are purified from cell bodies of the transformant or culture medium to be used as an antigen, or polypeptides consisting of amino acid sequences shown in the above figures are chemically synthesized, cojugated with a carrier such as KLH (Keyhole Limpet Hemocyanin) and purified to be used as an antigen.

Animals are inoculated with the antigen thus prepared, alone or together with a suitable adjuvant such as Freund's complete adjuvant (FCA) or Freund's incomplete adjuvant (FIA), subjected to boosting at two to four-week intervals. After boosting, the blood is drawn from the animals and antiserum is obtained therefrom. Animals to be immunized may be selected from rat, mouse, rabbit, sheep, horse, fowl, goat, pig, cattle and the like, depending on the kind of the antibody to be desired. Polyclonal antibodies may be obtained by purification of the antiserum by known methods such as salting-out, ion-exchange chromatography, affinity chromatography and any combination thereof.

Monoclonal antibodies may be prepared as follows. Antibody-producing cells such as spleen cells and lymphocytes are collected from the immunized animals, fused with myeloma and the like by known methods using polyethyleneglycol, Sendai virus, electrical pulse to give hybridomas. Clones which produce the antibodies bonding to Meltrins of the present invention are then selected and cultured. Monoclonal antibodies of the present invention are purified from the culture supernatant of the selected clones by known methods such as salting-out, ion-exchange chromatography, affinity chromatography and any combination thereof.

The present antibodies may be neutralizing antibodies, which inhibit the fusion, adhesion or aggregation of cells by Meltrins. The neutralizing antibodies of the present invention include those that can completely inhibit the activity of Meltrins, and those partially inhibit the same.

The neutralizing antibodies may be screened by adding antiserum or culture supernatant of the hybridomas to the culture system of Meltrin-expressing cells to evaluate the degree of inhibition of fusion or aggregation of cells. After the screening, the desired antibodies may be purified from the thus selected antiserum or culture supernatant of the hybridomas by the known methods.

The antibodies of the present invention include Fab, F(ab'), F(ab')$_2$ and Fv, as long as they recognize and bond to the present polypeptides or any part thereof. A single chain Fv may be also included in the present antibodies, which is obtained by constructing a gene encoding the single chain Fv wherein H and L chains are linked into a single chain and being expressed by a suitable host cell. Chimera antibodies, human antibodies and humanized antibodies are also included in the present invention, as long as they recognize and bond to the present polypeptides or any part thereof.

For example, the chimera antibodies may be prepared by substituting a gene encoding the constant region of human antibodies for a gene encoding the constant region of the mouse antibodies recognizing Meltrins or the polypeptides of the present invention, expressing the thus reconstituted gene in animal cells. The human antibodies may be prepared by, for example, in vitro sensitization method (Borrebaeck, C. A. K. J. Immunol., Meth., 123, 157, 1989) or the method using SCID mouse (Toshio KUDO, Tissue Culture, 19, 61-65, 1993). The humanized antibodies may be prepared by reconstituting a gene so that complementary determining regions (CDR) of the human antibodies are replaced with those of the mouse antibodies, and expressing the gene in animal cells (Carter et al., Pro. Nat. Acad. Sci, 89, 4285, 1992).

If necessary, amino acids in a framework of the variable region of the humanized antibodies thus reconstituted may be replaced, so that the framework should have a high homology to that of the mouse antibodies and CDR of said humanized antibodies may form an appropriate antigen-binding site. The preferred examples of the humanized antibodies are those having the same CDR as the neutralizing antibodies F932-15-2 and F937-9-2. For the preparation of these preferred humanized antibodies, the DNA encoding the antibodies is prepared from the hyridoma F932-15-2 or F937-9-2, and linked with the DNAs encoding human antibodies so that the sequences other than CDRs should originate in the human antibodies. Any variation may be optionally introduced into the DNA encoding the framework portion. The thus obtained DNA is then inserted into a suitable expression vector to transform a suitable cell, and the humanized antibodies are purified from the culture supernatant of the transformant.

The present antibodies may be labelled with fluorescent substances, enzymes, luminescent substances or radioisotopes to detect Meltrins or their decomposed products present in body fluid or tissues. Since it is considered that Meltrins are involved in formation of myotubes, resorption of bone and metastasis of cancers as already mentioned in the above, the detection of the existence of Meltrins in body fluid or tissues would make it possible to estimate the progress of diseases and prognosis and to confirm the effects of treatments. The present antibodies may be also used to provide an antibody affinity column, or to detect Meltrins in a fraction during the course of purification of Meltrins.

The neutralizing antibodies of the present invention may serve as an effective ingredient of a medical composition for inhibiting bone resorption, inflammatory diseases, blood coagulation and metastasis of cancers, owing to their ability to inhibit fusion or adhesion of cells. They may serve as an agent used in culture to inhibit the aggregation of cultured cells. When used as the effective ingredient of the medical composition, the human or humanized antibodies are preferred from the viewpoint of their antigenicity.

Also, the present invention relates to a vector comprising the DNA of the present invention. The present vector may further contain, if necessary, an enhancer sequence, promoter sequence, ribosome-binding sequence, base sequence for amplification of the number of copies, sequence encoding signal peptides, sequences encoding other polypeptides, poly (A)-additional sequence, splicing sequence, origin of replication, base sequence of the gene for selective markers and so on.

The present vector may be prepared by inserting the DNAs of the present invention into any vectors according to known methods (e.g., Molecular Cloning, a Laboratory Manual 2nd ed., Cold Spring Harbor Laboratory, New York, 1989). The preferable examples of the DNAs encoding Meltrins or any part thereof have been already disclosed in the present specification. The present vectors include a plasmid vector, phage vector and virus vector; pUC118, pBR322, pSV2-dhfr, pBluescriptII, PHIL-S1, λZap II, λgt10, pAc700, YRP17, pEF-BOS and pEFN-II being preferred.

The preferred vectors of the present invention may optionally comprise the origin of replication, selective markers, and promoter in addition to the DNAs encoding Meltrins or the polypeptides comprising at least any part thereof so as to be used to express Meltrins or the same polypeptides. As the origin of replication, ColE1, R factor, F factor and so on may be used in the vectors for $E.$ $coli$; SV40- or adenovirus-derived ones in the vectors for animal cells; and ARS1-derived one in the vectors for yeast. As the promoter, trp, lac and tac promoters may be used in the vectors for $E.$ $coli$; SV40-, cytomegalovirus-, and adenovirus-derived ones, and those intrinsically existing in the genes of human or animals such as the promoter region of an elongation factor 1α in the vectors for animal cells; and α promoter in the vectors for yeast, especially AOX1 promoter in the case of $Pichia$ yeast. In the addition to the above sequences, the present vectors may further comprise, if necessary, RNA splicing site, signal for poly-adenylation and the like for the transformation of eucaryotic cells. The present vectors may be used for the production of Meltrins or any part thereof by means of genetic engineering, and used in gene therapy for Meltrins-related diseases.

The present invention therefore relates to transformants transformed by the above vectors.

The present transformants may be prepared by transforming suitable host cells by the above vectors according to known methods (e.g., Idenshi Kogaku Handbook (Handbook of gene technology), extra edition of Jikkenigaku, Yodo, 1991)). The host cells may be selected from procaryotic ones such as $E.$ $coli$ and $Bacillus$, or eucaryotic cells such as yeast, insect cells, and animal ones. The preferred transformants of the present invention are those derived from $E.$ $coli$, yeast or CHO cell as a host cell to express Meltrins or the polypeptides of the present invention.

The present invention further relates to a process for producing Meltrins or the present polypeptides comprising at least any part thereof, comprising the step of culturing the above transformants.

In the present producing process, the transformants of the present invention are cultured, optionally with amplification of the gene or expression-induction, if necessary, according to known methods (e.g., Biseibutsugaku Jikkenho (Laboratory manual of microbiology), Tokyo Kagaku Dojin, 1992). The culture mixture, i.e., the cells and culture supernatant, is collected and optionally subjected to concentration, solubilization, dialysis, and various chromatography to purify Meltrins or the present polypeptides comprising any part thereof. The purification of the present polypeptides may be carried out by an optional combination of the above known methods for the purification of proteins, and an efficient purification could be performed by using an affinity column with the antibodies of the present invention.

In the present producing process, the polypeptides of the present invention may be produced by the transformants as a fused protein with other proteins such as β-galactosidase. In such case, the fused protein should be treated with chemicals such as cyanogen bromide or enzymes such as protease in a certain step in the purification process, so that the polypeptides of the present invention may be excised.

The present invention relates to medical compositions comprising a novel effective ingredient, which is Meltrins of the present invention or Meltrin-antagonist. The "Meltrin-antagonist" means a molecule which is able to inhibit fusion, adhesion or aggregation of cells through Meltrins. It includes, for example, the present antibodies recognizing Meltrins and having a neutralizing activity, the fragments of the same antibodies, the polypeptides consisting of any part of Meltrins or any combination thereof in any order, the antisense oligonucleotides for the DNAs encoding Meltrins or derivatives thereof.

The antibodies recognizing Meltrins may be prepared by the methods already mentioned in the above, and from which the antibodies which may completely or partially neutralize fusion, adhesion or aggregation of muscle cells, osteoclasts or cancer cells are selected and used as the effective ingredient of the present medical compositions. The antibodies to be used as the effective ingredient include those prepared by administering any polypeptides as the antigen into any animals, as long as they may recognize human Meltrins and inhibit fusion, adhesion or aggregation of human muscle cells, osteoclast or cancer cells. They may be polyclonal or monoclonal ones, being preferably the human or humanized antibodies, considering the fact that the medical compositions will be administered to human. The human or humanized antibodies may be prepared according to the methods already described in the above.

The above fragments to be used as the effective ingredient in the present medical compositions include Fab, F(ab'), F(ab')$_2$ and Fv.

The polypeptides having any part of Meltrins or any combination thereof in any order may be used as the effective ingredient of the medical compositions, as long as they have the activity of inhibiting fusion, adhesion or aggregation of cells.

The preferable examples of the above polypeptides include those comprising a part or the whole of the disintegrin domain of Meltrins, those comprising the metalloproteinase, disintegrin and cysteine-rich regions of Meltrins, those comprising the disintegrin domain, but not comprising the transmembrane domain of Meltrins, and those comprising at least the metalloproteinase and disintegrin domains, but not comprising the transmembrane domain of Meltrins. These polypeptides may be chemically synthesized or produced by means of genetic engineering, as already mentioned in the above.

The antisense oligonucleotides or derivatives thereof to be used as the effective ingredient of the medical compositions may have any base sequences or any structure, as long as they are suitable for administration to human, and will complementarily bond to the gene for Meltrins to completely or partially inhibit their expression.

As already mentioned, Meltrins are involved in formation of osteoclasts and metastasis of cancer cells. Accordingly, the medical comosition comprising the Meltrin-antagonist as the effective ingredient may be used for the purpose of inhibition of bone resorption or metastasis of cancers. The antagonist against human Meltrin α or β is more preferably used as the effective ingredient in the medical composition for inhibition of bone resorption, while the antagonist against human Meltrin γ is more preferably used as the effective ingredient in the medical composition for inhibition of cancer metastasis.

The Meltrins or Meltrin antagonist used as the effective ingredient in the present medical composition may be formed into their salts or be modified with pharmaceutically acceptable chemical agents, as long as they will never lose their essential activities. There may be exemplified as the salts those with inorganic acids such as hydrochloric acid, phosphoric acid, hydrobromic acid and sulfuric acid; those with organic acids such as maleic acid, succinic acid, malic acid and tartaric acid.

The medical compositions of the present invention include those administered by any route such as oral, subcutaneous, intravenous, intramuscular, intraperitoneal, intracutaneous, and intraintestinal ones.

Any administration methods and intervals may be adopted. The present medical compositions may comprise, depending on the administration route, pharmaceutically acceptable auxiliaries such as fillers, packing agents, thickeners, binding agents, humidifying agents, disintegrating agents, surfactants, solution aids, buffers, pain-easing agents, preservatives and stabilizers. In the case of injections, for example, they may comprise stabilizers such as gelatin, human serum albumin (HSA) and polyethylene glycol; alcohols and saccharides such as D-mannitol, D-sorbitol, and glucose; and surfactants such as Polysorbate 80™.

The medical compositions of the present invention may be mainly used for the prevention and treatment of osteoporosis and hypercalcemia, or the prevention of infiltration and metastasis of cancers.

The present medical compositions may be administered in an amount of about 0.1~100 mg/kg/day, preferably of about 1~50 mg/kg/day, more preferably of about 1~10 mg/kg/day, depending on the conditions or ages of patients, or administration routes. It may also be continuously administered by an intravenous drip, or administered by a single dose or doses at appropriate intervals per day.

The present medical compositions may be formulated according to the conventional manners. The injection, for example, may be formulated by dissolving the Meltrins or their antagonists aseptically prepared to a pharmaceutically acceptable purity into physiological saline, buffers and the like, followed by addition of gelatin or HSA, if necessary. Such injections may also be lyophilized, which will be dissolved into distilled water for the injections, physiological saline and the like when they are used.

The screening of the substances which may bind to Meltrins, inhibit the activity of Meltrins or regulate their expression may be carried out by using the Meltrins, various polypeptides, DNAs encoding them and the like.

BRIEF DESCRIPTION OF THE DRAWINGS

FIG. 1a~FIG. 1b show the comparison between parts of mouse Meltrins α, β, γ (referred to as "Mα", "Mβ", "Mγ") (SEQ ID NOS: 2, 4(residues 429-578), and 6 (residues 426-575), respectively) and the known sequences (macrophage specific antigen (MS2), Jararhagin (JR), fertilin-α (fα) (SEQ ID NOS: 45, 46, and 47, respectively).

FIG. 2a~FIG. 2j show the amino acid sequence (SEQ ID NO. 2) of mouse Meltrin α and its corresponding DNA sequence (SEQ ID NO: 1).

FIG. 3a~FIG. 3j show the amino acid sequence (SEQ ID NO: 4) of mouse Meltrin β and its corresponding DNA sequence (SEQ ID NO: 3), wherein "N" means unidentified base.

FIG. 4a~FIG. 4i show the amino acid sequence (SEQ ID NO: 6) of mouse Meltrin γ and its corresponding DNA sequence (SEQ ID NO: 5). "N" means unidentified base.

FIG. 5a~FIG. 5j show the result of DNA sequence analysis of the DNA inserted into pBSMelα, which comprises the base sequence encoding mouse Meltrin α(SEQ ID NO: 1). "N", "M", "W" and "S" mean unidentified bases.

FIG. 6a~FIG. 6h show the result of DNA sequence analysis of the DNA inserted into pBSMelβ, which comprises the base sequence encoding mouse Meltrin β(SEQ ID NO: 3). "N", "M", "W" and "S" mean unidentified bases.

FIG. 7a~FIG. 7e show the result of DNA sequence analysis of the DNA inserted into pBSMelγ, which comprises the base sequence encoding mouse Meltrin γ(SEQ ID NO: 5). "N", "M", "W" and "S" mean unidentified bases.

FIG. 12a~FIG. 12b show the result of base sequence analysis of the DNA inserted into pBShuMα300, which encodes human Meltrin α(SEQ ID NO: 7 and 8). "N" and "X" mean unidentified bases and unidentified amino acids, respectively.

FIG. 13a~FIG. 13d show the result of base sequence analysis of the DNA inserted into pBShuMγG238, which encodes human Meltrin γ(SEQ ID NO: 9 and 10).

FIG. 15a~FIG. 15f show partial amino acid sequence (SEQ ID NO: 12) and its corresponding base sequence (SEQ ID NO: 11) of human Meltrin α, determined based on the result of analysis of the DNA inserted into pMelα-26N, pMelα-25C.

FIG. 16 shows amino acid sequence (SEQ ID NO: 14) and its corresponding base sequence (SEQ ID NO: 13) of human Meltrin β.

FIG. 17a~FIG. 17c show partial amino acid sequence (SEQ ID NO: 16) and its corresponding base sequence (SEQ ID NO: 15) of human Meltrin β, determined based on the result of analysis of the DNA inserted into pMelβ-24C, pMelβ-24N.

FIG. 18a shows schematically the sites of the peptides administered as the antigens in mouse Meltrin α.

FIG. 18b shows amino acid sequences of the peptides administered (SEQ ID NOS: 48-55). as the antigens.

FIG. 23a~FIG. 23b show the amino acid sequence (SEQ ID NO: 18) comprising the transmembrane domain of human Meltrin α and its corresponding base sequence (SEQ ID NO: 17).

FIG. 24a~FIG. 24e show the result of base sequence analysis of the DNA inserted into pMelβ-24C, pMelβ-24N (SEQ ID NOS: 19 and 20).

BEST MODE FOR CARRYING OUT THE INVENTION

Figure 8:
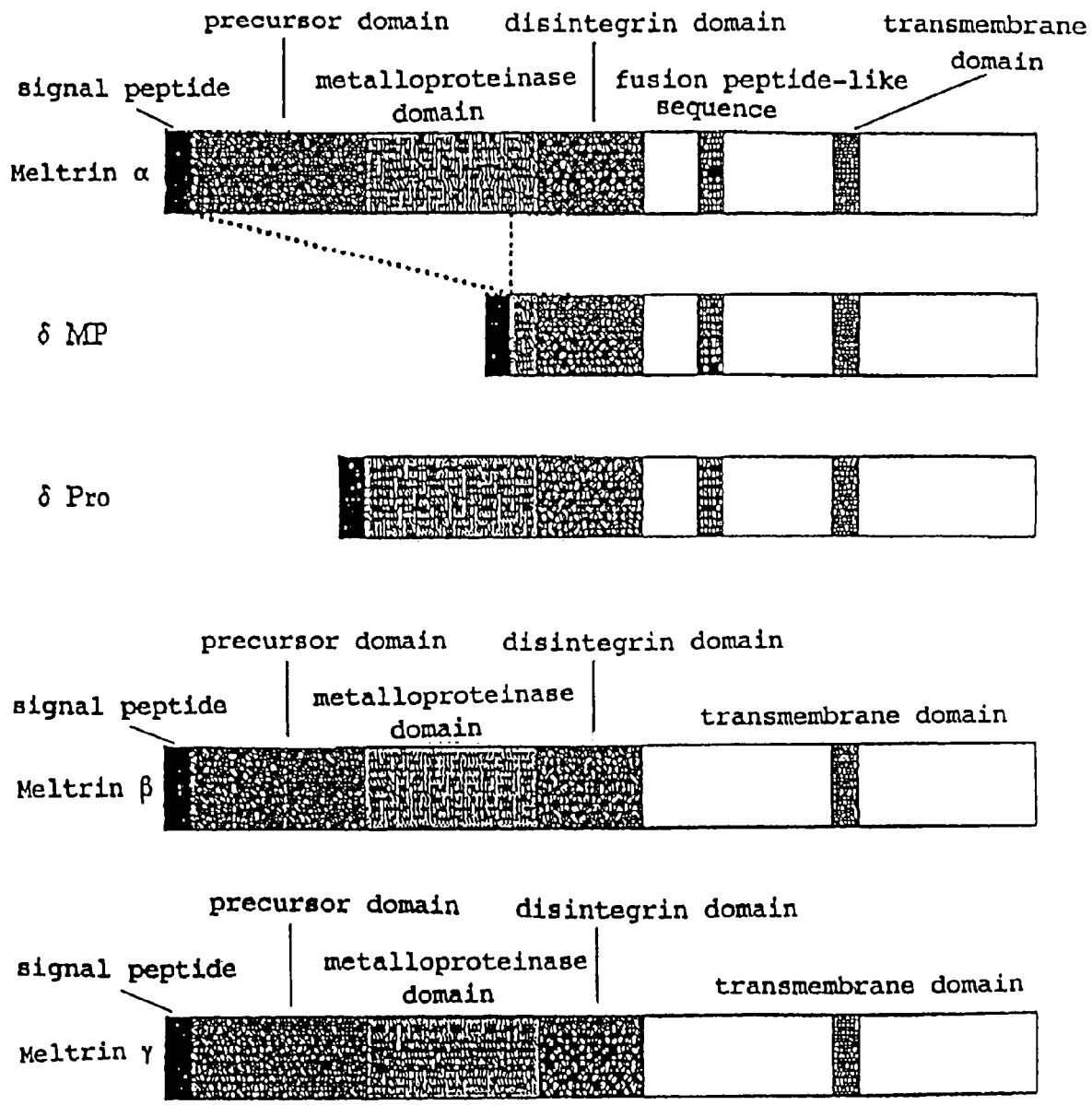
FIG. 8 shows schematically the structures of Meltrins α, β, γ δMP, δPro.

The present invention will be further illustrated by the following Examples, which should not be construed to limit the scope of the present invention.

EXAMPLES

The abbreviations used in the following description are based on the conventional ones in the art.

The processes used in the following Examples are based on Sambrook J. et al., Molecular Cloning, a Laboratory Manual 2nd ed., Cold Spring Harbor Laboratory, New York, 1989; E. Harlow, D. Lane et al., Antibodies, A Laboratory Manual, Cold Spring Harbor Laboratory; and the like.

Example 1

Acquisition of the DNAs Encoding Mouse Meltrins by RT-PCR (1) Preparation of RNA, cDNA A myogenic cell line derived from fetal fibroblast C3H10T1/2, (a clone transfected by the gene encoding "myogenin", a muscle differentiation-controlling factor and expressing the myogenin) was proliferated to the extent of $10^6$ cells/φ 10 cm plate in DMEM supplemented with 10% fetal bovine serum (Moregate), and cultured at 37° C. for 2 days in differentiation medium (DMEM containing 2% horse serum from GIBCO) for differentiation and induction. Total RNA was separated according to the Guanidine isothiocyanate/acid phenol method (Chomczynski P. and Sacchi N., Anal. Biochem., 162, 156-159, 1987), and poly (A) RNA was selectively separated by repeating twice oligo(dT)-cellulose column chromatography. By using the poly(A) RNA as a template and random primers (N6, Pharmacia), cDNAs were synthesized with MLV reverse transcriptase (GIBCO BRL) according to its manual for synthesis. The obtained cDNAs were then used as a template for the next PCR, and double strand DNAs were synthesized and inserted into a phage (λzapII(stratagene)) to give a cDNA library.

(2) RT-PCR

RT-PCR was carried out by using the cDNAs prepared in the above (1) as a template in the following steps:

A degenerative primer encoding the amino acid sequence EDCDCG (SEQ ID NO: 40) or EECDCG (SEQ ID NO: 41) was synthesized and used as a sense primer, and a degenerative primer encoding the amino acid sequence KCGKLIC (SEQ ID NO: 42) was synthesized and used as an antisense primer.

The primers were mixed with the above cDNAs, Taq polymerase and the reaction agents (Boehringer Manheim), and subjected to 36 reaction cycles of 95° C. for 1 min, 55° C. for 2 min, and 72° C. for 3 min. The amplification product of around 450 bp was then collected by 1.5% agarose gel electrophoresis.

Figure 1A:
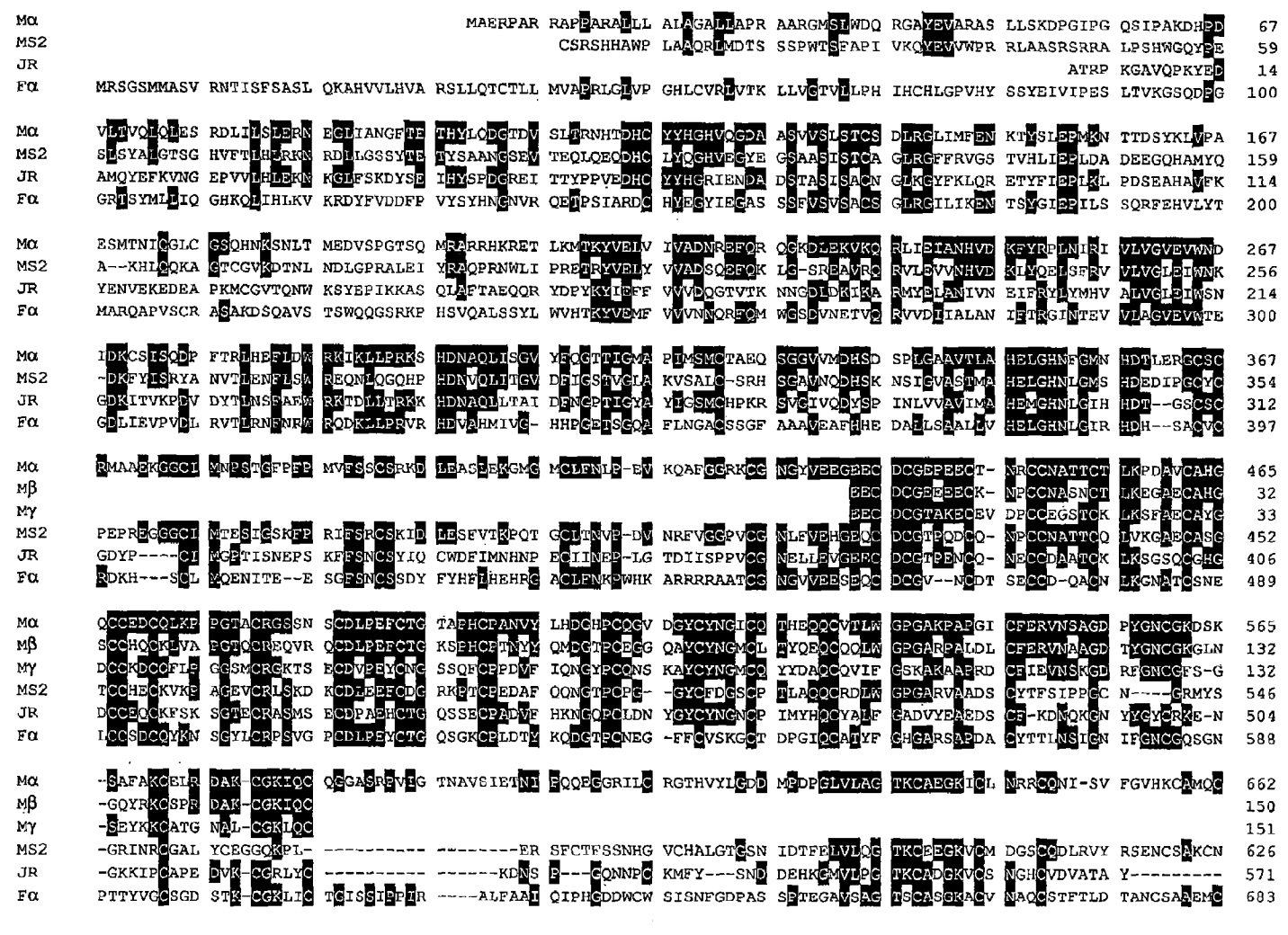

The amplified fragments thus obtained were inserted into a SmaI site in the plasmid pBS-SKII(−) (stratagene), and subjected to DNA sequence analysis by means of a DNA sequencer (370A type, Applied Biosystems). As a result, it was found that three kinds of molecules (DNA fragments) existed (FIG. 1), which were then used as a probe to screen the cDNA library so as to isolate cDNAs comprising an open reading frame with 903, 920 and 845 amino acid residues, respectively (FIG. 2a~FIG. 2j, FIG. 3a~FIG. 3j, FIG. 4a~FIG. 4i). The products of the respective genes were named Meltrins α, β, and γ (FIG. 5a~FIG. 5j, FIG. 6a~FIG. 6h, FIG. 7a~FIG. 7e). These cDNAs were inserted into pBS-SKII(−) to give the plasmids, "pBSMelα", "pBSMelβ", and "pBSMelγ", respectively.

E. coli strain JM109 was transformed according to a known method by the above plasmids "pBSMelα", "pBSMelβ", and "pBSMelγ", respectively, and the resulting transformants "JM109(pBSMelα)", "JM109(pBSMelβ)", and "JM109(pBSMelγ)" were deposited in the National Institute of Bioscience and Human-Technology, Agency of Industrial Science and Technology (1-3, Higashi 1-chome, Tsukuba-shi, Ibaraki-ken 350 Japan) on Feb. 19, 1996 under accession numbers FERM P-15451, FERM P-15452, and FERM P-15453, respectively, and then transferred on Oct. 8, 1996 to the deposit under the terms of the Budapest Treaty on the International Recognition of the Deposit of Microorganisms for the Purposes of Patent Procedure and Regulation under accession numbers FERM BP-5701, FERM BP-5702, and FERM BP-5703, respectively.

(3) Analysis of the Structure of Meltrins

From the structure analysis of Meltrins on the basis of the DNA sequences determined in the above (2), it was supposed that Meltrins α, β, and γ were a transmembrane-type protein consisting of an extracellular domain, transmembrane (TM) domain, and intracellular domain, and that the extracellular domain consists of a precursor domain (pro region) comprising a signal peptide-like sequence, metalloproteinase domain, disintegrin domain, and the following cysteine-rich region. A fusion peptide-like sequence was contained in the cysteine-rich domain of Meltrin α (FIG. 8).

Based on their homology to the snake venom, Jararhagin, it has been considered that in Meltrin α, the precursor domain corresponded to the sequence from N-terminal to Arg (No. 205) and to the bases No. 221-835, the metalloproteinase domain to the sequence from Glu (No. 206) to Pro (No. 414) and to the bases No. 836-1462, the disintegrin domain to the sequence from Phe (No. 420) to Gly (No. 509) and to the bases No. 1478-1747, the cysteine-rich region to the sequence from His (No. 510) to Gly (No. 706) and to the bases No. 1748-2338, the fusion peptide-like sequence to the sequence from Gly (No. 585) to Glu (No. 607) and to the bases No. 1973-2041, the transmembrane domain to the sequence from Leu (No. 707) to Leu (No. 727) and to the bases No. 2339-2401.

Similarly, it was considered that in Meltrin β, the precursor domain corresponded to the sequence from N-terminal to Arg (No. 204) and to the bases No. 63-674, the metalloproteinase domain to the sequence from Glu (No. 205) to Pro (No. 409) and to the bases No. 675-1289, the disintegrin domain to the sequence from Tyr (No. 415) to Gly (No. 504) and to the bases No. 1305-1574, the cysteine-rich region to the sequence from Thr (No. 505) to Pro (No. 706) and to the bases No. 1575-2180, the transmembrane domain to the sequence from Val (No. 707) to Arg (No. 729) or to Leu (No. 724) and to the bases No. 2181-2249 or 2181-2234.

Similarly, it was considered that in Meltrin γ, the precursor domain corresponded to the sequence from N-terminal to Arg (No. 205) and to the bases No. 69-683, the metalloproteinase domain to the sequence from Ala (No. 206) to Pro (No. 406) and to the bases No. 684-1292, the disintegrin domain to the sequence from Tyr (No. 412) to Gly (No. 502) and to the bases No. 1302-1574, the cysteine-rich region to the sequence from Tyr (No. 503) to Ala (No. 694) and to the bases No. 1575-2150, the transmembrane domain to the sequence from Leu (No. 695) to Ile (No. 714) and to the bases No. 2151-2210.

Example 2

Establishment of Anti-Meltrin α Antibodies (1) Preparation of Immunogen

A chimera polypeptide was prepared as follows, which consisted of glutathione-S-transferase (GST) (Smith, D. B. & Johnson, K. S., Gene, Vol. 67, 31-40, 1988) and the polypeptide having the amino acid sequence from Ser (No. 483) to Lys (No. 635) of Meltrin α in FIG. 2a~FIG. 2j, said polypeptide being attached to the C-terminal of GST. First, the plasmid, pGEX2T (Pharmacia) comprising the cDNA encoding GST was digested at a BamHI site and used as a vector. On the other hand, the cDNA corresponding to the amino acid sequence from Ser (No. 483) to Lys (No. 635) of Meltrin α in FIG. 2a~FIG. 2j was amplified from pBSMelα by PCR, and ligated with a BamHI linker by a DNA ligase. The resulting cDNA was then ligated with the above vector by a DNA ligase to give a plasmid, which was then transformed into E. coli strain NM522.

The transformed E. coli was cultured in L-broth with 1 mM IPTG to produce a large amount of the chimera polypeptide in the inclusion bodies upon expression-induction. The strain was suspended into MTPBS (150 mM NaCl, 16 mM $Na_2HPO_4$, 4 mM $NaH_2PO_4$, 0.1 mM PMSF), subjected to ultrasonication, and solubilized with 1% Triton. The supernatant of the thus treated mixture was collected. Glutathione agarose (Sigma) was mixed with the supernatant to adsorb the chimera polypeptide which was then eluted with an elution buffer (50 mM Tris-HCl, pH 8.0, 0.5 mM glutathione) and used as an immunogen.

(2) Preparation of Antiserum

The antigen (1 mg) prepared in the above (1) in 0.5 ml PBS and RIBI in PBS 0.5 ml (MPL+TDM+CWS Emulsion, Funakoshi) were mixed with each other, and subcutaneously or intracutaneously administered into a rabbit (12 weeks old, female). After boosting three times with 500%g dose at 4 week intervals, the blood was collected and serum was separated to give antiserum.

(3) Affinity Purification of Antiserum

The chimera polypeptide expressed in E. coli and solubilized in the above (1), or GST having no fused polypeptide was bound to the glutathione agarose beads. The resulting beads were washed with 0.2M sodium borate (pH 9.0), and mixed with dimethyl pimelidiate (a final concentration of 20 mM) so that the antigen was irreversibly bound to the beads, so as to give chimera polypeptide-affinity beads and GST-affinity beads, respectively.

The antiserum diluted ten times with 10 mM Tris-HCl (pH 7.5) was first mixed with the GST-affinity beads for anti-GST antibodies to be absorbed and removed, and then mixed with chimera polypeptide-affinity beads for anti-Meltrin α antibodies to be adsorbed thereon. The resulting chimera polypeptide-affinity beads were washed with 10 mM Tris (pH 7.5) and 500 mM NaCl, and the anti-Meltrin α antibodies were eluted with 100 mM glycine and collected as purified anti-Meltrin α antibodies.

(4) Western blotting

C2 cell was proliferated to the extent of $10^6$ cells/φ 10 cm plate in DMEM supplemented with 15% fetal bovine serum, then cultured at 37° C. in differentiation medium (DMEM supplemented with 2% horse serum) and collected on the second day (C2DM d2) and on the 4th day (C2DM d4).

Further, C2 cell transformed by pBOSMelα(+) prepared in the following Example 5 (3) was cultured in DMEM supplemented with 15% fetal bovine serum at 37° C. for three days, inoculated into a plastic dish (φ 6 cm) at a density of $2×10^5$/dish, further cultured for one day and transferred into the above differentiation medium for differentiation induction. After two day-culture in the differentiation medium, the cells were collected.

The collected C2DM d2, C2DM d4 or transformants by pBOSMelα(+) were mixed with SDS solubilizing buffer (100 mM Tris-HCl (pH 6.8), 4% SDS, 20% Glycerol), subjected to ultrasonication and centrifuged to give their supernatant as a sample. The sample were mixed with an equiamount of a gel loading buffer, supplied to SDS-PAGE, and electrophoresed. After the electrophoresis was finished, the contents were transferred to a membrane.

A membrane was washed twice with a washing solution. The antiserum prepared in the above (3) was diluted 20 times with 5% skim milk solution in TBS-T, into which the membrane was soaked and incubated at 37° C. for one hour. After the incubation, the membrane was washed twice with the washing solution. The membrane was then soaked into a biotin-labelled anti-rabbit immunoglobulin antibody (Daco) diluted 4,000 times with the above skim milk solution and incubated at 37° C. for one hour. After the incubation, the membrane was washed twice with the washing solution. The membrane was reacted with a peroxidase-labelled streptoavidin for one hour, washed twice, and detected by ECL system (Amersham).

Figure 9:
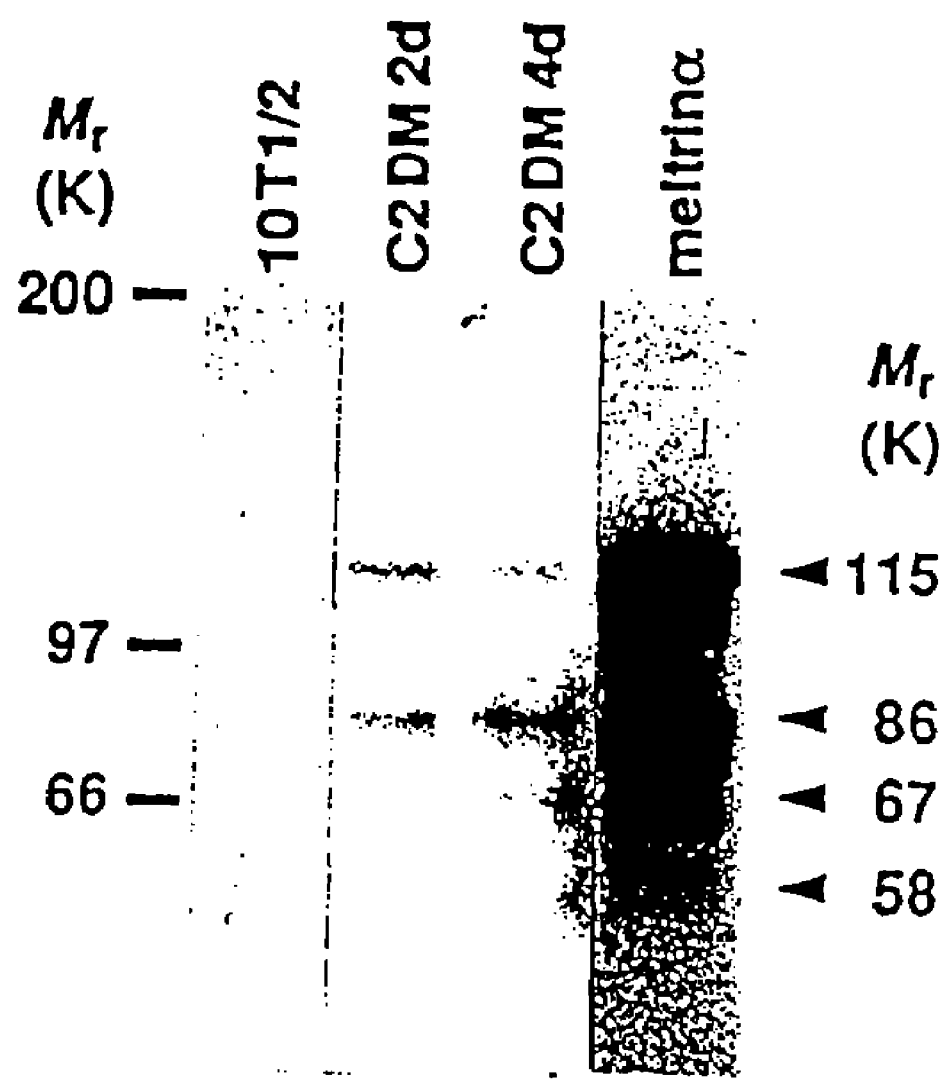
FIG. 9 is a photograph of electrophoresis showing the result of Western blotting.

The results are shown in FIG. 9.

The Western blotting revealed the bands at about 115 KD, 86 KD, 67 KD, and 58 KD, indicating that Meltrin α was expressed as a glycoprotein. It was also considered that the precursor domain was deleted in the molecule of 86 KD, and both the precursor and metalloproteinase domains were deleted in the molecule of 67 KD or 56 KD.

Example 3

Northern Blotting

Poly (A)$^+$ RNAs were prepared from various tissues of mouse (bone, brain, liver, heart and skeletal muscle of adult mouse; bone and skeletal muscle of newborn mouse; and bone and skeletal muscle of fetal mouse) by using a mRNA purification kit of Pharmacia according to the method described in Example 1. RNAs were denatured by heating at 65° C. for 5 min in 50% formamide, subjected to elecrtophoresis on 1.5% agarose gel comprising 6.6% formalin, and transferred onto a nylon membrane (Highbond-N, Amersham).

On the other hand, cDNAs encoding a part of the disintegrin and cysteine-rich regions (Glu(No. 434) Cys(No. 583) in FIG. 2a~FIG. 2j, Clu(No. 429)-Cys(No. 578) in FIG. 3a~FIG. 3j, Clu(No. 426)-Cys(No. 575) in FIG. 4a~FIG. 4i) were prepared by PCR, and labelled with $^{32}$P using a random primer labelling kit (Megaprime, Amersham). As a control probe, cDNA encoding G3PDH (glyceraldehyde 3-phosphate dehydrogenase) was also labelled with $^{32}$P in the same way. The above mRNAs were hybridized with the radiolabelled cDNAs under high stringency conditions according to the method of Sambrook J. et al. (Molecular Cloning: A Laboratory Manual, 2nd ed., Cold Spring Harbor Laboratory, New York, 1989).

Figure 10:
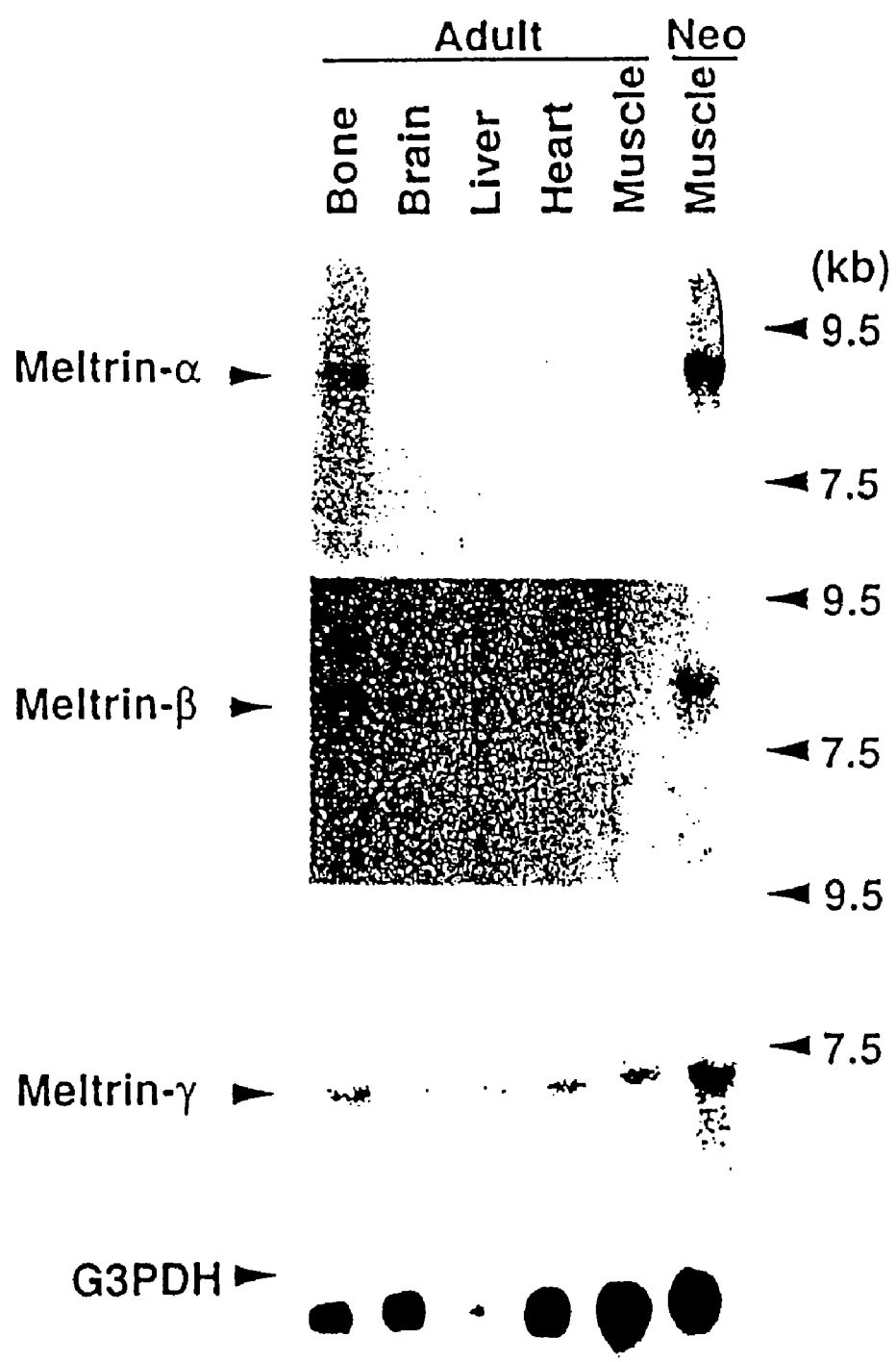
FIG. 10 is a photograph of electrophoresis showing the result of Northern blotting.

Their results are shown in FIG. 10.

FIG. 10 has revealed that Meltrin α and β were expressed only in bones of adult and newborn mice, and skeletal muscles of newborn and fetal mouses (the results from the fetal mouse are not shown in FIG. 10). There was no tissue-specificity in the expression of Meltrin γ, since it was universally expressed in all the tissues.

Example 4

Confirmation of Adhering Activity of Meltrin α

(1) Construction of Plasmids pBOSMelαδMP(+) and pBOSMelαδMP(−)

A deletion type Meltrin δMP wherein the precursor and metalloproteinase domains in the extracelluar domain of Meltrin α had been deleted was prepared in the following method.

The plasmid, pBSMelα was partially digested at MscI and subjected to electrophresis on 1% agarose gel to give a linear plasmid DNA. The resulting DNA was partially digested at NheI, treated with a Klenow fragment to generate blunt ends, and subjected to intramolecular ligation. Vectors having the right deletion were selected and their DNA sequences were confirmed. After digestion at multicloning sites of EcoRV and NotI in the vectors, a deletion type δMP fragment of about 5.8 kb was obtained.

On the other hand, the plasmid, pEFBOS (Mizushima S. & Nagata S, Nucleic Acid Res. Vol. 18, p. 5322, 1990) was digested by a restriction enzyme XbaI, dephosphorylated, treated with a Klenow fragment to generate blunt ends and subjected to electrophoresis on 1% agarose gel to give a linear plasmid DNA. The resulting linear DNA was then ligated with the above fragment of about 5.8 kb by a DNA ligase to give the plasmids pBOSMelαδMP(+) and pBOSMelαδMP(−). They were the constructs comprising the inserted DNA encoding the δMP fragment wherein the amino acid sequence of from Ile(55) to Glu(399) of Meltrin α was deleted, in sense direction and antisense direction, respectively.

(2) Construction of Plasmid pBOSMelα(+)

The plasmid, pBSMelα, was partially digested by EcORV and NotI to give a fragment of about 7 kb. The above pEFBOS plasmid was digested by a restriction enzyme XbaI, dephosphorylated, treated with a Klenow fragment to generate blunt ends, and subjected to electrophoresis on 1% agarose gel to give a linear plasmid DNA. The resulting linear DNA was then ligated with the above fragment of about 7 kb by a DNA ligase to give the plasmids pBOSMelα(+).

(3) Preparation of Plasmid pBOSMelαδPro(+)

There was a AflII site in the boundary region between the precursor and metalloproteinase domains of Meltrin α, and there was a NheI site in the boundary region between metalloproteinase and disintegrin domains of Meltrin α. On the other hand, there remained the NheI site in the boundary region between the signal peptide-like sequence and disintegrin domain in pBOSMelαδMP(+) prepared in the above (1).

Accordingly, pBOSMelα was digested at AflII, ligated with a NheI linker immediately before its metalloproteinase domain and digested at NheI, so that the metalloproteinase would be excised. The excised domain was inserted into the NheI site between the signal peptide-like sequence and the disintegrin domain of pBOSMelαδMP(+) to give the expression plasmid, pBOSMelαδPro(+) encoding δPro wherein there a deletion was found around the precursor domain (the amino acid sequence of from Ile(No. 55) to Glu(No. 206) of Meltrin α).

(4) Confirmation of Myoblast Fusion-Promoting Activity

Myoblast cell line C2 was transfected by the mixture comprising the plasmid pBOSMelα(+) or pBOSMelαδMP(+), and the plasmid pSV2NEO in a molar ratio of 20:1 by using LIPOFECTAMINE (Gibco BRL) according to its protocol. The transfected cells were diluted and inoculated on a plate (φ 10 cm) coated with collagen (IWAKI) so that the transformants would be obtained at a density of 10-20 clones per plate. The inoculated cells were cultured for 12 days in DMEM containing 20% fetal bovine serum and 5 ng/ml of bFGF (Gibco BRL) followed by isolation thereof.

For the purpose of the examination of myoblast fusion-promoting activity, the resulting transformants and the parent strain C2 were cultured for 3-4 days in the absence of bFGF, inoculated onto a plastic dish (φ 6 cm) at a density of $2 \times 10^5$/dish, and further cultured for one day, followed by the 4 day culture in the above differentiation medium for differentiation induction. Upon differentiation induction, C2 began to form myotubes. After the 4 day culture followed by fixation with methnol and staining with Giemsa and Wright's reagents (Merck), the number of nuclei were determined at any four independent fields of 1 mm$^2$ on the dish and fusion index was calculated as follows:

Fusion Index=100*(The number of nuclei in multi-cleate syncytium having three or more nuclei)/(The number of the total nuclei)

Further, the time course of the fusion index was observed after differentiation induction every one day for five days.

Figure 11A:
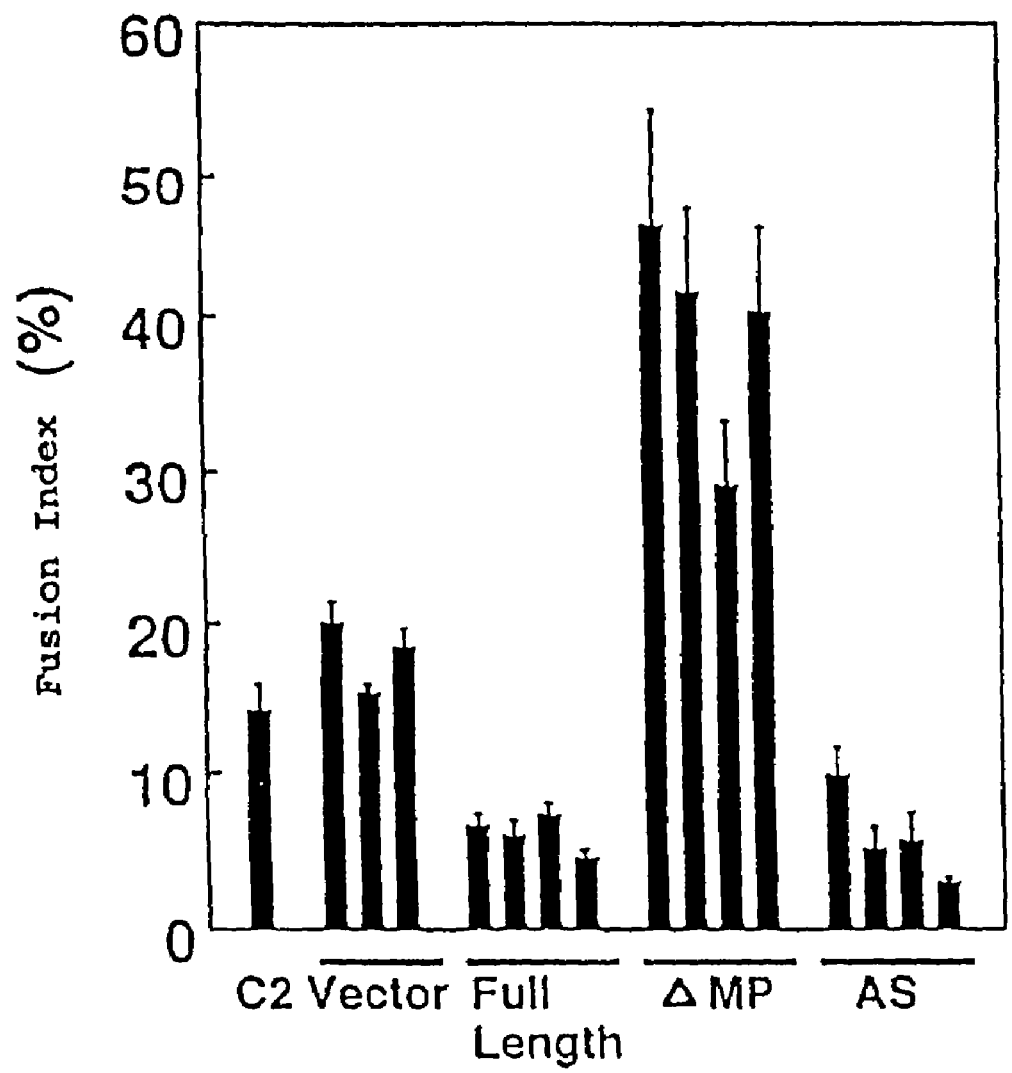
FIG. 11a~FIG. 11b show fusion-promoting activity of Meltrins for myoblast.
Figure 11B:
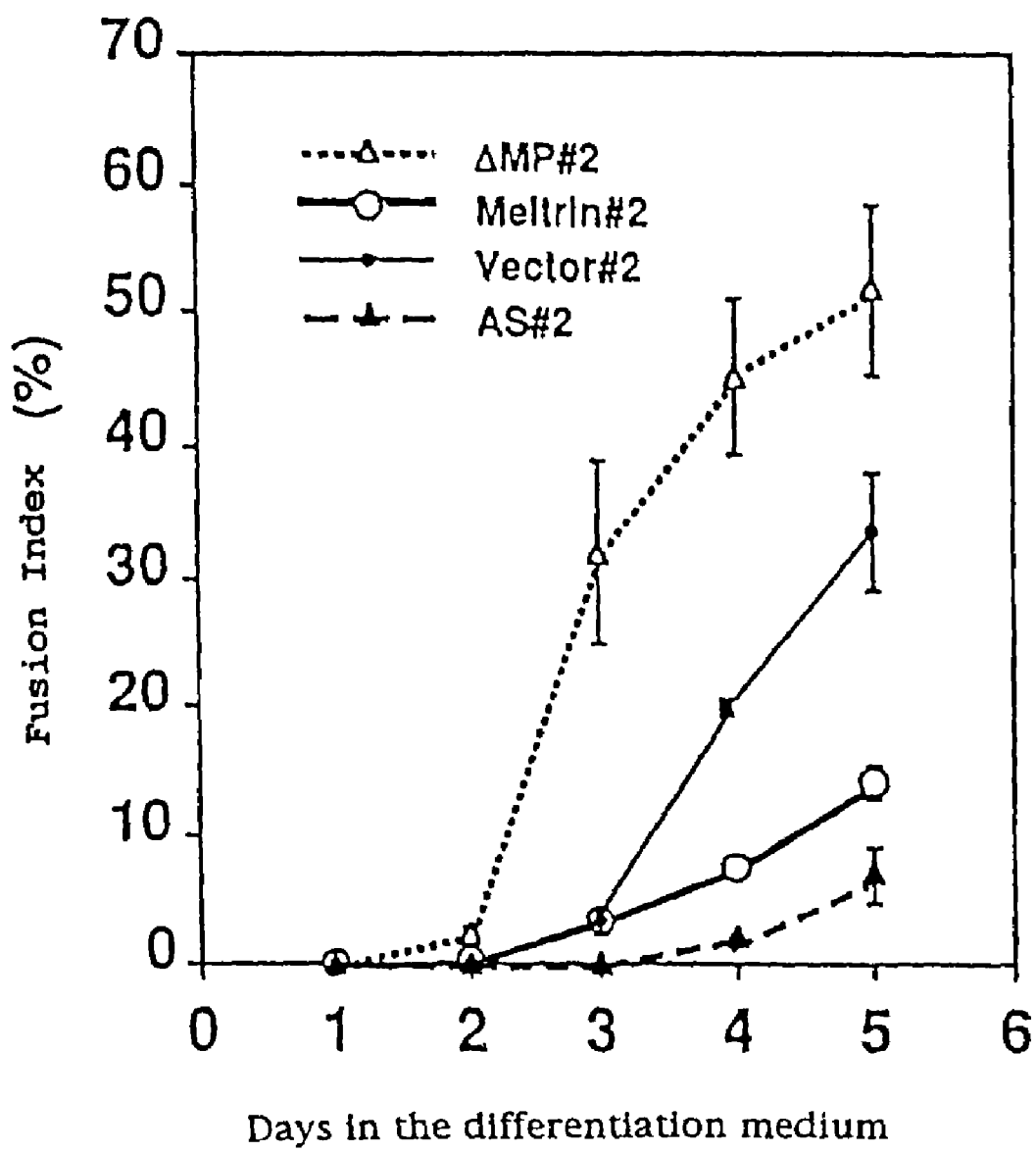

The results are shown in FIG. 11a~FIG. 11b. As seen from these figures, the fusion activity of the transformant expressing the full length of Meltrin α (pBOSMelα(+) which was referred to as "full length" in FIG. 11a) become lower than that of the parent cell, and it was therefore considered that the full length of Meltrin α would suppress the cell fusion in some way. On the other hand, the transformant harboring pBOSMelαδMP(+), which was referred to as "ΔMP" in the figures, significantly promoted the cell fusion activity. It was also observed that the transformant harboring pBOSMelαδPro(+) promoted the cell fusion activity.

On the other hand, the C2 cell transformed by the plasmid pBOSMelβ(+) prepared by the insertion of the DNA encoding the full length of Meltrin β in the same way as in the above (2) could not cause any significant change in the fusion activity for muscle cells. However, The C2 transformant cotransfected by pBOSMelα(+) and pBOSMelβ(+) promoted the cell fusion activity compared with that of parent cell.

On the other hand, neither the C2 cell transformed by the plasmid pBOSMelγ(+) prepared by the insertion of the DNA encoding the full length of Meltrin γ in the same way as in the above (2), nor the C2 transformant cotransfected by pBOSMelα(+) and pBOSMelγ(+) could cause any significant change in the fusion activity for muscle cells.

These results demonstrate that Meltrin α is involved in the fusion of muscle cells, and will show its activity to promote the cell fusion upon its processing. It is estimated that Meltrin α or Meltrin β does not act alone, but act in the form of a heteromer between them, since the transformant expressing both Meltrin α and Meltrin β promoted the fusion of muscle cells.

(5) Examination of the Function of Meltrins in Non-Muscle Cells

The mouse fibroblast L929 was transformed by pBOSMelα(+) or pBOSMelβ(+) and the transformants expressing Meltrin α or Meltrin β were isolated. These transformants did not aggregate, nor fuse with each other. This was also true for the case of the transformant expressing both Meltrin α and Meltrin β.

On the other hand, the L929 cells transformed by pBOSMelγ(+) could showed a significant aggregation activity upon the addition of calcium ion, after the cells had been torn from a plate in a medium comprising no calcium ion.

These results demonstrate that Meltrin γ has a cell aggregation activity, and by considering the similarity of these molecules it is suggested that myoblast fusion-promoting activity of Meltrin α and Meltrin β may be attributed to their myoblast aggregation-promoting activity.

Example 5

Inhibition of Adhering Activity by Antisense

The plasmid BOSMelαδMP(-) prepared in Example 4 (1) was mixed with the plasmid PSV2NEO at a molar ratio of 20:1, by which C2 cells were transformed according to the method of Example 4 (4) followed by isolation of the transformants expressing antisense RNA. The adhering activity of the thus isolated transformants was determined by the method of Example 4. The results are shown in FIG. 11a-FIG. 11b, which demonstrated that the fusion of C2 cells was inhibited by the expression of antisense RNA for δMP (referred to as "AS" in the figures).

The above results have revealed that Meltrin α plays an essential role in the cell fusion of muscle cells.

Example 6

Preparation of cDNA Fragments Encoding Human Meltrins α and γ

By using mRNA purified from human myelocytes (Clonetech Co.) as a template, cDNAs were prepared according to the method of Example 1 (1), and 36 cycles of PCR was then carried out by using the degenerative primer obtained in Example 1 (2) and said cDNAs as a template. The amplified product was inserted into a EcoRV site of pBS-SKII(-), and named "pBShuMα300." The results of DNA sequencing are shown in FIG. 12a and FIG. 12b.

It was found that the DNA sequence comprised the base sequence encoding the part from an intermediate position of the disintegrin domain to an intermediate position of the cysteine-rich region of human Meltrin α (the disintegrin domain is located to Gly (No. 36), followed by the cysteine-rich region in FIG. 12a and FIG. 12b).

On the other hand, by using a part of a human sequence (D-14665) registered with a data base, whose function had not yet identified, a sense primer (5'-CACGATGATGG-GAGAGATTG-3')(SEQ ID NO: 56) and antisense primer (3'-CACTCTGATTTCCTATGCCTC-5')(SEQ ID NO: 57) were synthesized. PCR was carried out according to the above method to give the amplified product, which was then inserted into the EcoRV site of pBS-SKII(-), and named "pBShuMγG238." The results of DNA sequencing are shown in FIG. 13a and FIG. 13b.

It was found that the DNA sequence comprised the base sequence encoding the part from an intermediate position of the metalloproteinase domain to an intermediate position of the cysteine-rich region of human Meltrin γ (the metalloproteinase domain is located from N-terminal to Pro (No. 40), the disintegrin domain from Lys (No. 41) to Gly (No. 136) or from Tyr (No. 46) to Gly (No. 136), followed by the cysteine-rich region from Tyr (No. 137)). The *E. coli* strain JM109 was transformed by those plasmids to give JM109(pB-ShuMα300) and JM109(pBShuMγG238), which were deposited in the National Institute of Bioscience and Human-Technology, Agency of Industrial Science and Technology (1-3, Higashi 1-chome, Tsukuba-shi, Ibaraki-ken 350 Japan) on Feb. 19, 1996 under accession numbers FERM P-15454 and 15455, respectively, and then transferred on Oct. 8, 1996 to the deposit under the terms of the Budapest Treaty on the International Recognition of the Deposit of Microorganisms for the Purposes of Patent Procedure and Regulation under accession numbers FERM BP-5704 and 5705, respectively.

Example 7

Preparation of cDNA Fragment Encoding Human Meltrin α by Usig cDNA Library Derived from Human Placenta −1

(1) First Screening

Based on the cDNA sequence of Meltrin α obtained in Example 6, sense primer MA-1 and antisense primer MA-2 were synthersized (see Table 1). The human placenta λgt11 cDNA library (Clonetech Co., code No. CLHL1008b) was inoculated onto LB plate (φ 10 cm) at such a density that 10,000 plaques per plate may be obtained. After the formation of plaques, SM buffer 5 ml was added to each plate, the plates were put by incubation at a room temperature for 4 hours, and phages were collected from each plate (plate lysate method). PCR was carried out by using the collected phage solution as a template. Thus, MA-1 and MA-2 primers, Ex Taq polymerase (TaKaRa Co.,), and its reagents (TaKaRa Co.,) were mixed, followed by 35 cycles of the reactions at 94° C. for 30 sec, 55° C. for 30 sec, and 72° C. for one min. A part of the amplified products was subjected to an agarose gel electrophoresis, and a phage solution of the clone comprising Meltrin α cDNA was selected.

(2) Second Screening

The phage solution of the desired clone obtained in the first screening was inoculated at such a density that 400 plaques per plate may be obtained. After the formation of plaques, phages were collected in the same manner as above and a phage solution comprising the desired clone was selected.

(3) Third Screening

The phage solution of the desired clone obtained in the second screening was inoculated at such a density that 40 plaques per plate may be obtained. After the formation of plaques, phages were collected in the same manner as above and a phage solution comprising the desired clone was selected.

(4) Forth Screening

The phage solution of the desired clone obtained in the third screening was inoculated at such a density that 10 plaques per plate may be obtained. After the formation of plaques, phages were collected in the same manner as above and a phage solution comprising the desired clone was selected.

(5) Final Screening

The phage solution of the desired clone obtained in the forth screening was inoculated at such a density that 20 plaques per plate may be obtained. After the formation of plaques, each plaque was stuck with a toothpick, and the sticking material was suspended as a template into PCR solution. The above 35 cycles of the PCR with MA-1 and MA-2 primers finally gave two positive clones. A single positive plaque comprising the desired clone was collected in SM buffer, and the phage was lysed thereinto.

PCR was carried out by using λgt11 Forward primer and λgt11 Reverse primer (Table 1) to give a fragment of human Meltrin α cDNA in the phage vector.

Figure 14A:
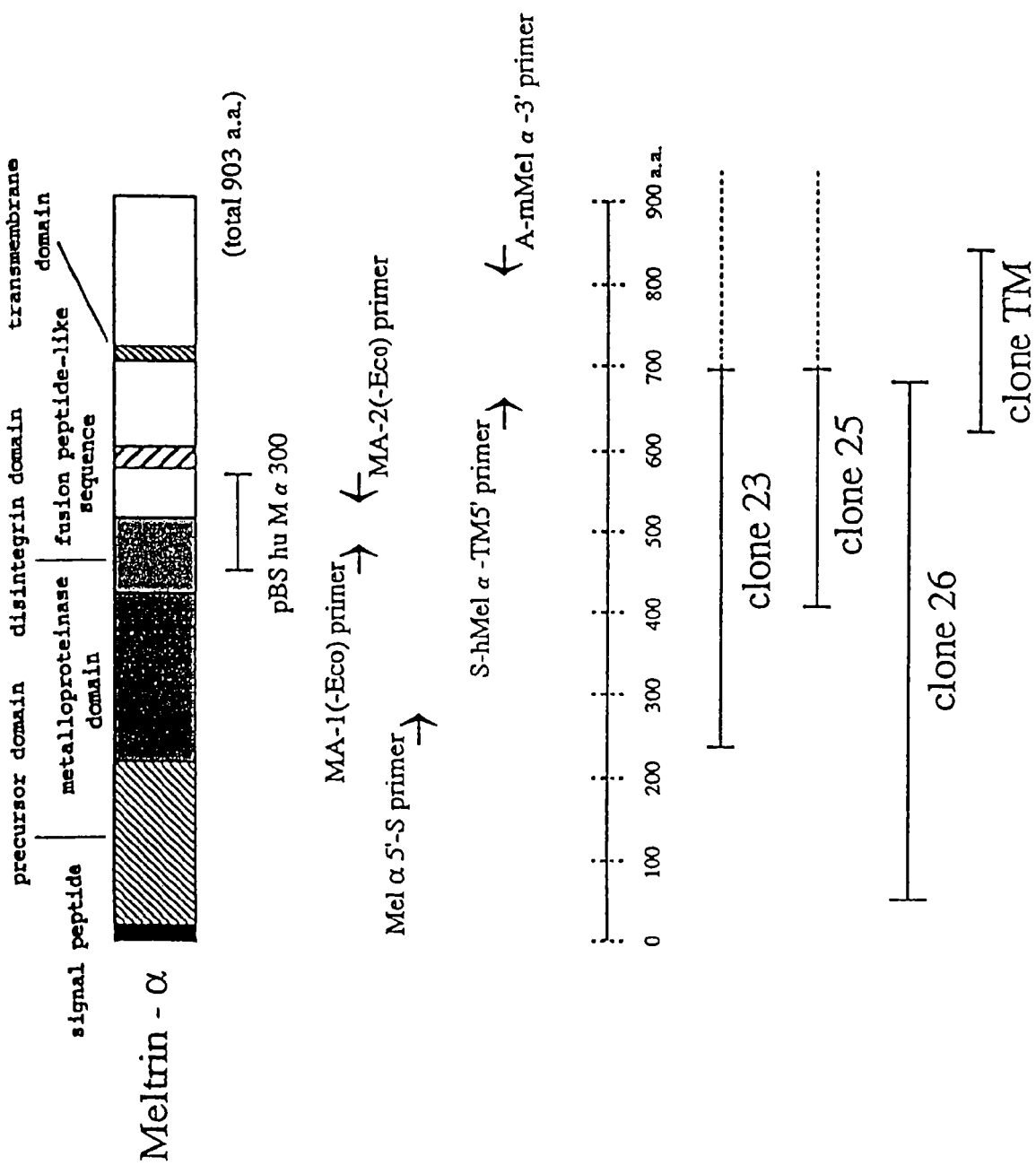
FIG. 14a shows schematically the cloning region in the cloning of human Meltrin α.
Figure 14B:
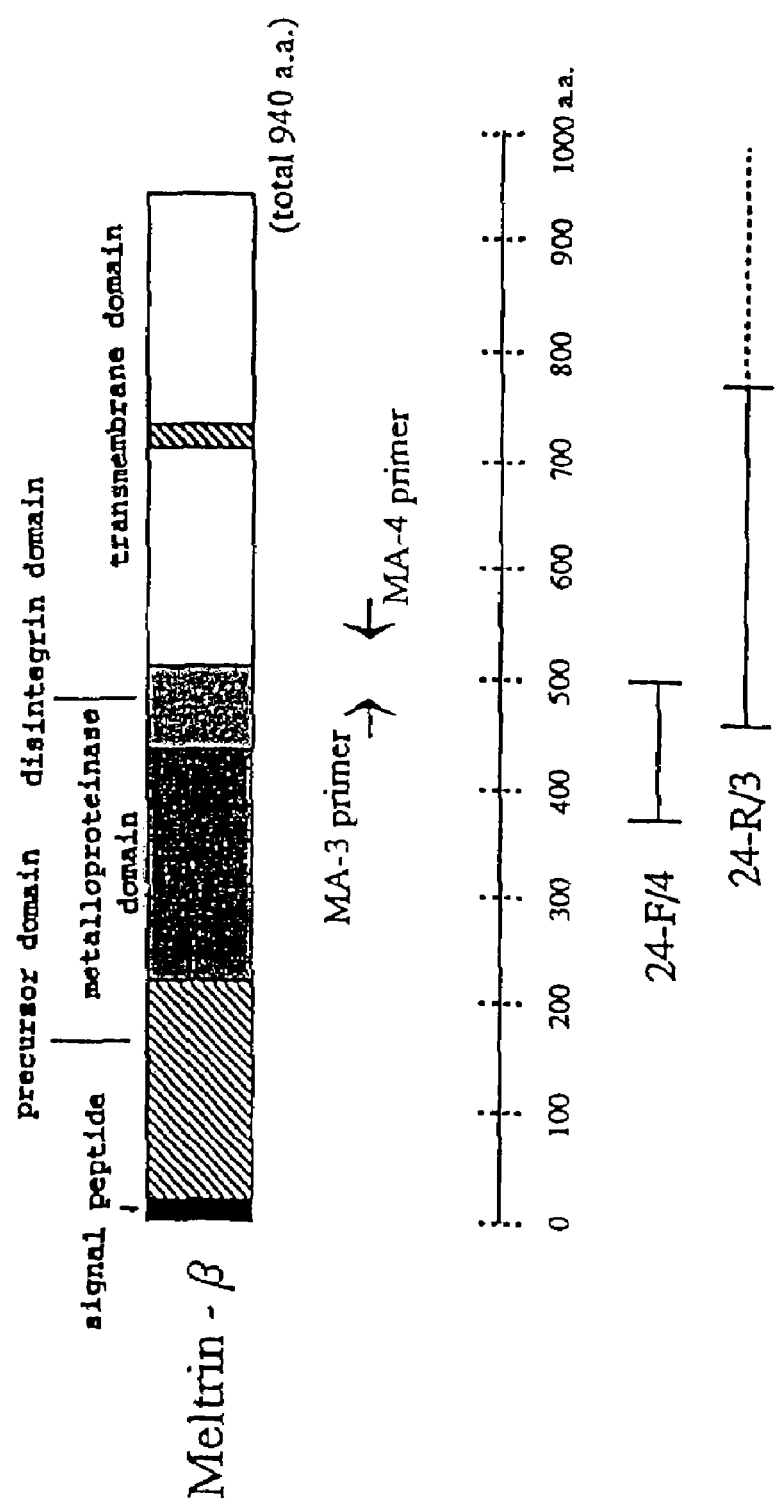
FIG. 14b shows schematically the cloning region in the cloning of human Meltrin β.

From a partial DNA sequencing of the terminal bases of the resulting fragments it was estimated that those cDNAs comprised the base sequences encoding human Meltrin α obtained in Example 6, and corresponded to about 650 amino acids (Clone 23) or about 500 amino acids (Clone 25) of mouse Meltrin (FIG. 14).

Example 8

Preparation of cDNA Fragment Encoding Human Meltrin α by using cDNA Library Derived from Human Placenta −2

A sense primer Mel α-5'S was designed based on the sequence encoding the N-terminal of the cDNA sequence of the clone 23 revealed in Example 7. The human placenta λgt11 cDNA library (Clonetech Co.) was screened by the sense primer Mel α-5'S and antisense primer MA-2 to give cDNA encoding about 700 amino acids (Clone 26) (FIG. 14*a*). For the purpose of the analysis of the base sequence of Meltrin gene, the four primers, λgt11 Forward-Eco, λgt11 Reverse-Eco, MA-1-Eco, and MA-2-Eco were synthesized (Table 1).

TABLE 1

The base sequences of the primers for PCR
(SEQ ID NOS: 29-39, respectively)

| | |
|---|---|
| MA-1: | 5' ACG ATG GGC ACT CAT GTC AG 3' |
| MA-2: | 5' CAT CTC GCA TTT GGC AAA GG 3' |
| λ gt11 Forward: | 5' GGT GGC GAC GAC TCC TGG AGC CCG 3' |
| λ gt11 Reverse: | 5' TTG ACA CCA GAC CAA CTG GTA ATG 3' |
| Mel α-5'S: | 5' CAC TGA ACA TTC GGA TCG TG 3' |
| λ gt11 Forward-Eco: | 5' CCG GAA TTC GGT GGC GAC GAC TCC TGG AGC CCG 3' |

TABLE 1-continued

The base sequences of the primers for PCR
(SEQ ID NOS: 29-39, respectively)

| | |
|---|---|
| λ gt11 Reverse-Eco: | 5' CCG GGA TTC TTG ACA CCA GAC CAA CTG GTA ATG 3' |
| MA-1-Eco: | 5' CCG GAA TTC ACG ATG GGC ACT CAT GTC AG 3' |
| MA-2-Eco: | 5' CCG GAA TTC CAT CTC GCA TTT GGC AAA GG 3' |
| S-hMeL α-TM5': | 5' GCA CAA AGT GTG CAG ATG GA |
| A-mMel α-3': | 5' CAG AGG CTT AGG AGG N |

The second half of the Meltrin gene was amplified by PCR using Clone 25 as a template, and MA-1-Eco and λgt11 Reverse-Eco primers. The first half of the Meltrin gene was amplified by PCR using Clone 26 as a template, and MA-2-Eco and λgt11 Forward-Eco primers. These cDNA fragments were digested at EcoRI and cloned into the EcoRI site of pUC 118 to give the plasmid vectors "pMelα-26N" and "pMelα-25C", respectively. The sequences of Meltrin α cDNA comprised in these plasmids were determined by a conventional method.

The E. coli strain JM109 was transformed by those plasmids according to the known method of Hanahan et al. to give JM109(pMelα-26N) and JM109(pMelα-25C), and were deposited in the National Institute of Bioscience and Human-Technology, Agency of Industrial Science and Technology (1-3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5689 and 5688, respectively.

The base sequence and its corresponding amino acid sequence of human Meltrin α which had been revealed by the base sequencing of pMelα-26N and pMelα-25C are shown in FIG. 15a~FIG. 15f.

Comparison of the DNA sequence thus obtained with that obtained in Example 6 indicated four discrepancies in base pairs, the three of which being silent mutation, and the other discrepancy causing substitution of Asp (No. 505) in the above figures for Glu in the sequence of Example 6.

The analysis of the structure of the base sequence showed that the DNA encoded the sequence from an intermediate part of the precursor domain to the C-terminal of Meltrin α. Thus, it has been considered that in the amino acid sequence shown in FIG. 15a~FIG. 15f, the partial sequence (C-terminal) of the precursor domain corresponds to the sequence from Gly N-terminal to Arg (No. 155) and to the bases No. 1-465, the metalloproteinase domain to the sequence from Glu (No. 156) to Pro (No. 364) and to the bases No. 466-1092, the disintegrin domain to the sequence from Glu (No. 365) or Phe (No. 370) to Gly (No. 459) and to the bases No. 1093 or 1108-1377, the cysteine-rich region to the sequence from His (No. 460) to Gln (No. 656) or Ala (No. 652) and to the bases No. 1378-1968 or 1956, the fusion peptide-like sequence to the sequence from Gly (No. 535) to Gln (No. 557) and to the bases No. 1603-1671. There was no transmembrane domain in this sequence, suggesting that human Meltrin α existed as a soluble protein without a transmembrane domain in a body. In other words, it is considered that Meltrin α having the amino acid sequence of FIG. 15a~FIG. 15f is extracellularly secreted and present in blood or body fluid. It is considered that such soluble Meltrin α takes a part in regulating adhesion, fusion and aggregation of cells in the body.

It is considered that Meltrin α having the amino acid sequence of FIG. 15a~FIG. 15f has generated as a result of an alternative splicing of the gene. It is also considered that the DNA encoding the region downstream of the cysteine-rich region, and the DNA encoding transmembrane domain and intracellular domain are located on different exons, and that the splicing out of either DNA would yield a soluble type Meltrin, or a membrane-binding type Meltrin.

Example 9

Preparation of cDNA Fragments Encoding Human Meltrins β

(1) Preparation of cDNA Fragment Encoding a Part of the Disintegrin Domain of Human Meltrin β

By using mRNA purified from human myelocytes (Clonetech Co.) as a template, cDNAs were prepared according to the method of Example 1 (1), and 36 cycles of PCR were then carried out by using the degenerative primers obtained in Example 1 (2) and said cDNAs as a template. The amplified product was inserted into pBS-SKII(-). The analysis of the resulting DNA sequence revealed that it was a partial sequence of Meltrin β. The determined DNA sequence is shown in FIG. 16.

(2) First Screening by Using cDNA Library Originated in Human Fetal Lung

Based on the partial cDNA sequence of Meltrin β obtained in the above (1), sense primer MA-3 and antisense primer MA-4 were synthersized (see Table 2). The human fetal lung λgt11 cDNA library (Clonetech Co., code No. CLHL1072) was inoculated onto LB plate (φ 10 cm) at such a density that 10,000 plaques per plate may be obtained. After the formation of plaques, SM buffer 5 ml was added to each plate. And the plates were put at a room temperature for 4 hours, and phages were collected from each plate (plate lysate method). PCR was carried out by using the collected phage solution as a template. Thus, MA-3 and MA-4 primers, Ex Taq polymerase (TaKaRa Co.,), and its reagents (TaKaRa Co.,) were mixed, followed by 35 cycles of the reactions at 94° C. for 30 sec, 55° C. for 30 sec, and 72° C. for one min by means of DNA thermal cycler (Perkin Elmer Co.,). A part of the amplified products was subjected to an agarose gel electrophoresis, and a phage solution of the clone comprising Meltrin β cDNA was selected.

(3) Second Screening

The phage solution of the desired clone obtained in the first screening was inoculated at such a density that 1000 plaques per plate may be obtained. After the formation of plaques, phages were collected in the same manner as above and a phage solution comprising the desired clone was selected.

(4) Third Screening

The phage solution of the desired clone obtained in the second screening was inoculated at such a density that 100 plaques per plate may be obtained. After the formation of plaques, phages were collected in the same manner as above and a phage solution comprising the desired clone was selected.

(5) Forth Screening

The phage solution of the desired clone obtained in the third screening was inoculated at such a density that 10 plaques per plate may be obtained. After the formation of plaques, phages were collected in the same manner as above and a phage solution comprising the desired clone was selected.

(6) Collection and Confirmation of DNA Fragment Comprising Partial cDNA Sequence The PCR was carried out using the phage solution of the desired clone obtained in the forth screening (#24) as a template, and a combination of λgt11 Forward primer (Table 1) and MA-4 primer or a combination of λgt11 Reverse primer (Table 1) and MA-3 primer to give amplified products with about 500 bp (24-F/4) and about 5 kbp (24-R/3), respectively. From a partial DNA sequencing of the terminal bases of the resulting two DNA fragments, it was estimated that those cDNA comprised the base sequences determined in the above (1).

(7) Analysis of Base Sequences

For the purpose of subcloning of the cDNA fragments comprising the cDNA partial sequence of human Meltrin β, two primers MA-3-Eco and MA-4-Eco were newly synthersized (see Table 2).

The PCR was carried out using the phage solution (#24) as a template, and a combination of λgt11 Forward-Eco primer (Table 1) and MA-4-Eco primer or a combination of λgt11 Reverse-Eco primer (Table 1) and MA-3-Eco primer. The resulting amplified products were digested with EcoRI and inserted into the EcoRI site of pUC118 to give the plasmids, "pMelβ-24C" and "pMelβ-24N", respectively. The sequence of Meltrin β cDNA comprised in these plasmids was determined by a conventional method.

The *E. coli* strain JM109 was transformed by those plasmids according to the known method of Hanahan et al. to give JM109(pMelβ-24C) and JM109(pMelβ-24N), and were deposited in the National Institute of Bioscience and Human-Technology, Agency of Industrial Science and Technology (1-3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5690 and 5691, respectively.

The base sequence and its corresponding amino acid sequence which had been revealed by the base sequencing of pMelβ-24C and pMelβ-24N are shown in FIG. 24a~FIG. 24e.

Comparison of the DNA sequence thus obtained with that obtained in the above (1) showed one discrepancy in base pairs, which was a silent mutation, causing no change of amino acid.

The analysis of the structure of the base sequence showed that the DNA encoded the sequence from an intermediate part of the metalloproteinase domain to the C-terminal of human Meltrin-β. Thus, it has been considered that in the sequence shown in FIG. 24a~FIG. 24e, the partial sequence at C-terminal of the metalloproteinase domain corresponds to the sequence from Gly (N-terminal) to Pro (No. 36) and to the bases No. 2-109, the disintegrin domain to the sequence from Asp (No. 37) or Tyr (No. 42) to Gly (No. 131) and to the bases No. 110 or 125-394, the cysteine-rich region to the sequence from Thr (No. 132) to Pro (No. 330) and to the bases No. 395-991, the transmembrane domain to the sequence from Val (No. 331) to Met (No. 348) or Arg (No. 353) and to the bases No. 992-1045 or 1060. It is considered that the sequence from Tyr (No. 349) or Gln (No. 354) corresponds to the intracellular domain. However, as homology analysis to mouse Meltrin β shows a very low homology in the sequence from Pro (No. 395), it is estimated that the sequence up to His (No. 394) is involved in the function of extracellular domain of human Meltrin β. The sequence up to Pro (No. 395) in FIG. 24a~FIG. 24e is shown in FIG. 17a~FIG. 17c.

TABLE 2

The base sequences of the primers for PCR
(SEQ ID NOS: 58-61, respectively)

| | |
|---|---|
| MA-3: | 5' TGC TGC CAC CAG TGT AAG 3' |
| MA-4: | 5' TCC TGG TAG GTG AGG CAC ATG 3' |
| MA-3-Eco: | 5' CCG GAA TTC TGC TGC CAC CAG TGT AAG 3' |
| MA-4-Eco: | 5' CCG GAA TTC TCC TGG TAG GTG AGG CAC ATG 3' |

Example 10

Preparation of Anti-Meltrin α Monoclonal Antibodies (1) Selection of Peptides

Based on the amino acid sequence of mouse Meltrin α determined in Example 1, their epitopes were analysed.

Eight kinds of peptide sequences were selected as a potential epitope, based on the secondary structure estimated from the regions wherein discrepancy in amino acids is seen between Meltrins α and β, the estimated non-RGD region, and the region wherein metalloproteinase had been cleaved (FIGS. 18a and b). These eight kinds of peptides were synthesized by Peptide Synthesizer (ABI 432A) so that they would have Cys at their C-terminal, cleaved, and purified by HPLC of a reverse phase column (YMC-ODS).

(2) Preparation of Antiserum

After lyophilization of the peptides obtained in the above (1), each peptide 0.55 mg was dissolved in 0.1 M phosphate buffer (pH 7.0) 55 μl. Maleimidated KLH (Boehringer Mannheim) 0.77 mg was dissolved in distilled water 77 μl. The two resulting solutions were combined, and reacted at a room temperature for two hours, followed by the purification by Nick column (Pharmacia) equilibrated with physiological saline to give antigens to be used in the following experiments.

Each antigen 50 μg was diluted with physiological saline to 0.1 ml, mixed with the same amount of Freund's complete adjuvant (DIFCO) and administered intraperitoneally into Wistar rat (5 weeks old, female). The antigen was mixed with the same amount of Freund's incomplete adjuvant (DIFCO) and administered two weeks later in the same way as above.

(3) Evaluation of Antiserum (Plate Assay)

After one week from the administration, the blood was drawn from the eyeground of the rat, and an increase of the antibody titer for the administered peptides was confirmed by the reaction between immobilized peptides and the antiserum according to a plate assay as follows.

First, 50 mM phosphate buffered saline (0.9% NaCl, pH 7.2) comprising 0.5 mg/ml of Sulfo-SMCC (Pierce) was poured into each well of an amino plate (Sumitomo Bakelite). After incubation at 37° C. for 2 hours, the wells were washed five times with ion-exchanged water, and the above buffer comprising 0.5 μg/ml of each peptide was added. After incubation at 37° C. for one hour, the well were blocked by 0.076M phosphate buffered saline (0.45% NaCl, pH 6.4), which will be referred to hereinafter as "PBS", comprising 0.1% of BSA and 4 mg/ml of cysteamine. The blocking agent was removed, each antiserum diluted 1,000 to 100,000 times with PBS was added followed by incubation at 37° C. for one hour. After two repeats of washing of the wells with 0.9% NaCl comprising 0.005% Tween20, an anti-rat immunoglobulin antibody labelled with peroxidase (Dako) and diluted with PBS comprising 10% rabbit serum was added to each well followed by incubation at 37° C. for one hour. Upon the completion of the reaction, the wells were washed five times with a washing liquid and two times with ion-exchanged water. And 0.1M McIlvaine buffer (pH 5.0) comprising 3 mg/ml of o-phenylene diamine and 0.027% hydro peroxide was added and reacted for 5 min. The reaction was terminated by the addition of 1N HCl, and absorbance at 490 nm was measured. The results are shown in Table 3, in which (++) means a strong reactivity, and (+) means a week reactivity.

TABLE 3

Reaction of antiserum with the peptide antigens

| peptide antigens | Reaction of Antiserum |
|---|---|
| 1 ProA | ++ |
| 2 MP-A | ++ |
| 3 MP-B | ++ |
| 4 DC-A | + |
| 5 DC-B | + |
| 6 DC-C | ++ |
| 7 DC-D | N.D. |
| 8 DEA | ++ |

N.D. (not determined)

(4) Evaluation of Antiserum (Western Blotting)

For the confirmation of the binding of the antiserum prepared in the above (2) to Meltrins, Western blotting was carried out.

Mouse myoblast C2 was transformed by pBOSMelαδPro (+) and pBOSMelβ(+), which will be referred to hereinafter as "#9-3", and mouse myoblast C2 was transformed by pBOSMelαδMP(+), which will be referred to hereinafter as "#3-5."

The transformed C2 cells of $1 \times 10^7$ cells were washed with PBS− (GIBCO BRL) and collected by centrifugation. The density of the collected cells was adjusted to $5 \times 10^6$ cells/ml, mixed with a proteolysis inhibitor, Cφmplete (Boehringer Manheim) in amount of one 25th of the volume of the cell mixture, and mixed with SDS to a final concentration of 0.2%. After incubation at a room temperature for 30 min, the cells were subjected to sonication at 4° C. for 10 sec (1 sec×10), and centrifuged. The resulting supernatant was collected and used as a cell lysate. Another cell lysate was prepared from fibroblast L929 (ATCC No. CCL-1) in the same way, and used as a negative control.

The resulting cell lysate (10 μl) was mixed with an equiamount of a gel loading buffer (0.25M Tris-HCl, 2% SDS, 30% Glycerol, 0.01% BPB (pH 6.8)), the resulting solution (6 μl) was applied to SDS-PAGE of 4~20T % (Tefco), and electrophoresed under 25 mA at a room temperature for about one hour. After the completion of the electrophoresis, the contents were transferred to PVDF membrane (Millipore) under the conditions of 150 mA, 4° C. and 45 min. The membrane was blocked by shaking in 4% skim milk (Meiji Milk Co.) at a room temperature for one hour, and each lane was cut. Each excised lane was soaked and shaken in antiserum (1 ml) diluted 500 times with 50 mM Tris-HCl (pH 7.2) comprising 0.05% Tween20 (referred to hereinafter as "T-TBS") and 4% skim milk at a room temperature for one hour. After the completion of the reaction, each lane was washed two times with T-PBS, soaked in 1 ml of an anti-rat immunoglobulins antibody labelled with HRPO (Dako) diluted 500 times with T-PBS comprising 4% skim milk, and reacted at a room temperature for one hour. After washing five times with T-PBS, it was detected by ECL system (Amersham). The results are shown in Table 4. Bands were detected in the three kinds of the antiserums by the Western blotting.

TABLE 4

Reaction of antiserum with the cell lysate in Western blotting

| Peptide antigens | Western blottting |
|---|---|
| 1 ProA | + |
| 2 MP-A | − |
| 3 MP-B | − |
| 4 DC-A | N.D. |
| 5 DC-B | N.D. |
| 6 DC-C | + |
| 7 DC-D | N.D. |
| 8 DEA | + |

N.D. (not determined)

(5) Preparation of Monoclonal Antibody

The antigens (ProA, MP-B, DC-C, DEA) (50 μg each) were diluted with 400 μl of physiological saline, and injected into the tail vein of the rats whose antibody titer had increased. Three days later, cell fusion was carried out by using myeloma P3X63Ag8U.1 according to the known method (Monoclonal antibody Jikken Sosa Nyumon (Guide of monoclonal antibody preparation), Tamie Ando and Jo Chiba, Koudan-sha Scientific). Six days later, the culture supernatant was collected and subjected to the plate assay according to the method of the above (3). The wells that showed reactivity with the peptide antigens were subjected to cloning by limiting dilution (Monoclonal antibody Jikken Sosa Nyumon (Guide of monoclonal antibody preparation), Tamie Ando and Jo Chiba, Koudan-sha Scientific). After cloning, the screening by the plate assay was performed again to give 27 clones of the hybridomas producing an anti-mouse Meltrin α monoclonal antibody which reacted with the peptide antigens. The results are shown in Table 5.

TABLE 5

Hybridomas producing anti-Meltrin peptides monoclonal antibody

| Peptide antigens | Hybridoma No. | The number of Hb |
|---|---|---|
| ProA | F936 | 10 |
| MP-B | F939 | 4 |
| DC-C | F933 | 4 |
| DEA | F934 | 8 |

Purified antibodies were obtained from the thus established anti-Meltrin monoclonal antibody-producing hybridoma cell lines by the following method.

The hybridomas were cultured in RPMI1640 supplemented with 10% fetal bovine serum and 1 ng/ml of human IL6 till a final density of $2 \times 10^5$ cells/ml. The medium was then exchanged with a serum-free medium (Hybridoma-SFM, GIBCO BRL), and the culture was continued until the cells died. The resulting culture supernatant was filtered through filter paper for the removal of the cells, and subjected to purification by Protein G column (Prosep-G, Bioprocessing INC) as follows. The culture supernatant (1 L) was applied to Prosep-G column (20 ml) at a flow rate of 10 ml/min, followed by washing with 0.1M phosphate buffer (pH 7.5) comprising 0.15M NaCl. After the absorbance at 280 nm had decreased, the bound monoclonal antibody was eluted by 0.1M citric acid buffer (pH 3.0). After neutralization of the pH, the eluate was concentrated with DIAFLO (Grace Japan), and dialysed against 0.076M phosphate buffered saline (pH 6.4) comprising 0.45% NaCl. The concentration of the purified antibody was calculated on the basis of the absorbance at 280 nm.

(6) Evaluation of Monoclonal Antibody

Figure 19:
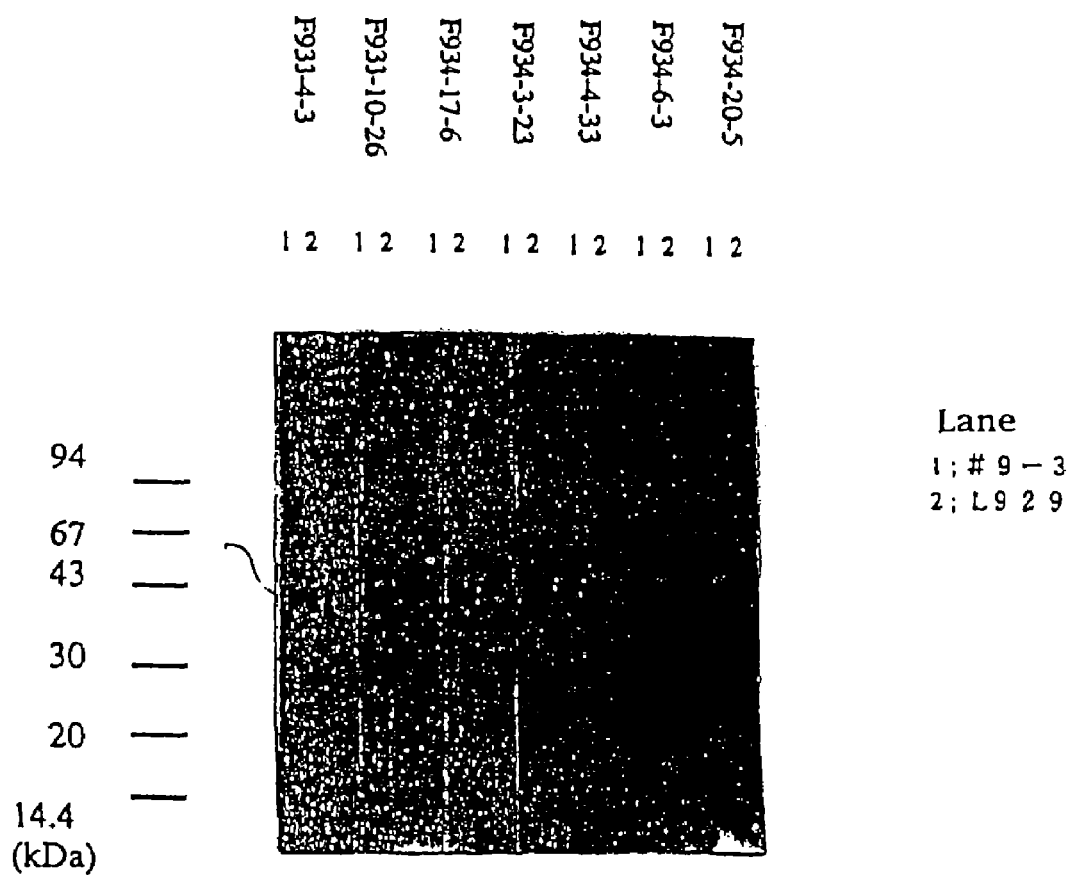
FIG. 19 is a photograph of electrophoresis showing the result of Western blotting with anti-mouse Meltrin α antibodies.

The binding activity of 7 lots of the purified antibodies (10 μg/ml each) obtained in the above (5) to Meltrin was confirmed by Western blotting according to the method of the above (4) using the cell lysate of #9-3 cell. The results are shown in FIG. 19. The band of about 67 kDa specific to the cell lysate of #9-3 cell was detected by the reaction with F933-4-3 (subclass IgG2a), F933-10-26 (subclass IgG2a), F934-17-6 (subclass IgG2a), F934-3-23 (subclass IgG2a), F934-4-33 (subclass IgG2a), F934-6-3 (subclass IgG2a), and F934-20-5 (subclass IgG2c). As these bands were not detected in the case of the cell lysate of L929 cell, it was confirmed that the monoclonal antibodies obtained in the above (5) were bound to Meltrin.

Example 11

Preparation of Anti-Mouse Meltrin Monoclonal Antibody (1) Preparation of the Antigen to be Administered and Immunization of Rat Rats were immunized with #9-3 and #3-5 cells as the antigen to be administered as follows. The cells used as the antigen to be administered were cultured in the absence of bFGF. First, the cells cultured in four dishes to a density of about $5 \times 10^5$ cells/φ 10 cm dish were subcultured in 20 dishes to until the same density as the above, then again subcultured in 40 dishes (φ 15 cm) up to a density of about $5-6 \times 10^6$ cells/dish, and further cultured in a differentiation medium (DMEM supplemented with 2% horse serum) for two days to finally form myotube. These cells were then scraped with a silicon rubber Policeman, washed two times with PBS, and suspended into the medium comprising 10% DMSO for storage at $-80°$ C.

The #9-3 and #3-5 cells were suspended in physiological saline (200 μl), mixed with an equiamount of Freund's complete adjuvant (DIFCO) and intraperitoneally administered into Wistar rat (5 weeks old, female) in an amount of $1 \times 10^7$ cells/rat. The antigen was mixed with the same amount of Freund's incomplete adjuvant (DIFCO) and administered two weeks later in the same way as above.

(2) Evaluation of Antiserum

After one week from the boosting, the blood was drawn from the eyeground of the rat, and a binding of antiserum to Meltrin was determined by using the cell extract according to the plate assay of Example 10 (3). The cell extracts of #9-3, #3-5 and L929 cells were prepared according to the method of Example 10 (4), except that NP-40 (Nacarai Tesque Co.) was used at a final concentration of 0.5% as a surfactant.

First, each cell extract was diluted with PBS to a concentration of 40 μg/ml, each 50 μl of which was separately poured into each well of an immuno plate (Maxisorp Nunc). After incubation at $56°$ C. for 30 min for binding of the antigen, the wells were washed five times with ion-exchanged water, blocked by 20% Block Ace (Yukijirushi Milk Co.)/PBS 100 μl, followed by incubation at a room temperature for 30 min. After removal of the blocking agent, each antiserum (50 μl) was added and incubated at $37°$ C. for one hour. After two repeats of washing of the wells with the washing liquid, 50 μl of an anti-rat immunoglobulins antibody labelled with peroxidase (Dako) and diluted 1,000 times with 10% Block Ace/PBS was added to each well followed by incubation at $37°$ C. for one hour. Upon the completion of the reaction, the wells were washed five times with the washing liquid and two times with ion-exchanged water, and 50 μl of 0.1 M McIlvaine buffer (pH 5.0) comprising 3 mg/ml of o-phenylene diamine and 0.027% hydro peroxide was added and reacted for 10 min. The reaction was terminated by the addition of 1N HCl (50 μl), and the absorbance at 490 nm was measured.

Western blotting was also carried out by using the cell extract of L4-3 described in the following (4) to confirm its binding to Meltrin. The results are shown in Table 6.

It was confirmed that the antiserum obtained from the rats immunized with #9-3 and #3-5 cells reacted with the corresponding cell extract, and were bound to Meltrin in the Western blotting.

TABLE 6

Reaction of antiserum of the rats immunized with #9-3 and #3-5 cells to Meltrin

| Antiserum | Plate Assay | | | Western blotting |
| --- | --- | --- | --- | --- |
| | #9-3 | #3-5 | L929 | L4-3 |
| rat immunized with #9-3 cell | + | N.D. | − | + |
| rat immunized with #3-5 cell | N.D. | + | − | + |

N.D. (not determined)

(3) Preparation of Monoclonal Antibody

The #9-3 and #3-5 cells ($1 \times 10^7$ cells each) were suspended in physiological saline (200 μl), and intraperitoneally administered into the rat whose antibody titer had increased. Three days later, cell fusion was carried out by using myeloma P3X63Ag8U.1 according to the known method (Monoclonal antibody Jikken Sosa Nyumon (Guide of monoclonal antibody preparation), Tamie Ando and Jo Chiba, Koudan-sha Scientific). Six days later, the culture supernatant was screened by its reactivity with the immobilized cell extracts. The wells that showed reactivity with the cell extracts were subjected to cloning by limiting dilution (Monoclonal antibody Jikken Sosa Nyumon (Guide of monoclonal antibody preparation), Tamie Ando and Jo Chiba, Koudan-sha Scientific). After cloning, the above screening was repeated to give 13 clones, 5 clone from the rat immunized with #9-3 (δpro; hybridoma No. F932) and 8 clones from the rat immunized with #3-5 (δMP; hybridoma No. F937).

(4) Evaluation of Monoclonal Antibody

The monoclonal antibodies F932-15-2 (subclass IgG1) and F937-9-2 (subclass IgG1) that showed a high reactivity with the cell extracts were evaluated.

First, the staining of myotube formed by C2 cells was examined by a cell immunofluorescence staining method. C2 cells were suspended in 10% FCS/DMEM at a density of $3\times10^4$ cells/ml, each 100 µl of which was then separately poured into the wells of chamber slide (Lab-TEK, Nunc Co.). After the culture at 37° C. and 5% $CO_2$ for two days, the medium was exchanged with 2% horse serum/DMEM. The cell staining was carried out by using myotube formed two days later. The cells were washed two times with PBS-, and 4% formaldehyde was added followed by the reaction at a room temperature for 30 min to fix the cells. The cells were washed three times with PBS- and blocked with 20% Block Ace/T-PBS. After removal of the blocking agent, antibodies diluted to 10 µg/ml with 20% Block Ace/T-PBS was added and reacted at a room temperature for one hour. After three repeats of washing of the wells with PBS-, an anti-rat immunoglobulins antibody FITC (Dako) diluted 20 times with 10% rabbit serum/T-PBS was added to each well followed by incubation a room temperature for one hour. After the completion of the incubation, the cells were washed three times with PBS-, and subjected to fluorescence microscopy. It was observed that myotube was stained by both the antibodies, but not stained by rat IgG (ZYMED) used as a negative control.

Next, L929 cells expressing mouse Meltrin α or β were prepared and subjected to cell staining for the purpose of confirmation of the specificity of the above antibodies. Thus, fibroblast L929 was transfected with the mixture comprising the plasmids pBOSMelα(+) and pBOSMelβ(+) prepared in Example 4, and the plasmid pSV2NEO in a molar ratio of 12:12:1 by using LIPOFECTAMINE (Gibco BRL) according to its protocol to give L4-3 cells expressing mouse Meltrins α and β. Similarly, L929 was transfected with the mixture comprising the plasmids pBOSMelβ(+) and the plasmid pSV2NEO in a molar ratio of 20:1 to give L2-10 cells expressing mouse Meltrin β. Similarly, L929 was transfected with the plasmids pBOSMelαδPro(+) to give L8-5 cells expressing mouse Meltrin α δPro. The transfected cells were cultured in 10% FCS/DMEM and subcultured onto a chamber slide. The specificity of the antibodies was confirmed by cell staining using L929, L4-3, L2-10 and L8-5 cells. The results shown in Table 7 indicated that F932-15-2 was bound to Meltrins α and β, and F937-9-2 was bound to Meltrin α.

The hybridoma expressing the monoclonal antibody F932-15-2 was deposited with the National Institute of Bioscience and Human-Technology, Agency of Industrial Science and Technology (1-3, Higashi 1-chome, Tsukuba-shi, Ibaraki-ken 350 Japan) on Oct. 3, 1996 under the terms of the Budapest Treaty on the International Recognition of the Deposit of Microorganisms for the Purposes of Patent Procedure and Regulation under accession numbers FERM BP-5687.

TABLE 7

| Cell | Expression | F932-15-2 | F937-9-2 |
|---|---|---|---|
| L929 | — | − | − |
| L4-3 | α and β | + | + |
| L2-10 | β | + | − |
| L8-5 | α (δPro) | + | + |

(5) Determination of Neutralizing Activity

Figure 20:
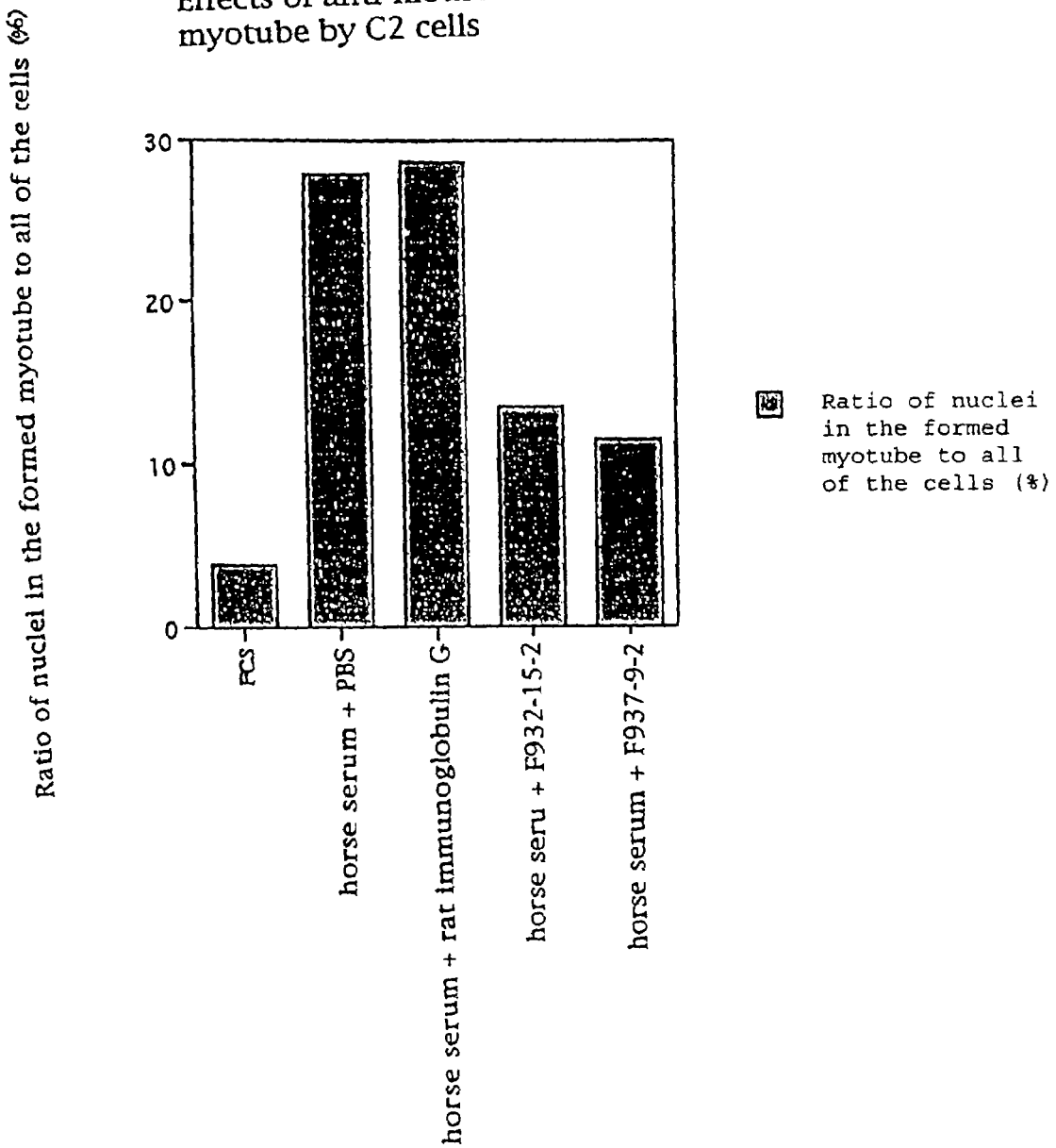
FIG. 20 is a graph showing the inhibition of myotube formation by anti-mouse Meltrin antibodies.

The neutralizing activity of the monoclonal antibodies obtained in the above (3) was confirmed by their inhibition of the formation of myotube by C2 cells. C2 cells were cultured in a collagen-coated dish containing 10% FCS/DMEM till 80% of confluence, followed by exchange of the medium with 2% horse serum/DMEM supplemented with 0 or 40 µg/ml of the antibodies to be tested. The formation of byotube was then observed and the ratio of nuclei in the formed myotube was calculated. As seen from FIG. 20, the formation of myotube on the day 2 was inhibited, showing that both F932-15-2 and F937-9-2 have the neutralizing activity.

Example 12

The Activity of Meltrin Neutralizing Antibodies to Inhibit the Formation of Bone Resorption Area (Pit) in Mouse Unfractionated Bone Cells Femur and tibia extracted from 13-day-old ICR mouse were crushed in MEM α medium (GIBCO) supplemented with 5% FBS. After being allowed to stand still for 2 min, the precipitated bone residues were removed. The supernatant of the suspending cells was adjusted to $1\times10^7$ cells/ml, 100 µl of which was then added to each well of a 96 well microplate provided with ivory fragments. The ivory fragments had been thinly sliced, punched into 6 mm in diameter, washed with 70% ethanol and sterilized. The mouse Meltrin-neutralizing antibody (F932-15-2) obtained in Example 11, and rat IgG were diluted with MEM α medium (GIBCO) supplemented with 5% FBS to final concentrations of 5, 50, and 500 µg/ml, 100.1 of which was then added to each well. After incubation at 37° C. and 5% $CO_2$ for three days, the cells were removed with a scraper, and resorption area was stained with an acid hematoxylin solution (SIGMA) for about 7 min and the number of the stained resorption area was calculated using an ocular micrometer under a microscope by counting the number of squares wherein resorption fossa was contained.

Figure 21:
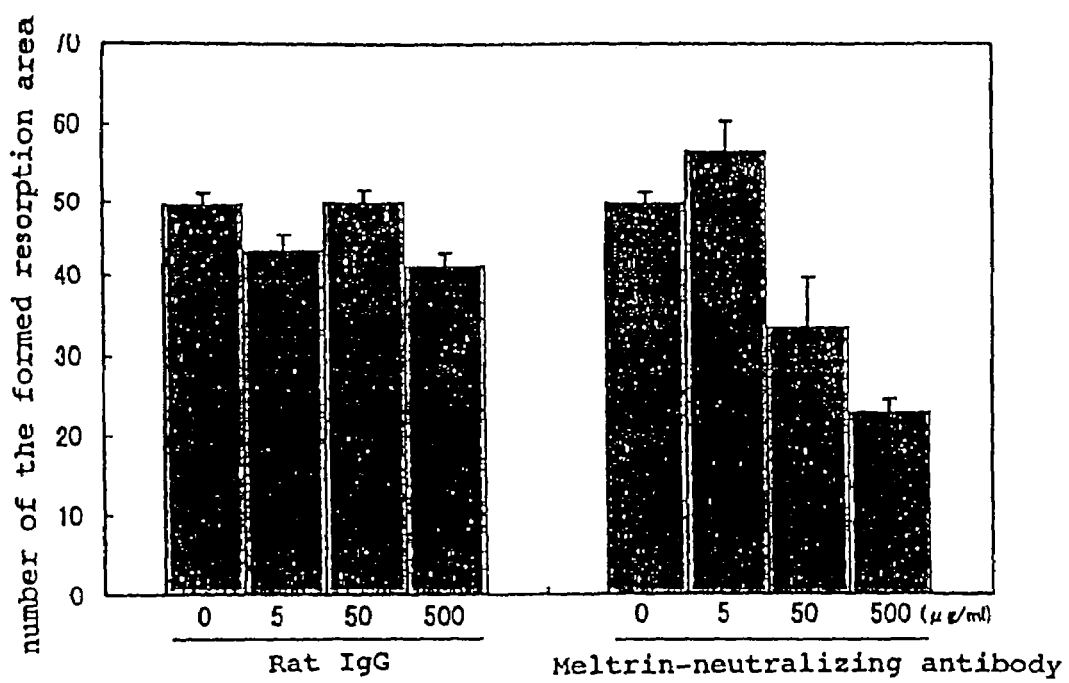
FIG. 21 is a graph showing the effects by anti-mouse Meltrin antibodies on the formation of pit (bone-resorption area) by mouse all bone cells.

The results are shown in FIG. 21, which demonstrates that the number of the formed resorption area was inhibited in a dose-depending manner by the mouse Meltrin-neutralizing antibody. Accordingly, it was suggested that the Meltrin-neutralizing antibody would affect directly or indirectly osteoclast and inhibit bone resorption.

Example 13

Serum Ca-Decreasing Activity of Meltrin-Neutralizing Antibody in Mouse Having Enhanced Bone Resorption Seven-week-old ICR mice (male) were fed for five days with low Ca feed with Ca content of 0.02% or less. The mouse Meltrin-neutralizing antibody (F932-15-2) obtained in Example 11 was injected into the tail vein of the mice (one group consisting of five mice) at doses of 0.1 mg and 1 mg per mouse). Rat IgG (1 mg per mouse) and phosphate buffer physiological saline were also injected as a control in the same way. Before injection and one day later, the blood was collected from the vein under eyes, and serum was separated. The value of Ca in the serum was then determined by an autoanalyzer (COBAS FARAII, ROCHE) using Ca determination kit (CalciumHR-II, WAKO Pure Pharmaceuticals). The results are shown in FIG. 22.

Figure 22:
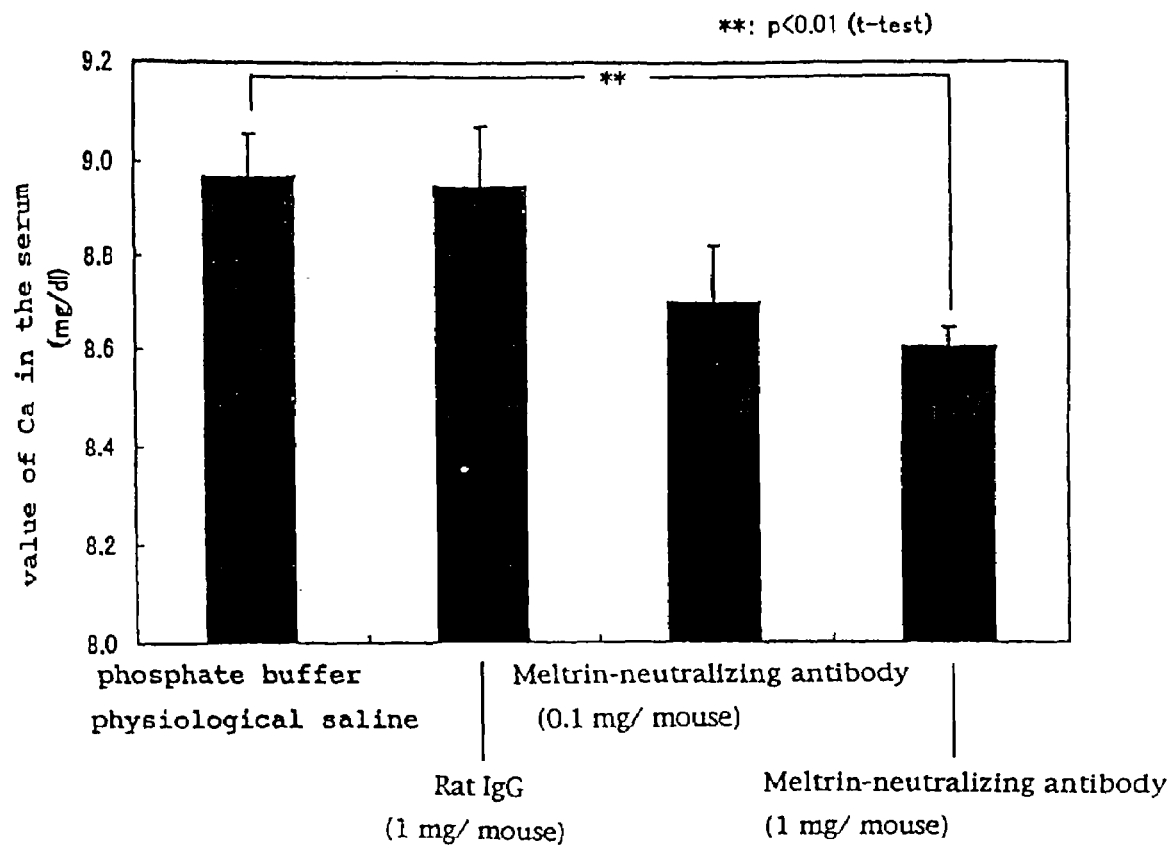
FIG. 22 is a graph showing the effects on the serum Ca values of the mouse fed with low Ca-content feed by anti-mouse Meltrin antibodies.

As seen from FIG. 22, the serum Ca value after one day from the injection in the groups treated with the mouse Meltrin-neutralizing antibody was lower than that of the groups treated with rat IgG or physiological saline. These results suggested that the Meltrin-neutralizing antibody would inhibit an unhealthily enhanced bone resorption due to hyperparathyroidism or malignant hypercalcemia.

Example 14

Preparation of cDNA Fragment Encoding Human Meltrin α Comprising Transmembrane Domain A sense primer S-hMelα-TM5' was synthesized based on the partial cDNA sequence of human Meltrin α obtained in Example 8, and an antisense primer A-mMelα-3' was synthersized based on the cDNA sequence of mouse Meltrin α (see Table 1).

PCR was carried out by mixing the human placenta λgt11 cDNA library (Clonetech Co., code No. CLHL1008b) as a template, with S-hMelα-TM5' and A-mMelα-3' primers, Ex Taq polymerase (TaKaRa Co.,), and its reagents (TaKaRa Co.,), followed by 35 cycles of the reactions at 94° C. for 30 sec, 55° C. for 30 sec, and 72° C. for one min. The base sequencing of the resulting amplified fragment (clone TM) suggested that the fragment was a human cDNA fragment corresponding to about 220 amino acids comprising the transmembrane domain of mouse Meltrin.

The obtained base sequence and its corresponding amino acid sequence are shown in FIG. 23a~FIG. 23b.

Example 15

Acute Toxicity Test

The mouse Meltrin-neutralizing antibody (F932-15-2) obtained in Example 11 was injected into seven-week-old ICR male mice (one group consisting of five mice) at doses of 1 mg and 3 mg per mouse). Phosphate buffer physiological saline was also injected into a control group in the same way. Neither significant decrease of body weight nor side effect was observed in any group after the injection. No dead mouse was observed, either.

Reference Example 1

Preparation of Monoclonal Antibody Recognizing Human Meltrin (1) Preparation of Antibody Using a Peptide Having the Amino Acid Sequence Derived from Human Meltrin as an Antigen In consideration of the results obtained in Example 10, the sequence "GKVSKSSFAKCEMRDAKC" (SEQ ID NO: 62) corresponding to DC-C in the amino acid sequence of human Meltrin α obtained in Example 8 was synthesized in the same way as in Example 10 (1), purified and conjugated with maleimidated KLH to give an antigen to be administered. 20 μg of the antigen was dissolved in 0.1 ml of physiological saline and mixed with an equiamount of FCA followed by injection to ddy mouse (5 weeks old, female). The same amount of the antigen was mixed with FIA and injected two weeks later. The blood was collected from the eyeground one week later and antiserum was prepared. Evaluation of the reactivity of the resulting antiserum with the administered peptide according to the method of Example 10 (3) revealed its specific reactivity with the administered peptide. Accordingly, mouse, rat, hamster and the like are immunized with the peptide antigen, and monoclonal antibody may be prepared in the same manner as in Example 10 (5). Such antibody may also be used in Western blotting.

As it is estimated that the amino acid sequence in FIG. 15a~FIG. 15f is Meltrin α of a soluble type, an antibody, which may be effectively used in the determination of soluble Meltrin in the body, may be prepared by immunization of a peptide having the amino acid sequence adjacent to C-terminal of the above sequence.

Similarly, antibodies recognizing human Meltrin β and Meltrin γ may be prepared by chemically synthesizing peptides having the amino acid sequences of suitable parts in the amino acid sequences in FIG. 17a~FIG. 17c or FIG. 13a~FIG. 13d and injecting the thus synthesized peptides into animals. In any case, the amino acid sequence will be selected from the extracellular domain.

For the preparation of an antibody specific to each one of Meltrins α, β and γ, the amino acid sequence should be selected from the parts with a low homology among them, and a peptide having the thus selected amino acid sequence is synthesized and injected to animals such as mouse, rat and hamster in the same way as in Example 10 (2).

In any case, monoclonal antibodies are prepared in the same way as in Example 10 (5).

(2) Preparation of Anti-Meltrin Monoclonal Antibody Using Cells Expressing Human Meltrin as an Antigen DNA encoding the amino acid sequence wherein the amino acid sequence located downstream of the transmembrane domain shown in FIG. 23a~FIG. 23b is fused downstream of the sequence from the metalloproteinase or the disintegrin domain to the cysteine-rich region shown in FIG. 15a~FIG. 15f is prepared, and inserted into an expression vector pEF-BOS, followed by transformation of C2 cells by the resulting vector. The transformant is treated as in Example 11 (1), and used as an antigen for immunization of animals such as mouse, rat and hamster. Antibodies recognizing human Meltrin α is screened as in Example 11 (2), and monoclonal antibodies are prepared as in Example 11 (3).

Similarly, DNA encoding the amino acid sequence shown in FIG. 17a~FIG. 17c or the sequence located downstream of the disintegrin domain of the above sequence is prepared, and inserted into an expression vector pEFBOS, followed by transformation of C2 cells by the resulting vector. The transformant is treated as in Example 11 (1), and used as an antigen for immunization of animals such as mouse, rat and hamster. Antibodies recognizing human Meltrin β is screened as in Example 11 (2), and monoclonal antibodies are prepared as in Example 11 (3).

Similarly, DNA encoding the amino acid sequence shown in FIG. 13a~FIG. 13d or the sequence located downstream of the disintegrin domain of the above sequence is prepared, and inserted into an expression vector pEFBOS, followed by transformation of C2 cells by the resulting vector. The transformant is treated as in Example 11 (1), and used as an antigen for immunization of animals such as mouse, rat and hamster. Antibodies recognizing human Meltrin γ is screened as in Example 11 (2), and monoclonal antibodies are prepared as in Example 11 (3).

The invention claimed is:

1. An isolated polypeptide comprising amino acid residues 156 to 686 of SEQ ID NO: 12.

2. An isolated polypeptide consisting of amino acid residues 460 to 656 of SEQ ID NO: 12.

3. An isolated soluble meltrin polypeptide which comprises amino acid residues 156 to 686 of SEQ ID NO:12.

4. An isolated polypeptide comprising amino acid residues 1 to 686 of SEQ ID NO: 12.

5. An isolated soluble meltrin polypeptide which comprises amino acid residues 1 to 686 of SEQ ID NO:12.

6. A polypeptide produced by a process of expressing from a transformant the polypeptide, wherein said transformant comprises a DNA sequence selected from the group consisting of:
   a) the DNA sequence encoding the polypeptide according to one of claims 1 to 5,
   b) base number 466 to 2058 of SEQ ID NO: 11,
   c) base number 1 to 2058 of SEQ ID NO:11, and
   d) SEQ ID NO:11;
   wherein the polypeptide is encoded by said DNA sequence.

7. The polypeptide of claim 6, which is in isolated form.

* * * * *

UNITED STATES PATENT AND TRADEMARK OFFICE
CERTIFICATE OF CORRECTION

| | |
|---|---|
| PATENT NO. | : 7,605,226 B2 |
| APPLICATION NO. | : 11/276738 |
| DATED | : October 20, 2009 |
| INVENTOR(S) | : Fujisawa et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 48 days.

Signed and Sealed this

Fifth Day of October, 2010

David J. Kappos
*Director of the United States Patent and Trademark Office*

SEQUENCE LISTING

```
<160> NUMBER OF SEQ ID NOS: 44

<210> SEQ ID NO 1
<211> LENGTH: 6915
<212> TYPE: DNA
<213> ORGANISM: Unknown Organism
<220> FEATURE:
<223> OTHER INFORMATION: Description of Unknown Organism:
      JM109(pBSMel-alpha), mouse meltrin alpha
```

-continued

```
<220> FEATURE:
<221> NAME/KEY: CDS
<222> LOCATION: (221)..(2929)
<220> FEATURE:
<221> NAME/KEY: unsure
<222> LOCATION: (2930)..(6915)
<223> OTHER INFORMATION: Nucleotide "n" is unknown

<400> SEQUENCE: 1
gccagagtag cgcgcgcgcg cacgcacaca cacggggagg ggagaaagtt tttttttgaa      60
aaaatgaaag gctagactcg ctgctcagcg acccgggcgc tgcgcgaggg ggtcgcggca     120
gactcagggc agtaggactt ccccccagctc ggcgcccgcg tgggatgctg cagcgctggc   180
cgcggggccc ccgaagcagc tgcacgccag gccggcgaca atg gca gag cgc ccg      235
                                              Met Ala Glu Arg Pro
                                                1               5 gcg cgg cgc gcg ccc ccc gcc cgc gcc ctc ctg ctg gcc ctg gct ggg      283
Ala Arg Arg Ala Pro Pro Ala Arg Ala Leu Leu Leu Ala Leu Ala Gly
             10                  15                  20 gcc ctg ctg gcg ccc cgt gca gcc cga ggg atg agt ttg tgg gac cag      331
Ala Leu Leu Ala Pro Arg Ala Ala Arg Gly Met Ser Leu Trp Asp Gln
         25                  30                  35 aga gga gct tac gaa gtg gcc aga gcc tcc ctt ctg agc aag gac cct      379
Arg Gly Ala Tyr Glu Val Ala Arg Ala Ser Leu Leu Ser Lys Asp Pro
     40                  45                  50 ggg atc cca gga cag agc atc cca gcc aag gat cat cca gac gtg ctg      427
Gly Ile Pro Gly Gln Ser Ile Pro Ala Lys Asp His Pro Asp Val Leu
 55                  60                  65 act gtg caa ctg cag ctg gag agc cga gac ctg atc ctc agc ctg gaa      475
Thr Val Gln Leu Gln Leu Glu Ser Arg Asp Leu Ile Leu Ser Leu Glu
 70                  75                  80                  85 agg aat gag gga ctc att gcc aat ggc ttc acg gag acc cat tat ctg      523
Arg Asn Glu Gly Leu Ile Ala Asn Gly Phe Thr Glu Thr His Tyr Leu
             90                  95                 100 caa gat ggt act gat gtc tct ctc act cga aat cac acg gat cat tgt      571
Gln Asp Gly Thr Asp Val Ser Leu Thr Arg Asn His Thr Asp His Cys
        105                 110                 115 tac tac cat gga cat gtg caa gga gat gct gca tca gtg gtc agc ctc      619
Tyr Tyr His Gly His Val Gln Gly Asp Ala Ala Ser Val Val Ser Leu
    120                 125                 130 agt act tgc tct gat ctc cgg gga ctt atc atg ttt gaa aat aaa acg      667
Ser Thr Cys Ser Asp Leu Arg Gly Leu Ile Met Phe Glu Asn Lys Thr
135                 140                 145 tac agc tta gag cca atg aaa aac acc act gac agc tac aaa ctc gtc      715
Tyr Ser Leu Glu Pro Met Lys Asn Thr Thr Asp Ser Tyr Lys Leu Val
150                 155                 160                 165 cca gct gag agc atg acg aac atc caa ggg ctg tgt ggg tca cag cat      763
Pro Ala Glu Ser Met Thr Asn Ile Gln Gly Leu Cys Gly Ser Gln His
            170                 175                 180 aac aag tcc aac ctc acc atg gaa gat gtc tcc cct gga acc tct caa      811
Asn Lys Ser Asn Leu Thr Met Glu Asp Val Ser Pro Gly Thr Ser Gln
        185                 190                 195 atg cgg gca aga agg cat aag aga gag acc ctt aag atg acc aag tac      859
Met Arg Ala Arg Arg His Lys Arg Glu Thr Leu Lys Met Thr Lys Tyr
    200                 205                 210 gta gag ctg gtt att gtg gca gac aac aga gag ttt cag agg caa gga      907
Val Glu Leu Val Ile Val Ala Asp Asn Arg Glu Phe Gln Arg Gln Gly
215                 220                 225 aaa gac ctg gag aaa gtt aag cag cga tta ata gag atc gcc aat cac      955
Lys Asp Leu Glu Lys Val Lys Gln Arg Leu Ile Glu Ile Ala Asn His
230                 235                 240                 245
```

```
gtt gac aag ttt tac aga cca ctg aac atc cgg atc gtg ctg gta gga    1003
Val Asp Lys Phe Tyr Arg Pro Leu Asn Ile Arg Ile Val Leu Val Gly
            250                 255                 260 gtg gaa gtg tgg aat gac atc gac aaa tgc tct ata agc cag gac cca    1051
Val Glu Val Trp Asn Asp Ile Asp Lys Cys Ser Ile Ser Gln Asp Pro
        265                 270                 275 ttc acc agg ctc cat gag ttt cta gac tgg aga aag ata aag ctt cta    1099
Phe Thr Arg Leu His Glu Phe Leu Asp Trp Arg Lys Ile Lys Leu Leu
    280                 285                 290 cct cga aaa tcc cac gac aat gct cag ctt atc agt ggg gtt tat ttc    1147
Pro Arg Lys Ser His Asp Asn Ala Gln Leu Ile Ser Gly Val Tyr Phe
295                 300                 305 caa gga acc acc atc ggc atg gca ccc atc atg agc atg tgc act gca    1195
Gln Gly Thr Thr Ile Gly Met Ala Pro Ile Met Ser Met Cys Thr Ala
310                 315                 320                 325 gaa cag tct gga gga gtt gtc atg gac cat tca gac agc ccc ctt ggt    1243
Glu Gln Ser Gly Gly Val Val Met Asp His Ser Asp Ser Pro Leu Gly
                330                 335                 340 gcc gca gtg acc ttg gca cat gag ctg ggc cac aac ttc ggg atg aac    1291
Ala Ala Val Thr Leu Ala His Glu Leu Gly His Asn Phe Gly Met Asn
            345                 350                 355 cat gac aca ctg gag agg ggc tgc agc tgc aga atg gcc gca gag aaa    1339
His Asp Thr Leu Glu Arg Gly Cys Ser Cys Arg Met Ala Ala Glu Lys
        360                 365                 370 gga ggc tgc atc atg aac ccg tcc acg ggg ttc cca ttc ccc atg gtg    1387
Gly Gly Cys Ile Met Asn Pro Ser Thr Gly Phe Pro Phe Pro Met Val
    375                 380                 385 ttc agc agc tgc agc agg aag gac ctg gag gct agc ctg gag aag ggc    1435
Phe Ser Ser Cys Ser Arg Lys Asp Leu Glu Ala Ser Leu Glu Lys Gly
390                 395                 400                 405 atg ggg atg tgc ctc ttc aac cta cca gag gtc aag cag gcc ttt ggg    1483
Met Gly Met Cys Leu Phe Asn Leu Pro Glu Val Lys Gln Ala Phe Gly
                410                 415                 420 ggc cgg aag tgt gga aat ggc tat gtg gaa gag gga gaa gag tgt gac    1531
Gly Arg Lys Cys Gly Asn Gly Tyr Val Glu Glu Gly Glu Glu Cys Asp
            425                 430                 435 tgc gga gaa ccg gag gaa tgc acg aat cgc tgc tgt aac gct acc acc    1579
Cys Gly Glu Pro Glu Glu Cys Thr Asn Arg Cys Cys Asn Ala Thr Thr
        440                 445                 450 tgt act ctg aag cca gat gct gtg tgc gcg cac ggg cag tgc tgt gaa    1627
Cys Thr Leu Lys Pro Asp Ala Val Cys Ala His Gly Gln Cys Cys Glu
    455                 460                 465 gac tgt cag ctg aag cct cca gga act gca tgc agg ggc tcc agc aac    1675
Asp Cys Gln Leu Lys Pro Pro Gly Thr Ala Cys Arg Gly Ser Ser Asn
470                 475                 480                 485 tcc tgt gac ctc cca gaa ttc tgc aca ggg act gcc cct cac tgt cca    1723
Ser Cys Asp Leu Pro Glu Phe Cys Thr Gly Thr Ala Pro His Cys Pro
                490                 495                 500 gcc aat gtg tac cta cat gat ggc cac ccg tgt cag ggc gtg gat ggt    1771
Ala Asn Val Tyr Leu His Asp Gly His Pro Cys Gln Gly Val Asp Gly
            505                 510                 515 tac tgc tac aac ggc atc tgc cag acc cat gag cag cag tgt gtc acg    1819
Tyr Cys Tyr Asn Gly Ile Cys Gln Thr His Glu Gln Gln Cys Val Thr
        520                 525                 530 ctc tgg gga cca ggt gct aaa ccg gct cct ggc atc tgc ttt gag cga    1867
Leu Trp Gly Pro Gly Ala Lys Pro Ala Pro Gly Ile Cys Phe Glu Arg
    535                 540                 545 gtc aac tct gca gga gat cct tat ggt aac tgt ggc aaa gac tcc aag    1915
Val Asn Ser Ala Gly Asp Pro Tyr Gly Asn Cys Gly Lys Asp Ser Lys
550                 555                 560                 565
```

```
                                                    -continued agc gcc ttc gcc aaa tgt gag ctg aga gat gcc aag tgt ggg aaa atc    1963
Ser Ala Phe Ala Lys Cys Glu Leu Arg Asp Ala Lys Cys Gly Lys Ile
                570             575                 580 cag tgt caa ggt ggt gca agc cga cct gtc att ggt acc aat gct gtt    2011
Gln Cys Gln Gly Gly Ala Ser Arg Pro Val Ile Gly Thr Asn Ala Val
585                 590                 595 tcc ata gaa aca aat atc cca cag cag gaa gga ggt cgg att ctg tgc    2059
Ser Ile Glu Thr Asn Ile Pro Gln Gln Glu Gly Gly Arg Ile Leu Cys
                600             605                 610 cgg ggg acc cat gtg tac ttg ggt gat gac atg cca gac cca ggg ctt    2107
Arg Gly Thr His Val Tyr Leu Gly Asp Asp Met Pro Asp Pro Gly Leu
615                 620                 625 gtg ctt gca gga aca aag tgt gca gaa gga aaa atc tgc ctc aat cgt    2155
Val Leu Ala Gly Thr Lys Cys Ala Glu Gly Lys Ile Cys Leu Asn Arg
630                 635                 640                 645 cga tgt cag aat atc agt gtc ttc ggc gtt cac aag tgt gcc atg cag    2203
Arg Cys Gln Asn Ile Ser Val Phe Gly Val His Lys Cys Ala Met Gln
                650             655                 660 tgc cac ggc cga ggg gta tgt aac aac agg aag aat tgc cac tgt gaa    2251
Cys His Gly Arg Gly Val Cys Asn Asn Arg Lys Asn Cys His Cys Glu
                665             670                 675 gcc cac tgg gct cca ccc ttc tgt gac aag ttt ggc ttt gga gga agc    2299
Ala His Trp Ala Pro Pro Phe Cys Asp Lys Phe Gly Phe Gly Gly Ser
                680             685                 690 aca gac agt ggt ccc atc agg caa gca gat aac cag ggc ttg act gta    2347
Thr Asp Ser Gly Pro Ile Arg Gln Ala Asp Asn Gln Gly Leu Thr Val
695                 700             705 gga atc ctg gtg agc atc ctg tgt ctt ctt gct gct gga ttt gtg gtg    2395
Gly Ile Leu Val Ser Ile Leu Cys Leu Leu Ala Ala Gly Phe Val Val
710                 715             720                 725 tat ctc aaa agg aag acg ttg atg cgg ctg ctg ttc aca cat aaa aaa    2443
Tyr Leu Lys Arg Lys Thr Leu Met Arg Leu Leu Phe Thr His Lys Lys
                730             735                 740 acc acc atg gaa aag cta agg tgt gtg cac cct tcc cgg aca ccc agt    2491
Thr Thr Met Glu Lys Leu Arg Cys Val His Pro Ser Arg Thr Pro Ser
                745             750                 755 ggc cct cac ctt ggc cag gct cac cac acc ccc ggg aaa ggc ctg ctg    2539
Gly Pro His Leu Gly Gln Ala His His Thr Pro Gly Lys Gly Leu Leu
                760             765                 770 atg aac cgg gca cca cat ttc aat acc ccc aag gac agg cac tcg ctg    2587
Met Asn Arg Ala Pro His Phe Asn Thr Pro Lys Asp Arg His Ser Leu
775                 780             785 aaa tgc cag aac atg gac atc agc agg ccc ctc gac gct cga gcc gtc    2635
Lys Cys Gln Asn Met Asp Ile Ser Arg Pro Leu Asp Ala Arg Ala Val
790                 795             800                 805 cca cag ctt cag tca cct cag cga gtg ctc ctg cct ctc cac cag acc    2683
Pro Gln Leu Gln Ser Pro Gln Arg Val Leu Leu Pro Leu His Gln Thr
                810             815                 820 cca cgt gca ccc agt ggc cct gcc agg ccc ctg ccc gcc agt cct gca    2731
Pro Arg Ala Pro Ser Gly Pro Ala Arg Pro Leu Pro Ala Ser Pro Ala
825                 830             835 gtc agg cag gcc cag ggc att cga aaa ccc agt cct cct cag aag cct    2779
Val Arg Gln Ala Gln Gly Ile Arg Lys Pro Ser Pro Pro Gln Lys Pro
                840             845                 850 ctg cct gct gat cca ctg agc agg act tct cgg ctc act agt gcc ttg    2827
Leu Pro Ala Asp Pro Leu Ser Arg Thr Ser Arg Leu Thr Ser Ala Leu
855                 860             865 gtg agg acc cca ggg cag cag gaa cct ggg cac cgc cca gcc ccc atc    2875
Val Arg Thr Pro Gly Gln Gln Glu Pro Gly His Arg Pro Ala Pro Ile
870                 875             880                 885
```

| | |
|---|---|
| aga cct gcc cct aag cat caa gta ccc aga cct tcc cac aat gcc tat<br>Arg Pro Ala Pro Lys His Gln Val Pro Arg Pro Ser His Asn Ala Tyr<br>                      890                     895                   900 | 2923 |
| atc aag tgagaagcca gcccagaccg gtcctcaaca gtgaagacag aagtttgcac<br>Ile Lys | 2979 |
| tatcttcagc tccattggag ttgttgttgt accaactttc cgagtttcta aagtgtttaa | 3039 |
| aacaccattc tctccagacc ctggagccac tgccatcggt gctgtgctgt ggtgctttgt | 3099 |
| gtacttgctc aggaacttgt aagttattaa tttatgcaga gtgtctatta ctgcgcaggg | 3159 |
| cgccgtagca ggcatttgta ccatcacagg gcttttctac agaaggaagg ctcctcgtgc | 3219 |
| ttttgttttt ctggaggact tgaaataccc tgcttgatgg gacctaagat gagatgttta | 3279 |
| ctttctattc aaggccttat cggaaaatag ctccccacct tcccaaggct gttatggtac | 3339 |
| cagacacaca gctcaggaca ccccagggag aacctggcat gggttttctt tgtttgcttt | 3399 |
| catttttatct tttatatttt ggtatcccta tcttgggttg tagccagggc cttcaggaag | 3459 |
| gtcttgggcc actgcatgct aatggccttc aggtcctgca ccctgaagct ctcagacaac | 3519 |
| aagtaggatc tgcttttctag ccagcagctt tggagagaac ctggggtact gaaaagaagg | 3579 |
| tttggggtgt ggttatacca ggatggagac tggaatccta atctgggcaa acatctgacc | 3639 |
| ttgagctgag cagccatgag cacctctagg aagcaaggac ggctgaggtg ctgcacaagg | 3699 |
| ctctgctttg agagctggca ggggcttctc tctggctgcc ctttgcagag tgctagctgg | 3759 |
| catggcatgt tgtttacatc gggaacagtg gtgtttctac aagaaagcca ctgcctgggc | 3819 |
| actgcagacc tccgtctcct gcccatttag agctaagcaa attaccacat tgtcttctgg | 3879 |
| actgtaatac aatgaccctg tgttctgaca gatagaggag gctttctatg gaaccataac | 3939 |
| tattttcana tgtgaactag taaccagatc tagtcgatca actctggaga tagaaatctc | 3999 |
| cttttttactg caaggctcga cttattaaaa attaggcaga atccatatgc ttgcaaaagc | 4059 |
| tataaccacg tggaatgctc ttctcatggc acagcctgag tctggtatcc ttattagtag | 4119 |
| ccattggaca aagcacccaa agttacctgt gtgttctctt caaggcatcc taatttcttc | 4179 |
| agcatagaga gactcggtct tcctcacatt ctgaacatac ctatcaatga ctaagncagc | 4239 |
| aaggcaatcc gtttccgaat actgagttgc tcacggnaag gcaacctcag cccaggnaaa | 4299 |
| cttttttcct ctgntctttc agtatgtgac tggggagcta ccttcagaag caaattttca | 4359 |
| aggtggnctc aaccccatng gatgaaagnt atttttttaa aaaataatta atggtaatgc | 4419 |
| cagagggctt tcctggcntc cagatngggg cgtaggnttg actagctttc acgacagaag | 4479 |
| gtaaatgaca gcagtcctct acctcgtctg actgctttaa gatcaaggct tcttttggaag | 4539 |
| ggtaactaac attaatggct ggcctgtgcc ttgaagcaga agggaaaata cagataagga | 4599 |
| atttggtttg ctttctagaa tccaaaactg tatccagcat tgggaagcat ggtcttcatg | 4659 |
| actgggtaaa taaatccacg tcacagatgc ataaaagaat aactcttatg acatgcctct | 4719 |
| ttttgtggca cagagacaat attgctgcca ctgagatgca tacaaaattt ctgtaactga | 4779 |
| tatgtcattc agtagttgta ttaaggccaa acatccacaa ctgtaaagac ttatagagtt | 4839 |
| gtgtgggcgt tgtcttgtga gacacacaaa gcctcagctg aagcgtatga gctcctcctc | 4899 |
| caggtgggag tgatggggag gctagaaaca cacaaagaca acagaagagc tttggtttgg | 4959 |
| ggggggtgca gagagagtgt ggtttagagg aagttggagc catgatcttc tgccatctcc | 5019 |
| ccagtgtcca ctaaggatgc cgatggtgcc ttaccagctg tgcagtgctg gctgcttgct | 5079 |
| tttacagagc catgcattca tttctgaata agaacatatt taatcctgaa attcccttac | 5139 |

```
aggacagaca gtgttactaa aggaattcct ctaagataca gtagttgtca attaaagcat    5199
atttagcagt aacttcaatt ttaacaaaat tgggacccaa tagccagcat gagggttctt    5259
tgacagaggg tagtttctct ctcccttttct ccatccttca aatgacaaga cgtcaaaact   5319
aatacagttc atttgcagtc catctcatgc ttatacatac tagaggtatg actaaagttg    5379
gttgagtcat gggagaccat ccctgagaaa gtccagtcgg tcaagagcct tgccaggtgg    5439
cgtggctgga cgtcctcctt tgttcctgc actgaggaat agttataggt tatgtgaccc     5499
cacttcacag gcaagtggga ggcgaacctt gcaggcatgc cccttaaaag ctggtctcag    5559
acctacaata gtcctgagtc tgttttccca gcacacagag agcaacaatg cagttttcca    5619
tttcaaaata tgcatgccga gtttgcgctc tgtgtgagtg tttccaggtt acacatatgg    5679
gatgacatca cagaaaccac acaagcaaca aattaaattc tacgggaaga atcctcctg     5739 actggtctct gaggagacat ttttatgcct tcttaacttt attaggaact ctcaggctga    5799
agctaggggt cattgtcccc caacaaatca atacaaagcc atcaatgnac tctcgaagaa    5859
ctgccaaacc ctgatctgtg tgaatgttct caggagcctg tgatccccat ggtgctanaa    5919
agaggctgga gctgggccaa caagaaggcc taagagtcct cctgcctctc agcagatgtt    5979
tactgagcac tctgagccag aagcaccccg acaaccagga ggacgatngc tgggcagtag    6039
ggcgcccagc cacttgcagc tcttttcctct gaggcccgct ttgtgttta attcccttct    6099 gtcaggcccc aancagngga cactgtccta tagacctccc tctnagtttt cagacggcct    6159
aagccataca caaatgcccc agactaagaa acaccaatac ntcccagcag tccccaagaa    6219
ctggttttta aacactatga caagtagaag agggtgtcac agaggccatt ttttttcttt    6279
tctttccact catactggaa cctaggtcct ctctctacac tcctagttcc tttacacaac    6339
tcggcagtgg ctccattaca ccaaggacac agaaaaacac aggtaccgat ttgccttcct    6399
ctcctgccaa tcacaagtgc cttactctga ccagacccat gacaaaacct ctgtcatcca    6459
agagagccaa ctctctacct tgttactac ttcaagccaa tgtggtaact gctaaccttc     6519
aagggtcacc taaacagtat agtccaacct tcaccaggac catagcacag agcaacctcc    6579
agnacacaca cacacacaca ccttgaatct atcccacagc atatcaaccc acagtgacct    6639
ccctcccacc gccttgttct aattacaagg tgaagatggc catagaaaat caagttagca    6699
ctaattacaa aatgcttttg atgcaacctg aatttcccaa tggcacctat tgctttgaaa    6759
ctctgatgag ttaagtcatg ctctgggagc tgtgagcccc atgctcagat ccactgggca    6819 gggggggactc cttgcaggag acatgggcac acatatgaat gtaccatttc catgcctttt    6879
gtggagtaca gacatataaa cataaatact tccatt                              6915
```

<210> SEQ ID NO 2
<211> LENGTH: 903
<212> TYPE: PRT
<213> ORGANISM: Unknown Organism
<220> FEATURE:
<223> OTHER INFORMATION: Description of Unknown Organism:
    JM109(pBSMel-alpha), mouse meltrin alpha

<400> SEQUENCE: 2

Met Ala Glu Arg Pro Ala Arg Arg Ala Pro Pro Ala Arg Ala Leu Leu
  1               5                  10                  15

Leu Ala Leu Ala Gly Ala Leu Leu Ala Pro Arg Ala Ala Arg Gly Met
             20                  25                  30

Ser Leu Trp Asp Gln Arg Gly Ala Tyr Glu Val Ala Arg Ala Ser Leu
         35                  40                  45

```
Leu Ser Lys Asp Pro Gly Ile Pro Gly Gln Ser Ile Pro Ala Lys Asp
     50                  55                  60

His Pro Asp Val Leu Thr Val Gln Leu Gln Leu Glu Ser Arg Asp Leu
 65                  70                  75                  80

Ile Leu Ser Leu Glu Arg Asn Glu Gly Leu Ile Ala Asn Gly Phe Thr
                 85                  90                  95

Glu Thr His Tyr Leu Gln Asp Gly Thr Asp Val Ser Leu Thr Arg Asn
            100                 105                 110

His Thr Asp His Cys Tyr Tyr His Gly His Val Gln Gly Asp Ala Ala
        115                 120                 125

Ser Val Val Ser Leu Ser Thr Cys Ser Asp Leu Arg Gly Leu Ile Met
    130                 135                 140

Phe Glu Asn Lys Thr Tyr Ser Leu Glu Pro Met Lys Asn Thr Thr Asp
145                 150                 155                 160

Ser Tyr Lys Leu Val Pro Ala Glu Ser Met Thr Asn Ile Gln Gly Leu
                165                 170                 175

Cys Gly Ser Gln His Asn Lys Ser Asn Leu Thr Met Glu Asp Val Ser
            180                 185                 190

Pro Gly Thr Ser Gln Met Arg Ala Arg Arg His Lys Arg Glu Thr Leu
        195                 200                 205

Lys Met Thr Lys Tyr Val Glu Leu Val Ile Val Ala Asp Asn Arg Glu
    210                 215                 220

Phe Gln Arg Gln Gly Lys Asp Leu Glu Lys Val Lys Gln Arg Leu Ile
225                 230                 235                 240

Glu Ile Ala Asn His Val Asp Lys Phe Tyr Arg Pro Leu Asn Ile Arg
                245                 250                 255

Ile Val Leu Val Gly Val Glu Val Trp Asn Asp Ile Asp Lys Cys Ser
            260                 265                 270

Ile Ser Gln Asp Pro Phe Thr Arg Leu His Glu Phe Leu Asp Trp Arg
        275                 280                 285

Lys Ile Lys Leu Leu Pro Arg Lys Ser His Asp Asn Ala Gln Leu Ile
    290                 295                 300

Ser Gly Val Tyr Phe Gln Gly Thr Thr Ile Gly Met Ala Pro Ile Met
305                 310                 315                 320

Ser Met Cys Thr Ala Glu Gln Ser Gly Gly Val Val Met Asp His Ser
                325                 330                 335

Asp Ser Pro Leu Gly Ala Ala Val Thr Leu Ala His Glu Leu Gly His
            340                 345                 350

Asn Phe Gly Met Asn His Asp Thr Leu Glu Arg Gly Cys Ser Cys Arg
        355                 360                 365

Met Ala Ala Glu Lys Gly Gly Cys Ile Met Asn Pro Ser Thr Gly Phe
    370                 375                 380

Pro Phe Pro Met Val Phe Ser Ser Cys Ser Arg Lys Asp Leu Glu Ala
385                 390                 395                 400

Ser Leu Glu Lys Gly Met Gly Met Cys Leu Phe Asn Leu Pro Glu Val
                405                 410                 415

Lys Gln Ala Phe Gly Gly Arg Lys Cys Gly Asn Gly Tyr Val Glu Glu
            420                 425                 430

Gly Glu Glu Cys Asp Cys Gly Glu Pro Glu Glu Cys Thr Asn Arg Cys
        435                 440                 445

Cys Asn Ala Thr Thr Cys Thr Leu Lys Pro Asp Ala Val Cys Ala His
    450                 455                 460
```

```
Gly Gln Cys Cys Glu Asp Cys Gln Leu Lys Pro Pro Gly Thr Ala Cys
465                 470                 475                 480

Arg Gly Ser Ser Asn Ser Cys Asp Leu Pro Glu Phe Cys Thr Gly Thr
                485                 490                 495

Ala Pro His Cys Pro Ala Asn Val Tyr Leu His Asp Gly His Pro Cys
            500                 505                 510

Gln Gly Val Asp Gly Tyr Cys Tyr Asn Gly Ile Cys Gln Thr His Glu
        515                 520                 525

Gln Gln Cys Val Thr Leu Trp Gly Pro Gly Ala Lys Pro Ala Pro Gly
530                 535                 540

Ile Cys Phe Glu Arg Val Asn Ser Ala Gly Asp Pro Tyr Gly Asn Cys
545                 550                 555                 560

Gly Lys Asp Ser Lys Ser Ala Phe Ala Lys Cys Glu Leu Arg Asp Ala
                565                 570                 575

Lys Cys Gly Lys Ile Gln Cys Gln Gly Gly Ala Ser Arg Pro Val Ile
                580                 585                 590

Gly Thr Asn Ala Val Ser Ile Glu Thr Asn Ile Pro Gln Gln Glu Gly
            595                 600                 605

Gly Arg Ile Leu Cys Arg Gly Thr His Val Tyr Leu Gly Asp Asp Met
610                 615                 620

Pro Asp Pro Gly Leu Val Leu Ala Gly Thr Lys Cys Ala Glu Gly Lys
625                 630                 635                 640

Ile Cys Leu Asn Arg Arg Cys Gln Asn Ile Ser Val Phe Gly Val His
                645                 650                 655

Lys Cys Ala Met Gln Cys His Gly Arg Gly Val Cys Asn Asn Arg Lys
                660                 665                 670

Asn Cys His Cys Glu Ala His Trp Ala Pro Pro Phe Cys Asp Lys Phe
            675                 680                 685

Gly Phe Gly Gly Ser Thr Asp Ser Gly Pro Ile Arg Gln Ala Asp Asn
        690                 695                 700

Gln Gly Leu Thr Val Gly Ile Leu Val Ser Ile Leu Cys Leu Leu Ala
705                 710                 715                 720

Ala Gly Phe Val Val Tyr Leu Lys Arg Lys Thr Leu Met Arg Leu Leu
                725                 730                 735

Phe Thr His Lys Lys Thr Thr Met Glu Lys Leu Arg Cys Val His Pro
                740                 745                 750

Ser Arg Thr Pro Ser Gly Pro His Leu Gly Gln Ala His His Thr Pro
        755                 760                 765

Gly Lys Gly Leu Leu Met Asn Arg Ala Pro His Phe Asn Thr Pro Lys
770                 775                 780

Asp Arg His Ser Leu Lys Cys Gln Asn Met Asp Ile Ser Arg Pro Leu
785                 790                 795                 800

Asp Ala Arg Ala Val Pro Gln Leu Gln Ser Pro Gln Arg Val Leu Leu
                805                 810                 815

Pro Leu His Gln Thr Pro Arg Ala Pro Ser Gly Pro Ala Arg Pro Leu
            820                 825                 830

Pro Ala Ser Pro Ala Val Arg Gln Ala Gln Gly Ile Arg Lys Pro Ser
        835                 840                 845

Pro Pro Gln Lys Pro Leu Pro Ala Asp Pro Leu Ser Arg Thr Ser Arg
850                 855                 860

Leu Thr Ser Ala Leu Val Arg Thr Pro Gly Gln Gln Glu Pro Gly His
865                 870                 875                 880
```

```
Arg Pro Ala Pro Ile Arg Pro Ala Pro Lys His Gln Val Pro Arg Pro
            885                 890                 895

Ser His Asn Ala Tyr Ile Lys
            900

<210> SEQ ID NO 3
<211> LENGTH: 6352
<212> TYPE: DNA
<213> ORGANISM: Unknown Organism
<220> FEATURE:
<223> OTHER INFORMATION: Description of Unknown Organism: Clone:
      JM109(pBSMel-beta), mouse beta meltrin
<220> FEATURE:
<221> NAME/KEY: CDS
<222> LOCATION: (63)..(2822)
<220> FEATURE:
<221> NAME/KEY: unsure
<222> LOCATION: (1782)..(2822)
<223> OTHER INFORMATION: Amino Acid "Xaa" unknown

<400> SEQUENCE: 3
ggccgggggc aggcaatggc aggggatgtg tgattgcgga cagtgagagg gccgttgcta        60 tc atg ccc ggg cgc gcg ggc gtc gcc cgg ttc tgc ttg ctg gct ctc         107
   Met Pro Gly Arg Ala Gly Val Ala Arg Phe Cys Leu Leu Ala Leu
   1               5                  10                  15 gct ctg cag cta cat tgg ccg ctg gcg gcg tgc gag ccg gga tgg acc        155
Ala Leu Gln Leu His Trp Pro Leu Ala Ala Cys Glu Pro Gly Trp Thr
                20                  25                  30 aca aga gga agc caa gaa ggt agc cct ccg cta cag cat gaa ctc ata        203
Thr Arg Gly Ser Gln Glu Gly Ser Pro Pro Leu Gln His Glu Leu Ile
            35                  40                  45 ata cct cag tgg cgg act tca gaa agc cct ggg aga gga aag cat cca        251
Ile Pro Gln Trp Arg Thr Ser Glu Ser Pro Gly Arg Gly Lys His Pro
        50                  55                  60 ctc aga gca gag ctc agg gtc atg gct gaa ggg cga gag ctg atc cta        299
Leu Arg Ala Glu Leu Arg Val Met Ala Glu Gly Arg Glu Leu Ile Leu
    65                  70                  75 gac ctg gag aag aac gag cac ctt ttt gct cca gcc tac aca gaa acc        347
Asp Leu Glu Lys Asn Glu His Leu Phe Ala Pro Ala Tyr Thr Glu Thr
80                  85                  90                  95 tgc tac act gca agt ggc aat cct caa acc agc acg ctg aag tct gag        395
Cys Tyr Thr Ala Ser Gly Asn Pro Gln Thr Ser Thr Leu Lys Ser Glu
                100                 105                 110 gat cac tgc ttt tac cac ggg act gtg agg gac gtg gat gag tcc agt        443
Asp His Cys Phe Tyr His Gly Thr Val Arg Asp Val Asp Glu Ser Ser
            115                 120                 125 gtc acg ctc agc acc tgc cgg gga att aga gga ctg att ata gtg aga        491
Val Thr Leu Ser Thr Cys Arg Gly Ile Arg Gly Leu Ile Ile Val Arg
        130                 135                 140 agt aac ctc agc tac atc atc gag ccc gtc cct aac agc gac agc caa        539
Ser Asn Leu Ser Tyr Ile Ile Glu Pro Val Pro Asn Ser Asp Ser Gln
    145                 150                 155 cac cgt att tac aga tcc gaa cat ctc acg ctg ccc ccg ggg aac tgt        587
His Arg Ile Tyr Arg Ser Glu His Leu Thr Leu Pro Pro Gly Asn Cys
160                 165                 170                 175 ggg ttc gag cac tcc ggg ccc acc tcg aag gac tgg gcc ctt cag ttt        635
Gly Phe Glu His Ser Gly Pro Thr Ser Lys Asp Trp Ala Leu Gln Phe
                180                 185                 190 aca cat cag acc aaa aag caa cct cgc aga atg aaa cgg gaa gat cta        683
Thr His Gln Thr Lys Lys Gln Pro Arg Arg Met Lys Arg Glu Asp Leu
            195                 200                 205
```

| | | |
|---|---|---|
| cac tct atg aag tac gtg gag ctt tac ctg gtg gct gat tat gca gag<br>His Ser Met Lys Tyr Val Glu Leu Tyr Leu Val Ala Asp Tyr Ala Glu<br>210 215 220 | | 731 |
| ttt cag aag aat cga cat gac cag gat gcc acc aaa cgc aag ctc atg<br>Phe Gln Lys Asn Arg His Asp Gln Asp Ala Thr Lys Arg Lys Leu Met<br>225 230 235 | | 779 |
| gag att gcc aac tat gtt gat aag ttt tac cgc tcc ctg aac atc cga<br>Glu Ile Ala Asn Tyr Val Asp Lys Phe Tyr Arg Ser Leu Asn Ile Arg<br>240 245 250 255 | | 827 |
| att gca ctt gtc ggc ttg gag gtg tgg acg cat ggg gat aag tgt gaa<br>Ile Ala Leu Val Gly Leu Glu Val Trp Thr His Gly Asp Lys Cys Glu<br>260 265 270 | | 875 |
| gtt tca gag aat ccc tac tct acc ctc tgg tcc ttt ctt agt tgg agg<br>Val Ser Glu Asn Pro Tyr Ser Thr Leu Trp Ser Phe Leu Ser Trp Arg<br>275 280 285 | | 923 |
| cgc aag ctg ctt gct cag aag agc cat gac aat gct cag cta atc acg<br>Arg Lys Leu Leu Ala Gln Lys Ser His Asp Asn Ala Gln Leu Ile Thr<br>290 295 300 | | 971 |
| ggc agg tcc ttc caa ggc acc acc att ggc ctg gcc ccc ctc atg gcc<br>Gly Arg Ser Phe Gln Gly Thr Thr Ile Gly Leu Ala Pro Leu Met Ala<br>305 310 315 | | 1019 |
| atg tgc tcc gtg tac cag tct gga gga gtt agc atg gac cac tcc gag<br>Met Cys Ser Val Tyr Gln Ser Gly Gly Val Ser Met Asp His Ser Glu<br>320 325 330 335 | | 1067 |
| aat gcc att ggt gta gcc tcc act gtg gcc cat gag att ggc cac aac<br>Asn Ala Ile Gly Val Ala Ser Thr Val Ala His Glu Ile Gly His Asn<br>340 345 350 | | 1115 |
| ttt ggc atg agc cat gat tct gca cac tgc tgt tct gcc agt gca gcc<br>Phe Gly Met Ser His Asp Ser Ala His Cys Cys Ser Ala Ser Ala Ala<br>355 360 365 | | 1163 |
| gat ggc ggc tgc atc atg gcc gcc gcc acc ggg cac cct ttc ccc aaa<br>Asp Gly Gly Cys Ile Met Ala Ala Ala Thr Gly His Pro Phe Pro Lys<br>370 375 380 | | 1211 |
| gtg ttc agt tgg tgt aac agg aag gag ctg gac agg tat ctg cag aca<br>Val Phe Ser Trp Cys Asn Arg Lys Glu Leu Asp Arg Tyr Leu Gln Thr<br>385 390 395 | | 1259 |
| gga gga ggg atg tgt ctc tcc aac atg ccg gac act agg acg ctg tat<br>Gly Gly Gly Met Cys Leu Ser Asn Met Pro Asp Thr Arg Thr Leu Tyr<br>400 405 410 415 | | 1307 |
| gga ggc cgg agg tgt ggc aac ggg tac ctg gaa gac ggt gaa gaa tgt<br>Gly Gly Arg Arg Cys Gly Asn Gly Tyr Leu Glu Asp Gly Glu Glu Cys<br>420 425 430 | | 1355 |
| gac tgt gga gaa gag gag gaa tgt aag aac cct tgc tgc aat gcc tcc<br>Asp Cys Gly Glu Glu Glu Glu Cys Lys Asn Pro Cys Cys Asn Ala Ser<br>435 440 445 | | 1403 |
| aac tgc act ctg aag gaa ggg gca gag tgt gcc cat ggt tcc tgc tgc<br>Asn Cys Thr Leu Lys Glu Gly Ala Glu Cys Ala His Gly Ser Cys Cys<br>450 455 460 | | 1451 |
| cac cag tgc aag ctg gtg gct cct gga acc cag tgt cgg gag cag gtt<br>His Gln Cys Lys Leu Val Ala Pro Gly Thr Gln Cys Arg Glu Gln Val<br>465 470 475 | | 1499 |
| cgg caa tgt gac ctc ccc gag ttc tgc acc ggc aag tct ccc cac tgc<br>Arg Gln Cys Asp Leu Pro Glu Phe Cys Thr Gly Lys Ser Pro His Cys<br>480 485 490 495 | | 1547 |
| ccc acc aac tat tat cag atg gat ggc acc ccc tgc gag ggt ggc cag<br>Pro Thr Asn Tyr Tyr Gln Met Asp Gly Thr Pro Cys Glu Gly Gly Gln<br>500 505 510 | | 1595 |
| gcc tac tgc tac aac ggc atg tgc ctc act tac cag gaa cag tgc cag<br>Ala Tyr Cys Tyr Asn Gly Met Cys Leu Thr Tyr Gln Glu Gln Cys Gln<br>515 520 525 | | 1643 |

```
cag ctg tgg gga cct gga gcc cgg cct gcc ctc gat ctt tgc ttt gag    1691
Gln Leu Trp Gly Pro Gly Ala Arg Pro Ala Leu Asp Leu Cys Phe Glu
        530                 535                 540 agg gtg aat gct gct ggt gac acc tat gga aac tgt ggc aag ggc ttg    1739
Arg Val Asn Ala Ala Gly Asp Thr Tyr Gly Asn Cys Gly Lys Gly Leu
545                 550                 555 aat ggc caa tac agg aag tgc agt ccc agg gat gcc aag tgt ggs aag    1787
Asn Gly Gln Tyr Arg Lys Cys Ser Pro Arg Asp Ala Lys Cys Xaa Lys
560                 565                 570                 575 att cag tgc cag agc acc cag gcc cgg ccc ctg gaa tcc aac gca gta    1835
Ile Gln Cys Gln Ser Thr Gln Ala Arg Pro Leu Glu Ser Asn Ala Val
                580                 585                 590 tct att gac acc acc atc acc ttg aac ggg agg cgg atc cac tgt cgg    1883
Ser Ile Asp Thr Thr Ile Thr Leu Asn Gly Arg Arg Ile His Cys Arg
            595                 600                 605 ggc acc cac gtc tac cgg ggt cct gag gag gag gaa ggg gaa ggt gac    1931
Gly Thr His Val Tyr Arg Gly Pro Glu Glu Glu Glu Gly Glu Gly Asp
        610                 615                 620 atg ctg gac cca ggg ctg gtg atg act gga acc aag tgt ggc cac aac    1979
Met Leu Asp Pro Gly Leu Val Met Thr Gly Thr Lys Cys Gly His Asn
625                 630                 635 cat att tgc ttc gag ggg cag tgc agg aac acc tcc ttc ttt gag acg    2027
His Ile Cys Phe Glu Gly Gln Cys Arg Asn Thr Ser Phe Phe Glu Thr
640                 645                 650                 655 gaa ggc tgt ggg aaa aag tgc aat ggc cac ggg gtc tgc aac aac aac    2075
Glu Gly Cys Gly Lys Lys Cys Asn Gly His Gly Val Cys Asn Asn Asn
                660                 665                 670 aag aac tgt cat tgc ttc cct ggc tgg tct cca cct ttc tgt aac acc    2123
Lys Asn Cys His Cys Phe Pro Gly Trp Ser Pro Pro Phe Cys Asn Thr
            675                 680                 685 ccg gga gat ggt ggc agc gtc gac agt ggt cct ttg ccc cct aag agt    2171
Pro Gly Asp Gly Gly Ser Val Asp Ser Gly Pro Leu Pro Pro Lys Ser
        690                 695                 700 gtg ggt ccc gtg atc gct ggg gtg ttt tca gct ctc ttc gtg ttg gca    2219
Val Gly Pro Val Ile Ala Gly Val Phe Ser Ala Leu Phe Val Leu Ala
705                 710                 715 gtt ctg gtg cta ctg tgt cac tgc tac aga cag agc cac aaa ctg ggc    2267
Val Leu Val Leu Leu Cys His Cys Tyr Arg Gln Ser His Lys Leu Gly
720                 725                 730                 735 aaa ccc tcg gct ctc cct ttc aag ctg cgg cat cag ttc agt tgt ccc    2315
Lys Pro Ser Ala Leu Pro Phe Lys Leu Arg His Gln Phe Ser Cys Pro
                740                 745                 750 ttc agg gta tct cag agt ggt gga act ggc cat gcc aac cca act ttc    2363
Phe Arg Val Ser Gln Ser Gly Gly Thr Gly His Ala Asn Pro Thr Phe
            755                 760                 765 aag ttg cag acc ccc cag ggc aag cga aag gtg act aac acc cct gaa    2411
Lys Leu Gln Thr Pro Gln Gly Lys Arg Lys Val Thr Asn Thr Pro Glu
        770                 775                 780 tcc ctc cgg aag ccg tcc cac ccc cct ctc cgg ccc cct cca gac tac    2459
Ser Leu Arg Lys Pro Ser His Pro Pro Leu Arg Pro Pro Pro Asp Tyr
785                 790                 795 ctc cgc gtt gaa tcg cca cct gca cca ttg tcg gca cat ctg aac agg    2507
Leu Arg Val Glu Ser Pro Pro Ala Pro Leu Ser Ala His Leu Asn Arg
800                 805                 810                 815 gct gct ggg agc tcc cca gaa gct ggg gct cga ata gaa aga aag gag    2555
Ala Ala Gly Ser Ser Pro Glu Ala Gly Ala Arg Ile Glu Arg Lys Glu
                820                 825                 830 tca gcc agg agg cct ccc cca agc cga ccc atg ccc cct gca cct aac    2603
Ser Ala Arg Arg Pro Pro Pro Ser Arg Pro Met Pro Pro Ala Pro Asn
            835                 840                 845
```

| | |
|---|---|
| tgc cta ctg tcc cag gac ttc tcc agg cct cga cca cct cag aag gca<br>Cys Leu Leu Ser Gln Asp Phe Ser Arg Pro Arg Pro Pro Gln Lys Ala<br>850       855       860 | 2651 |
| ctc cca gcc aat ccg gtg cca ggc caa agg acc ggt ccc agg tca gga<br>Leu Pro Ala Asn Pro Val Pro Gly Gln Arg Thr Gly Pro Arg Ser Gly<br>865       870       875 | 2699 |
| ggc acc tcc ctg ctt cag ccc cct act tct ggt cct cag ccc ccc agg<br>Gly Thr Ser Leu Leu Gln Pro Pro Thr Ser Gly Pro Gln Pro Pro Arg<br>880       885       890       895 | 2747 |
| cct cca gca gtg cct gtt cca aag cta ccc gag tac cga tca cag agg<br>Pro Pro Ala Val Pro Val Pro Lys Leu Pro Glu Tyr Arg Ser Gln Arg<br>900       905       910 | 2795 |
| gtt gga gca ata att agc tcc aag atc tagaagtgtc gagaagtttc<br>Val Gly Ala Ile Ile Ser Ser Lys Ile<br>915       920 | 2842 |
| ttgttccgat ggaagactcc ggatgccatg aaggtccag aagaaagacg ccttctcacc | 2902 |
| catcctgaag ctttggcagc cttctggaac gtccctcatc cccagaatct cccttcttac | 2962 |
| ccgagtgcct cctgcttcct ccgaggccca gggggactca tatccaatgg ctcctaagtg | 3022 |
| tttgtcctgt gcaatataca gcccaggag ggaagggaag cacggcgagg agggtgggaa | 3082 |
| aggttctccc tcagcccact agccaagagc taccagcgat gctcagggaa ggcttgagct | 3142 |
| ggggtcctcc tctgcggagc ttggagaagg tacccatcct ggtcctatgc tggcaggaac | 3202 |
| acacgcgagt gtcactgatt ggcctccttc tgggatccca ggctgctgag aagctactg | 3262 |
| ctacatccct accccaaggg gcttggtcaa ggtgcctgty cctggctctc tggctgcatg | 3322 |
| taataagcca tgctcccctc ccctgccttt cttcacattc ccactcccat atttacacgg | 3382 |
| gtcactctga ctcagacagg tactatttgt aagtagcata gacagcaggg gggtggggtg | 3442 |
| gtcaacctgt gtcccctctg agccgttatg ccaaaggtca ctaaggacat ttagaatccc | 3502 |
| catccatcca tccatccatc catccatcca tccattcatc catccccagt gttccatgtg | 3562 |
| tcaccttctc cttttccagc atccctatcc tatggtgctt tggtggtgaa ctatggcagt | 3622 |
| cctgacttgc tgatgaccat atgctggtga cctacaaatc gggatcctgc catatggggt | 3682 |
| cgccactgga ctttctgcac tggttctcaa gagcgttgag ccgagtgggc gtgtatgttt | 3742 |
| gtgtgtgtgt gtgtgtgtgt gtgtgtgtgt gtgtgtgtgt gtgtgtgtgt gtgtgtgtgt | 3802 |
| gaaagagaca gaggcaatga gagagacaga catgcaggca ggccgacagc tctgcatgta | 3862 |
| cttgtgtttt acggcctcaa gcagtataag ggacctcctc cttatttctg actcatatct | 3922 |
| aagtaaggtt ccccaggacm agccacagct gtactgaggg gggctgacat gtttggcatc | 3982 |
| ctggctatag tattgtatac acagggccac cagccccgcc ctagtggtca gctctgaggg | 4042 |
| gggactggtg actctgaaca gatcgatgtc aacagccatg gtgaaccaga tctgggcagg | 4102 |
| gttccccaaa ctctattcaa ccagagtttt atcacgcanc tcatcgggtc tctcctggtt | 4162 |
| gctgccccga ggtgatcgtc atggaaaatg ctgagaaggt gggaatggga tggggtggac | 4222 |
| cttctcttgc ttggtgctcc gctatttgga acagttctta cacatttgct gggcctggcc | 4282 |
| tctgagaggc catcttccac ccccagaaag gtgctaatgg cactgcagag ggctctctag | 4342 |
| gggcctcccc gccccaacag caagcagttg ttagctcttg aaccctcca gaggaagagg | 4402 |
| caagcgtttg acttccccctt taccacctga ggcctcctta tatctcttcc cagagtaagc | 4462 |
| tttgggattg tagacatgtg ggagctatga cagacgtggc ctggggtaga aagatctcag | 4522 |
| gaaagcacct ttctccttttt cagggtgacc gtgctcttca cactctctga ggcctcagtc | 4582 |
| catgtcctat atcagtttct cttttgtgtg ctttaccaag tggccggtga ctacaggcca | 4642 |

-continued

```
ccccgattct caccacaaag ttagaaaccc tccactttct gtcccttgaa ccatatcaga     4702
aaaagaccca tttccttgct ctttggtaat cacttctgtt ttttcttctt cattactgtg     4762
ctaccacctc catcccatga cattattctg tgangtgtaa gaggacggtg ttttnttant     4822
cttgggagan atgtcggcag ctgctctaca cacaacttca ctcaaggctt tgtctccaga     4882
ggccagctag gctgtcacag gcaggaatcc cttcccatct gctttgtgaa gggtcccata     4942
caggtgtatc tagacttcaa ggacagggtt tgtctcacag gattgtcact taggagatga     5002
aagaatatta ccacatgagg aggaggggca gttgcaacag aacactttgg tcttcctaca     5062
ccaagtctgt gagggcatcc aagactgaat gaaagcgctt ttcttatgca tacaatgtga     5122
gcaagaacaa gaactgttta aggcacctct gttcccagcc actgaagaga gacgtcagaa     5182
gatgttagaa taggtcaaaa ccaaggctct ggtggactga gggaaggttt gtagctgcgt     5242
ttagtggtat acatctttag tcccagcata ggcaggtgaa tctcgagttt gaagctagcc     5302
tggtctaaaa aggaagttcc aagactgcca gggccacaca gaggaaaaaa aaaaaccctc     5362
tagaaaaaca aaaatgaaga caggttctca tgtatcgtag attggccttt aagtcacttt     5422
accaaggatg atctttgaac tcctgagtac agactgcggg tgtgtgctac catgctttat     5482
gtggccctgg gttcaaacac agcccttcat atgtatatag ccaaacactc tacaactgag     5542
ctacatcctc cagcctaggc tgtaaatgtt ttttggagct agattagctg cctgccaacc     5602
ttagaactgc aaagccattc ctgacctgta aacctcagct ctccatctct ataagaggta     5662
tagcctgggc taataccgtc caagttacaa ctccttgctt gctttctgtt ccttctagcc     5722
ttggtgactt ccaccaggaa gagaataccc cctctctacc cctgctccaa gacactgtag     5782
atgctagtgt cggagtgttc tctgtaacgc gacagttcct tctgttgcaa tagcccccct     5842
gcaacactgc aataatcctt cagtgtctcc cctgggctca attcacttcc ttatttgaca     5902
aagtggaggt gagacttgta ttcttaaaat tggaggctag ttattttgtc aaatgcatgt     5962
aatgaacaga cccgaaggaa tcctccacac acaagccagg gaacaccaac tggaaaggta     6022
ccccgtccca gggaagcctg ctagggagag gttctgtaga atccgagcct agcaccccaa     6082
agtcatgcac ccagtatcct cttgtatgac tgtatatgtc tatgtctggg atccagggca     6142
aatgtgaatt tccttttgat ttgggagatt gttcacagga agtagtcctc ccctctcatg     6202
tcctcctatt gattgtttac aatatttgta catctatgca aaatacttga atgggccatg     6262
gtgccttgtt ttttgttgtt gttgttattt ttttctcctt gtttgtattt aattaaaaca     6322
aattgtcatg aggaaaaaaa aaaaaaaaaa                                      6352
```

<210> SEQ ID NO 4
<211> LENGTH: 920
<212> TYPE: PRT
<213> ORGANISM: Unknown Organism
<220> FEATURE:
<223> OTHER INFORMATION: Description of Unknown Organism: Clone:
      JM109(pBSMel-beta), mouse beta meltrin
<220> FEATURE:
<221> NAME/KEY: Unsure
<222> LOCATION: 574
<223> OTHER INFORMATION: Amino acid "Xaa" is unknown

<400> SEQUENCE: 4

Met Pro Gly Arg Ala Gly Val Ala Arg Phe Cys Leu Leu Ala Leu Ala
1               5                   10                  15

Leu Gln Leu His Trp Pro Leu Ala Ala Cys Glu Pro Gly Trp Thr Thr
            20                  25                  30

-continued

```
Arg Gly Ser Gln Glu Gly Ser Pro Pro Leu Gln His Glu Leu Ile Ile
            35                  40                  45
Pro Gln Trp Arg Thr Ser Glu Ser Pro Gly Arg Gly Lys His Pro Leu
        50                  55                  60
Arg Ala Glu Leu Arg Val Met Ala Glu Gly Arg Glu Leu Ile Leu Asp
65                  70                  75                  80
Leu Glu Lys Asn Glu His Leu Phe Ala Pro Ala Tyr Thr Glu Thr Cys
                85                  90                  95
Tyr Thr Ala Ser Gly Asn Pro Gln Thr Ser Thr Leu Lys Ser Glu Asp
            100                 105                 110
His Cys Phe Tyr His Gly Thr Val Arg Asp Val Asp Glu Ser Ser Val
        115                 120                 125
Thr Leu Ser Thr Cys Arg Gly Ile Arg Gly Leu Ile Ile Val Arg Ser
130                 135                 140
Asn Leu Ser Tyr Ile Ile Glu Pro Val Pro Asn Ser Asp Ser Gln His
145                 150                 155                 160
Arg Ile Tyr Arg Ser Glu His Leu Thr Leu Pro Pro Gly Asn Cys Gly
                165                 170                 175
Phe Glu His Ser Gly Pro Thr Ser Lys Asp Trp Ala Leu Gln Phe Thr
            180                 185                 190
His Gln Thr Lys Lys Gln Pro Arg Arg Met Lys Arg Glu Asp Leu His
        195                 200                 205
Ser Met Lys Tyr Val Glu Leu Tyr Leu Val Ala Asp Tyr Ala Glu Phe
210                 215                 220
Gln Lys Asn Arg His Asp Gln Asp Ala Thr Lys Arg Lys Leu Met Glu
225                 230                 235                 240
Ile Ala Asn Tyr Val Asp Lys Phe Tyr Arg Ser Leu Asn Ile Arg Ile
                245                 250                 255
Ala Leu Val Gly Leu Glu Val Trp Thr His Gly Asp Lys Cys Glu Val
            260                 265                 270
Ser Glu Asn Pro Tyr Ser Thr Leu Trp Ser Phe Leu Ser Trp Arg Arg
        275                 280                 285
Lys Leu Leu Ala Gln Lys Ser His Asp Asn Ala Gln Leu Ile Thr Gly
290                 295                 300
Arg Ser Phe Gln Gly Thr Thr Ile Gly Leu Ala Pro Leu Met Ala Met
305                 310                 315                 320
Cys Ser Val Tyr Gln Ser Gly Gly Val Ser Met Asp His Ser Glu Asn
                325                 330                 335
Ala Ile Gly Val Ala Ser Thr Val Ala His Glu Ile Gly His Asn Phe
            340                 345                 350
Gly Met Ser His Asp Ser Ala His Cys Cys Ser Ala Ser Ala Ala Asp
        355                 360                 365
Gly Gly Cys Ile Met Ala Ala Ala Thr Gly His Pro Phe Pro Lys Val
370                 375                 380
Phe Ser Trp Cys Asn Arg Lys Glu Leu Asp Arg Tyr Leu Gln Thr Gly
385                 390                 395                 400
Gly Gly Met Cys Leu Ser Asn Met Pro Asp Thr Arg Thr Leu Tyr Gly
                405                 410                 415
Gly Arg Arg Cys Gly Asn Gly Tyr Leu Glu Asp Gly Glu Glu Cys Asp
            420                 425                 430
Cys Gly Glu Glu Glu Glu Cys Lys Asn Pro Cys Cys Asn Ala Ser Asn
        435                 440                 445
```

-continued

```
Cys Thr Leu Lys Glu Gly Ala Glu Cys Ala His Gly Ser Cys Cys His
    450                 455                 460
Gln Cys Lys Leu Val Ala Pro Gly Thr Gln Cys Arg Glu Gln Val Arg
465                 470                 475                 480
Gln Cys Asp Leu Pro Glu Phe Cys Thr Gly Lys Ser Pro His Cys Pro
                    485                 490                 495
Thr Asn Tyr Tyr Gln Met Asp Gly Thr Pro Cys Glu Gly Gly Gln Ala
                500                 505                 510
Tyr Cys Tyr Asn Gly Met Cys Leu Thr Tyr Gln Glu Gln Cys Gln Gln
            515                 520                 525
Leu Trp Gly Pro Gly Ala Arg Pro Ala Leu Asp Leu Cys Phe Glu Arg
    530                 535                 540
Val Asn Ala Ala Gly Asp Thr Tyr Gly Asn Cys Gly Lys Gly Leu Asn
545                 550                 555                 560
Gly Gln Tyr Arg Lys Cys Ser Pro Arg Asp Ala Lys Cys Xaa Lys Ile
                565                 570                 575
Gln Cys Gln Ser Thr Gln Ala Arg Pro Leu Glu Ser Asn Ala Val Ser
                580                 585                 590
Ile Asp Thr Thr Ile Thr Leu Asn Gly Arg Arg Ile His Cys Arg Gly
            595                 600                 605
Thr His Val Tyr Arg Gly Pro Glu Glu Glu Gly Glu Gly Asp Met
    610                 615                 620
Leu Asp Pro Gly Leu Val Met Thr Gly Thr Lys Cys Gly His Asn His
625                 630                 635                 640
Ile Cys Phe Glu Gly Gln Cys Arg Asn Thr Ser Phe Phe Glu Thr Glu
                645                 650                 655
Gly Cys Gly Lys Lys Cys Asn Gly His Gly Val Cys Asn Asn Asn Lys
                660                 665                 670
Asn Cys His Cys Phe Pro Gly Trp Ser Pro Pro Phe Cys Asn Thr Pro
            675                 680                 685
Gly Asp Gly Gly Ser Val Asp Ser Gly Pro Leu Pro Pro Lys Ser Val
    690                 695                 700
Gly Pro Val Ile Ala Gly Val Phe Ser Ala Leu Phe Val Leu Ala Val
705                 710                 715                 720
Leu Val Leu Leu Cys His Cys Tyr Arg Gln Ser His Lys Leu Gly Lys
                725                 730                 735
Pro Ser Ala Leu Pro Phe Lys Leu Arg His Gln Phe Ser Cys Pro Phe
                740                 745                 750
Arg Val Ser Gln Ser Gly Gly Thr Gly His Ala Asn Pro Thr Phe Lys
            755                 760                 765
Leu Gln Thr Pro Gln Gly Lys Arg Lys Val Thr Asn Thr Pro Glu Ser
    770                 775                 780
Leu Arg Lys Pro Ser His Pro Leu Arg Pro Pro Asp Tyr Leu
785                 790                 795                 800
Arg Val Glu Ser Pro Pro Ala Pro Leu Ser Ala His Leu Asn Arg Ala
                805                 810                 815
Ala Gly Ser Ser Pro Glu Ala Gly Ala Arg Ile Glu Lys Glu Ser
            820                 825                 830
Ala Arg Arg Pro Pro Ser Arg Pro Met Pro Pro Ala Pro Asn Cys
    835                 840                 845
Leu Leu Ser Gln Asp Phe Ser Arg Pro Arg Pro Pro Gln Lys Ala Leu
850                 855                 860
```

```
                Pro Ala Asn Pro Val Pro Gly Gln Arg Thr Gly Pro Arg Ser Gly Gly
                865                 870                 875                 880

Thr Ser Leu Leu Gln Pro Pro Thr Ser Gly Pro Gln Pro Pro Arg Pro
                                885                 890                 895

Pro Ala Val Pro Val Pro Lys Leu Pro Glu Tyr Arg Ser Gln Arg Val
                            900                 905                 910

Gly Ala Ile Ile Ser Ser Lys Ile
                        915                 920

<210> SEQ ID NO 5
<211> LENGTH: 3931
<212> TYPE: DNA
<213> ORGANISM: Unknown Organism
<220> FEATURE:
<223> OTHER INFORMATION: Description of Unknown Organism: Clone,
      JM109(pBSMel-gamma), mouse meltrin gamma
<220> FEATURE:
<221> NAME/KEY: CDS
<222> LOCATION: (69)..(2603)

<400> SEQUENCE: 5
gttgcaagga tgaccgaagn ncggaggcgg cggccgcgcg ttgagcggaa cctgccgaag          60 ccctcgct atg ggg ccg cgc gcg ctc tcg ccc ctt gcc tct ctg cga cta         110
         Met Gly Pro Arg Ala Leu Ser Pro Leu Ala Ser Leu Arg Leu
             1               5                  10 agg tgg ctg ctg gcg tgt ggc ttg ctg ggc cca gtc ctc gag gcc ggg          158
Arg Trp Leu Leu Ala Cys Gly Leu Leu Gly Pro Val Leu Glu Ala Gly
15              20                  25                  30 cga cca gac ttg gaa cag act gtc cat ctt tct tct tat gaa att att          206
Arg Pro Asp Leu Glu Gln Thr Val His Leu Ser Ser Tyr Glu Ile Ile
                35                  40                  45 act cct tgg aga tta act aga gaa aga agg gaa gct ctg ggg ccc agt          254
Thr Pro Trp Arg Leu Thr Arg Glu Arg Arg Glu Ala Leu Gly Pro Ser
            50                  55                  60 tca cag cag atc tct tac gtc atc cag gcc caa gga aaa cag cat att          302
Ser Gln Gln Ile Ser Tyr Val Ile Gln Ala Gln Gly Lys Gln His Ile
65              70                  75 att cac ttg gaa aga aac aca gac ctt tta cct aat gat ttt gta gtt          350
Ile His Leu Glu Arg Asn Thr Asp Leu Leu Pro Asn Asp Phe Val Val
    80                  85                  90 tac acc tac gac aag gaa ggc tcc cta ctc tct gac cat ccc aac gta          398
Tyr Thr Tyr Asp Lys Glu Gly Ser Leu Leu Ser Asp His Pro Asn Val
95                  100                 105                 110 cag agc cat tgt cac tat cga ggc tat gtg gag gga gtg cag aat tcc          446
Gln Ser His Cys His Tyr Arg Gly Tyr Val Glu Gly Val Gln Asn Ser
                115                 120                 125 gcg gtt gct gtg agc gcc tgc ttt gga ctc aga ggc ttg ctg cat ttg          494
Ala Val Ala Val Ser Ala Cys Phe Gly Leu Arg Gly Leu Leu His Leu
            130                 135                 140 gag aat gcc agt ttt gga att gaa cct ctg cac aac agc tca cac ttt          542
Glu Asn Ala Ser Phe Gly Ile Glu Pro Leu His Asn Ser Ser His Phe
145                 150                 155 gag cac ata ttt tac ccc atg gat ggc atc cac cag gag cct ctg aga          590
Glu His Ile Phe Tyr Pro Met Asp Gly Ile His Gln Glu Pro Leu Arg
    160                 165                 170 tgt gga gtc tct aac agg gac aca gag aag gaa ggc aca cag ggg gat          638
Cys Gly Val Ser Asn Arg Asp Thr Glu Lys Glu Gly Thr Gln Gly Asp
175                 180                 185                 190 gag gag gag cat ccg agt gtc act cag ctg ctg cgc aga aga aga gct          686
Glu Glu Glu His Pro Ser Val Thr Gln Leu Leu Arg Arg Arg Arg Ala
                195                 200                 205
```

```
gtt cta cca cag acc cgc tat gtg gag ctg ttc att gtt gta gac aag      734
Val Leu Pro Gln Thr Arg Tyr Val Glu Leu Phe Ile Val Val Asp Lys
            210                 215                 220 gaa agg tac gac atg atg gga cgg aac cag act gct gtg aga gaa gag      782
Glu Arg Tyr Asp Met Met Gly Arg Asn Gln Thr Ala Val Arg Glu Glu
                225                 230                 235 atg att cgc tta gca aac tac ctg gat agc atg tac atc atg tta aac      830
Met Ile Arg Leu Ala Asn Tyr Leu Asp Ser Met Tyr Ile Met Leu Asn
    240                 245                 250 att cga att gtg ctg gtt gga cta gaa att tgg aca gac aga aat cct      878
Ile Arg Ile Val Leu Val Gly Leu Glu Ile Trp Thr Asp Arg Asn Pro
255                 260                 265                 270 atc aat ata att gga gga gct gga gat gtg ctg ggc aac ttt gtt cag      926
Ile Asn Ile Ile Gly Gly Ala Gly Asp Val Leu Gly Asn Phe Val Gln
                275                 280                 285 tgg cgg gaa aag ttc ctt ata act cgt cgg aga cac gac agt gca cag      974
Trp Arg Glu Lys Phe Leu Ile Thr Arg Arg Arg His Asp Ser Ala Gln
                290                 295                 300 ttg gtt ttg aag aaa ggc ttt ggt gga act gca gga atg gcg ttt gta     1022
Leu Val Leu Lys Lys Gly Phe Gly Gly Thr Ala Gly Met Ala Phe Val
    305                 310                 315 gga aca gta tgt tca agg agc cac gca ggt ggg atc aat gtg ttt ggg     1070
Gly Thr Val Cys Ser Arg Ser His Ala Gly Gly Ile Asn Val Phe Gly
320                 325                 330 caa atc act gtg gag aca ttt gca tcc att gtt gct cat gaa ttg ggg     1118
Gln Ile Thr Val Glu Thr Phe Ala Ser Ile Val Ala His Glu Leu Gly
335                 340                 345                 350 cat aac ctt gga atg aat cat gat gat ggg aga gag tgt ttc tgt gga     1166
His Asn Leu Gly Met Asn His Asp Asp Gly Arg Glu Cys Phe Cys Gly
                355                 360                 365 gca aag agc tgt atc atg aat tca gga gca tcc ggg tcc aga aac ttt     1214
Ala Lys Ser Cys Ile Met Asn Ser Gly Ala Ser Gly Ser Arg Asn Phe
                370                 375                 380 agc agt tgc agt gcg gag gac ttt gag aag tta acg ttg aat aag gga     1262
Ser Ser Cys Ser Ala Glu Asp Phe Glu Lys Leu Thr Leu Asn Lys Gly
    385                 390                 395 gga agc tgc ctg ctt aac atc ccg aag cct gac gaa gcc tac agc gcg     1310
Gly Ser Cys Leu Leu Asn Ile Pro Lys Pro Asp Glu Ala Tyr Ser Ala
400                 405                 410 ccc tcc tgt ggt aat aag ctg gtg gac cct gga gag gag tgt gac tgc     1358
Pro Ser Cys Gly Asn Lys Leu Val Asp Pro Gly Glu Glu Cys Asp Cys
415                 420                 425                 430 ggc aca gcg aag gag tgt gag gtg gac cca tgc tgt gaa gga agc act     1406
Gly Thr Ala Lys Glu Cys Glu Val Asp Pro Cys Cys Glu Gly Ser Thr
                435                 440                 445 tgt aag ctc aag tca ttt gct gag tgt gca tat ggc gac tgt tgt aaa     1454
Cys Lys Leu Lys Ser Phe Ala Glu Cys Ala Tyr Gly Asp Cys Cys Lys
                450                 455                 460 gat tgc cag ttc ctt cca gga ggc tcc atg tgc aga ggg aag acc agt     1502
Asp Cys Gln Phe Leu Pro Gly Gly Ser Met Cys Arg Gly Lys Thr Ser
    465                 470                 475 gag tgt gat gtt cct gag tac tgc aac ggt tcc tct cag ttc tgc ccg     1550
Glu Cys Asp Val Pro Glu Tyr Cys Asn Gly Ser Ser Gln Phe Cys Pro
    480                 485                 490 cca gat gtc ttc att cag aat gga tat cct tgc cag aac agc aaa gcc     1598
Pro Asp Val Phe Ile Gln Asn Gly Tyr Pro Cys Gln Asn Ser Lys Ala
495                 500                 505                 510 tac tgc tac aat ggc atg tgc caa tat tat gac gcg cag tgt cag gtc     1646
Tyr Cys Tyr Asn Gly Met Cys Gln Tyr Tyr Asp Ala Gln Cys Gln Val
                515                 520                 525
```

```
atc ttt ggt tca aag gct aag gct gcc cca aga gat tgc ttc att gaa     1694
Ile Phe Gly Ser Lys Ala Lys Ala Ala Pro Arg Asp Cys Phe Ile Glu
            530                 535                 540 gtc aat tct aaa ggt gac aga ttt ggc aac tgt ggt ttc tcc ggc agt     1742
Val Asn Ser Lys Gly Asp Arg Phe Gly Asn Cys Gly Phe Ser Gly Ser
545                 550                 555 gag tac aag aag tgt gcc act ggg aac gcg ctg tgt gga aag ctt caa     1790
Glu Tyr Lys Lys Cys Ala Thr Gly Asn Ala Leu Cys Gly Lys Leu Gln
        560                 565                 570 tgc gag aat gta cag gac atg ccg gtg ttt gga ata gta cca gct atc     1838
Cys Glu Asn Val Gln Asp Met Pro Val Phe Gly Ile Val Pro Ala Ile
575                 580                 585                 590 att cag aca ccc agt cga ggc acc aaa tgc tgg ggt gtg gat ttc cag     1886
Ile Gln Thr Pro Ser Arg Gly Thr Lys Cys Trp Gly Val Asp Phe Gln
            595                 600                 605 ctt ggt tcc gac gtt cca gac cca ggg atg gtg aat gaa ggc acc aaa     1934
Leu Gly Ser Asp Val Pro Asp Pro Gly Met Val Asn Glu Gly Thr Lys
        610                 615                 620 tgt gat gct ggc aag att tgc agg aat ttt cag tgt gta aat gct tct     1982
Cys Asp Ala Gly Lys Ile Cys Arg Asn Phe Gln Cys Val Asn Ala Ser
625                 630                 635 gtc ctg aat tat gac tgt gac att cag gga aaa tgt cat ggc cat ggg     2030
Val Leu Asn Tyr Asp Cys Asp Ile Gln Gly Lys Cys His Gly His Gly
            640                 645                 650 gta tgt aac agc aat aag aat tgt cac tgt gaa gat ggc tgg gct ccc     2078
Val Cys Asn Ser Asn Lys Asn Cys His Cys Glu Asp Gly Trp Ala Pro
655                 660                 665                 670 cca cac tgt gac acc aaa gga tat gga gga agc gtg gac agc ggg ccg     2126
Pro His Cys Asp Thr Lys Gly Tyr Gly Gly Ser Val Asp Ser Gly Pro
            675                 680                 685 acg tat aat gca aag agc aca gca ctg agg gac ggg ctt ctg gtc ttc     2174
Thr Tyr Asn Ala Lys Ser Thr Ala Leu Arg Asp Gly Leu Leu Val Phe
        690                 695                 700 ttc ttc cta atc gtc ccc ctt gtt gcg gct gcc att ttc ctc ttt atc     2222
Phe Phe Leu Ile Val Pro Leu Val Ala Ala Ala Ile Phe Leu Phe Ile
            705                 710                 715 aag aga gat gaa cta cgg aaa acc ttc agg aag aag aga tca caa atg     2270
Lys Arg Asp Glu Leu Arg Lys Thr Phe Arg Lys Lys Arg Ser Gln Met
        720                 725                 730 tca gat ggc aga aat caa gca aac gtc tct aga cag cca gga gat cct     2318
Ser Asp Gly Arg Asn Gln Ala Asn Val Ser Arg Gln Pro Gly Asp Pro
735                 740                 745                 750 agt atc tcc aga cca cca ggg gca cca aat gtc tcc aga cca cca ggg     2366
Ser Ile Ser Arg Pro Pro Gly Gly Pro Asn Val Ser Arg Pro Pro Gly
            755                 760                 765 ggc cca ggt gtc tcc aga cca cca ggg ggc cca ggt gtc tcc aga cca     2414
Gly Pro Gly Val Ser Arg Pro Pro Gly Gly Pro Gly Val Ser Arg Pro
        770                 775                 780 cca ggg ggc cca ggt gtc tcc aga ccg cca cct ggg cat gga aac aga     2462
Pro Gly Gly Pro Gly Val Ser Arg Pro Pro Gly His Gly Asn Arg
                785                 790                 795 ttc cca gta cca acc tac gcc gcc aag cag cct gcg cag ttc ccg tca     2510
Phe Pro Val Pro Thr Tyr Ala Ala Lys Gln Pro Ala Gln Phe Pro Ser
        800                 805                 810 agg cca cct cca cca caa ccg aaa ata tct tct cag gga aac ttg att     2558
Arg Pro Pro Pro Pro Gln Pro Lys Ile Ser Ser Gln Gly Asn Leu Ile
815                 820                 825                 830 ccg gct cgg ccc gct cct gca cct cct tta tat agc tcc ctc acc         2603
Pro Ala Arg Pro Ala Pro Ala Pro Pro Leu Tyr Ser Ser Leu Thr
                835                 840                 845
```

-continued

```
tgatagtaga atattagaat cttattttt aaatgtcttc agggaactga gcaaatgttt    2663 gttgttttt ttttcctgat gttttcttga aaagcctttc tcttccaacc atgaatgaac    2723
acaaaccacc acaaaacaag ctttattaac acaggagcct agtggggatt gcgaaacaca    2783
ggaatgtgca ggcgctccgg ggggtgtaaa gtgaacgttt ccatcgttag aatgttttct    2843
ctggccattt gtggatttaa tgcacttgac gtggattaag ttattctgag catgttactg    2903
taatgattct caaattaact gtattagtgt aagctttgtc actatgcgct aaacgtaatc    2963 ctgactttt gacccagtt accattaata gtttctggtt gaccatttga acatgtatta    3023
acttaggaag actaattgcc aataacgtct gcattttcat cttgcatgga ttaacagcca    3083
tttatatgga cttatgtctc ttaatgcaca aagaagcaga tatctcgaag gagcttacac    3143
aagaaccaca attactagat catgatatac ttggaaagtg tgaaatatgg tgtgtactca    3203
gttattggct tccatttttw atgatctttc aactataaca attatgatag aaatcgattt    3263
aacacaatca gttatgggct tccatttca aatatctttt caactgtaat gactatgaca    3323
ggaactgatt caactctcaa ttttctttat gcatcatggt aaagcattgc agcagtgttg    3383
ttttgtttga agtgcacact ctatggtacg aggtgtttag tatacccaag cagataggtg    3443
tcgatcgaac aggagcaggg agaatacttc caacagttga ggtgttacca aaccacttga    3503
gaattcatga gcactttaac tctaaactct gaatttcaaa gcttgatgtg aagtcctcta    3563
gaatgtttac atttactaag gtgtgctggg tcctgtctct tttgactaat attttcgtaa    3623
acattaggct ggagaaagga aggaagcagt ggtttcctta gataactaca gaattatact    3683
ggtctctggg attactctct cagctgtatt aaaatgaatt tgtactttga aaggaatgat    3743
attgacacta aaattttaaa catttaaatt ttttcataat ctttcataaa gaagtttaat    3803
aataggtata ttaactgaat ttcattagtt ttttaaaata atattgtttg tgtatatata    3863
catattaaaa taaaaacatt tacaacaaat aaaatacttg aaattctaaa aaaaaaaaa    3923 aaaaaaaa                                                              3931
```

<210> SEQ ID NO 6
<211> LENGTH: 845
<212> TYPE: PRT
<213> ORGANISM: Unknown Organism
<220> FEATURE:
<223> OTHER INFORMATION: Description of Unknown Organism: Clone,
      JM109(pBSMel-gamma), mouse meltrin gamma

<400> SEQUENCE: 6

```
Met Gly Pro Arg Ala Leu Ser Pro Leu Ala Ser Leu Arg Leu Arg Trp
  1               5                  10                  15

Leu Leu Ala Cys Gly Leu Leu Gly Pro Val Leu Glu Ala Gly Arg Pro
             20                  25                  30

Asp Leu Glu Gln Thr Val His Leu Ser Ser Tyr Glu Ile Ile Thr Pro
         35                  40                  45

Trp Arg Leu Thr Arg Glu Arg Arg Glu Ala Leu Gly Pro Ser Ser Gln
     50                  55                  60

Gln Ile Ser Tyr Val Ile Gln Ala Gln Gly Lys Gln His Ile Ile His
 65                  70                  75                  80

Leu Glu Arg Asn Thr Asp Leu Leu Pro Asn Asp Phe Val Val Tyr Thr
                 85                  90                  95

Tyr Asp Lys Glu Gly Ser Leu Leu Ser Asp His Pro Asn Val Gln Ser
            100                 105                 110
```

```
His Cys His Tyr Arg Gly Tyr Val Glu Gly Val Gln Asn Ser Ala Val
            115                 120                 125
Ala Val Ser Ala Cys Phe Gly Leu Arg Gly Leu Leu His Leu Glu Asn
        130                 135                 140
Ala Ser Phe Gly Ile Glu Pro Leu His Asn Ser Ser Phe Glu His
    145                 150                 155                 160
Ile Phe Tyr Pro Met Asp Gly Ile His Gln Glu Pro Leu Arg Cys Gly
                165                 170                 175
Val Ser Asn Arg Asp Thr Glu Lys Glu Gly Thr Gln Gly Asp Glu Glu
            180                 185                 190
Glu His Pro Ser Val Thr Gln Leu Leu Arg Arg Arg Ala Val Leu
        195                 200                 205
Pro Gln Thr Arg Tyr Val Glu Leu Phe Ile Val Asp Lys Glu Arg
    210                 215                 220
Tyr Asp Met Met Gly Arg Asn Gln Thr Ala Val Arg Glu Glu Met Ile
225                 230                 235                 240
Arg Leu Ala Asn Tyr Leu Asp Ser Met Tyr Ile Met Leu Asn Ile Arg
            245                 250                 255
Ile Val Leu Val Gly Leu Glu Ile Trp Thr Asp Arg Asn Pro Ile Asn
        260                 265                 270
Ile Ile Gly Gly Ala Gly Asp Val Leu Gly Asn Phe Val Gln Trp Arg
    275                 280                 285
Glu Lys Phe Leu Ile Thr Arg Arg His Asp Ser Ala Gln Leu Val
290                 295                 300
Leu Lys Lys Gly Phe Gly Gly Thr Ala Gly Met Ala Phe Val Gly Thr
305                 310                 315                 320
Val Cys Ser Arg Ser His Ala Gly Gly Ile Asn Val Phe Gly Gln Ile
            325                 330                 335
Thr Val Glu Thr Phe Ala Ser Ile Val Ala His Glu Leu Gly His Asn
        340                 345                 350
Leu Gly Met Asn His Asp Asp Gly Arg Glu Cys Phe Cys Gly Ala Lys
    355                 360                 365
Ser Cys Ile Met Asn Ser Gly Ala Ser Gly Ser Arg Asn Phe Ser Ser
370                 375                 380
Cys Ser Ala Glu Asp Phe Glu Lys Leu Thr Leu Asn Lys Gly Gly Ser
385                 390                 395                 400
Cys Leu Leu Asn Ile Pro Lys Pro Asp Glu Ala Tyr Ser Ala Pro Ser
            405                 410                 415
Cys Gly Asn Lys Leu Val Asp Pro Gly Glu Glu Cys Asp Cys Gly Thr
        420                 425                 430
Ala Lys Glu Cys Glu Val Asp Pro Cys Cys Glu Gly Ser Thr Cys Lys
    435                 440                 445
Leu Lys Ser Phe Ala Glu Cys Ala Tyr Gly Asp Cys Cys Lys Asp Cys
450                 455                 460
Gln Phe Leu Pro Gly Gly Ser Met Cys Arg Gly Lys Thr Ser Glu Cys
465                 470                 475                 480
Asp Val Pro Glu Tyr Cys Asn Gly Ser Ser Gln Phe Cys Pro Pro Asp
            485                 490                 495
Val Phe Ile Gln Asn Gly Tyr Pro Cys Gln Asn Ser Lys Ala Tyr Cys
        500                 505                 510
Tyr Asn Gly Met Cys Gln Tyr Tyr Asp Ala Gln Cys Gln Val Ile Phe
    515                 520                 525
```

-continued

Gly Ser Lys Ala Lys Ala Ala Pro Arg Asp Cys Phe Ile Glu Val Asn
530                 535                 540

Ser Lys Gly Asp Arg Phe Gly Asn Cys Gly Phe Ser Gly Ser Glu Tyr
545                 550                 555                 560

Lys Lys Cys Ala Thr Gly Asn Ala Leu Cys Gly Lys Leu Gln Cys Glu
        565                 570                 575

Asn Val Gln Asp Met Pro Val Phe Gly Ile Val Pro Ala Ile Ile Gln
        580                 585                 590

Thr Pro Ser Arg Gly Thr Lys Cys Trp Gly Val Asp Phe Gln Leu Gly
        595                 600                 605

Ser Asp Val Pro Asp Pro Gly Met Val Asn Glu Gly Thr Lys Cys Asp
610                 615                 620

Ala Gly Lys Ile Cys Arg Asn Phe Gln Cys Val Asn Ala Ser Val Leu
625                 630                 635                 640

Asn Tyr Asp Cys Asp Ile Gln Gly Lys Cys His Gly His Gly Val Cys
            645                 650                 655

Asn Ser Asn Lys Asn Cys His Cys Glu Asp Gly Trp Ala Pro Pro His
            660                 665                 670

Cys Asp Thr Lys Gly Tyr Gly Gly Ser Val Asp Ser Gly Pro Thr Tyr
        675                 680                 685

Asn Ala Lys Ser Thr Ala Leu Arg Asp Gly Leu Leu Val Phe Phe Phe
        690                 695                 700

Leu Ile Val Pro Leu Val Ala Ala Ile Phe Leu Phe Ile Lys Arg
705                 710                 715                 720

Asp Glu Leu Arg Lys Thr Phe Arg Lys Arg Ser Gln Met Ser Asp
            725                 730                 735

Gly Arg Asn Gln Ala Asn Val Ser Arg Gln Pro Gly Asp Pro Ser Ile
            740                 745                 750

Ser Arg Pro Pro Gly Gly Pro Asn Val Ser Arg Pro Pro Gly Gly Pro
        755                 760                 765

Gly Val Ser Arg Pro Pro Gly Gly Pro Gly Val Ser Arg Pro Pro Gly
        770                 775                 780

Gly Pro Gly Val Ser Arg Pro Pro Gly His Gly Asn Arg Phe Pro
785                 790                 795                 800

Val Pro Thr Tyr Ala Ala Lys Gln Pro Ala Gln Phe Pro Ser Arg Pro
            805                 810                 815

Pro Pro Pro Gln Pro Lys Ile Ser Ser Gln Gly Asn Leu Ile Pro Ala
            820                 825                 830

Arg Pro Ala Pro Ala Pro Pro Leu Tyr Ser Ser Leu Thr
        835                 840                 845

<210> SEQ ID NO 7
<211> LENGTH: 321
<212> TYPE: DNA
<213> ORGANISM: Unknown Organism
<220> FEATURE:
<223> OTHER INFORMATION: Description of Unknown Organism: Clone:
      JM109(pBShuM-alpha 300), human meltrin alpha
<220> FEATURE:
<221> NAME/KEY: CDS
<222> LOCATION: (1)..(321)
<220> FEATURE:
<221> NAME/KEY: unsure
<222> LOCATION: (139)..(321)
<223> OTHER INFORMATION: Amino Acid "Xaa" is unknown

<400> SEQUENCE: 7

```
aag cct gca gga aca gcg tgc agg gac tcc agc aac tcc tgt gac ctc        48
Lys Pro Ala Gly Thr Ala Cys Arg Asp Ser Ser Asn Ser Cys Asp Leu
 1               5                  10                  15 cca gag ttc tgc aca ggg gcc agc cct cac tgc cca gcc aac gtg tac        96
Pro Glu Phe Cys Thr Gly Ala Ser Pro His Cys Pro Ala Asn Val Tyr
            20                  25                  30 ctg cac gat ggg cac tca tgt cag gat gtg gac ggc tac tgc tan aat       144
Leu His Asp Gly His Ser Cys Gln Asp Val Asp Gly Tyr Cys Xaa Asn
        35                  40                  45 ggc atc tgc cag act cac gag cag cag tgt gtc acg ctc tgg gga cca       192
Gly Ile Cys Gln Thr His Glu Gln Gln Cys Val Thr Leu Trp Gly Pro
    50                  55                  60 ggt gct aaa cct gcc cct ggg atc tgc ttt gag aga gtc aat tct gca       240
Gly Ala Lys Pro Ala Pro Gly Ile Cys Phe Glu Arg Val Asn Ser Ala
65                  70                  75                  80 ggt gaa cct tat ggc aac tgt ggc aaa gtc tcg aag agt tcc ttt gcc       288
Gly Glu Pro Tyr Gly Asn Cys Gly Lys Val Ser Lys Ser Ser Phe Ala
                85                  90                  95 aaa tgc gag atg aga gat gct aaa tgc ggc aag                           321
Lys Cys Glu Met Arg Asp Ala Lys Cys Gly Lys
            100                 105
```

<210> SEQ ID NO 8
<211> LENGTH: 107
<212> TYPE: PRT
<213> ORGANISM: Unknown Organism
<220> FEATURE:
<223> OTHER INFORMATION: Description of Unknown Organism: Clone:
    JM109(pBShuM-alpha 300), human meltrin alpha
<220> FEATURE:
<221> NAME/KEY: Unsure
<222> LOCATION: 47
<223> OTHER INFORMATION: Amino acid "Xaa" is unknown

<400> SEQUENCE: 8

```
Lys Pro Ala Gly Thr Ala Cys Arg Asp Ser Ser Asn Ser Cys Asp Leu
 1               5                  10                  15

Pro Glu Phe Cys Thr Gly Ala Ser Pro His Cys Pro Ala Asn Val Tyr
            20                  25                  30

Leu His Asp Gly His Ser Cys Gln Asp Val Asp Gly Tyr Cys Xaa Asn
        35                  40                  45

Gly Ile Cys Gln Thr His Glu Gln Gln Cys Val Thr Leu Trp Gly Pro
    50                  55                  60

Gly Ala Lys Pro Ala Pro Gly Ile Cys Phe Glu Arg Val Asn Ser Ala
65                  70                  75                  80

Gly Glu Pro Tyr Gly Asn Cys Gly Lys Val Ser Lys Ser Ser Phe Ala
                85                  90                  95

Lys Cys Glu Met Arg Asp Ala Lys Cys Gly Lys
            100                 105
```

<210> SEQ ID NO 9
<211> LENGTH: 967
<212> TYPE: DNA
<213> ORGANISM: Unknown Organism
<220> FEATURE:
<223> OTHER INFORMATION: Description of Unknown Organism:  Clone:
    JM109(pBShuM-gamma-G238), human meltrin gamma
<220> FEATURE:
<221> NAME/KEY: CDS
<222> LOCATION: (1)..(966)

<400> SEQUENCE: 9

```
gca aag agc tgc atc atg aat tca gga gca tcg ggt tcc aga aac ttt         48
Ala Lys Ser Cys Ile Met Asn Ser Gly Ala Ser Gly Ser Arg Asn Phe
 1               5                  10                  15 agc agt tgc agt gca gag gac ttt gag aag tta act tta aat aaa gga         96
Ser Ser Cys Ser Ala Glu Asp Phe Glu Lys Leu Thr Leu Asn Lys Gly
             20                  25                  30 gga aac tgc ctt ctt aat att cca aag cct gat gaa gcc tat agt gct        144
Gly Asn Cys Leu Leu Asn Ile Pro Lys Pro Asp Glu Ala Tyr Ser Ala
         35                  40                  45 ccc tcc tgt ggt aat aag ttg gtg gac gct ggg gaa gag tgt gac tgt        192
Pro Ser Cys Gly Asn Lys Leu Val Asp Ala Gly Glu Glu Cys Asp Cys
     50                  55                  60 ggt act cca aag gaa tgt gaa ttg gac cct tgc tgc gaa gga agt acc        240
Gly Thr Pro Lys Glu Cys Glu Leu Asp Pro Cys Cys Glu Gly Ser Thr
 65                  70                  75                  80 tgt aag ctt aaa tca ttt gct gag tgt gca tat ggt gac tgt tgt aaa        288
Cys Lys Leu Lys Ser Phe Ala Glu Cys Ala Tyr Gly Asp Cys Cys Lys
                 85                  90                  95 gac tgt cgg ttc ctt cca gga ggt act tta tgc cga gga aaa acc agt        336
Asp Cys Arg Phe Leu Pro Gly Gly Thr Leu Cys Arg Gly Lys Thr Ser
            100                 105                 110 gag tgt gat gtt cca gag tac tgc aat ggt tct tct cag ttc tgt cag        384
Glu Cys Asp Val Pro Glu Tyr Cys Asn Gly Ser Ser Gln Phe Cys Gln
        115                 120                 125 cca gat gtt ttt att cag aat gga tat cct tgc cag aat aac aaa gcc        432
Pro Asp Val Phe Ile Gln Asn Gly Tyr Pro Cys Gln Asn Asn Lys Ala
    130                 135                 140 tat tgc tac aac ggc atg tgc cag tat tat gat gct caa tgt caa gtc        480
Tyr Cys Tyr Asn Gly Met Cys Gln Tyr Tyr Asp Ala Gln Cys Gln Val
145                 150                 155                 160 atc ttt ggc tca aaa gcc aag gct gcc ccc aaa gat tgt ttc att gaa        528
Ile Phe Gly Ser Lys Ala Lys Ala Ala Pro Lys Asp Cys Phe Ile Glu
                165                 170                 175 gtg aat tct aaa ggt gac aga ttt ggc aat tgt ggt ttc tct ggc aat        576
Val Asn Ser Lys Gly Asp Arg Phe Gly Asn Cys Gly Phe Ser Gly Asn
            180                 185                 190 gaa tac aag aag tgt gcc act ggg aat gct ttg tgt gga aag ctt cag        624
Glu Tyr Lys Lys Cys Ala Thr Gly Asn Ala Leu Cys Gly Lys Leu Gln
        195                 200                 205 tgt gag aat gta caa gag ata cct gta ttt gga att gtg cct gct att        672
Cys Glu Asn Val Gln Glu Ile Pro Val Phe Gly Ile Val Pro Ala Ile
    210                 215                 220 att caa acg cct agt cga ggc acc aaa tgt tgg ggt gtg gat ttc cag        720
Ile Gln Thr Pro Ser Arg Gly Thr Lys Cys Trp Gly Val Asp Phe Gln
225                 230                 235                 240 cta gga tca gat gtt cca gat cct ggg atg gtt aac gaa ggc aca aaa        768
Leu Gly Ser Asp Val Pro Asp Pro Gly Met Val Asn Glu Gly Thr Lys
                245                 250                 255 tgt ggt gct gga aag atc tgt aga aac ttc cag tgt gta gat gct tct        816
Cys Gly Ala Gly Lys Ile Cys Arg Asn Phe Gln Cys Val Asp Ala Ser
            260                 265                 270 gtt ctg aat tat gac tgt gat gtt cag aaa aag tgt cat gga cat ggg        864
Val Leu Asn Tyr Asp Cys Asp Val Gln Lys Lys Cys His Gly His Gly
        275                 280                 285 gta tgt aat agc aat aag aat tgt cac tgt gaa aat ggc tgg ctc ccc        912
Val Cys Asn Ser Asn Lys Asn Cys His Cys Glu Asn Gly Trp Leu Pro
    290                 295                 300
```

```
caa att gtg aga cta aag gat acg aga tca agc tta tcg ata ccg tcg    960
Gln Ile Val Arg Leu Lys Asp Thr Arg Ser Ser Leu Ser Ile Pro Ser
305             310                 315                 320 acc tcg a                                                          967
Thr Ser
```

<210> SEQ ID NO 10
<211> LENGTH: 322
<212> TYPE: PRT
<213> ORGANISM: Unknown Organism
<220> FEATURE:
<223> OTHER INFORMATION: Description of Unknown Organism: Clone:
      JM109(pBShuM-gamma-G238), human meltrin gamma

<400> SEQUENCE: 10

```
Ala Lys Ser Cys Ile Met Asn Ser Gly Ala Gly Ser Arg Asn Phe
 1               5                  10                  15

Ser Ser Cys Ser Ala Glu Asp Phe Glu Lys Leu Thr Leu Asn Lys Gly
                20                  25                  30

Gly Asn Cys Leu Leu Asn Ile Pro Lys Pro Asp Glu Ala Tyr Ser Ala
             35                  40                  45

Pro Ser Cys Gly Asn Lys Leu Val Asp Ala Gly Glu Glu Cys Asp Cys
 50                      55                  60

Gly Thr Pro Lys Glu Cys Glu Leu Asp Pro Cys Cys Glu Gly Ser Thr
 65                  70                  75                  80

Cys Lys Leu Lys Ser Phe Ala Glu Cys Ala Tyr Gly Asp Cys Cys Lys
                85                  90                  95

Asp Cys Arg Phe Leu Pro Gly Gly Thr Leu Cys Arg Gly Lys Thr Ser
            100                 105                 110

Glu Cys Asp Val Pro Glu Tyr Cys Asn Gly Ser Ser Gln Phe Cys Gln
        115                 120                 125

Pro Asp Val Phe Ile Gln Asn Gly Tyr Pro Cys Gln Asn Asn Lys Ala
    130                 135                 140

Tyr Cys Tyr Asn Gly Met Cys Gln Tyr Tyr Asp Ala Gln Cys Gln Val
145                 150                 155                 160

Ile Phe Gly Ser Lys Ala Lys Ala Ala Pro Lys Asp Cys Phe Ile Glu
                165                 170                 175

Val Asn Ser Lys Gly Asp Arg Phe Gly Asn Cys Gly Phe Ser Gly Asn
            180                 185                 190

Glu Tyr Lys Lys Cys Ala Thr Gly Asn Ala Leu Cys Gly Lys Leu Gln
        195                 200                 205

Cys Glu Asn Val Gln Glu Ile Pro Val Phe Gly Ile Val Pro Ala Ile
    210                 215                 220

Ile Gln Thr Pro Ser Arg Gly Thr Lys Cys Trp Gly Val Asp Phe Gln
225                 230                 235                 240

Leu Gly Ser Asp Val Pro Asp Pro Gly Met Val Asn Glu Gly Thr Lys
                245                 250                 255

Cys Gly Ala Gly Lys Ile Cys Arg Asn Phe Gln Cys Val Asp Ala Ser
            260                 265                 270

Val Leu Asn Tyr Asp Cys Asp Val Gln Lys Lys Cys His Gly His Gly
        275                 280                 285

Val Cys Asn Ser Asn Lys Asn Cys His Cys Glu Asn Gly Trp Leu Pro
    290                 295                 300

Gln Ile Val Arg Leu Lys Asp Thr Arg Ser Ser Leu Ser Ile Pro Ser
305                 310                 315                 320

Thr Ser
```

<210> SEQ ID NO 11
<211> LENGTH: 2848
<212> TYPE: DNA
<213> ORGANISM: Unknown Organism
<220> FEATURE:
<223> OTHER INFORMATION: Description of Unknown Organism: Clones:
    JM109(pMel-alpha-25C), human meltrin alpha, and
    JM109(pMel-alpha-26N), human meltrin alpha
<220> FEATURE:
<223> OTHER INFORMATION: CDC at (1) ... (2058)

<400> SEQUENCE: 11

```
ggggacctct ggatcccagt gaagagcttc gactccaaga atcatccaga agtgctgaat      60
attcgactac aacgggaaag caagaactg atcataaatc tggaaagaaa tgaaggtctc     120
attgccagca gtttcacgga aacccactat ctgcaagacg gtactgatgt ctccctcgct    180
cgaaattaca cgggtcactg ttactaccat ggacatgtac ggggatattc tgattcagca    240
gtcagtctca gcacgtgttc tggtctcagg ggacttattg ggtttgaaaa tgaaagctat    300
gtcttagaac caatgaaaag tgcaaccaac agatacaaac tcttcccagc gaagaagctg    360
aaaagcgtcc ggggatcatg tggatcacat cacaacacac caaacctcgc tgcaaagaat    420
gtgtttccac caccctctca gacatgggca agaaggcata aagagagac cctcaaggca     480
actaagtatg tggagctggt gatcgtggca gacaaccgag agtttcagag gcaaggaaaa    540
gatctggaaa aagttaagca gcgattaata gagattgcta atcacgttga caagttttac    600
agaccactga acattcggat cgtgttggta ggcgtggaag tgtggaatga catggacaaa    660
tgctctgtaa gtcaggaccc attcaccagc ctccatgaat ttctggactg gaggaagatg    720
aagcttctac ctcgcaaatc ccatgacaat gcgcagcttg tcagtggggt ttatttccaa    780
gggaccacca tcggcatggc cccaatcatg agcatgtgca cggcagacca gtctggggga    840
attgtcatgg accattcaga caatcccctt ggtgcagccg tgaccctggc acatgagctg    900
ggccacaatt cgggatgaa tcatgacaca ctggacaggg gctgtagctg tcaaatggcg     960
gttgagaaag gaggctgcat catgaacgct tccaccgggt acccatttcc catggtgttc   1020
agcagttgca gcaggaagga cttggagacc agcctggaga aaggaatggg ggtgtgcctg   1080
tttaacctgc cggaagtcag ggagtctttc ggggccaga agtgtgggaa cagatttgtg    1140
gaagaaggag aggagtgtga ctgtgggag ccagaggaat gtatgaatcg ctgctgcaat    1200
gccaccacct gtaccctgaa gccggacgct gtgtgcgcac atgggctgtg ctgtgaagac   1260
tgccagctga agcctgcagg aacagcgtgc agggactcca gcaactcctg tgacctccca   1320
gagttctgca caggggccag ccctcactgc ccagccaacg tgtacctgca cgatgggcac   1380
tcatgtcagg atgtgacgg ctactgctac aatggcatct gccagactca cgagcagcag    1440
tgtgtcacgc tctgggacc aggtgctaaa cctgcccctg ggatctgctt tgagagagtc   1500
aattctgcag gtgatcctta tggcaactgt ggcaaagtct cgaagagttc ctttgccaaa   1560
tgcgagatga gagatgctaa atgtggaaaa atccagtgtc aaggaggtgc cagccggcca   1620
gtcattggta ccaatgccgt ttccatagaa acaaacatcc ccctgcagca aggaggccgg   1680
attctgtgcc gggggaccca cgtgtacttg gcgatgaca tgccggaccc agggcttgtg    1740
cttgcaggca caaagtgtgc agatggaaaa atctgcctga atcgtcaatg tcaaaatatt   1800
agtgtctttg gggttcacga gtgtgcaatg cagtgccacg gcagggggt gtgcaacaac   1860
aggaagaact gccactgcga ggcccactgg gcacctccct tctgtgacaa gtttggcttt   1920
ggaggaagca cagacagcgg ccccatccgg caagcagaag caaggcagga agctgcagag   1980
```

-continued

```
tccaacaggg agcgcggcca gggccaggag cccgtgggat cgcaggagca tgcgtctact   2040
gcctcactga cactcatctg agccctccca tgacatggag accgtgacca gtgctgctgc   2100
agaggaggtc acgcgtcccc aaggcctcct gtgactggca gcattgactc tgtggctttg   2160
ccatcgtttc catgacaaca gacacaacac agttctcggg gctcaggagg ggaagtccag   2220
cctaccaggc acgtctgcag aaacagtgca aggaagggca gcgacttcct ggttgagctt   2280
ctgctaaaac atggacatgc ttcagtgctg ctcctgagag agtagcaggt taccactctg   2340
gcaggcccca gccctgcagc aaggaggaag aggactcaaa agtctggcct ttcactgagc   2400
ccccacagca gtgggggaga agcaagggtt gggcccagtg tcccctttcc ccagtgacac   2460
ctcagccttg gcagccctga tgactggtct ctggctgcaa cttaatgctc tgatatggct   2520
tttagcattt attatatgaa aatagcaggg ttttagtttt taatttatca gagaccctgc   2580
cacccattcc atctccatcc aagcaaactg aatggcattg aaacaaactg agaagaagg    2640
taggagaaag ggcggtgaac tctggctctt tgctgtggac atgcgtgacc agcagtactc   2700
aggtttgagg gtttgcagaa agccagggaa cccacagagt caccaaccct tcatttaaca   2760
agtaagaatg ttaaaaagtg aaaacaatgt aagagcctaa ctccatcccc cgtggccatt   2820
actgcataaa atagagtgca tcccgccc                                      2848
```

<210> SEQ ID NO 12
<211> LENGTH: 686
<212> TYPE: PRT
<213> ORGANISM: Unknown Organism
<220> FEATURE:
<223> OTHER INFORMATION: Description of Unknown Organism:  Clones:
    JM109(pMel-alpha-25C), human meltrin alpha, and
    JM109 (pMel-alpha-26N), human meltrin alpha

<400> SEQUENCE: 12

```
Gly Asp Leu Trp Ile Pro Val Lys Ser Phe Asp Ser Lys Asn His Pro
  1               5                  10                  15

Glu Val Leu Asn Ile Arg Leu Gln Arg Glu Ser Lys Glu Leu Ile Ile
             20                  25                  30

Asn Leu Glu Arg Asn Glu Gly Leu Ile Ala Ser Ser Phe Thr Glu Thr
         35                  40                  45

His Tyr Leu Gln Asp Gly Thr Asp Val Ser Leu Ala Arg Asn Tyr Thr
     50                  55                  60

Gly His Cys Tyr Tyr His Gly His Val Arg Gly Tyr Ser Asp Ser Ala
 65                  70                  75                  80

Val Ser Leu Ser Thr Cys Ser Gly Leu Arg Gly Leu Ile Gly Phe Glu
                 85                  90                  95

Asn Glu Ser Tyr Val Leu Glu Pro Met Lys Ser Ala Thr Asn Arg Tyr
            100                 105                 110

Lys Leu Phe Pro Ala Lys Lys Leu Lys Ser Val Arg Gly Ser Cys Gly
        115                 120                 125

Ser His His Asn Thr Pro Asn Leu Ala Ala Lys Asn Val Phe Pro Pro
    130                 135                 140

Pro Ser Gln Thr Trp Ala Arg Arg His Lys Arg Glu Thr Leu Lys Ala
145                 150                 155                 160

Thr Lys Tyr Val Glu Leu Val Ile Val Ala Asp Asn Arg Glu Phe Gln
                165                 170                 175

Arg Gln Gly Lys Asp Leu Glu Lys Val Lys Gln Arg Leu Ile Glu Ile
            180                 185                 190
```

```
Ala Asn His Val Asp Lys Phe Tyr Arg Pro Leu Asn Ile Arg Ile Val
        195                 200                 205

Leu Val Gly Val Glu Val Trp Asn Asp Met Asp Lys Cys Ser Val Ser
210                 215                 220

Gln Asp Pro Phe Thr Ser Leu His Glu Phe Leu Asp Trp Arg Lys Met
225                 230                 235                 240

Lys Leu Leu Pro Arg Lys Ser His Asp Asn Ala Gln Leu Val Ser Gly
                245                 250                 255

Val Tyr Phe Gln Gly Thr Thr Ile Gly Met Ala Pro Ile Met Ser Met
                260                 265                 270

Cys Thr Ala Asp Gln Ser Gly Gly Ile Val Met Asp His Ser Asp Asn
                275                 280                 285

Pro Leu Gly Ala Ala Val Thr Leu Ala His Glu Leu Gly His Asn Phe
290                 295                 300

Gly Met Asn His Asp Thr Leu Asp Arg Gly Cys Ser Cys Gln Met Ala
305                 310                 315                 320

Val Glu Lys Gly Gly Cys Ile Met Asn Ala Ser Thr Gly Tyr Pro Phe
                325                 330                 335

Pro Met Val Phe Ser Ser Cys Ser Arg Lys Asp Leu Glu Thr Ser Leu
                340                 345                 350

Glu Lys Gly Met Gly Val Cys Leu Phe Asn Leu Pro Glu Val Arg Glu
                355                 360                 365

Ser Phe Gly Gly Gln Lys Cys Gly Asn Arg Phe Val Glu Glu Gly Glu
                370                 375                 380

Glu Cys Asp Cys Gly Glu Pro Glu Glu Cys Met Asn Arg Cys Cys Asn
385                 390                 395                 400

Ala Thr Thr Cys Thr Leu Lys Pro Asp Ala Val Cys Ala His Gly Leu
                405                 410                 415

Cys Cys Glu Asp Cys Gln Leu Lys Pro Ala Gly Thr Ala Cys Arg Asp
                420                 425                 430

Ser Ser Asn Ser Cys Asp Leu Pro Glu Phe Cys Thr Gly Ala Ser Pro
                435                 440                 445

His Cys Pro Ala Asn Val Tyr Leu His Asp Gly His Ser Cys Gln Asp
                450                 455                 460

Val Asp Gly Tyr Cys Tyr Asn Gly Ile Cys Gln Thr His Glu Gln Gln
465                 470                 475                 480

Cys Val Thr Leu Trp Gly Pro Gly Ala Lys Pro Ala Pro Gly Ile Cys
                485                 490                 495

Phe Glu Arg Val Asn Ser Ala Gly Asp Pro Tyr Gly Asn Cys Gly Lys
                500                 505                 510

Val Ser Lys Ser Ser Phe Ala Lys Cys Glu Met Arg Asp Ala Lys Cys
                515                 520                 525

Gly Lys Ile Gln Cys Gln Gly Gly Ala Ser Arg Pro Val Ile Gly Thr
                530                 535                 540

Asn Ala Val Ser Ile Glu Thr Asn Ile Pro Leu Gln Gln Gly Gly Arg
545                 550                 555                 560

Ile Leu Cys Arg Gly Thr His Val Tyr Leu Gly Asp Asp Met Pro Asp
                565                 570                 575

Pro Gly Leu Val Leu Ala Gly Thr Lys Cys Ala Asp Gly Lys Ile Cys
                580                 585                 590

Leu Asn Arg Gln Cys Gln Asn Ile Ser Val Phe Gly Val His Glu Cys
                595                 600                 605
```

```
Ala Met Gln Cys His Gly Arg Gly Val Cys Asn Asn Arg Lys Asn Cys
        610                 615                 620

His Cys Glu Ala His Trp Ala Pro Pro Phe Cys Asp Lys Phe Gly Phe
625                 630                 635                 640

Gly Gly Ser Thr Asp Ser Gly Pro Ile Arg Gln Ala Glu Ala Arg Gln
                645                 650                 655

Glu Ala Ala Glu Ser Asn Arg Glu Arg Gly Gln Gly Gln Glu Pro Val
                660                 665                 670

Gly Ser Gln Glu His Ala Ser Thr Ala Ser Leu Thr Leu Ile
            675                 680                 685

<210> SEQ ID NO 13
<211> LENGTH: 394
<212> TYPE: DNA
<213> ORGANISM: Unknown Organism
<220> FEATURE:
<223> OTHER INFORMATION: Description of Unknown Organism: Partial
      sequence of human meltrin beta derived from cDNA
<220> FEATURE:
<221> NAME/KEY: CDS
<222> LOCATION: (1)..(393)

<400> SEQUENCE: 13 ggg gaa gag tgt gat tgt gga gaa gaa gag gaa tgt aac aac ccc tgc      48
Gly Glu Glu Cys Asp Cys Gly Glu Glu Glu Glu Cys Asn Asn Pro Cys
 1                5                  10                 15 tgc aat gcc tct aat tgt acc ctg agg ccg ggg gcg gag tgt gct cac      96
Cys Asn Ala Ser Asn Cys Thr Leu Arg Pro Gly Ala Glu Cys Ala His
             20                  25                  30 ggc tcc tgc tgc cac cag tgt aag ctg ttg gct cct ggg acc ctg tgc     144
Gly Ser Cys Cys His Gln Cys Lys Leu Leu Ala Pro Gly Thr Leu Cys
         35                  40                  45 cgc gag cag gcc agg cag tgt gac ctc ccg gag ttc tgt acg ggc aag     192
Arg Glu Gln Ala Arg Gln Cys Asp Leu Pro Glu Phe Cys Thr Gly Lys
     50                  55                  60 tct ccc cac tgc cct acc aac ttc tac cag atg gat ggt acc ccc tgt     240
Ser Pro His Cys Pro Thr Asn Phe Tyr Gln Met Asp Gly Thr Pro Cys
 65                  70                  75                  80 gag ggc ggc cag gcc tac tgc tac aac ggc atg tgc ctc acc tac cag     288
Glu Gly Gly Gln Ala Tyr Cys Tyr Asn Gly Met Cys Leu Thr Tyr Gln
                 85                  90                  95 gag cag tgc cag cag ctg tgg gga ccc gga gcc cga cct gcc cct gac     336
Glu Gln Cys Gln Gln Leu Trp Gly Pro Gly Ala Arg Pro Ala Pro Asp
            100                 105                 110 ctc tgc ttc gag aag gtg aat gtg gca gga gac acc ttt gga aac tgt     384
Leu Cys Phe Glu Lys Val Asn Val Ala Gly Asp Thr Phe Gly Asn Cys
        115                 120                 125 gga aag gac a                                                       394
Gly Lys Asp
    130

<210> SEQ ID NO 14
<211> LENGTH: 131
<212> TYPE: PRT
<213> ORGANISM: Unknown Organism
<220> FEATURE:
<223> OTHER INFORMATION: Description of Unknown Organism: Partial
      sequence of human meltrin beta derived from cDNA
```

<400> SEQUENCE: 14

```
Gly Glu Glu Cys Asp Cys Gly Glu Glu Glu Cys Asn Asn Pro Cys
 1               5                  10                  15

Cys Asn Ala Ser Asn Cys Thr Leu Arg Pro Gly Ala Glu Cys Ala His
             20                  25                  30

Gly Ser Cys Cys His Gln Cys Lys Leu Leu Ala Pro Gly Thr Leu Cys
         35                  40                  45

Arg Glu Gln Ala Arg Gln Cys Asp Leu Pro Glu Phe Cys Thr Gly Lys
     50                  55                  60

Ser Pro His Cys Pro Thr Asn Phe Tyr Gln Met Asp Gly Thr Pro Cys
 65                  70                  75                  80

Glu Gly Gly Gln Ala Tyr Cys Tyr Asn Gly Met Cys Leu Thr Tyr Gln
                 85                  90                  95

Glu Gln Cys Gln Gln Leu Trp Gly Pro Gly Ala Arg Pro Ala Pro Asp
            100                 105                 110

Leu Cys Phe Glu Lys Val Asn Val Ala Gly Asp Thr Phe Gly Asn Cys
        115                 120                 125

Gly Lys Asp
        130
```

<210> SEQ ID NO 15
<211> LENGTH: 1183
<212> TYPE: DNA
<213> ORGANISM: Unknown Organism
<220> FEATURE:
<223> OTHER INFORMATION: Description of Unknown Organism: Human meltrin beta derived from cDNA
<220> FEATURE:
<221> NAME/KEY: CDS
<222> LOCATION: (2)..(1183)

<400> SEQUENCE: 15

```
c gga gct gcc act ggg cac ccc ttt ccc aaa gtg ttc aat gga tgc aac      49
  Gly Ala Ala Thr Gly His Pro Phe Pro Lys Val Phe Asn Gly Cys Asn
   1               5                  10                  15 agg agg gag ctg gac agg tat ctg cag tca ggt ggt gga atg tgt ctc       97
Arg Arg Glu Leu Asp Arg Tyr Leu Gln Ser Gly Gly Gly Met Cys Leu
             20                  25                  30 tcc aac atg cca gac acc agg atg ttg tat gga ggc cgg agg tgt ggg      145
Ser Asn Met Pro Asp Thr Arg Met Leu Tyr Gly Gly Arg Arg Cys Gly
         35                  40                  45 aac ggg tat ctg gaa gat ggg gaa gag tgt gac tgt gga gaa gaa gag      193
Asn Gly Tyr Leu Glu Asp Gly Glu Glu Cys Asp Cys Gly Glu Glu Glu
     50                  55                  60 gaa tgt aac aac ccc tgc tgc aat gcc tct aat tgt acc ctg agg ccg      241
Glu Cys Asn Asn Pro Cys Cys Asn Ala Ser Asn Cys Thr Leu Arg Pro
 65                  70                  75                  80 ggg gcg gag tgt gct cac ggc tcc tgc tgc cac cag tgt aag ctg ttg      289
Gly Ala Glu Cys Ala His Gly Ser Cys Cys His Gln Cys Lys Leu Leu
                 85                  90                  95 gct cct ggg acc ctg tgc cgc gag cag gcc agg cag tgt gac ctc ccg      337
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag      385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc      433
Met Asp Gly Thr Pro Cys Glu Gly Gly Gln Ala Tyr Cys Tyr Asn Gly
    130                 135                 140
```

```
atg tgc ctc acc tac cag gag cag tgc cag cag ctg tgg gga ccc gga      481
Met Cys Leu Thr Tyr Gln Glu Gln Cys Gln Gln Leu Trp Gly Pro Gly
145                 150                 155                 160 gcc cga cct gcc cct gac ctc tgc ttc gag aag gtg aat gtg gca gga      529
Ala Arg Pro Ala Pro Asp Leu Cys Phe Glu Lys Val Asn Val Ala Gly
                165                 170                 175 gac acc ttt gga aac tgt gga aag gac atg aat ggt gaa cac agg aag      577
Asp Thr Phe Gly Asn Cys Gly Lys Asp Met Asn Gly Glu His Arg Lys
            180                 185                 190 tgc aac atg aga gat gcg aag tgt ggg aag atc cag tgt cag agc tct      625
Cys Asn Met Arg Asp Ala Lys Cys Gly Lys Ile Gln Cys Gln Ser Ser
        195                 200                 205 gag gcc cgg ccc ctg gag tcc aac gcg gtg ccc att gac acc act atc      673
Glu Ala Arg Pro Leu Glu Ser Asn Ala Val Pro Ile Asp Thr Thr Ile
    210                 215                 220 atc atg aat ggg agg cag atc cag tgc cgg ggc acc cac gtc tac cga      721
Ile Met Asn Gly Arg Gln Ile Gln Cys Arg Gly Thr His Val Tyr Arg
225                 230                 235                 240 ggt cct gag gag gag ggt gac atg ctg gac cca ggg ctg gtg atg act      769
Gly Pro Glu Glu Glu Gly Asp Met Leu Asp Pro Gly Leu Val Met Thr
                245                 250                 255 gga acc aag tgt ggc tac aac cat att tgc ctt gag ggg cag tgc agg      817
Gly Thr Lys Cys Gly Tyr Asn His Ile Cys Leu Glu Gly Gln Cys Arg
            260                 265                 270 aac acc tcc ttc ttt gaa act gaa ggc tgt ggg aag aag tgc aat ggc      865
Asn Thr Ser Phe Phe Glu Thr Glu Gly Cys Gly Lys Lys Cys Asn Gly
        275                 280                 285 cat ggg gtc tgt aac aac aac cag aac tgc cac tgc ctg ccg ggc tgg      913
His Gly Val Cys Asn Asn Asn Gln Asn Cys His Cys Leu Pro Gly Trp
    290                 295                 300 gcc ccg ccc ttc tgc aac aca ccg ggc cac ggg ggc agt atc gac agt      961
Ala Pro Pro Phe Cys Asn Thr Pro Gly His Gly Gly Ser Ile Asp Ser
305                 310                 315                 320 ggg cct atg ccc cct gag agt gtg ggt cct gtg gta gct gga gtg ttg     1009
Gly Pro Met Pro Pro Glu Ser Val Gly Pro Val Val Ala Gly Val Leu
                325                 330                 335 gtg gcc atc ttg gtg ctg gcg gtc ctc atg ctg atg tac tac tgc tgc     1057
Val Ala Ile Leu Val Leu Ala Val Leu Met Leu Met Tyr Tyr Cys Cys
            340                 345                 350 aga cag aac aac aaa cta ggc caa ctc aag ccc tca gct ctc cct tcc     1105
Arg Gln Asn Asn Lys Leu Gly Gln Leu Lys Pro Ser Ala Leu Pro Ser
        355                 360                 365 aag ctg agg caa cag ttc agt tgt ccc ttc agg gtt tct cag aac agc     1153
Lys Leu Arg Gln Gln Phe Ser Cys Pro Phe Arg Val Ser Gln Asn Ser
    370                 375                 380 ggg act ggt cat gcc aac cca act ttc aag                             1183
Gly Thr Gly His Ala Asn Pro Thr Phe Lys
385                 390
```

<210> SEQ ID NO 16
<211> LENGTH: 394
<212> TYPE: PRT
<213> ORGANISM: Unknown Organism
<220> FEATURE:
<223> OTHER INFORMATION: Description of Unknown Organism: Human meltrin
      beta derived from cDNA

```
<400> SEQUENCE: 16

Gly Ala Ala Thr Gly His Pro Phe Pro Lys Val Phe Asn Gly Cys Asn
 1               5                  10                  15

Arg Arg Glu Leu Asp Arg Tyr Leu Gln Ser Gly Gly Met Cys Leu
            20                  25                  30

Ser Asn Met Pro Asp Thr Arg Met Leu Tyr Gly Gly Arg Arg Cys Gly
            35                  40                  45

Asn Gly Tyr Leu Glu Asp Gly Glu Glu Cys Asp Cys Gly Glu Glu Glu
        50                  55                  60

Glu Cys Asn Asn Pro Cys Cys Asn Ala Ser Asn Cys Thr Leu Arg Pro
 65                 70                  75                  80

Gly Ala Glu Cys Ala His Gly Ser Cys Cys His Gln Cys Lys Leu Leu
                85                  90                  95

Ala Pro Gly Thr Leu Cys Arg Glu Gln Ala Arg Gln Cys Asp Leu Pro
            100                 105                 110

Glu Phe Cys Thr Gly Lys Ser Pro His Cys Pro Thr Asn Phe Tyr Gln
            115                 120                 125

Met Asp Gly Thr Pro Cys Glu Gly Gly Gln Ala Tyr Cys Tyr Asn Gly
130                 135                 140

Met Cys Leu Thr Tyr Gln Glu Gln Cys Gln Gln Leu Trp Gly Pro Gly
145                 150                 155                 160

Ala Arg Pro Ala Pro Asp Leu Cys Phe Glu Lys Val Asn Val Ala Gly
                165                 170                 175

Asp Thr Phe Gly Asn Cys Gly Lys Asp Met Asn Gly Glu His Arg Lys
            180                 185                 190

Cys Asn Met Arg Asp Ala Lys Cys Gly Lys Ile Gln Cys Gln Ser Ser
            195                 200                 205

Glu Ala Arg Pro Leu Glu Ser Asn Ala Val Pro Ile Asp Thr Thr Ile
        210                 215                 220

Ile Met Asn Gly Arg Gln Ile Gln Cys Arg Gly Thr His Val Tyr Arg
225                 230                 235                 240

Gly Pro Glu Glu Glu Gly Asp Met Leu Asp Pro Gly Leu Val Met Thr
                245                 250                 255

Gly Thr Lys Cys Gly Tyr Asn His Ile Cys Leu Glu Gly Gln Cys Arg
            260                 265                 270

Asn Thr Ser Phe Phe Glu Thr Glu Gly Cys Gly Lys Lys Cys Asn Gly
            275                 280                 285

His Gly Val Cys Asn Asn Gln Asn Cys His Cys Leu Pro Gly Trp
290                 295                 300

Ala Pro Pro Phe Cys Asn Thr Pro Gly His Gly Gly Ser Ile Asp Ser
305                 310                 315                 320

Gly Pro Met Pro Pro Glu Ser Val Gly Pro Val Val Ala Gly Val Leu
                325                 330                 335

Val Ala Ile Leu Val Leu Ala Val Leu Met Leu Met Tyr Tyr Cys Cys
            340                 345                 350

Arg Gln Asn Asn Lys Leu Gly Gln Leu Lys Pro Ser Ala Leu Pro Ser
            355                 360                 365

Lys Leu Arg Gln Gln Phe Ser Cys Pro Phe Arg Val Ser Gln Asn Ser
        370                 375                 380

Gly Thr Gly His Ala Asn Pro Thr Phe Lys
385                 390
```

<210> SEQ ID NO 17
<211> LENGTH: 624
<212> TYPE: DNA
<213> ORGANISM: Unknown Organism
<220> FEATURE:
<223> OTHER INFORMATION: Description of Unknown Organism: Clone TM:
      Human meltrin alpha derived from cDNA
<220> FEATURE:
<221> NAME/KEY: CDS
<222> LOCATION: (3)..(623)

<400> SEQUENCE: 17

```
gc aca aag tgt gca gat gga aaa atc tgc ctg aat cgt caa tgt caa        47
   Thr Lys Cys Ala Asp Gly Lys Ile Cys Leu Asn Arg Gln Cys Gln
    1               5                  10                  15 aat att agt gtc ttt ggg gtt cac gag tgt gca atg cag tgc cac ggc       95
Asn Ile Ser Val Phe Gly Val His Glu Cys Ala Met Gln Cys His Gly
            20                  25                  30 aga ggg gtg tgc aac aac agg aag aac tgc cac tgc gag gcc cac tgg      143
Arg Gly Val Cys Asn Asn Arg Lys Asn Cys His Cys Glu Ala His Trp
        35                  40                  45 gca cct ccc ttc tgt gac aag ttt ggc ttt gga gga agc aca gac agc      191
Ala Pro Pro Phe Cys Asp Lys Phe Gly Phe Gly Gly Ser Thr Asp Ser
    50                  55                  60 ggc ccc atc cgg caa gca gat aac caa ggt tta acc ata gga att ctg      239
Gly Pro Ile Arg Gln Ala Asp Asn Gln Gly Leu Thr Ile Gly Ile Leu
65                  70                  75 gtg acc atc ctg tgt ctt ctt gct gcc gga ttt gtg gtt tat ctc aaa      287
Val Thr Ile Leu Cys Leu Leu Ala Ala Gly Phe Val Val Tyr Leu Lys
 80                  85                  90                  95 agg aag acc ttg ata cga ctg ctg ttt aca aat aag aag acc acc att      335
Arg Lys Thr Leu Ile Arg Leu Leu Phe Thr Asn Lys Lys Thr Thr Ile
                100                 105                 110 gaa aaa cta agg tgt gtg cgc cct tcc cgg cca ccc gtg gct tca caa      383
Glu Lys Leu Arg Cys Val Arg Pro Ser Arg Pro Pro Val Gly Phe Gln
            115                 120                 125 ccc tgt cag gct cac ctc ggc cac ctt gga aaa ggc ctg atg agg aag      431
Pro Cys Gln Ala His Leu Gly His Leu Gly Lys Gly Leu Met Arg Lys
        130                 135                 140 ccg cca gat tcc tac cca ccg aag gac aat ccc agg aga ttg ctg cag      479
Pro Pro Asp Ser Tyr Pro Pro Lys Asp Asn Pro Arg Arg Leu Leu Gln
    145                 150                 155 tgt cag aat gtt gac atc agc aga ccc ctc aac ggc ctg aat gtc cct      527
Cys Gln Asn Val Asp Ile Ser Arg Pro Leu Asn Gly Leu Asn Val Pro
160                 165                 170                 175 cag ccc cag tca act cag cga gtg ctt cct ccc ctc cac cgg gct cca      575
Gln Pro Gln Ser Thr Gln Arg Val Leu Pro Pro Leu His Arg Ala Pro
                180                 185                 190 cgt gca cct agc gtc cct gcc aga ccc ctg cca gcc aag cct gca ctt a   624
Arg Ala Pro Ser Val Pro Ala Arg Pro Leu Pro Ala Lys Pro Ala Leu
            195                 200                 205
```

<210> SEQ ID NO 18
<211> LENGTH: 207
<212> TYPE: PRT
<213> ORGANISM: Unknown Organism
<220> FEATURE:
<223> OTHER INFORMATION: Description of Unknown Organism: Clone TM:
      Human meltrin alpha derived from cDNA

```
<400> SEQUENCE: 18

Thr Lys Cys Ala Asp Gly Lys Ile Cys Leu Asn Arg Gln Cys Gln Asn
  1               5                  10                  15

Ile Ser Val Phe Gly Val His Glu Cys Ala Met Gln Cys His Gly Arg
             20                  25                  30

Gly Val Cys Asn Asn Arg Lys Asn Cys His Cys Glu Ala His Trp Ala
         35                  40                  45

Pro Pro Phe Cys Asp Lys Phe Gly Phe Gly Gly Ser Thr Asp Ser Gly
     50                  55                  60

Pro Ile Arg Gln Ala Asp Asn Gln Gly Leu Thr Ile Gly Ile Leu Val
 65                  70                  75                  80

Thr Ile Leu Cys Leu Leu Ala Ala Gly Phe Val Val Tyr Leu Lys Arg
                 85                  90                  95

Lys Thr Leu Ile Arg Leu Leu Phe Thr Asn Lys Lys Thr Thr Ile Glu
            100                 105                 110

Lys Leu Arg Cys Val Arg Pro Ser Arg Pro Pro Arg Gly Phe Gln Pro
        115                 120                 125

Cys Gln Ala His Leu Gly His Leu Gly Lys Gly Leu Met Arg Lys Pro
    130                 135                 140

Pro Asp Ser Tyr Pro Pro Lys Asp Asn Pro Arg Arg Leu Leu Gln Cys
145                 150                 155                 160

Gln Asn Val Asp Ile Ser Arg Pro Leu Asn Gly Leu Asn Val Pro Gln
                165                 170                 175

Pro Gln Ser Thr Gln Arg Val Leu Pro Pro Leu His Arg Ala Pro Arg
            180                 185                 190

Ala Pro Ser Val Pro Ala Arg Pro Leu Pro Ala Lys Pro Ala Leu
        195                 200                 205

<210> SEQ ID NO 19
<211> LENGTH: 2669
<212> TYPE: DNA
<213> ORGANISM: Unknown Organism
<220> FEATURE:
<223> OTHER INFORMATION: Description of Unknown Organism:  Clones:
      JM109(pMel-beta-24C) and JM109(pMel-beta-24N),
      both human meltrin beta
<220> FEATURE:
<221> NAME/KEY: CDS
<222> LOCATION: (2)..(1282)

<400> SEQUENCE: 19 c gga gct gcc act ggg cac ccc ttt ccc aaa gtg ttc aat gga tgc aac      49
  Gly Ala Ala Thr Gly His Pro Phe Pro Lys Val Phe Asn Gly Cys Asn
   1               5                  10                  15 agg agg gag ctg gac agg tat ctg cag tca ggt ggt gga atg tgt ctc       97
Arg Arg Glu Leu Asp Arg Tyr Leu Gln Ser Gly Gly Gly Met Cys Leu
             20                  25                  30 tcc aac atg cca gac acc agg atg ttg tat gga ggc cgg agg tgt ggg      145
Ser Asn Met Pro Asp Thr Arg Met Leu Tyr Gly Gly Arg Arg Cys Gly
         35                  40                  45 aac ggg tat ctg gaa gat ggg gaa gag tgt gac tgt gga gaa gaa gag      193
Asn Gly Tyr Leu Glu Asp Gly Glu Glu Cys Asp Cys Gly Glu Glu Glu
     50                  55                  60 gaa tgt aac aac ccc tgc tgc aat gcc tct aat tgt acc ctg agg ccg      241
Glu Cys Asn Asn Pro Cys Cys Asn Ala Ser Asn Cys Thr Leu Arg Pro
 65                  70                  75                  80 ggg gcg gag tgt gct cac ggc tcc tgc tgc cac cag tgt aag ctg ttg      289
Gly Ala Glu Cys Ala His Gly Ser Cys Cys His Gln Cys Lys Leu Leu
                 85                  90                  95
```

```
gct cct ggg acc ctg tgc cgc gag cag gcc agg cag tgt gac ctc ccg     337
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag     385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc     433
Met Asp Gly Thr Pro Cys Glu Gly Gly Gln Ala Tyr Cys Tyr Asn Gly
130                 135                 140 atg tgc ctc acc tac cag gag cag tgc cag cag ctg tgg gga ccc gga     481
Met Cys Leu Thr Tyr Gln Glu Gln Cys Gln Gln Leu Trp Gly Pro Gly
145                 150                 155                 160 gcc cga cct gcc cct gac ctc tgc ttc gag aag gtg aat gtg gca gga     529
Ala Arg Pro Ala Pro Asp Leu Cys Phe Glu Lys Val Asn Val Ala Gly
                165                 170                 175 gac acc ttt gga aac tgt gga aag gac atg aat ggt gaa cac agg aag     577
Asp Thr Phe Gly Asn Cys Gly Lys Asp Met Asn Gly Glu His Arg Lys
            180                 185                 190 tgc aac atg aga gat gcg aag tgt ggg aag atc cag tgt cag agc tct     625
Cys Asn Met Arg Asp Ala Lys Cys Gly Lys Ile Gln Cys Gln Ser Ser
        195                 200                 205 gag gcc cgg ccc ctg gag tcc aac gcg gtg ccc att gac acc act atc     673
Glu Ala Arg Pro Leu Glu Ser Asn Ala Val Pro Ile Asp Thr Thr Ile
210                 215                 220 atc atg aat ggg agg cag atc cag tgc cgg ggc acc cac gtc tac cga     721
Ile Met Asn Gly Arg Gln Ile Gln Cys Arg Gly Thr His Val Tyr Arg
225                 230                 235                 240 ggt cct gag gag gag ggt gac atg ctg gac cca ggg ctg gtg atg act     769
Gly Pro Glu Glu Glu Gly Asp Met Leu Asp Pro Gly Leu Val Met Thr
                245                 250                 255 gga acc aag tgt ggc tac aac cat att tgc ctt gag ggg cag tgc agg     817
Gly Thr Lys Cys Gly Tyr Asn His Ile Cys Leu Glu Gly Gln Cys Arg
            260                 265                 270 aac acc tcc ttc ttt gaa act gaa ggc tgt ggg aag aag tgc aat ggc     865
Asn Thr Ser Phe Phe Glu Thr Glu Gly Cys Gly Lys Lys Cys Asn Gly
        275                 280                 285 cat ggg gtc tgt aac aac aac cag aac tgc cac tgc ctg ccg ggc tgg     913
His Gly Val Cys Asn Asn Asn Gln Asn Cys His Cys Leu Pro Gly Trp
290                 295                 300 gcc ccg ccc ttc tgc aac aca ccg ggc cac ggg ggc agt atc gac agt     961
Ala Pro Pro Phe Cys Asn Thr Pro Gly His Gly Gly Ser Ile Asp Ser
305                 310                 315                 320 ggg cct atg ccc cct gag agt gtg ggt cct gtg gta gct gga gtg ttg    1009
Gly Pro Met Pro Pro Glu Ser Val Gly Pro Val Val Ala Gly Val Leu
                325                 330                 335 gtg gcc atc ttg gtg ctg gcg gtc ctc atg ctg atg tac tac tgc tgc    1057
Val Ala Ile Leu Val Leu Ala Val Leu Met Leu Met Tyr Tyr Cys Cys
            340                 345                 350 aga cag aac aac aaa cta ggc caa ctc aag ccc tca gct ctc cct tcc    1105
Arg Gln Asn Asn Lys Leu Gly Gln Leu Lys Pro Ser Ala Leu Pro Ser
        355                 360                 365 aag ctg agg caa cag ttc agt tgt ccc ttc agg gtt tct cag aac agc    1153
Lys Leu Arg Gln Gln Phe Ser Cys Pro Phe Arg Val Ser Gln Asn Ser
370                 375                 380 ggg act ggt cat gcc aac cca act ttc aag ccg gaa ttc cgg gcc ccc    1201
Gly Thr Gly His Ala Asn Pro Thr Phe Lys Pro Glu Phe Arg Ala Pro
385                 390                 395                 400 cac agc cca cac cac cat gac aag ggc cac caa ttc cac ggc cac acc    1249
His Ser Pro His His His Asp Lys Gly His Gln Phe His Gly His Thr
                405                 410                 415
```

```
ctc ctc cac tct ggg gac gac ccg gat cct cac tgagctgacc acaacagcca    1302
Leu Leu His Ser Gly Asp Asp Pro Asp Pro His
        420                 425 ctacaactgc agccactgga tccacggcca ccctgtcctc caccccaggg accacctgga    1362
tcctcacaga gccgagcact atagccaccg tgatggtgcc caccggttcc acggccaccg    1422
cctcctccac tctgggaaca gctcacaccc caaagtggt gaccaccatg gccactatgc     1482
ccacagccca tgcctccacg gttcccagct cgtccaccgt ggggaccacc cgcacccctg    1542
cagtgctccc cagcagcctg ccaaccttca gcgtgtccac tgtgtcctcc tcagtcctca    1602
ccaccctgag acccactggc ttccccagct cccacttctc tactccctgc ttctgcaggg    1662
catttggaca gttttctcg cccggggaag tcatctacaa taagaccgac cgagccggct     1722
gccatttcta cgcagtgtgc aatcagcact gtgacattga ccgcttccag ggcgcctgtc    1782
ccacctcccc accgccagtg tcctccgccc cgctgtcctc gccctcccct gccctggct     1842
gtgacaatgc catccctctc cggcaggtga atgagacctg gacctggag aactgcacgg     1902
tggccaggtg cgtgggtgac aaccgtgtcg tcctgctgga cccaaagcct gtggccaacg    1962
tcacctgcgt gaacaagcac ctgcccatca aagtgtcgga cccgagccag ccctgtgact    2022
tccactatga gtgcgagtgc atctgcagca tgtggggcgg ctcccactat tccacctttg    2082
acggcacctc ttacaccttc cggggcaact gcacctatgt cctcatgaga gagatccatg    2142
cacgctttgg gaatctcagc ctctacctgg acaaccacta ctgcacggcc tctgccactg    2202
ccgctgccgc ccgctgcccc cgcgccctca gcatccacta caagtccatg gatatcgtcc    2262
tcactgtcac catggtgcat gggaaggagg agggcctgat cctgtttgac caaattccgg    2322
tgagcagcgg tttcagcaag aacggcgtgc ttgtgtctgt gctggggacc accaccatgc    2382
gtgtggacat tcctgccctg ggcgtgagcg tcaccttcaa tggccaagtc ttccaggccc    2442
ggctgcccta cagcctcttc cacaacaaca ccgagggcca gtgcggcacc tgcaccaaca    2502
accagaggga cgactgtctc cagcgggacg gaaccactgc cgccagttgc aaggacatgg    2562
ccaagacgtg gctggtcccc gacagcagaa aggatggctg ctgggccccg actggcacac    2622
cccccactgc cagccccgca gccccggtgt ctagcacacc cacccccg                 2669
```

<210> SEQ ID NO 20
<211> LENGTH: 427
<212> TYPE: PRT
<213> ORGANISM: Unknown Organism
<220> FEATURE:
<223> OTHER INFORMATION: Description of Unknown Organism: Clones:
      JM109(pMel-beta-24C) and JM109(pMel-beta-24N),
      both human meltrin beta

<400> SEQUENCE: 20

Gly Ala Ala Thr Gly His Pro Phe Pro Lys Val Phe Asn Gly Cys Asn
 1               5                  10                  15

Arg Arg Glu Leu Asp Arg Tyr Leu Gln Ser Gly Gly Met Cys Leu
             20                  25                  30

Ser Asn Met Pro Asp Thr Arg Met Leu Tyr Gly Gly Arg Arg Cys Gly
         35                  40                  45

Asn Gly Tyr Leu Glu Asp Gly Glu Glu Cys Asp Cys Gly Glu Glu Glu
     50                  55                  60

Glu Cys Asn Asn Pro Cys Cys Asn Ala Ser Asn Cys Thr Leu Arg Pro
 65                  70                  75                  80

Gly Ala Glu Cys Ala His Gly Ser Cys Cys His Gln Cys Lys Leu Leu
                 85                  90                  95

-continued

Ala Pro Gly Thr Leu Cys Arg Glu Gln Ala Arg Gln Cys Asp Leu Pro
            100                 105                 110

Glu Phe Cys Thr Gly Lys Ser Pro His Cys Pro Thr Asn Phe Tyr Gln
        115                 120                 125

Met Asp Gly Thr Pro Cys Glu Gly Gln Ala Tyr Cys Tyr Asn Gly
    130                 135                 140

Met Cys Leu Thr Tyr Gln Glu Gln Cys Gln Gln Leu Trp Gly Pro Gly
145                 150                 155                 160

Ala Arg Pro Ala Pro Asp Leu Cys Phe Glu Lys Val Asn Val Ala Gly
                165                 170                 175

Asp Thr Phe Gly Asn Cys Gly Lys Asp Met Asn Gly Glu His Arg Lys
            180                 185                 190

Cys Asn Met Arg Asp Ala Lys Cys Gly Lys Ile Gln Cys Gln Ser Ser
            195                 200                 205

Glu Ala Arg Pro Leu Glu Ser Asn Ala Val Pro Ile Asp Thr Thr Ile
            210                 215                 220

Ile Met Asn Gly Arg Gln Ile Gln Cys Arg Gly Thr His Val Tyr Arg
225                 230                 235                 240

Gly Pro Glu Glu Gly Asp Met Leu Asp Pro Gly Leu Val Met Thr
                245                 250                 255

Gly Thr Lys Cys Gly Tyr Asn His Ile Cys Leu Glu Gly Gln Cys Arg
            260                 265                 270

Asn Thr Ser Phe Phe Glu Thr Glu Gly Cys Gly Lys Lys Cys Asn Gly
            275                 280                 285

His Gly Val Cys Asn Asn Asn Gln Asn Cys His Cys Leu Pro Gly Trp
            290                 295                 300

Ala Pro Pro Phe Cys Asn Thr Pro Gly His Gly Gly Ser Ile Asp Ser
305                 310                 315                 320

Gly Pro Met Pro Pro Glu Ser Val Gly Pro Val Val Ala Gly Val Leu
                325                 330                 335

Val Ala Ile Leu Val Leu Ala Val Leu Met Leu Met Tyr Tyr Cys Cys
            340                 345                 350

Arg Gln Asn Asn Lys Leu Gly Gln Leu Lys Pro Ser Ala Leu Pro Ser
            355                 360                 365

Lys Leu Arg Gln Gln Phe Ser Cys Pro Phe Arg Val Ser Gln Asn Ser
            370                 375                 380

Gly Thr Gly His Ala Asn Pro Thr Phe Lys Pro Glu Phe Arg Ala Pro
385                 390                 395                 400

His Ser Pro His His His Asp Lys Gly His Gln Phe His Gly His Thr
                405                 410                 415

Leu Leu His Ser Gly Asp Asp Pro Asp Pro His
            420                 425

<210> SEQ ID NO 21
<211> LENGTH: 1483
<212> TYPE: DNA
<213> ORGANISM: Unknown Organism
<220> FEATURE:
<223> OTHER INFORMATION: Description of Unknown Organism: Clone:
      JM109(pMel-alpha-25C), human meltrin alpha
<220> FEATURE:
<221> NAME/KEY: CDS
<222> LOCATION: (1)..(687)

<400> SEQUENCE: 21

```
gat ggg cac tca tgt cag gat gtg gac ggc tac tgc tac aat ggc atc        48
Asp Gly His Ser Cys Gln Asp Val Asp Gly Tyr Cys Tyr Asn Gly Ile
1               5                   10                  15 tgc cag act cac gag cag cag tgt gtc acg ctc tgg gga cca ggt gct        96
Cys Gln Thr His Glu Gln Gln Cys Val Thr Leu Trp Gly Pro Gly Ala
                20                  25                  30 aaa cct gcc cct ggg atc tgc ttt gag aga gtc aat tct gca ggt gat       144
Lys Pro Ala Pro Gly Ile Cys Phe Glu Arg Val Asn Ser Ala Gly Asp
            35                  40                  45 cct tat ggc aac tgt ggc aaa gtc tcg aag agt tcc ttt gcc aaa tgc       192
Pro Tyr Gly Asn Cys Gly Lys Val Ser Lys Ser Ser Phe Ala Lys Cys
        50                  55                  60 gag atg aga gat gct aaa tgt gga aaa atc cag tgt caa gga ggt gcc       240
Glu Met Arg Asp Ala Lys Cys Gly Lys Ile Gln Cys Gln Gly Gly Ala
65                  70                  75                  80 agc cgg cca gtc att ggt acc aat gcc gtt tcc ata gaa aca aac atc       288
Ser Arg Pro Val Ile Gly Thr Asn Ala Val Ser Ile Glu Thr Asn Ile
                85                  90                  95 ccc ctg cag caa gga ggc cgg att ctg tgc cgg ggg acc cac gtg tac       336
Pro Leu Gln Gln Gly Gly Arg Ile Leu Cys Arg Gly Thr His Val Tyr
            100                 105                 110 ttg ggc gat gac atg ccg gac cca ggg ctt gtg ctt gca ggc aca aag       384
Leu Gly Asp Asp Met Pro Asp Pro Gly Leu Val Leu Ala Gly Thr Lys
        115                 120                 125 tgt gca gat gga aaa atc tgc ctg aat cgt caa tgt caa aat att agt       432
Cys Ala Asp Gly Lys Ile Cys Leu Asn Arg Gln Cys Gln Asn Ile Ser
130                 135                 140 gtc ttt ggg gtt cac gag tgt gca atg cag tgc cac ggc aga ggg gtg       480
Val Phe Gly Val His Glu Cys Ala Met Gln Cys His Gly Arg Gly Val
145                 150                 155                 160 tgc aac aac agg aag aac tgc cac tgc gag gcc cac tgg gca cct ccc       528
Cys Asn Asn Arg Lys Asn Cys His Cys Glu Ala His Trp Ala Pro Pro
                165                 170                 175 ttc tgt gac aag ttt ggc ttt gga gga agc aca gac agc ggc ccc atc       576
Phe Cys Asp Lys Phe Gly Phe Gly Gly Ser Thr Asp Ser Gly Pro Ile
            180                 185                 190 cgg caa gca gaa gca agg cag gaa gct gca gag tcc aac agg gag cgc       624
Arg Gln Ala Glu Ala Arg Gln Glu Ala Ala Glu Ser Asn Arg Glu Arg
        195                 200                 205 ggc cag ggc cag gag ccc gtg gga tcg cag gag cat gcg tct act gcc       672
Gly Gln Gly Gln Glu Pro Val Gly Ser Gln Glu His Ala Ser Thr Ala
210                 215                 220 tca ctg aca ctc atc tgagccctcc catgacatgg agaccgtgac cagtgctgct       727
Ser Leu Thr Leu Ile
225 gcagaggagg tcacgcgtcc ccaaggcctc ctgtgactgg cagcattgac tctgtggctt      787 tgccatcgtt tccatgacaa cagacacaac acagttctcg gggctcagga ggggaagtcc      847 agcctaccag gcacgtctgc agaaacagtg caaggaaggg cagcgacttc ctggttgagc      907 ttctgctaaa acatggacat gcttcagtgc tgctcctgag agagtagcag gttaccactc      967 tggcaggccc cagccctgca gcaaggagga agaggactca aaagtctggc ctttcactga     1027 gcccccacag cagtggggga gaagcaaggg ttgggcccag tgtccccttt ccccagtgac     1087 acctcagcct tggcagccct gatgactggt ctctggctgc aacttaatgc tctgatatgg     1147 cttttagcat ttattatatg aaaatagcag ggttttagtt tttaatttat cagagaccct     1207 gccacccatt ccatctccat ccaagcaaac tgaatggcat tgaaacaaac tggagaagaa     1267
```

-continued

```
ggtaggagaa agggcggtga actctggctc tttgctgtgg acatgcgtga ccagcagtac    1327
tcaggtttga gggtttgcag aaagccaggg aacccacaga gtcaccaacc cttcatttaa    1387
caagtaagaa tgttaaaaag tgaaaacaat gtaagagcct aactccatcc cccgtggcca    1447
ttactgcata aatagagtg catcccgccc gaattc                                1483
```

<210> SEQ ID NO 22
<211> LENGTH: 229
<212> TYPE: PRT
<213> ORGANISM: Unknown Organism
<220> FEATURE:
<223> OTHER INFORMATION: Description of Unknown Organism: Clone: JM109(pMel-alpha-25C), human meltrin alpha

<400> SEQUENCE: 22

```
Asp Gly His Ser Cys Gln Asp Val Asp Gly Tyr Cys Tyr Asn Gly Ile
 1               5                  10                  15

Cys Gln Thr His Glu Gln Gln Cys Val Thr Leu Trp Gly Pro Gly Ala
            20                  25                  30

Lys Pro Ala Pro Gly Ile Cys Phe Glu Arg Val Asn Ser Ala Gly Asp
        35                  40                  45

Pro Tyr Gly Asn Cys Gly Lys Val Ser Lys Ser Ser Phe Ala Lys Cys
    50                  55                  60

Glu Met Arg Asp Ala Lys Cys Gly Lys Ile Gln Cys Gln Gly Gly Ala
65                  70                  75                  80

Ser Arg Pro Val Ile Gly Thr Asn Ala Val Ser Ile Glu Thr Asn Ile
                85                  90                  95

Pro Leu Gln Gln Gly Gly Arg Ile Leu Cys Arg Gly Thr His Val Tyr
            100                 105                 110

Leu Gly Asp Asp Met Pro Asp Pro Gly Leu Val Leu Ala Gly Thr Lys
        115                 120                 125

Cys Ala Asp Gly Lys Ile Cys Leu Asn Arg Gln Cys Gln Asn Ile Ser
    130                 135                 140

Val Phe Gly Val His Glu Cys Ala Met Gln Cys His Gly Arg Gly Val
145                 150                 155                 160

Cys Asn Asn Arg Lys Asn Cys His Cys Glu Ala His Trp Ala Pro Pro
                165                 170                 175

Phe Cys Asp Lys Phe Gly Phe Gly Gly Ser Thr Asp Ser Gly Pro Ile
            180                 185                 190

Arg Gln Ala Glu Ala Arg Gln Glu Ala Ala Glu Ser Asn Arg Glu Arg
        195                 200                 205

Gly Gln Gly Gln Glu Pro Val Gly Ser Gln Glu His Ala Ser Thr Ala
    210                 215                 220

Ser Leu Thr Leu Ile
225
```

<210> SEQ ID NO 23
<211> LENGTH: 1569
<212> TYPE: DNA
<213> ORGANISM: Unknown Organism
<220> FEATURE:
<223> OTHER INFORMATION: Description of Unknown Organism: Clone: JM109(pMel-alpha-26N), human meltrin alpha
<220> FEATURE:
<221> NAME/KEY: CDS
<222> LOCATION: (1)..(1569)

<400> SEQUENCE: 23

| | | |
|---|---|---|
| ggg gac ctc tgg atc cca gtg aag agc ttc gac tcc aag aat cat cca<br>Gly Asp Leu Trp Ile Pro Val Lys Ser Phe Asp Ser Lys Asn His Pro<br>1                  5                    10                15 | 48 |
| gaa gtg ctg aat att cga cta caa cgg gaa agc aaa gaa ctg atc ata<br>Glu Val Leu Asn Ile Arg Leu Gln Arg Glu Ser Lys Glu Leu Ile Ile<br>                  20                    25                    30 | 96 |
| aat ctg gaa aga aat gaa ggt ctc att gcc agc agt ttc acg gaa acc<br>Asn Leu Glu Arg Asn Glu Gly Leu Ile Ala Ser Ser Phe Thr Glu Thr<br>        35                    40                    45 | 144 |
| cac tat ctg caa gac ggt act gat gtc tcc ctc gct cga aat tac acg<br>His Tyr Leu Gln Asp Gly Thr Asp Val Ser Leu Ala Arg Asn Tyr Thr<br>50                    55                    60 | 192 |
| ggt cac tgt tac tac cat gga cat gta cgg gga tat tct gat tca gca<br>Gly His Cys Tyr Tyr His Gly His Val Arg Gly Tyr Ser Asp Ser Ala<br>65                    70                    75                    80 | 240 |
| gtc agt ctc agc acg tgt tct ggt ctc agg gga ctt att ggg ttt gaa<br>Val Ser Leu Ser Thr Cys Ser Gly Leu Arg Gly Leu Ile Gly Phe Glu<br>                  85                    90                    95 | 288 |
| aat gaa agc tat gtc tta gaa cca atg aaa agt gca acc aac aga tac<br>Asn Glu Ser Tyr Val Leu Glu Pro Met Lys Ser Ala Thr Asn Arg Tyr<br>        100                    105                    110 | 336 |
| aaa ctc ttc cca gcg aag aag ctg aaa agc gtc cgg gga tca tgt gga<br>Lys Leu Phe Pro Ala Lys Lys Leu Lys Ser Val Arg Gly Ser Cys Gly<br>            115                    120                    125 | 384 |
| tca cat cac aac aca cca aac ctc gct gca aag aat gtg ttt cca cca<br>Ser His His Asn Thr Pro Asn Leu Ala Ala Lys Asn Val Phe Pro Pro<br>130                    135                    140 | 432 |
| ccc tct cag aca tgg gca aga agg cat aaa aga gag acc ctc aag gca<br>Pro Ser Gln Thr Trp Ala Arg Arg His Lys Arg Glu Thr Leu Lys Ala<br>145                    150                    155                    160 | 480 |
| act aag tat gtg gag ctg gtg atc gtg gca gac aac cga gag ttt cag<br>Thr Lys Tyr Val Glu Leu Val Ile Val Ala Asp Asn Arg Glu Phe Gln<br>                  165                    170                    175 | 528 |
| agg caa gga aaa gat ctg gaa aaa gtt aag cag cga tta ata gag att<br>Arg Gln Gly Lys Asp Leu Glu Lys Val Lys Gln Arg Leu Ile Glu Ile<br>                    180                    185                    190 | 576 |
| gct aat cac gtt gac aag ttt tac aga cca ctg aac att cgg atc gtg<br>Ala Asn His Val Asp Lys Phe Tyr Arg Pro Leu Asn Ile Arg Ile Val<br>            195                    200                    205 | 624 |
| ttg gta ggc gtg gaa gtg tgg aat gac atg gac aaa tgc tct gta agt<br>Leu Val Gly Val Glu Val Trp Asn Asp Met Asp Lys Cys Ser Val Ser<br>210                    215                    220 | 672 |
| cag gac cca ttc acc agc ctc cat gaa ttt ctg gac tgg agg aag atg<br>Gln Asp Pro Phe Thr Ser Leu His Glu Phe Leu Asp Trp Arg Lys Met<br>225                    230                    235                    240 | 720 |
| aag ctt cta cct cgc aaa tcc cat gac aat gcg cag ctt gtc agt ggg<br>Lys Leu Leu Pro Arg Lys Ser His Asp Asn Ala Gln Leu Val Ser Gly<br>                  245                    250                    255 | 768 |
| gtt tat ttc caa ggg acc acc atc ggc atg gcc cca atc atg agc atg<br>Val Tyr Phe Gln Gly Thr Thr Ile Gly Met Ala Pro Ile Met Ser Met<br>        260                    265                    270 | 816 |
| tgc acg gca gac cag tct ggg gga att gtc atg gac cat tca gac aat<br>Cys Thr Ala Asp Gln Ser Gly Gly Ile Val Met Asp His Ser Asp Asn<br>            275                    280                    285 | 864 |
| ccc ctt ggt gca gcc gtg acc ctg gca cat gag ctg ggc cac aat ttc<br>Pro Leu Gly Ala Ala Val Thr Leu Ala His Glu Leu Gly His Asn Phe<br>290                    295                    300 | 912 |

```
ggg atg aat cat gac aca ctg gac agg ggc tgt agc tgt caa atg gcg      960
Gly Met Asn His Asp Thr Leu Asp Arg Gly Cys Ser Cys Gln Met Ala
305                 310                 315                 320 gtt gag aaa gga ggc tgc atc atg aac gct tcc acc ggg tac cca ttt     1008
Val Glu Lys Gly Gly Cys Ile Met Asn Ala Ser Thr Gly Tyr Pro Phe
                325                 330                 335 ccc atg gtg ttc agc agt tgc agc agg aag gac ttg gag acc agc ctg     1056
Pro Met Val Phe Ser Ser Cys Ser Arg Lys Asp Leu Glu Thr Ser Leu
            340                 345                 350 gag aaa gga atg ggg gtg tgc ctg ttt aac ctg ccg gaa gtc agg gag     1104
Glu Lys Gly Met Gly Val Cys Leu Phe Asn Leu Pro Glu Val Arg Glu
        355                 360                 365 tct ttc ggg ggc cag aag tgt ggg aac aga ttt gtg gaa gaa gga gag     1152
Ser Phe Gly Gly Gln Lys Cys Gly Asn Arg Phe Val Glu Glu Gly Glu
    370                 375                 380 gag tgt gac tgt ggg gag cca gag gaa tgt atg aat cgc tgc tgc aat     1200
Glu Cys Asp Cys Gly Glu Pro Glu Glu Cys Met Asn Arg Cys Cys Asn
385                 390                 395                 400 gcc acc acc tgt acc ctg aag ccg gac gct gtg tgc gca cat ggg ctg     1248
Ala Thr Thr Cys Thr Leu Lys Pro Asp Ala Val Cys Ala His Gly Leu
                405                 410                 415 tgc tgt gaa gac tgc cag ctg aag cct gca gga aca gcg tgc agg gac     1296
Cys Cys Glu Asp Cys Gln Leu Lys Pro Ala Gly Thr Ala Cys Arg Asp
            420                 425                 430 tcc agc aac tcc tgt gac ctc cca gag ttc tgc aca ggg gcc agc cct     1344
Ser Ser Asn Ser Cys Asp Leu Pro Glu Phe Cys Thr Gly Ala Ser Pro
        435                 440                 445 cac tgc cca gcc aac gtg tac ctg cac gat ggg cac tca tgt cag gat     1392
His Cys Pro Ala Asn Val Tyr Leu His Asp Gly His Ser Cys Gln Asp
    450                 455                 460 gtg gac ggc tac tgc tac aat ggc atc tgc cag act cac gag cag cag     1440
Val Asp Gly Tyr Cys Tyr Asn Gly Ile Cys Gln Thr His Glu Gln Gln
465                 470                 475                 480 tgt gtc acg ctc tgg gga cca ggt gct aaa cct gcc cct ggg atc tgc     1488
Cys Val Thr Leu Trp Gly Pro Gly Ala Lys Pro Ala Pro Gly Ile Cys
                485                 490                 495 ttt gag aga gtc aat tct gca ggt gat cct tat ggc aac tgt ggc aaa     1536
Phe Glu Arg Val Asn Ser Ala Gly Asp Pro Tyr Gly Asn Cys Gly Lys
            500                 505                 510 gtc tcg aag agt tcc ttt gcc aaa tgc gag atg                         1569
Val Ser Lys Ser Ser Phe Ala Lys Cys Glu Met
        515                 520
```

<210> SEQ ID NO 24
<211> LENGTH: 523
<212> TYPE: PRT
<213> ORGANISM: Unknown Organism
<220> FEATURE:
<223> OTHER INFORMATION: Description of Unknown Organism: Clone:
    JM109(pMel-alpha-26N), human meltrin alpha

<400> SEQUENCE: 24

```
Gly Asp Leu Trp Ile Pro Val Lys Ser Phe Asp Ser Lys Asn His Pro
1               5                   10                  15

Glu Val Leu Asn Ile Arg Leu Gln Arg Glu Ser Lys Glu Leu Ile Ile
            20                  25                  30

Asn Leu Glu Arg Asn Glu Gly Leu Ile Ala Ser Ser Phe Thr Glu Thr
        35                  40                  45

His Tyr Leu Gln Asp Gly Thr Asp Val Ser Leu Ala Arg Asn Tyr Thr
    50                  55                  60
```

```
Gly His Cys Tyr Tyr His Gly His Val Arg Gly Tyr Ser Asp Ser Ala
 65                  70                  75                  80

Val Ser Leu Ser Thr Cys Ser Gly Leu Arg Gly Leu Ile Gly Phe Glu
                 85                  90                  95

Asn Glu Ser Tyr Val Leu Glu Pro Met Lys Ser Ala Thr Asn Arg Tyr
            100                 105                 110

Lys Leu Phe Pro Ala Lys Lys Leu Lys Ser Val Arg Gly Ser Cys Gly
        115                 120                 125

Ser His His Asn Thr Pro Asn Leu Ala Ala Lys Asn Val Phe Pro Pro
    130                 135                 140

Pro Ser Gln Thr Trp Ala Arg Arg His Lys Arg Glu Thr Leu Lys Ala
145                 150                 155                 160

Thr Lys Tyr Val Glu Leu Val Ile Val Ala Asp Asn Arg Glu Phe Gln
                165                 170                 175

Arg Gln Gly Lys Asp Leu Glu Lys Val Lys Gln Arg Leu Ile Glu Ile
            180                 185                 190

Ala Asn His Val Asp Lys Phe Tyr Arg Pro Leu Asn Ile Arg Ile Val
        195                 200                 205

Leu Val Gly Val Glu Val Trp Asn Asp Met Asp Lys Cys Ser Val Ser
    210                 215                 220

Gln Asp Pro Phe Thr Ser Leu His Glu Phe Leu Asp Trp Arg Lys Met
225                 230                 235                 240

Lys Leu Leu Pro Arg Lys Ser His Asp Asn Ala Gln Leu Val Ser Gly
                245                 250                 255

Val Tyr Phe Gln Gly Thr Thr Ile Gly Met Ala Pro Ile Met Ser Met
            260                 265                 270

Cys Thr Ala Asp Gln Ser Gly Gly Ile Val Met Asp His Ser Asp Asn
        275                 280                 285

Pro Leu Gly Ala Ala Val Thr Leu Ala His Glu Leu Gly His Asn Phe
    290                 295                 300

Gly Met Asn His Asp Thr Leu Asp Arg Gly Cys Ser Cys Gln Met Ala
305                 310                 315                 320

Val Glu Lys Gly Gly Cys Ile Met Asn Ala Ser Thr Gly Tyr Pro Phe
                325                 330                 335

Pro Met Val Phe Ser Ser Cys Ser Arg Lys Asp Leu Glu Thr Ser Leu
            340                 345                 350

Glu Lys Gly Met Gly Val Cys Leu Phe Asn Leu Pro Glu Val Arg Glu
        355                 360                 365

Ser Phe Gly Gly Gln Lys Cys Gly Asn Arg Phe Val Glu Glu Gly Glu
    370                 375                 380

Glu Cys Asp Cys Gly Glu Pro Glu Glu Cys Met Asn Arg Cys Cys Asn
385                 390                 395                 400

Ala Thr Thr Cys Thr Leu Lys Pro Asp Ala Val Cys Ala His Gly Leu
                405                 410                 415

Cys Cys Glu Asp Cys Gln Leu Lys Pro Ala Gly Thr Ala Cys Arg Asp
            420                 425                 430

Ser Ser Asn Ser Cys Asp Leu Pro Glu Phe Cys Thr Gly Ala Ser Pro
        435                 440                 445

His Cys Pro Ala Asn Val Tyr Leu His Asp Gly His Ser Cys Gln Asp
    450                 455                 460

Val Asp Gly Tyr Cys Tyr Asn Gly Ile Cys Gln Thr His Glu Gln Gln
465                 470                 475                 480
```

```
Cys Val Thr Leu Trp Gly Pro Gly Ala Lys Pro Ala Pro Gly Ile Cys
            485                 490                 495

Phe Glu Arg Val Asn Ser Ala Gly Asp Pro Tyr Gly Asn Cys Gly Lys
            500                 505                 510

Val Ser Lys Ser Ser Phe Ala Lys Cys Glu Met
            515                 520

<210> SEQ ID NO 25
<211> LENGTH: 2404
<212> TYPE: DNA
<213> ORGANISM: Unknown Organism
<220> FEATURE:
<223> OTHER INFORMATION: Description of Unknown Organism: Clone:
      JM109(pMel-beta-24C), human meltrin beta
<220> FEATURE:
<221> NAME/KEY: CDS
<222> LOCATION: (1)..(1017)

<400> SEQUENCE: 25
```

| | | |
|---|---|---|
| tgc tgc cac cag tgt aag ctg ttg gct cct ggg acc ctg tgc cgc gag<br>Cys Cys His Gln Cys Lys Leu Leu Ala Pro Gly Thr Leu Cys Arg Glu<br>1               5                   10                  15 | 48 |
| cag gcc agg cag tgt gac ctc ccg gag ttc tgt acg ggc aag tct ccc<br>Gln Ala Arg Gln Cys Asp Leu Pro Glu Phe Cys Thr Gly Lys Ser Pro<br>            20                  25                  30 | 96 |
| cac tgc cct acc aac ttc tac cag atg gat ggt acc ccc tgt gag ggc<br>His Cys Pro Thr Asn Phe Tyr Gln Met Asp Gly Thr Pro Cys Glu Gly<br>        35                  40                  45 | 144 |
| ggc cag gcc tac tgc tac aac ggc atg tgc ctc acc tac cag gag cag<br>Gly Gln Ala Tyr Cys Tyr Asn Gly Met Cys Leu Thr Tyr Gln Glu Gln<br>    50                  55                  60 | 192 |
| tgc cag cag ctg tgg gga ccc gga gcc cga cct gcc cct gac ctc tgc<br>Cys Gln Gln Leu Trp Gly Pro Gly Ala Arg Pro Ala Pro Asp Leu Cys<br>65                  70                  75                  80 | 240 |
| ttc gag aag gtg aat gtg gca gga gac acc ttt gga aac tgt gga aag<br>Phe Glu Lys Val Asn Val Ala Gly Asp Thr Phe Gly Asn Cys Gly Lys<br>                85                  90                  95 | 288 |
| gac atg aat ggt gaa cac agg aag tgc aac atg aga gat gcg aag tgt<br>Asp Met Asn Gly Glu His Arg Lys Cys Asn Met Arg Asp Ala Lys Cys<br>            100                 105                 110 | 336 |
| ggg aag atc cag tgt cag agc tct gag gcc cgg ccc ctg gag tcc aac<br>Gly Lys Ile Gln Cys Gln Ser Ser Glu Ala Arg Pro Leu Glu Ser Asn<br>        115                 120                 125 | 384 |
| gcg gtg ccc att gac acc act atc atc atg aat ggg agg cag atc cag<br>Ala Val Pro Ile Asp Thr Thr Ile Ile Met Asn Gly Arg Gln Ile Gln<br>    130                 135                 140 | 432 |
| tgc cgg ggc acc cac gtc tac cga ggt cct gag gag gag ggt gac atg<br>Cys Arg Gly Thr His Val Tyr Arg Gly Pro Glu Glu Glu Gly Asp Met<br>145                 150                 155                 160 | 480 |
| ctg gac cca ggg ctg gtg atg act gga acc aag tgt ggc tac aac cat<br>Leu Asp Pro Gly Leu Val Met Thr Gly Thr Lys Cys Gly Tyr Asn His<br>                165                 170                 175 | 528 |
| att tgc ctt gag ggg cag tgc agg aac acc tcc ttc ttt gaa act gaa<br>Ile Cys Leu Glu Gly Gln Cys Arg Asn Thr Ser Phe Phe Glu Thr Glu<br>            180                 185                 190 | 576 |
| ggc tgt ggg aag aag tgc aat ggc cat ggg gtc tgt aac aac aac cag<br>Gly Cys Gly Lys Lys Cys Asn Gly His Gly Val Cys Asn Asn Asn Gln<br>        195                 200                 205 | 624 |
| aac tgc cac tgc ctg ccg ggc tgg gcc ccg ccc ttc tgc aac aca ccg<br>Asn Cys His Cys Leu Pro Gly Trp Ala Pro Pro Phe Cys Asn Thr Pro<br>    210                 215                 220 | 672 |

| | | |
|---|---|---|
| ggc cac ggg ggc agt atc gac agt ggg cct atg ccc cct gag agt gtg<br>Gly His Gly Gly Ser Ile Asp Ser Gly Pro Met Pro Pro Glu Ser Val<br>225                           230                       235                   240 | | 720 |
| ggt cct gtg gta gct gga gtg ttg gtg gcc atc ttg gtg ctg gcg gtc<br>Gly Pro Val Val Ala Gly Val Leu Val Ala Ile Leu Val Leu Ala Val<br>                  245                        250                     255 | | 768 |
| ctc atg ctg atg tac tac tgc tgc aga cag aac aac aaa cta ggc caa<br>Leu Met Leu Met Tyr Tyr Cys Cys Arg Gln Asn Asn Lys Leu Gly Gln<br>    260                             265                       270 | | 816 |
| ctc aag ccc tca gct ctc cct tcc aag ctg agg caa cag ttc agt tgt<br>Leu Lys Pro Ser Ala Leu Pro Ser Lys Leu Arg Gln Gln Phe Ser Cys<br>275                           280                       285 | | 864 |
| ccc ttc agg gtt tct cag aac agc ggg act ggt cat gcc aac cca act<br>Pro Phe Arg Val Ser Gln Asn Ser Gly Thr Gly His Ala Asn Pro Thr<br>    290                             295                     300 | | 912 |
| ttc aag ccg gaa ttc cgg gcc ccc cac agc cca cac cat gac aag<br>Phe Lys Pro Glu Phe Arg Ala Pro His Ser Pro His His Asp Lys<br>305                       310                     315                  320 | | 960 |
| ggc cac caa ttc cac ggc cac acc ctc ctc cac tct ggg gac gac ccg<br>Gly His Gln Phe His Gly His Thr Leu Leu His Ser Gly Asp Asp Pro<br>                         325                         330                     335 | | 1008 |
| gat cct cac tgagctgacc acaacagcca ctacaactgc agccactgga<br>Asp Pro His | | 1057 |
| tccacggcca ccctgtcctc caccccaggg accacctgga tcctcacaga gccgagcact | | 1117 |
| atagccaccg tgatggtgcc caccggttcc acggccaccg cctcctccac tctgggaaca | | 1177 |
| gctcacaccc ccaaagtggt gaccaccatg ccactatgc ccacagccac tgcctccacg | | 1237 |
| gttcccagct cgtccaccgt ggggaccacc cgcacccctg cagtgctccc cagcagcctg | | 1297 |
| ccaaccttca gcgtgtccac tgtgtcctcc tcagtcctca ccaccctgag acccactggc | | 1357 |
| ttccccagct cccacttctc tactccctgc ttctgcaggg catttggaca gttttctcg | | 1417 |
| cccggggaag tcatctacaa taagaccgac cgagccggct gccatttcta cgcagtgtgc | | 1477 |
| aatcagcact gtgacattga ccgcttccag ggcgcctgtc ccacctcccc accgccagtg | | 1537 |
| tcctccgccc cgctgtcctc gccctcccct gcccctggct gtgacaatgc catccctctc | | 1597 |
| cggcaggtga atgagacctg gaccctggag aactgcacgg tggccaggtg cgtgggtgac | | 1657 |
| aaccgtgtcg tcctgctgga cccaaagcct gtggccaacg tcacctgcgt gaacaagcac | | 1717 |
| ctgcccatca aagtgtcgga cccgagccag ccctgtgact ccactatga gtgcgagtgc | | 1777 |
| atctgcagca tgtggggcgg ctcccactat tccacctttg acggcacctc ttacaccttc | | 1837 |
| cggggcaact gcacctatgt cctcatgaga gagatccatg cacgctttgg aatctcagc | | 1897 |
| ctctacctgg acaaccacta ctgcacggcc tctgccactg ccgctgccgc ccgctgcccc | | 1957 |
| cgcgccctca gcatccacta caagtccatg gatatcgtcc tcactgtcac catggtgcat | | 2017 |
| gggaaggagg agggcctgat cctgtttgac caaattccgg tgagcagcgg tttcagcaag | | 2077 |
| aacggcgtgc ttgtgtctgt gctggggacc accaccatgc gtgtggacat tcctgccctg | | 2137 |
| ggcgtgagcg tcaccttcaa tggccaagtc ttccaggccc ggctgcccta cagcctcttc | | 2197 |
| cacaacaaca ccgagggcca gtgcggcacc tgcaccaaca ccagaggga cgactgtctc | | 2257 |
| cagcgggacg gaaccactgc cgccagttgc aaggacatgg ccaagacgtg gctggtcccc | | 2317 |
| gacagcagaa aggatggctg ctgggcccg actggcacac cccccactgc cagccccgca | | 2377 |
| gccccggtgt ctagcacacc caccccg | | 2404 |

```
<210> SEQ ID NO 26
<211> LENGTH: 339
<212> TYPE: PRT
<213> ORGANISM: Unknown Organism
<220> FEATURE:
<223> OTHER INFORMATION: Description of Unknown Organism: Clone:
      JM109(pMel-beta-24C), human meltrin beta

<400> SEQUENCE: 26

Cys Cys His Gln Cys Lys Leu Leu Ala Pro Gly Thr Leu Cys Arg Glu
  1               5                  10                  15

Gln Ala Arg Gln Cys Asp Leu Pro Glu Phe Cys Thr Gly Lys Ser Pro
             20                  25                  30

His Cys Pro Thr Asn Phe Tyr Gln Met Asp Gly Thr Pro Cys Glu Gly
         35                  40                  45

Gly Gln Ala Tyr Cys Tyr Asn Gly Met Cys Leu Thr Tyr Gln Glu Gln
     50                  55                  60

Cys Gln Gln Leu Trp Gly Pro Ala Arg Pro Ala Pro Asp Leu Cys
 65                  70                  75                  80

Phe Glu Lys Val Asn Val Ala Gly Asp Thr Phe Gly Asn Cys Gly Lys
                 85                  90                  95

Asp Met Asn Gly Glu His Arg Lys Cys Asn Met Arg Asp Ala Lys Cys
            100                 105                 110

Gly Lys Ile Gln Cys Gln Ser Ser Glu Ala Arg Pro Leu Glu Ser Asn
        115                 120                 125

Ala Val Pro Ile Asp Thr Thr Ile Ile Met Asn Gly Arg Gln Ile Gln
    130                 135                 140

Cys Arg Gly Thr His Val Tyr Arg Gly Pro Glu Glu Gly Asp Met
145                 150                 155                 160

Leu Asp Pro Gly Leu Val Met Thr Gly Thr Lys Cys Gly Tyr Asn His
                165                 170                 175

Ile Cys Leu Glu Gly Gln Cys Arg Asn Thr Ser Phe Phe Glu Thr Glu
            180                 185                 190

Gly Cys Gly Lys Lys Cys Asn Gly His Gly Val Cys Asn Asn Asn Gln
        195                 200                 205

Asn Cys His Cys Leu Pro Gly Trp Ala Pro Pro Phe Cys Asn Thr Pro
    210                 215                 220

Gly His Gly Gly Ser Ile Asp Ser Gly Pro Met Pro Pro Glu Ser Val
225                 230                 235                 240

Gly Pro Val Val Ala Gly Val Leu Val Ala Ile Leu Val Leu Ala Val
                245                 250                 255

Leu Met Leu Met Tyr Tyr Cys Cys Arg Gln Asn Asn Lys Leu Gly Gln
            260                 265                 270

Leu Lys Pro Ser Ala Leu Pro Ser Lys Leu Arg Gln Gln Phe Ser Cys
        275                 280                 285

Pro Phe Arg Val Ser Gln Asn Ser Gly Thr Gly His Ala Asn Pro Thr
    290                 295                 300

Phe Lys Pro Glu Phe Arg Ala Pro His Ser His His His Asp Lys
305                 310                 315                 320

Gly His Gln Phe His Gly His Thr Leu Leu His Ser Gly Asp Pro
                325                 330                 335

Asp Pro His
```

```
<210> SEQ ID NO 27
<211> LENGTH: 453
<212> TYPE: DNA
<213> ORGANISM: Unknown Organism
<220> FEATURE:
<223> OTHER INFORMATION: Description of Unknown Organism: Clone:
      JM109(pMel-beta-24N), human meltrin beta
<220> FEATURE:
<221> NAME/KEY: CDS
<222> LOCATION: (2)..(451)

<400> SEQUENCE: 27 c gga gct gcc act ggg cac ccc ttt ccc aaa gtg ttc aat gga tgc aac      49
  Gly Ala Ala Thr Gly His Pro Phe Pro Lys Val Phe Asn Gly Cys Asn
  1               5                  10                  15 agg agg gag ctg gac agg tat ctg cag tca ggt ggt gga atg tgt ctc        97
Arg Arg Glu Leu Asp Arg Tyr Leu Gln Ser Gly Gly Gly Met Cys Leu
             20                  25                  30 tcc aac atg cca gac acc agg atg ttg tat gga ggc cgg agg tgt ggg       145
Ser Asn Met Pro Asp Thr Arg Met Leu Tyr Gly Gly Arg Arg Cys Gly
         35                  40                  45 aac ggg tat ctg gaa gat ggg gaa gag tgt gac tgt gga gaa gaa gag       193
Asn Gly Tyr Leu Glu Asp Gly Glu Glu Cys Asp Cys Gly Glu Glu Glu
     50                  55                  60 gaa tgt aac aac ccc tgc tgc aat gcc tct aat tgt acc ctg agg ccg       241
Glu Cys Asn Asn Pro Cys Cys Asn Ala Ser Asn Cys Thr Leu Arg Pro
 65                  70                  75                  80 ggg gcg gag tgt gct cac ggc tcc tgc tgc cac cag tgt aag ctg ttg       289
Gly Ala Glu Cys Ala His Gly Ser Cys Cys His Gln Cys Lys Leu Leu
                 85                  90                  95 gct cct ggg acc ctg tgc cgc gag cag gcc agg cag tgt gac ctc ccg       337
Ala Pro Gly Thr Leu Cys Arg Glu Gln Ala Arg Gln Cys Asp Leu Pro
            100                 105                 110 gag ttc tgt acg ggc aag tct ccc cac tgc cct acc aac ttc tac cag       385
Glu Phe Cys Thr Gly Lys Ser Pro His Cys Pro Thr Asn Phe Tyr Gln
        115                 120                 125 atg gat ggt acc ccc tgt gag ggc ggc cag gcc tac tgc tac aac ggc       433
Met Asp Gly Thr Pro Cys Glu Gly Gly Gln Ala Tyr Cys Tyr Asn Gly
    130                 135                 140 atg tgc ctc acc tac cag ga                                            453
Met Cys Leu Thr Tyr Gln
145             150

<210> SEQ ID NO 28
<211> LENGTH: 150
<212> TYPE: PRT
<213> ORGANISM: Unknown Organism
<220> FEATURE:
<223> OTHER INFORMATION: Description of Unknown Organism: Clone:
      JM109(pMel-beta-24N), human meltrin beta

<400> SEQUENCE: 28

Gly Ala Ala Thr Gly His Pro Phe Pro Lys Val Phe Asn Gly Cys Asn
1               5                  10                  15

Arg Arg Glu Leu Asp Arg Tyr Leu Gln Ser Gly Gly Gly Met Cys Leu
            20                  25                  30

Ser Asn Met Pro Asp Thr Arg Met Leu Tyr Gly Gly Arg Arg Cys Gly
        35                  40                  45

Asn Gly Tyr Leu Glu Asp Gly Glu Glu Cys Asp Cys Gly Glu Glu Glu
    50                  55                  60

Glu Cys Asn Asn Pro Cys Cys Asn Ala Ser Asn Cys Thr Leu Arg Pro
65                  70                  75                  80
```

-continued

```
Gly Ala Glu Cys Ala His Gly Ser Cys Cys His Gln Cys Lys Leu Leu
                85                  90                  95
Ala Pro Gly Thr Leu Cys Arg Glu Gln Ala Arg Gln Cys Asp Leu Pro
            100                 105                 110
Glu Phe Cys Thr Gly Lys Ser Pro His Cys Pro Thr Asn Phe Tyr Gln
        115                 120                 125
Met Asp Gly Thr Pro Cys Glu Gly Gly Gln Ala Tyr Cys Tyr Asn Gly
    130                 135                 140
Met Cys Leu Thr Tyr Gln
145                 150

<210> SEQ ID NO 29
<211> LENGTH: 20
<212> TYPE: DNA
<213> ORGANISM: Unknown Organism
<220> FEATURE:
<223> OTHER INFORMATION: Description of Unknown Organism:  MA-1 Primer
      for PCR

<400> SEQUENCE: 29
acgatgggca ctcatgtcag                                                     20

<210> SEQ ID NO 30
<211> LENGTH: 20
<212> TYPE: DNA
<213> ORGANISM: Unknown Organism
<220> FEATURE:
<223> OTHER INFORMATION: Description of Unknown Organism:  MA-2 primer
      for PCR

<400> SEQUENCE: 30
catctcgcat ttggcaaagg                                                     20

<210> SEQ ID NO 31
<211> LENGTH: 24
<212> TYPE: DNA
<213> ORGANISM: Unknown Organism
<220> FEATURE:
<223> OTHER INFORMATION: Description of Unknown Organism:  lambda gt11
      forward primer for PCR

<400> SEQUENCE: 31
ggtggcgacg actcctggag cccg                                                24

<210> SEQ ID NO 32
<211> LENGTH: 24
<212> TYPE: DNA
<213> ORGANISM: Unknown Organism
<220> FEATURE:
<223> OTHER INFORMATION: Description of Unknown Organism:  lambda gt11
      reverse primer for PCR

<400> SEQUENCE: 32
ttgacaccag accaactggt aatg                                                24

<210> SEQ ID NO 33
<211> LENGTH: 20
<212> TYPE: DNA
<213> ORGANISM: Unknown Organism
<220> FEATURE:
<223> OTHER INFORMATION: Description of Unknown Organism:  Mel-alpha 5'S
      primer for PCR

<400> SEQUENCE: 33
cactgaacat tcggatcgtg                                                     20
```

```
<210> SEQ ID NO 34
<211> LENGTH: 33
<212> TYPE: DNA
<213> ORGANISM: Unknown Organism
<220> FEATURE:
<223> OTHER INFORMATION: Description of Unknown Organism: lambda gt11
      forward-Eco primer for PCR

<400> SEQUENCE: 34
ccggaattcg gtggcgacga ctcctggagc ccg                                   33

<210> SEQ ID NO 35
<211> LENGTH: 33
<212> TYPE: DNA
<213> ORGANISM: Unknown Organism
<220> FEATURE:
<223> OTHER INFORMATION: Description of Unknown Organism: lambda gt11
      Reverse-Eco Primer for PCR

<400> SEQUENCE: 35
ccggaattct tgacaccaga ccaactggta atg                                   33

<210> SEQ ID NO 36
<211> LENGTH: 29
<212> TYPE: DNA
<213> ORGANISM: Unknown Organism
<220> FEATURE:
<223> OTHER INFORMATION: Description of Unknown Organism: MA-1-Eco
      primer for PCR

<400> SEQUENCE: 36
ccggaattca cgatgggcac tcatgtcag                                        29

<210> SEQ ID NO 37
<211> LENGTH: 29
<212> TYPE: DNA
<213> ORGANISM: Unknown Organism
<220> FEATURE:
<223> OTHER INFORMATION: Description of Unknown Organism: MA-2 Eco
      Primer for PCR

<400> SEQUENCE: 37
ccggaattcc atctcgcatt tggcaaagg                                        29

<210> SEQ ID NO 38
<211> LENGTH: 20
<212> TYPE: DNA
<213> ORGANISM: Unknown Organism
<220> FEATURE:
<223> OTHER INFORMATION: Description of Unknown Organism: S-hMel
      alpha-TM5' primer for PCR

<400> SEQUENCE: 38
gcacaaagtg tgcagatgga                                                  20

<210> SEQ ID NO 39
<211> LENGTH: 19
<212> TYPE: DNA
<213> ORGANISM: Unknown Organism
<220> FEATURE:
<223> OTHER INFORMATION: Description of Unknown Organism: A-mMel
      alpha-3' primer for PCR
<220> FEATURE:
<221> NAME/KEY: Unsure
<222> LOCATION: 10
<223> OTHER INFORMATION: Nucleotide "n" is unknown
```

```
<400> SEQUENCE: 39
cagaggcttc tga    ggaggn                                              19

<210> SEQ ID NO 40
<211> LENGTH: 6
<212> TYPE: PRT
<213> ORGANISM: Unknown organism
<220> FEATURE:
<223> OTHER INFORMATION: Description of unknown organism:  a polypeptide

<400> SEQUENCE: 40

Glu Asp Cys Asp Cys Gly
 1               5

<210> SEQ ID NO 41
<211> LENGTH: 6
<212> TYPE: PRT
<213> ORGANISM: Unknown organism
<220> FEATURE:
<223> OTHER INFORMATION: Description of unknown organism: a polypeptide

<400> SEQUENCE: 41

Glu Glu Cys Asp Cys Gly
 1               5

<210> SEQ ID NO 42
<211> LENGTH: 7
<212> TYPE: PRT
<213> ORGANISM: Unknown organism
<220> FEATURE:
<223> OTHER INFORMATION: Description of unknown organism: a polypeptide

<400> SEQUENCE: 42

Lys Cys Gly Lys Leu Ile Cys
 1               5

<210> SEQ ID NO 43
<211> LENGTH: 20
<212> TYPE: DNA
<213> ORGANISM: Unknown organism
<220> FEATURE:
<223> OTHER INFORMATION: Description of unknown organism: sense primer
      for PCR

<400> SEQUENCE: 43
cacgatgatg ggagagattg                                                 20

<210> SEQ ID NO 44
<211> LENGTH: 21
<212> TYPE: DNA
<213> ORGANISM: Unknown organism
<220> FEATURE:
<223> OTHER INFORMATION: Description of unknown organism: antisense
      primer for PCR

<400> SEQUENCE: 44
ctccgtatcc tttagtctca c                                               21
```